(12) United States Patent
Zhang

(10) Patent No.: US 10,450,300 B2
(45) Date of Patent: Oct. 22, 2019

(54) WNT SIGNALING PATHWAY INHIBITORS AND THERAPEUTIC APPLICATIONS THEREOF

(71) Applicants: Suzhou Yunxuan Yiyao Keji Youxian Gongsi, Suzhou, Jiangsu (CN); Xiaohu Zhang, Suzhou, Jiangsu (CN)

(72) Inventor: Xiaohu Zhang, Jiangsu (CN)

(73) Assignee: Suzhou Yunxuan Yiyao Keji Youxian Gongsi, Suzhou (CN)

( * ) Notice: Subject to any disclaimer, the term of this patent is extended or adjusted under 35 U.S.C. 154(b) by 0 days.

(21) Appl. No.: 15/766,799

(22) PCT Filed: Oct. 6, 2016

(86) PCT No.: PCT/US2016/055851
§ 371 (c)(1),
(2) Date: Apr. 6, 2018

(87) PCT Pub. No.: WO2017/062688
PCT Pub. Date: Apr. 13, 2017

(65) Prior Publication Data
US 2018/0244651 A1 Aug. 30, 2018

(30) Foreign Application Priority Data

Oct. 8, 2015 (CN) ............... 2015 1 0645986
Mar. 31, 2016 (CN) ............... 2016 1 0195731
Mar. 31, 2016 (CN) ............... 2016 1 0195733
Aug. 16, 2016 (CN) ............... 2016 1 0670828
Sep. 26, 2016 (CN) ............... 2016 1 0850357
Sep. 26, 2016 (CN) ............... 2016 1 0850358
Sep. 26, 2016 (CN) ............... 2016 1 0850360

(51) Int. Cl.
| | | |
|---|---|---|
| C07D 401/14 | (2006.01) |
| A61K 45/06 | (2006.01) |
| A61K 31/444 | (2006.01) |
| A61K 31/4709 | (2006.01) |
| A61K 31/4725 | (2006.01) |
| A61K 31/506 | (2006.01) |
| A61K 31/517 | (2006.01) |
| A61K 31/53 | (2006.01) |
| A61K 31/541 | (2006.01) |
| A61P 35/02 | (2006.01) |
| C07D 401/04 | (2006.01) |
| C07D 401/12 | (2006.01) |
| C07D 403/12 | (2006.01) |
| C07D 409/14 | (2006.01) |
| C07D 417/14 | (2006.01) |
| C07D 471/04 | (2006.01) |
| C07D 487/04 | (2006.01) |
| C07D 498/04 | (2006.01) |
| C07D 513/04 | (2006.01) |

(52) U.S. Cl.
CPC .......... *C07D 401/14* (2013.01); *A61K 31/444* (2013.01); *A61K 31/4709* (2013.01); *A61K 31/4725* (2013.01); *A61K 31/506* (2013.01); *A61K 31/517* (2013.01); *A61K 31/53* (2013.01); *A61K 31/541* (2013.01); *A61K 45/06* (2013.01); *A61P 35/02* (2018.01); *C07D 401/04* (2013.01); *C07D 401/12* (2013.01); *C07D 403/12* (2013.01); *C07D 409/14* (2013.01); *C07D 417/14* (2013.01); *C07D 471/04* (2013.01); *C07D 487/04* (2013.01); *C07D 498/04* (2013.01); *C07D 513/04* (2013.01)

(58) Field of Classification Search
CPC ............................. C07D 43/54; C07D 401/14
USPC ............................................. 514/256
See application file for complete search history.

(56) References Cited

U.S. PATENT DOCUMENTS

| | | | |
|---|---|---|---|
| 4,617,393 A | 10/1986 | Bagli et al. | |
| 7,799,782 B2 * | 9/2010 | Munson | C07D 231/56 514/234.5 |
| 9,834,550 B2 * | 12/2017 | Kim | C07D 519/00 |
| 2011/0189097 A1 | 8/2011 | Agalliu et al. | |
| 2014/0179696 A1 | 6/2014 | Hood et al. | |

FOREIGN PATENT DOCUMENTS

| | | |
|---|---|---|
| JP | S61205261 A | 9/1986 |
| WO | 20080132502 A1 | 11/2008 |
| WO | 2010020810 A1 | 2/2010 |
| WO | 2010041054 A1 | 4/2010 |
| WO | WO2012149528 * | 11/2012 |
| WO | 2013110433 A1 | 8/2013 |

(Continued)

OTHER PUBLICATIONS

Murray et al. CAS: 160: 440290, 2013.*

(Continued)

*Primary Examiner* — Rei Tsang Shiao
(74) *Attorney, Agent, or Firm* — Fox Rothschild LLP

(57) ABSTRACT

Inhibitors of Wnt signaling pathway with structures of Formula I are disclosed, together with their pharmaceutical salts. Applications of compounds of Formula I in inhibiting or modulating the Wnt signaling pathway are also disclosed. Compounds of Formula I can treat disorders caused by aberrant activation of the Wnt signaling pathway.

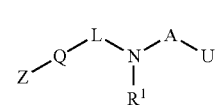

I

7 Claims, 3 Drawing Sheets

(56) References Cited

FOREIGN PATENT DOCUMENTS

| WO | 2014159733 A1 | 10/2014 |
| WO | 2014165232 A1 | 10/2014 |
| WO | 2016020295 A1 | 2/2016 |
| WO | 2016044787 A1 | 3/2016 |

OTHER PUBLICATIONS

Dastbaravardeh et al. CAS: 158: 104603, 2012.*
Chekler et al. CAS: 153: 609635, 2010.*
Kim et al. US 20160122343, see Kim et al. CAS: 164: 556329, 2016.*
Guan et al., "Discovery of novelJak2-Stat pathway inhibitors with exended residence time on target," Bioorganic & Medical Chemistry Letters (2013); 23:3105-3110.
European Search Report for EP Application No. 16854369.2 dated Apr. 11, 2019.

* cited by examiner

WNT SIGNALING PATHWAY INHIBITORS AND THERAPEUTIC APPLICATIONS THEREOF

CROSS REFERENCE TO RELATED APPLICATIONS

This application is the 35 U.S.C. § 371 National Phase Application of International Application Serial No. PCT/US2016/055851, filed on Oct. 6, 2016, which in turn claims the benefit of Chinese Patent Applications 201510645986.2, filed on Oct. 8, 2015; 201610195733.4, filed on Mar. 31, 2016; 201610195731.5, filed on Mar. 31, 2016; 201610670828.7, filed on Aug. 16, 2016; 201610850360.X, filed on Sep. 26, 2016; 201610850358.2, filed on Sep. 26, 2016; and 201610850357.8, filed on Sep. 26, 2016; all of which are hereby incorporated by reference.

FIELD OF INVENTION

The present invention generally relates to heterocyclic compounds and, more particularly, relates to novel heterocyclic compounds that are useful in therapies targeting the Wnt signaling pathway mediated diseases, such as cancer, in mammals.

BACKGROUND OF THE INVENTION

The Wnt signaling pathway has critical roles in developmental pathways, including regulatory roles in cell proliferation, tissue patterning, and cell fate, migration, morphogenesis and function, as well as cell survival and degeneration (Logan and Nusse, *Annu. Rev. Cell Dev. Biol.* (2004) 20:781-810). Recently during research on stem cells, Wnt signaling pathway has been found to regulate the maintenance of epidermal stem cells, intestinal stem cells, hematopoietic stem cells, neural stem cells, embryonic stem cells and tumor stem cells (Reya and Clevers, *Nature* (2005) 434:843-850).

The canonical Wnt signaling pathway is activated by Wnt proteins that interact with seven-pass transmembrane receptors of the Frizzled (Fzd) family and single-pass transmembrane co-receptors, such as lipoprotein receptor-related protein 5/6 (LRP5/6). Such interaction activates the Wnt signaling pathway by recruiting and activating the Dishevelled (Dvl) protein, which, in turn, silences glycogen synthase kinase 3β (GSK3β) within a destructive complex formed by adenomatous polyposis coli (APC) protein, GSK3β, Axin, and a priming kinase for β-catenin called casein kinase 1α (CK1α). The destructive complex can phosphorylate β-catenin for its degradation. By inhibiting the destructive complex, cytoplasmic β-catenin can be stabilized and accumulated in the presence of lymphoid enhancing factor/T-cell factor (LEF/TCF) transcription factors so that β-catenin can be translocated into the nucleus to activate β-catenin mediated gene expressions of dease-causing products, including c-Myc, cyclin-D1, survivin, gastrin, VEGF, ASEF, etc., to increase cell proliferation (Boutros and Mlodzik, *Mech. Dev.* (1999) 83:27-37; and Perrimon, *Cell* (1994) 76:781-4).

Mutations or deregulated expression of components of the Wnt signaling pathway have been linked to the formation and metastasis of numerous tumors. For example, in patients with colon cancer, gene mutations have been observed in regulators of the Wnt cascade, including APC, β-catenin, Axin and TCF, leading to over-expression of genes associated with cell proliferation (Klaus and Birchmeier, *Nat. Rev. Cancer* (2008) 8:387-98). Aberrant activation of the Wnt signaling pathway is associated with a variety of diseases including various cancers (Hoang et al., *Int. J. Cancer* (2004) 109:106-111), decrease of neural precursor cells (Chenn and Walsh, *Science* (2002) 297:365-9), pathogenesis of sporadic medulloblastoma (Dahmen et al., *Cancer Res.* (2001) 61:7039-43), malignant proliferation of cancer cells due to disruption of Wnt signaling pathway in stem and progenitor cells (Reya and Clevers, *Nature* (2005) 434:843-850).

Thus, there is a need for agents and methods that modulate the Wnt signaling pathway, thereby treating, and/or ameliorating Wnt signaling-related disorders.

SUMMARY OF THE INVENTION

In one aspect, the present invention provides compounds of Formula I:

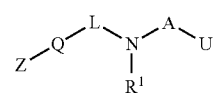

I or a pharmaceutically acceptable salt, solvate, stereoisomer or a tautomer thereof, wherein
A is A1, A2, A3 or A4;
U is U1, U2, U3 or U4;
L is L1, L2, or L3;
Q is Q1, Q2, Q3 or Q4;
Z is Z1, Z2, Z3 or Z4;
A1 is

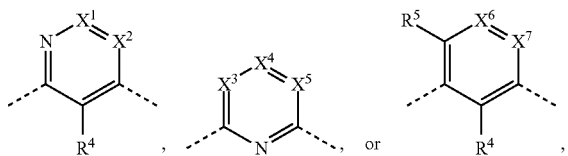

wherein $X^1$ to $X^7$ are independently selected from N and C—$R^{13}$;
A2 is

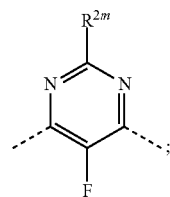

A3 is

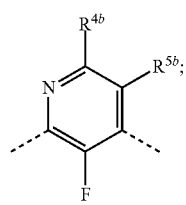

A4 is

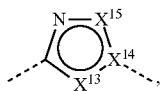

wherein $X^{13}$ and $X^{15}$ are independently O, N, S or C—$R^{4c}$, and $X^{14}$ is N or C;

U1 is

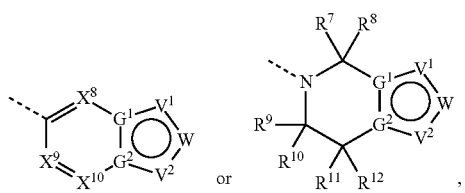

wherein $X^8$ to $X^{10}$ are independently selected from N and C—$R^{14}$;

$G^1$ and $G^2$ are independently selected from N and C;

$V^1$ and $V^2$ are independently selected from N, O, S and C—$R^{15}$;

W is $V^3$, $V^4$—V or $V^4$=$V^5$, wherein $V^3$ to $V^5$ are independently selected from N, O, S and C—$R^{16}$, wherein $V^4$ connects with $V^1$; and $V^5$ connects with $V^2$;

U2 is $C_6$-$C_{10}$ aryl, 5-12 membered heteroaryl, 11-13 membered heterocyclophenyl or 10-13 membered heterocycloheteroaryl, wherein heterocycle and heteroaryl comprises 1 to 4 heteroatoms independently selected from N, O and S; and $C_6$-$C_{10}$ aryl, 5-12 membered heteroaryl, 11-13 membered heterocyclophenyl and 10-13 membered heterocycloheteroaryl are unsubstituted or substituted with 1 to 4 $R^{6a}$ groups;

U3 is —$OR^{14b}$, —$NR^{14b}R^{15b}$, $C_6$-$C_{12}$ aryl unsubstituted or substituted with 1-6 $R^{13b}$ group, 5-14 membered heteroaryl unsubstituted or substituted with 1-6 $R^{13b}$ group, 11-13 membered heterocyclophenyl unsubstituted or substituted with 1-6 $R^{13b}$ group, 10-13 membered heterocycloheteroaryl unsubstituted or substituted with 1-6 $R^{13b}$ group, $C_2$-$C_8$ alkenyl substituted with 5-6 membered aryl or heteroaryl, $C_2$-$C_8$ alkynyl substituted with 5-6 membered aryl or herteroaryl, or

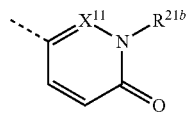

unsubstituted or substituted with 1 to 2 $R^{13b}$ groups, wherein heterocycle and heteroaryl comprises 1 to 4 heteroatoms independently selected from N, O and S; and $X^{11}$ is N or C—$R^{13b}$;

U4 is

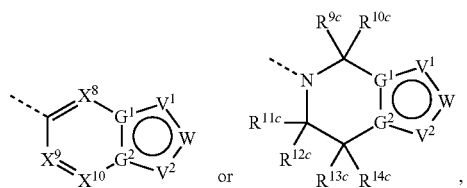

wherein $X^8$ to $X^{10}$ are independently selected from N and C—$R^{15c}$;

$G^1$ and $G^2$ are independently selected from N and C;

$V^1$ and $V^2$ are independently selected from N, O, S and C—$R^{16c}$;

W is $V^3$, $V^4$—$V_5$ or $V^4$=$V^5$, wherein $V^3$ to $V^5$ are independently selected from N, O, S and C—$R^{17c}$, wherein $V^4$ connects with $V^1$; and $V^5$ connects with $V^2$;

L1 is

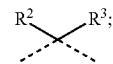

L2 is

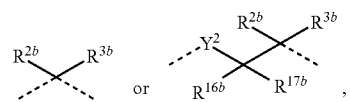

wherein $Y^2$ is blank, —O—, —S—, —N($R^{18b}$)— or —C($R^{18b}$)($R^{19b}$)—

L3 is —C($R^{2c}$)($R^{3c}$)— or —$NHCH_2CH_2$—;

Q1 is $C_6$-$C_{10}$ arylene or 5-12 membered heteroarylene, wherein 5-12 membered heteroarylene comprises 1 to 4 heteroatoms independently selected from N, O and S; and $C_6$-$C_{10}$ aryl and 5-12 membered heteroarylene are unsubstituted or substituted with 1 to 4 $R^{17}$ groups;

Q2 is $C_6$-$C_{10}$ arylene or 5-10 membered heteroarylene, wherein 5-10 membered heteroarylene comprises 1 to 4 heteroatoms independently selected from N, O and S; and $C_6$-$C_{10}$ arylene and 5-10 membered heteroarylene are unsubstituted or substituted with 1 to 4 $R^{4a}$ groups;

Q3 is $C_6$-$C_{12}$ arylene unsubstituted or substituted with 1-6 $R^{6b}$ group, 5-14 membered heteroarylene unsubstituted or substituted with 1-6 $R^{6b}$ group, $C_3$-$C_6$ cycloalkylene unsubstituted or substituted with 1-6 $R^{6b}$ group, $C_3$-$C_6$ heterocylene unsubstituted or substituted with 1-6 $R^{6b}$ group, or

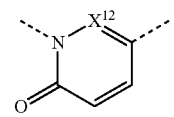

unsubstituted or substituted with 1 to 2 $R^{6b}$ groups, wherein heterocyclene and heteroarylene comprises 1 to 4 heteroatoms independently selected from N, O and S; and $X^{12}$ is N or C—$R^{6b}$;

Q4 is $C_6$-$C_{10}$ arylene or 5-12 membered heteroarylene, wherein 5-12 membered heteroarylene comprises 1 to 4 heteroatoms independently selected from N, O and S; and $C_6$-$C_{10}$ arylene and 5-12 membered heteroarylene are unsubstituted or substituted with 1 to 4 $R^{5c}$ groups;

Z1 is —CN, $C_6$ aryl, 5-6 membered heteroaryl, or

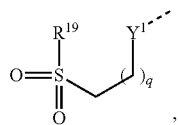

wherein 5-6 membered heteroaryl comprises 1 to 3 heteroatoms independently selected from N, O and S;

$C_6$ aryl and 5-6 membered heteroaryl are unsubstituted or substituted with 1 to 3 $R^{18}$ groups;

$Y^1$ is O or $NR^{20}$; and q is 0, 1, 2, or 3;

Z2 is H, —CN, halide, —OH, $C_1$-$C_8$ alkyl, $C_3$-$C_8$ cycloalkyl, $C_2$-$C_8$ alkenyl, $C_2$-$C_8$ alkynyl, $C_1$-$C_8$ alkylsulfonyl, $C_1$-$C_8$ acyl, aminoacyl, $C_1$-$C_8$ acylamino, $C_1$-$C_8$ alkylcarbamoylamino, $C_1$-$C_8$ alkoxycarbamoyl, $C_1$-$C_8$ alkylsulfonamido, $C_1$-$C_8$ alkylaminosulphonyl, $C_1$-$C_8$ alkoxy, $C_2$-$C_8$ alkoxyacyl, phenyl, 5-6 membered heteroaryl, or 5-7 membered heterocycle, wherein 5-6 membered heteroaryl and 5-7 membered heterocycle comprise one or more hetero atoms independently selected from N, O and S; and phenyl, 5-6 membered heteroaryl and 5-7 membered heterocycle are unsubstituted or substituted with 1 to 3 $R^{5a}$ groups;

Z3 is H, —CN, halide, —OH, $C_1$-$C_8$ alkyl unsubstituted or substituted with 1 to 3 $R^{12b}$ groups, $C_3$-$C_8$ cycloalkyl, $C_2$-$C_8$ alkenyl, $C_2$-$C_8$ alkynyl, $C_1$-$C_8$ alkylsulfonyl, $C_1$-$C_8$ acyl, aminoacyl, $C_1$-$C_8$ acylamino, $C_1$-$C_8$ alkylcarbamoylamino, $C_1$-$C_8$ alkoxycarbamoyl, $C_1$-$C_8$ alkylsulfonamido, $C_1$-$C_8$ alkylaminosulphonyl, $C_1$-$C_8$ alkoxy, $C_2$-$C_8$ alkoxyacyl, —N($R^{7b}$)($R^{8b}$) unsubstituted or substituted with 1 to 3 $R^{12b}$ groups, phenyl unsubstituted or substituted with 1 to 3 $R^{9b}$ groups, 5-6 membered heteroaryl unsubstituted or substituted with 1 to 3 $R^{10b}$ groups, or 5-7 membered heterocycle unsubstituted or substituted with 1 to 3 $R^{11b}$ groups, wherein 5-6 membered heteroaryl and 5-7 membered heterocycle comprises 1-3 hetero atoms independently selected from N, O and S;

Z4 is —CN, $C_6$ aryl, 5-6 membered heteroaryl, or

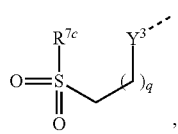

wherein 5-6 membered heteroaryl comprises 1 to 3 heteroatoms independently selected from N, O and S;

$C_6$ aryl and 5-6 membered heteroaryl are unsubstituted or substituted with 1 to 3 $R^{6c}$ groups;

$Y^3$ is O or $NR^{8c}$; and q is 0, 1, 2, or 3;

$R^1$ to $R^3$ are independently selected from H and $C_1$-$C_6$ alkyl, wherein $C_1$-$C_6$ alkyl is unsubstituted or substituted with 1 to 3 halide, —CN, —OH, $C_1$-$C_3$ alkyl, $C_3$-$C_5$ cycloalkyl, or $C_1$-$C_3$ alkoxy groups;

$R^4$ is H, halide, —CN, —OH, —$NO_2$, $C_1$-$C_6$ alkyl, $C_3$-$C_8$ cycloalkyl, or $C_1$-$C_6$ alkoxy, wherein $C_1$-$C_6$ alkyl, $C_3$-$C_8$ cycloalkyl and $C_1$-$C_6$ alkoxy are unsubstituted or substituted with 1 to 3 halide;

$R^5$ and $R^6$ are independently selected from H, halide, —CN, —OH, amino, $C_1$-$C_6$ alkyl, $C_3$-$C_6$ cycloalkyl and $C_1$-$C_6$ alkoxy, wherein $C_1$-$C_6$ alkyl, $C_3$-$C_6$ cycloalkyl and $C_1$-$C_6$ alkoxy are unsubstituted or substituted with 1 to 3 halide;

$R^7$ and $R^8$ are independently selected from H and $C_1$-$C_6$ alkyl, or $R^7$ and $R^8$ together are oxo (=O);

$R^9$ to $R^{12}$ are independently selected from H, $C_1$-$C_6$ alkyl;

$R^{13}$ is H, halide, —CN, —OH, amino, —$NO_2$, $C_1$-$C_6$ alkyl, $C_3$-$C_6$ cycloalkyl, $C_1$-$C_6$ alkoxy, $C_1$-$C_6$ alkylthio or 1-pyrrolidino, wherein amino, $C_1$-$C_6$ alkyl and $C_1$-$C_6$ alkoxy are unsubstituted or substituted with 1 to 3 halide, $C_1$-$C_3$ alkyl or $C_3$-$C_6$ cycloalkyl groups;

$R^{14}$ to $R^7$ are independently selected from H, halide, —CN, —OH, amino, $C_1$-$C_6$ alkyl, $C_3$-$C_6$ cycloalkyl, $C_1$-$C_6$ alkoxy and $C_1$-$C_6$ alkylthio, wherein amino, $C_1$-$C_6$ alkyl and $C_1$-$C_6$ alkoxy are unsubstituted or substituted with 1 to 3 halide, $C_1$-$C_3$ alkyl or $C_3$-$C_6$ cycloalkyl groups;

$R^{18}$ is H, halide, —CN, —OH, amino, $C_1$-$C_6$ alkyl, $C_3$-$C_6$ cycloalkyl or $C_1$-$C_6$ alkoxy, wherein amino, $C_1$-$C_6$ alkyl and $C_1$-$C_6$ alkoxy are unsubstituted or substituted with 1 to 3 halide, $C_1$-$C_3$ alkyl or $C_3$-$C_6$ cycloalkyl groups;

$R^{19}$ and $R^{20}$ are independently selected from H and $C_1$-$C_3$ alkyl, or $R^{19}$ and $R°$ together, with adjacent atoms they attached to, form a cyclic structure;

$R^{4a}$ and $R^{5a}$ are independently selected from halide, —CN, and —OH, or $R^{4a}$, $R^{5a}$ and $R^{6a}$ are independently selected from $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, $C_1$-$C_8$ alkylsulfonyl, $C_1$-$C_8$ acyl, aminoacyl, $C_1$-$C_8$ acylamino, $C_1$-$C_8$ alkylcarbamoylamino, $C_1$-$C_8$ alkoxycarbamoyl, $C_1$-$C_8$ alkylsulfonamido, $C_1$-$C_8$ alkylaminosulphonyl, $C_2$-$C_8$ alkoxyacyl, and 3-8 membered heterocycle, all of which are unsubstituted or substituted with 1-3 halide, —OH, —CN, $C_1$-$C_3$ alkyl, $C_1$-$C_3$ alkoxyl or $C_3$-$C_8$ cycloalkyl groups, wherein 3-8 membered heterocycle comprises one or more hetero atoms from N, O or S;

$R^{2m}$ is H, deuterium, tritium, halide, —OH, —CN, $C_1$-$C_8$ alkyl, $C_3$-$C_8$ cycloalkyl or $C_1$-$C_8$ alkoxy;

$R^{2b}$ and $R^{3b}$ are independently selected from H, $C_1$-$C_6$ alkyl unsubstituted or substituted with 1-3 groups selected from halide, —CN, —OH, $C_1$-$C_6$ alkyl, $C_3$-$C_5$ cycloalkyl and $C_1$-$C_3$ alkoxy;

$R^{4b}$ and $R^{5b}$ are independently selected from H, halide, —CN, amino, $C_1$-$C_8$ alkyl, $C_3$-$C_8$ cycloalkyl, $C_1$-$C_8$ alkoxy, and $C_1$-$C_3$ alkylamino;

$R^{6b}$ is H, halide, —CN or —OH, or $R^{6b}$ is selected from amino, $C_1$-$C_6$ alkyl, $C_3$-$C_6$ cycloalkyl, $C_1$-$C_6$ alkoxy, and $C_1$-$C_3$ alkylamino, all of which are unsubstituted or substituted with 1-3 halide, $C_1$-$C_3$ alkyl, or $C_3$-$C_6$ cycloalkyl groups;

$R^{7b}$ and $R^{8b}$ are independently selected from H, $C_1$-$C_8$ alkyl and $C_3$-$C_8$ cycloalkyl, the latter two of which are unsubstituted or substituted with 1-3 $R^{12b}$, or $R^7$ and $R^8$ together, with adjacent atoms they attached to, form a cyclic structure;

$R^{9b}$ and $R^{10b}$ are independently selected from H, halide, —CN and —OH, or $R^{9b}$ and $R^{10b}$ are independently selected from amino, $C_1$-$C_6$ alkyl, $C_3$-$C_6$ cycloalkyl, and $C_1$-$C_6$ alkoxy, all of which are unsubstituted or substituted with 1-3 halide, $C_1$-$C_3$ alkyl, or $C_3$-$C_6$ cycloalkyl groups;

$R^{11b}$ is H, halide, —CN, —OH, amino, $C_1$-$C_6$ alkyl unsubstituted or substituted with halide, $C_3$-$C_6$ cycloalkyl, oxo, or $C_1$-$C_6$ alkoxy;

$R^{12b}$ is H, —CN, —OH, amino, $C_1$-$C_6$ alkyl unsubstituted or substituted with halide, $C_3$-$C_6$ cycloalkyl, oxo, or $C_1$-$C_6$ alkoxy;

$R^{13b}$ is H, halide, —CN, —OH, amino, $C_1$-$C_6$ alkyl, $C_3$-$C_6$ cycloalkyl, $C_1$-$C_6$ alkoxy, $C_2$-$C_6$ alkylcarbamoylamino, $C_2$-$C_6$ alkoxycarbamoyl, $C_1$-$C_3$ alkylsulphonyl, —N($R^{16b}$)S(O)$_2$—$C_1$-$C_3$ alkyl, or —N($R^{16b}$)C(O)—$C_1$-$C_3$ alkyl;

$R^{14b}$ and $R^{15b}$ are independently selected from H, $C_3$-$C_6$ cycloalkyl unsubstituted or substituted with 1 to 3 $R^{20b}$ groups, $C_1$-$C_6$ alkyl unsubstituted or substituted with 1 to 3 $R^{20b}$ groups, 5-6 membered aryl unsubstituted or substituted with 1 to 3 $R^{20b}$ groups, 5-6 membered heteroaryl unsubstituted or substituted with 1 to 3 $R^{20b}$ groups, and 5-6 membered heterocycle unsubstituted or substituted with 1 to 3 $R^{20b}$ groups, wherein 5-6 membered heteroaryl and 5-7 membered heterocycle comprise 1 to 3 hetero atoms independently selected from N, O and S, or $R^{14b}$ and $R^{15b}$ together, with adjacent atoms they attached to, form a cyclic structure;

$R^{16b}$ to $R^{19b}$ are independently selected from H and $C_1$-$C_6$ alkyl unsubstituted or substituted with halide;

$R^{20b}$ is H, —CN, —OH, amino, $C_1$-$C_6$ alkyl, $C_3$-$C_6$ cycloalkyl, $C_1$-$C_6$ alkoxy, 5-6 membered aryl, or 5-6 membered heteroaryl, wherein 5-6 membered heteroaryl comprises 1 to 3 hetero atoms independently selected from N, O and S;

$R^{21b}$ is H or $C_1$-$C_6$ alkyl;

$R^{2c}$ and $R^{3c}$ are independently selected from H and $C_1$-$C_6$ alkyl unsubstituted or substituted with 1-3 halide;

$R^{4c}$ is H, halide, $C_1$-$C_3$ alkyl, $C_3$-$C_5$ cycloalkyl, or $C_1$-$C_3$ alkoxy;

$R^{5c}$ and $R^{6c}$ are independently selected from H, halide, —CN, —OH, amino, $C_1$-$C_6$ alkyl unsubstituted or substituted with 1-3 halide, $C_3$-$C_5$ cycloalkyl, and $C_1$-$C_6$ alkoxy;

$R^{7c}$ and $R^{8c}$ are independently selected from H and $C_1$-$C_6$ alkyl, or $R^{7c}$ and $R^{8c}$ together, with adjacent atoms they attached to, form a cyclic structure;

$R^{9c}$ to $R^{14c}$ are independently selected from H, $C_1$-$C_6$ alkyl and —CF$_3$;

$R^{15c}$ to $R^{17c}$ are independently selected from H, halide, —CN, —OH, amino, $C_1$-$C_6$ alkyl unsubstituted or substituted with 1-3 halide, $C_3$-$C_5$ cycloalkyl, and $C_1$-$C_6$ alkoxy.

In one embodiment, the compound of Formula I comprises Q which is

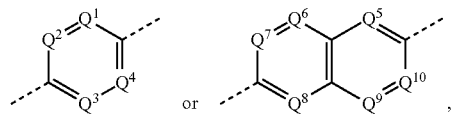

wherein $Q^1$ to $Q^{10}$ are independently N or C—$R^{17}$.

In another embodiment, the compound of Formula I comprises A which is

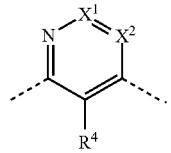

In one embodiment, the compound of Formula I comprises U which is

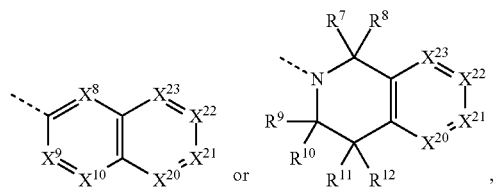

wherein $X^{20}$ to $X^{23}$ are independently N or C—$R^{15}$.

In another embodiment, the compound of Formula I comprises U which is selected from:

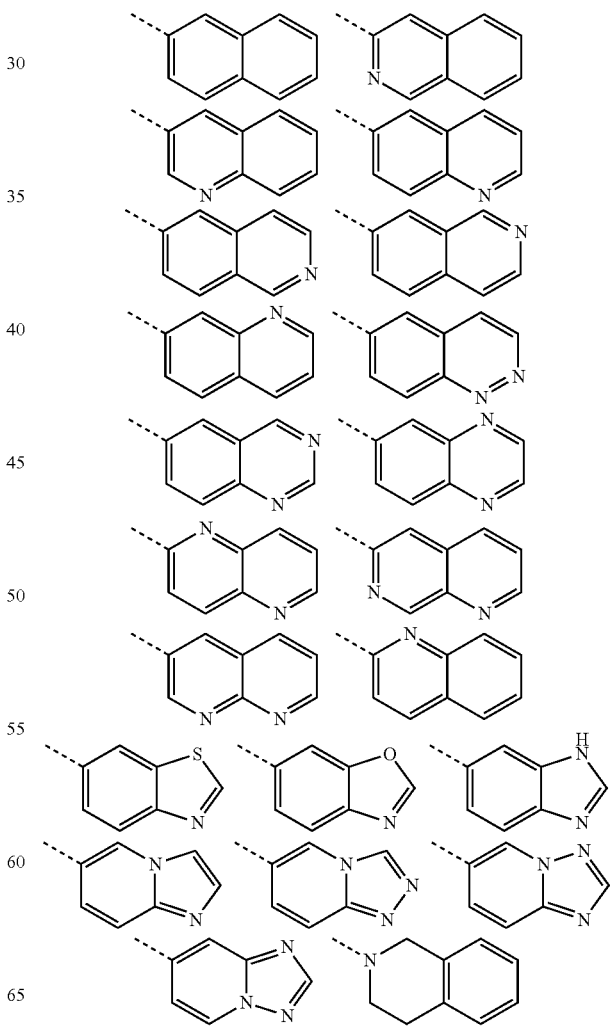

-continued
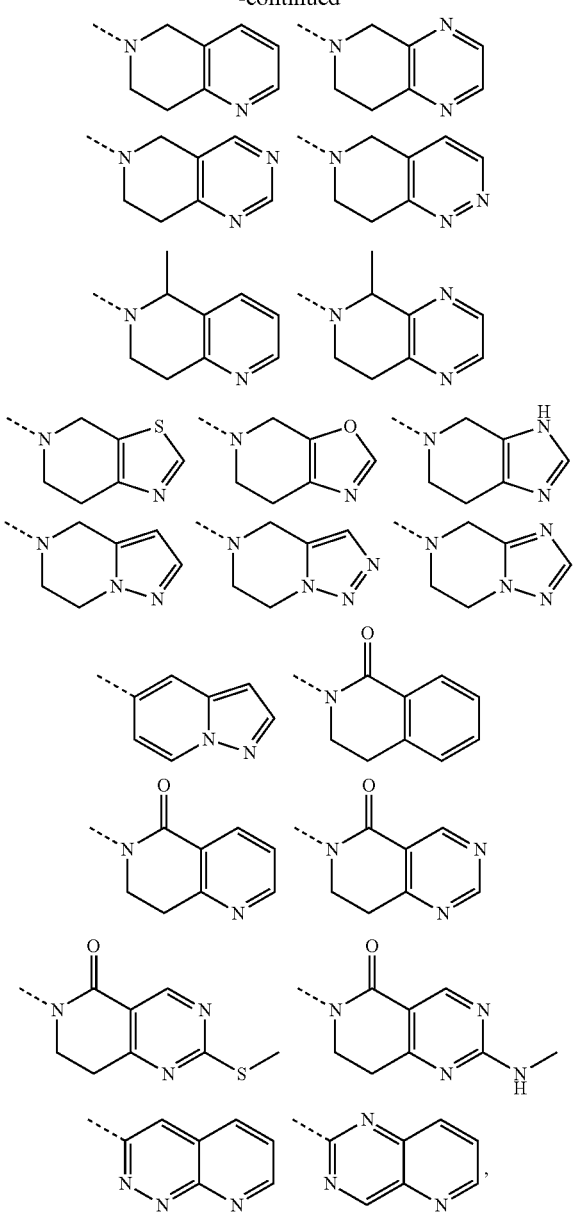
unsubstituted or substituted with 1 to 3 $R^{15}$ groups.
In one embodiment, the compound of Formula I comprises Q which is selected from:
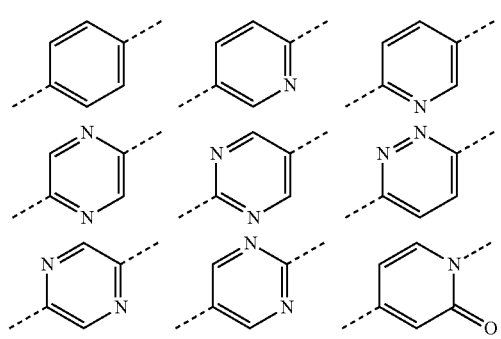
-continued
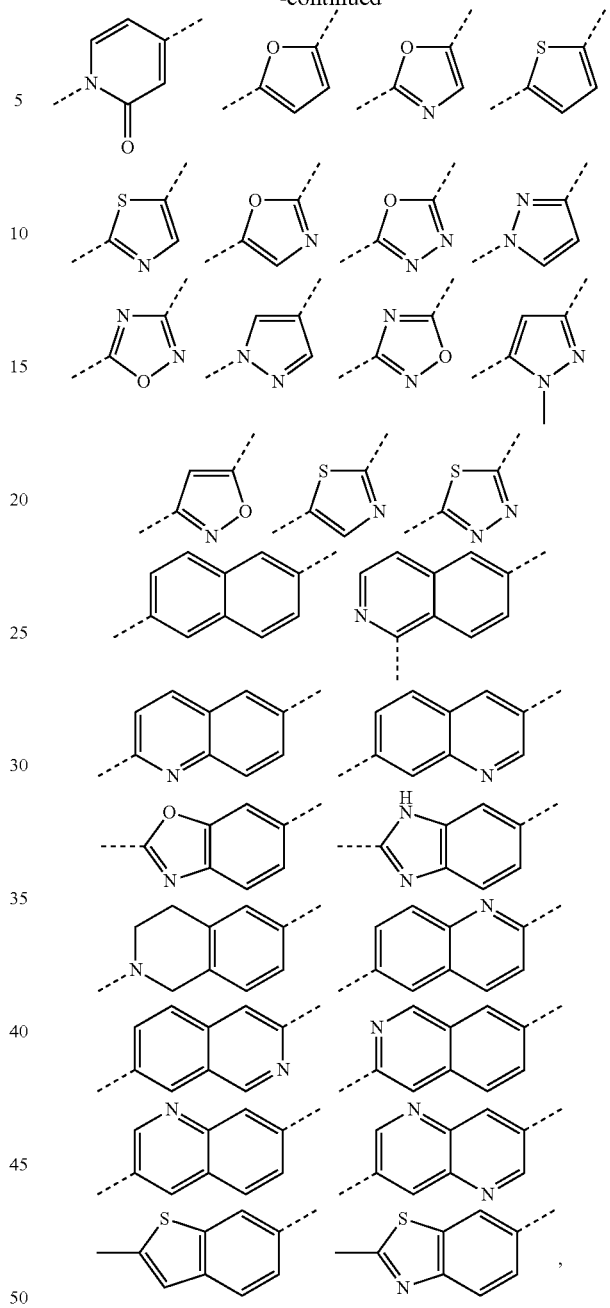
unsubstituted or substituted with 1 to 3 $R^{4a}$ groups.
In one embodiment, the compound of Formula I comprises Z which is selected from:
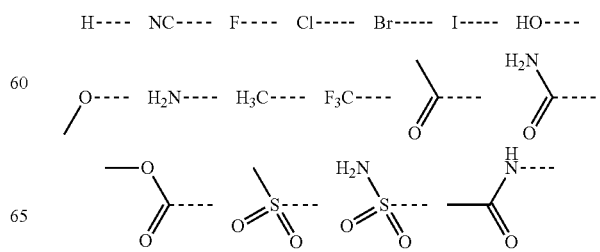

-continued
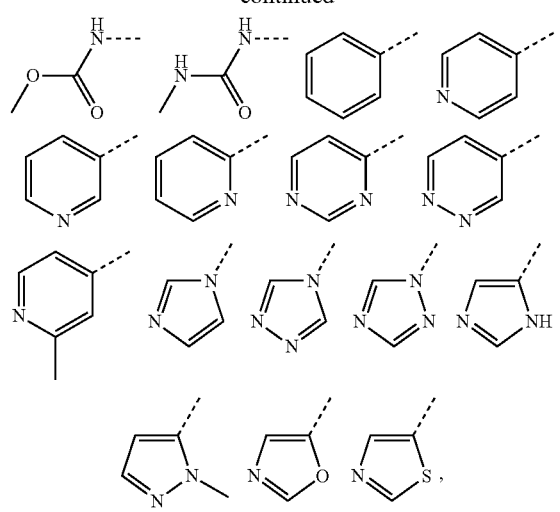
unsubstituted or substituted with 1 to 3 $R^{5a}$ groups.
In another embodiment, the compound of Formula I comprises Q which is selected from:
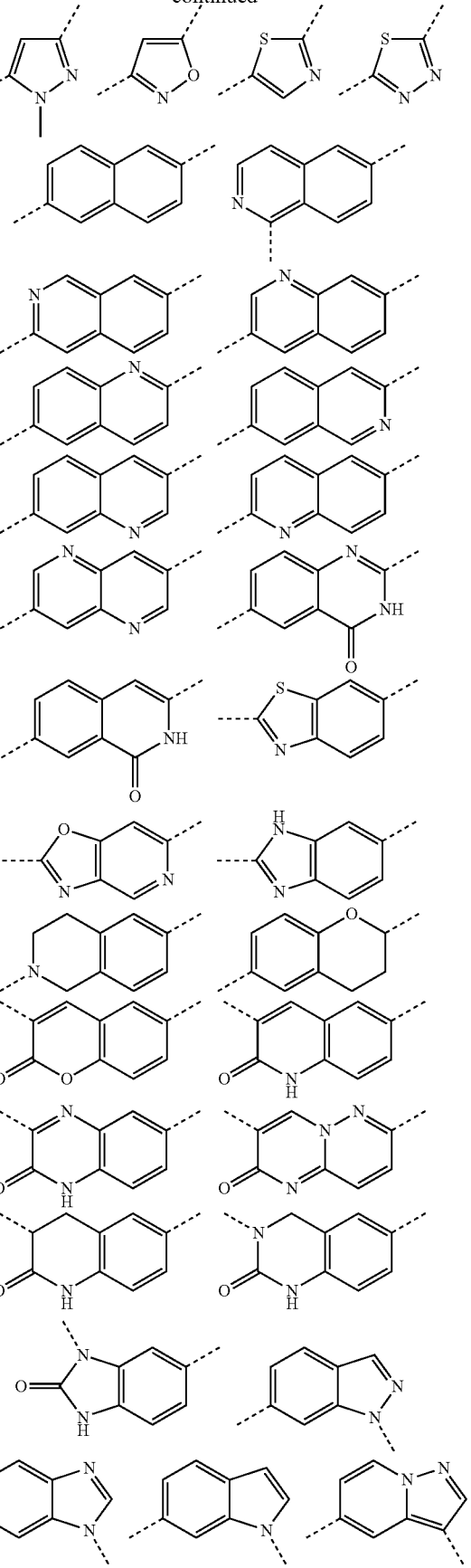

-continued
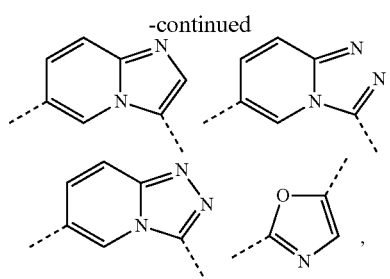
unsubstituted or substituted with 1 to 6 $R^{6b}$ groups.
In one embodiment, the compound of Formula I comprises Z which is selected from:
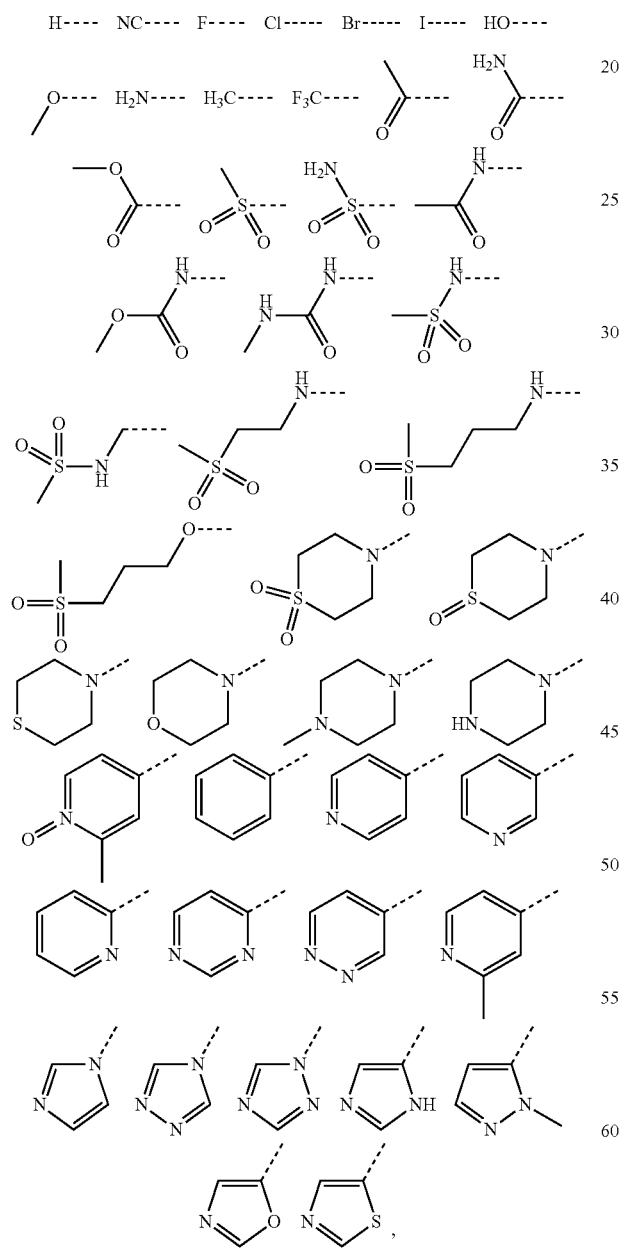
unsubstituted or substituted with 1-2 $R^{10b}$ groups.
In another embodiment, the compound of Formula I comprises U which is selected from:
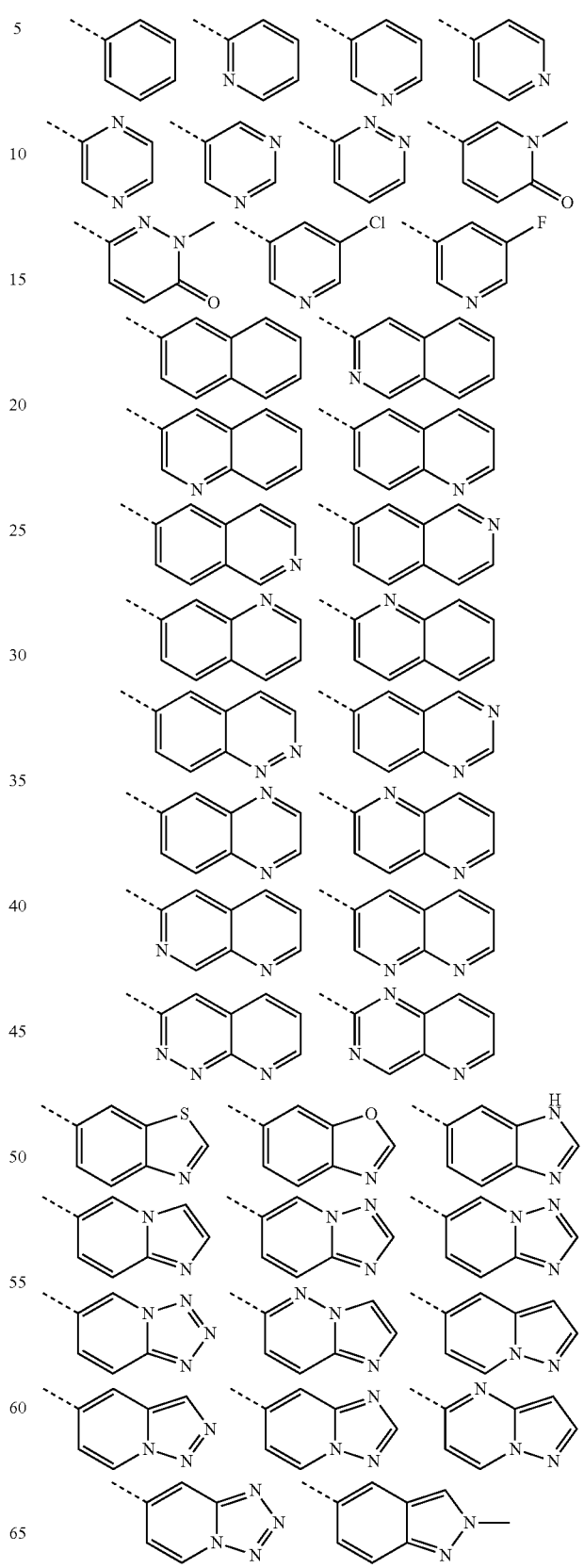

-continued
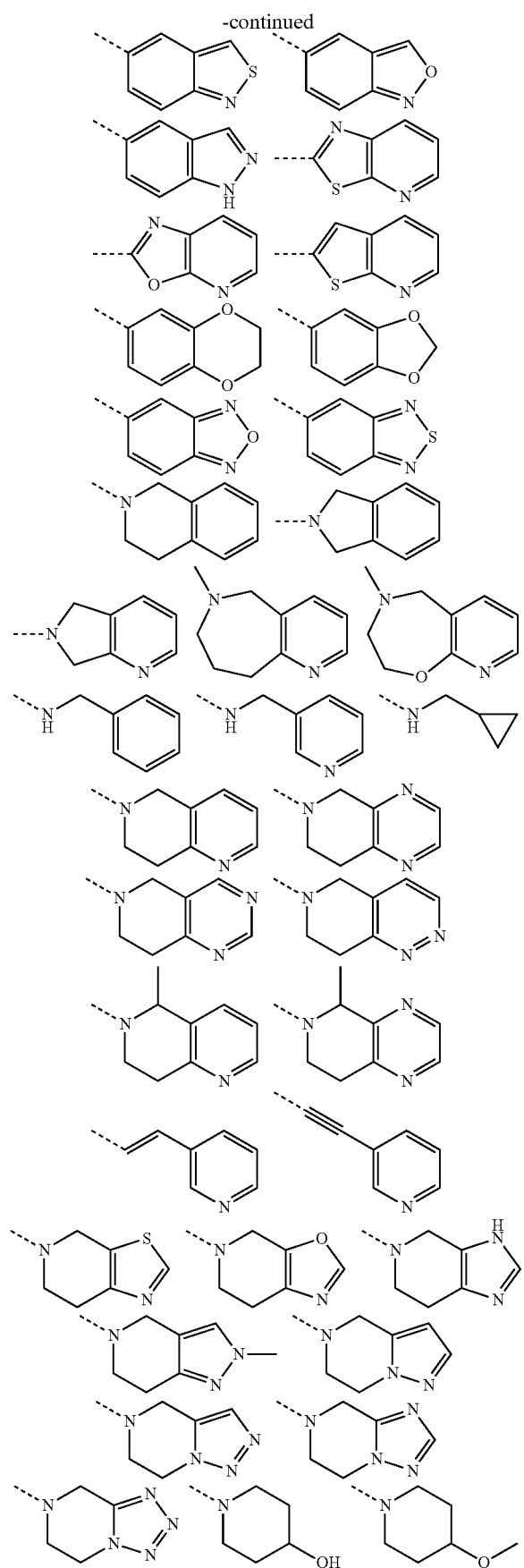
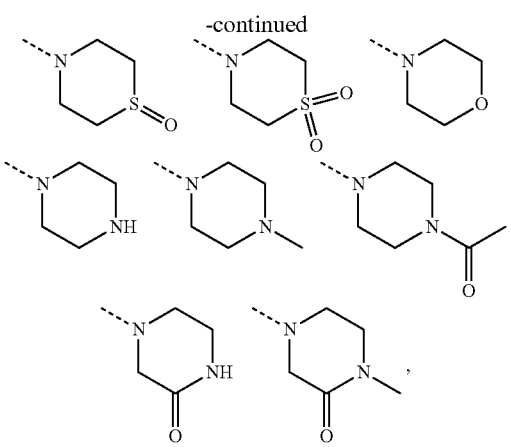
unsubstituted or substituted with 1-6 $R^{13c}$ groups.
In another embodiment, the compound of Formula I comprises Z which is
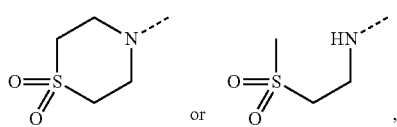
or Z is selected from:
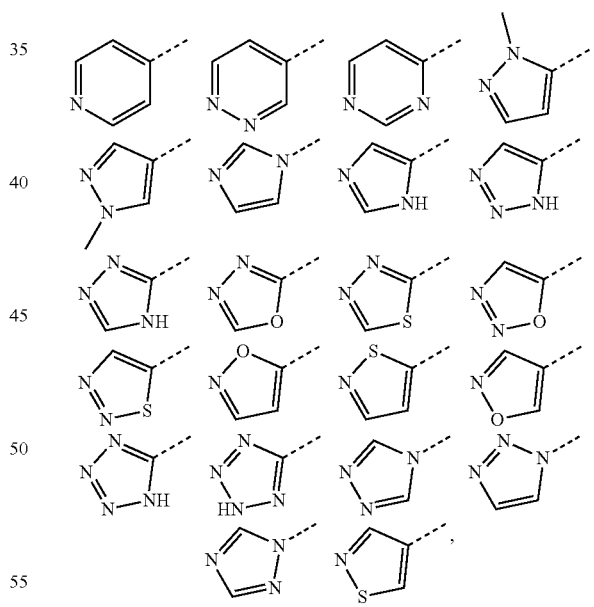
unsubstituted or substituted with 1-3 $R^{6c}$ groups.
In one embodiment, the compound of Formula I comprises A which is selected from:
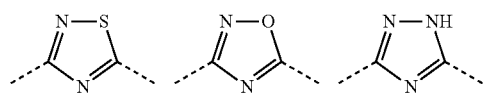

-continued

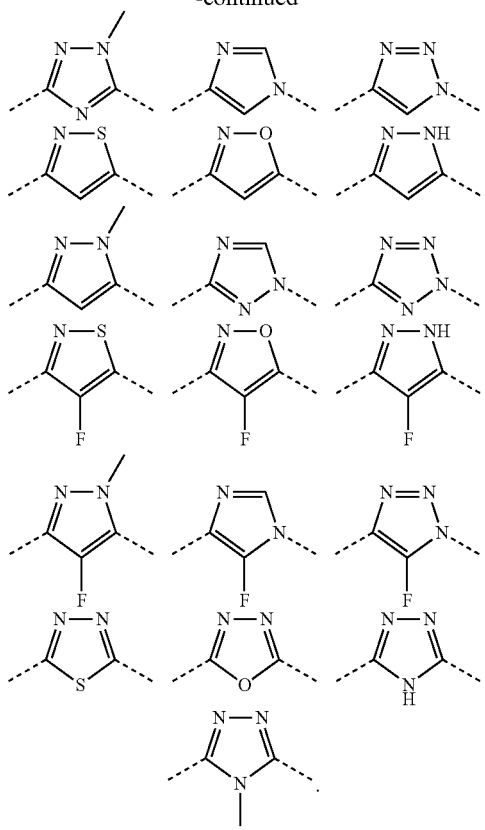

In another aspect, herein provides a pharmaceutical composition comprising a therapeutically effective amount of a compound of claim 1 and a pharmaceutically acceptable carrier.

In another aspect, herein provides a method for regulating the Wnt signaling pathway and/or treating a Wnt-mediated disorder in a mammal suffering therefrom. The method comprises administrating to a mammalian subject a therapeutically effective amount of at least one compound of formula I, or a pharmaceutical composition thereof, and optionally in combination with a second therapeutic agent.

In one embodiment, the method can treat a cell proliferative disorder selected from the group consisting of systemic sclerosis, skin fibrosis, idiopathic pulmonary fibrosis, renal fibrosis, liver fibrosis, drug-induced fibrosis, radiation-induced fibrosis, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomysarcoma, brain tumor, Wilms' tumor, basal cell carcinoma, melanoma, head and neck cancer, cervical cancer and prostate cancer.

In another aspect, herein provides compounds of formula I, wherein the compounds are the molecules shown in Table 1:

TABLE 1

Compounds of Formula I

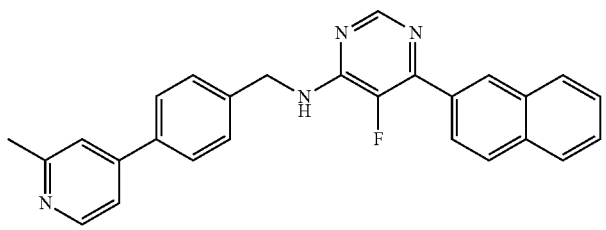 [SMILES: Cc1cc(-c2ccc(CNc3ncnc(-c4ccc5ccccc5c4)c3F)cc2)ccn1]

A-1

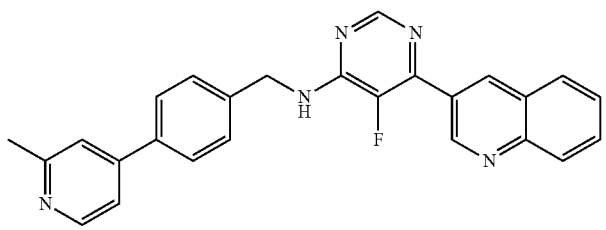 [SMILES: Cc1cc(-c2ccc(CNc3ncnc(-c4cnc5ccccc5c4)c3F)cc2)ccn1]

A-2

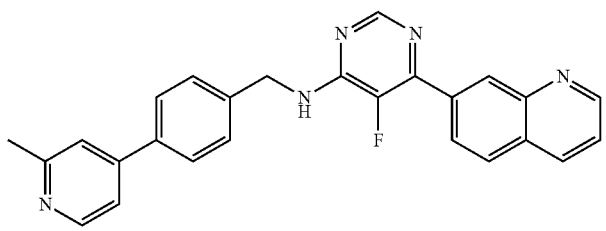 [SMILES: Cc1cc(-c2ccc(CNc3ncnc(-c4ccc5cccnc5c4)c3F)cc2)ccn1]

A-3

TABLE 1-continued
Compounds of Formula I
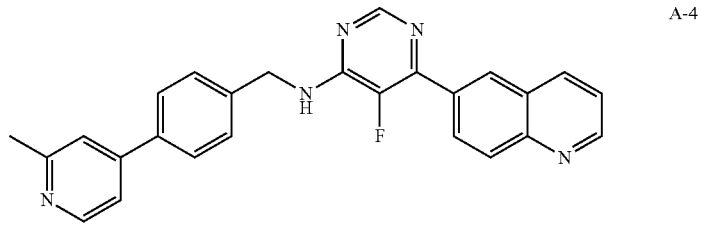
A-4
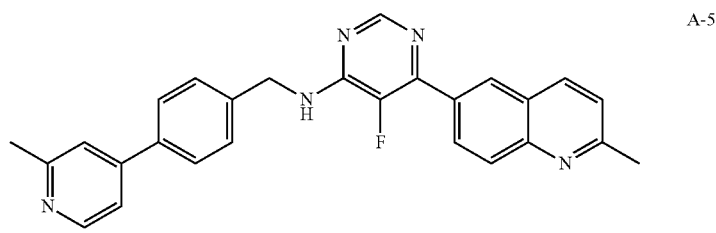
A-5
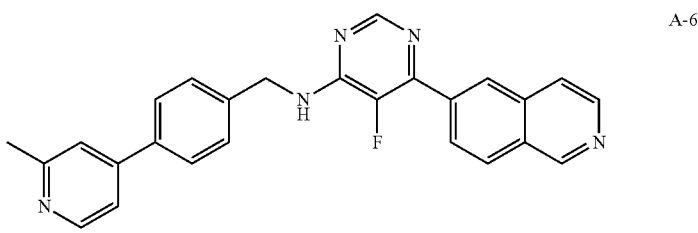
A-6
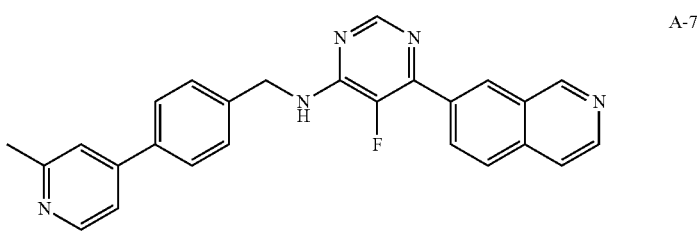
A-7
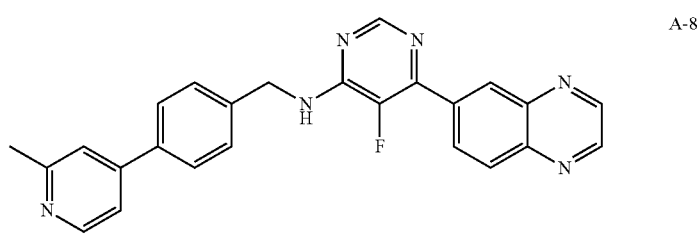
A-8
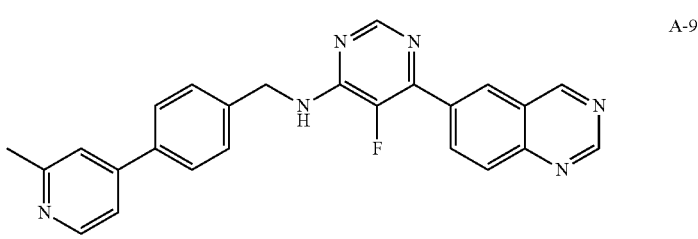
A-9

TABLE 1-continued
Compounds of Formula I
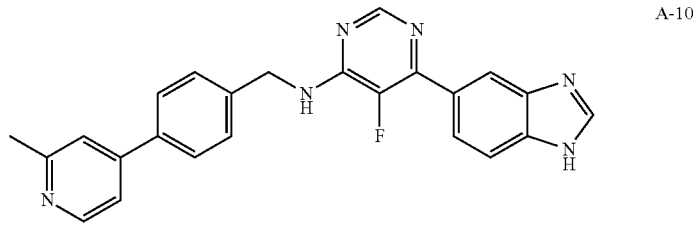
A-10
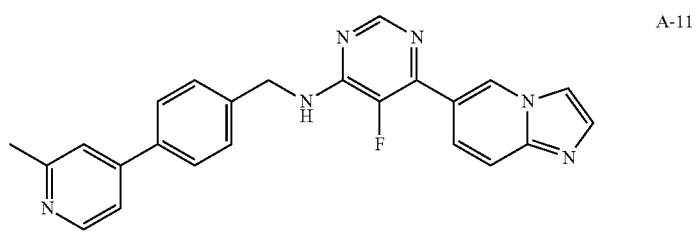
A-11
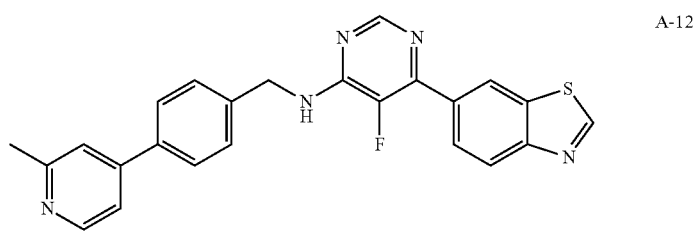
A-12
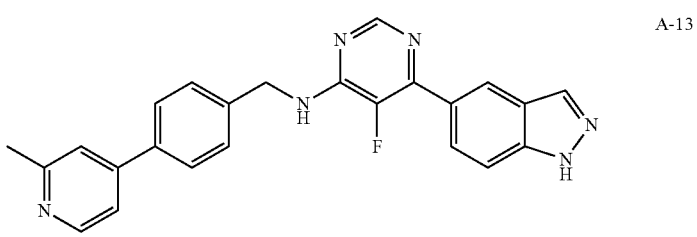
A-13
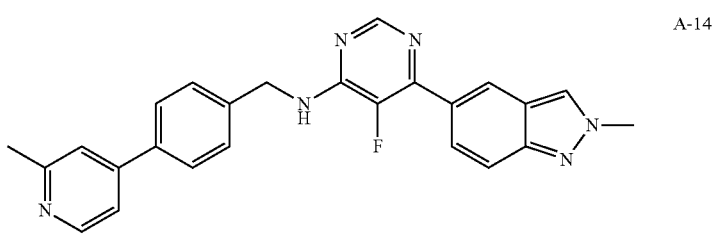
A-14
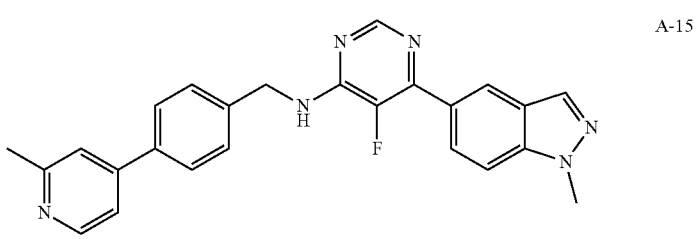
A-15

TABLE 1-continued
Compounds of Formula I
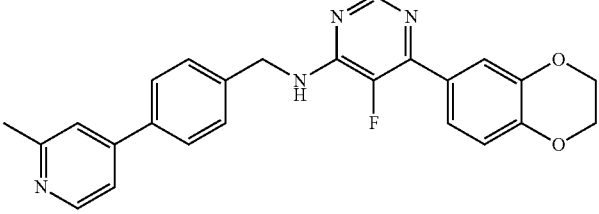
A-16
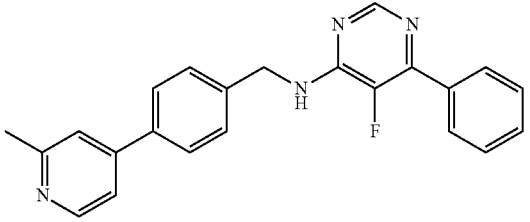 [SMILES: Cc1cc(-c2ccc(CNc3ncnc(-c4ccccc4)c3F)cc2)ccn1]
A-17
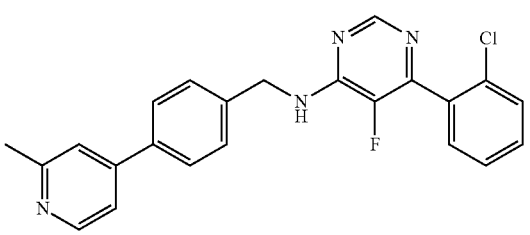 [SMILES: Cc1cc(-c2ccc(CNc3ncnc(-c4ccccc4Cl)c3F)cc2)ccn1]
A-18
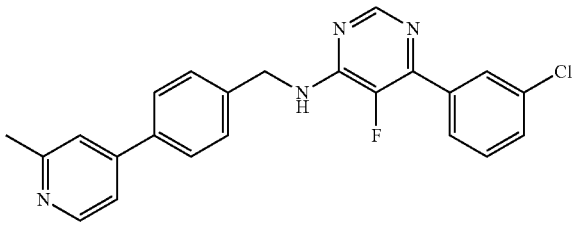 [SMILES: Cc1cc(-c2ccc(CNc3ncnc(-c4cccc(Cl)c4)c3F)cc2)ccn1]
A-19
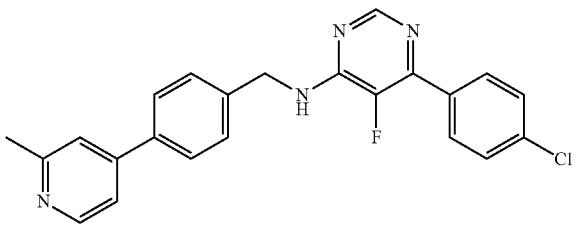 [SMILES: Cc1cc(-c2ccc(CNc3ncnc(-c4ccc(Cl)cc4)c3F)cc2)ccn1]
A-20
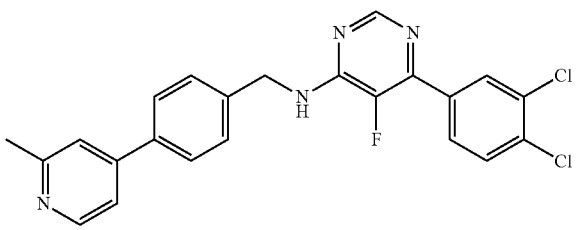 [SMILES: Cc1cc(-c2ccc(CNc3ncnc(-c4ccc(Cl)c(Cl)c4)c3F)cc2)ccn1]
A-21

TABLE 1-continued
Compounds of Formula I
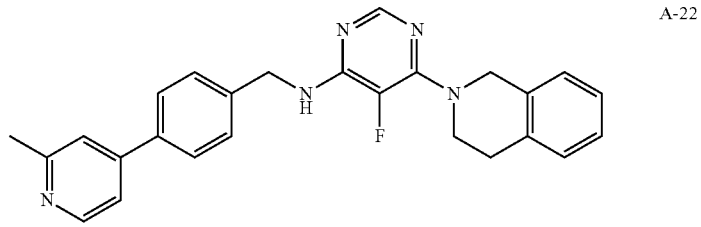
A-22
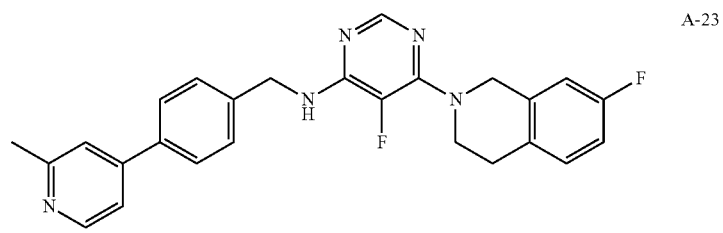
A-23
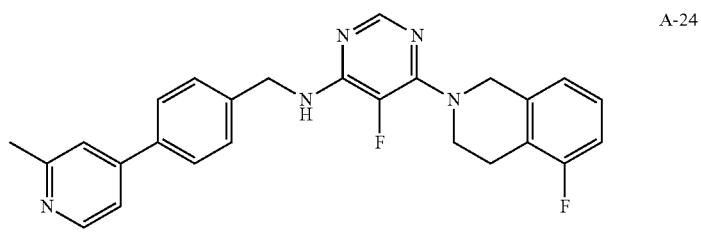
A-24
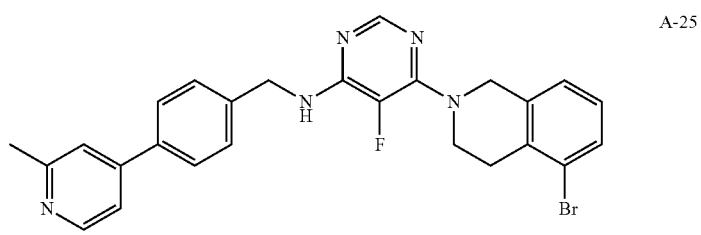
A-25
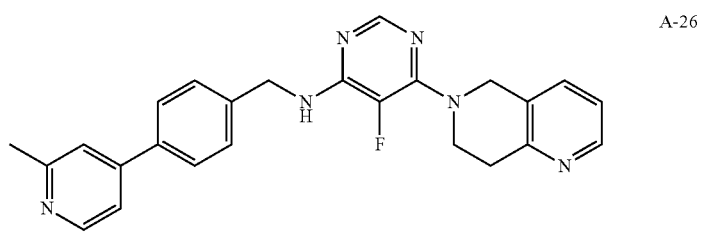
A-26
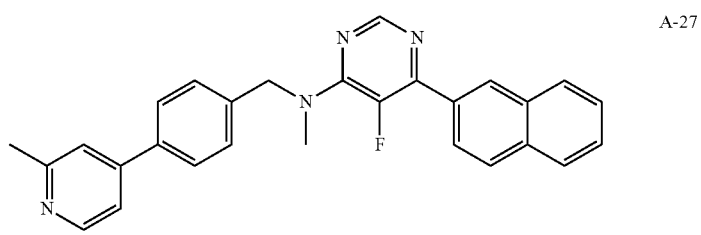
A-27

TABLE 1-continued

Compounds of Formula I

| | |
|---|---|
| (structure) | A-28 |
| (structure) | A-29 |
| (structure) | A-30 |
| (structure) | A-31 |
| (structure) | A-32 |
| (structure) | A-33 |
| (structure) | A-34 |

TABLE 1-continued
Compounds of Formula I
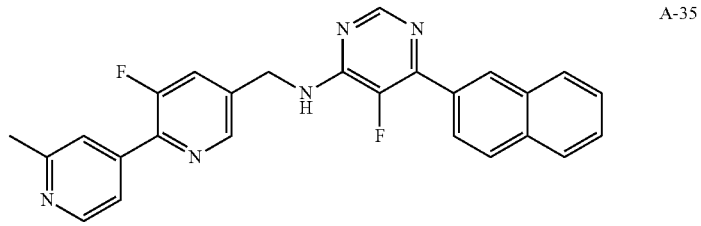
A-35
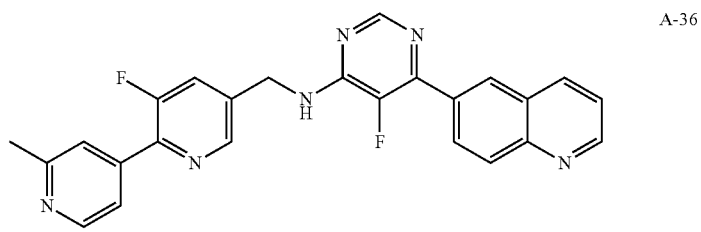
A-36
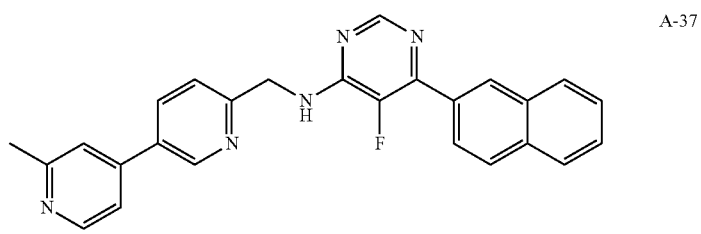
A-37
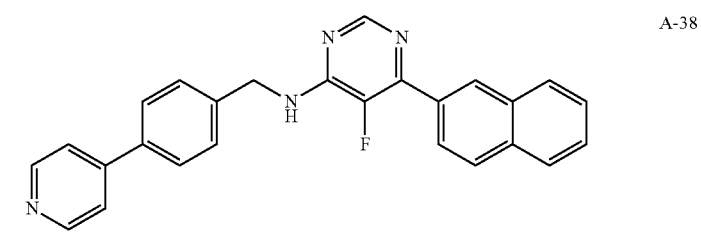
A-38
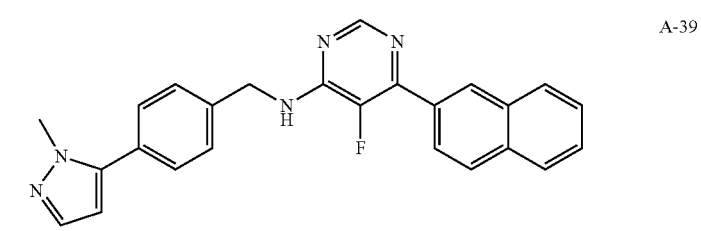
A-39
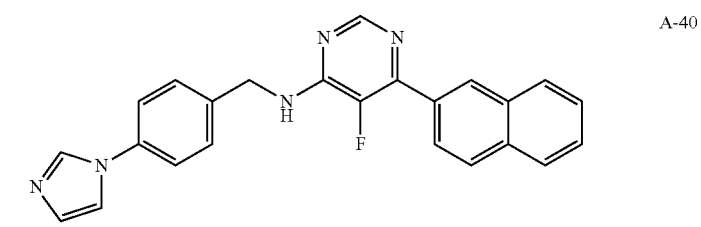
A-40
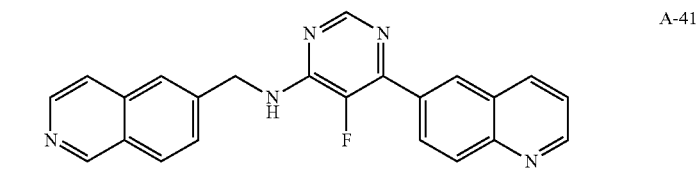
A-41

TABLE 1-continued
Compounds of Formula I
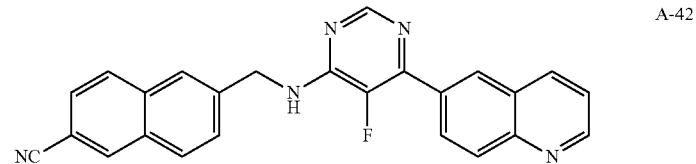
A-42
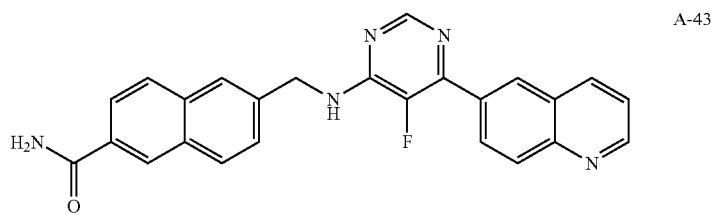
A-43
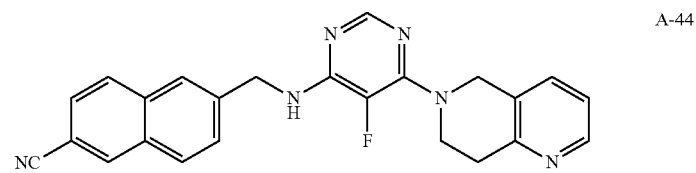
A-44
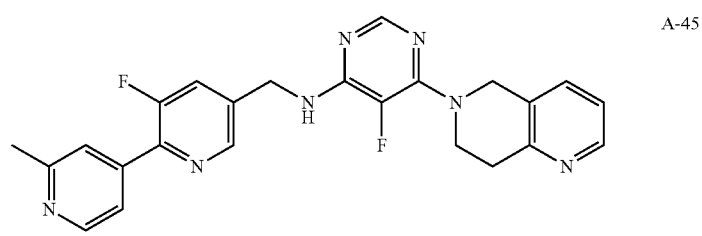
A-45
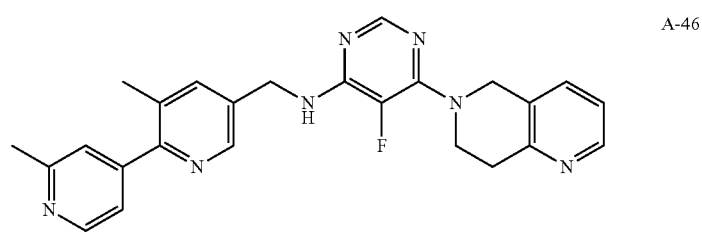
A-46
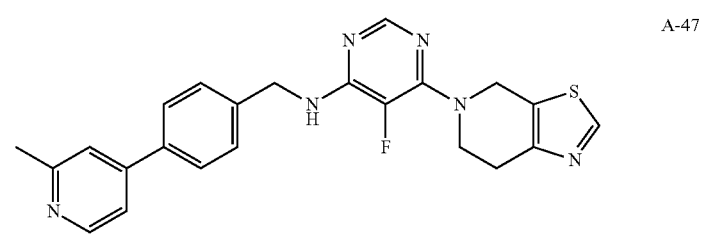
A-47
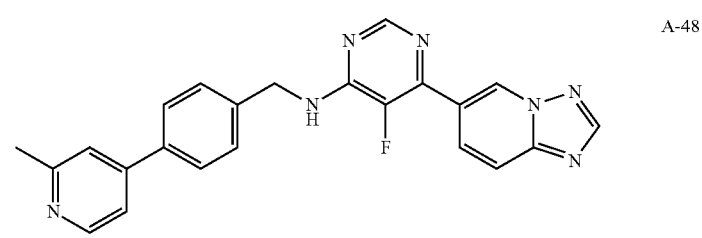
A-48

TABLE 1-continued
Compounds of Formula I
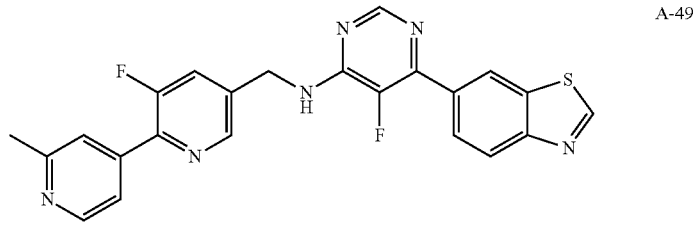
A-49
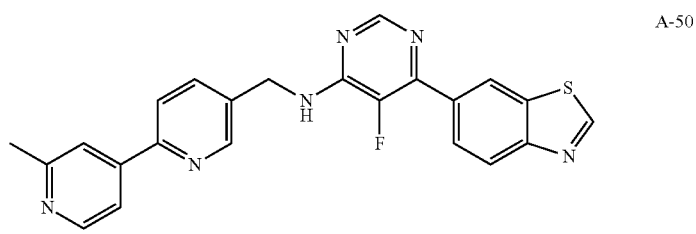
A-50
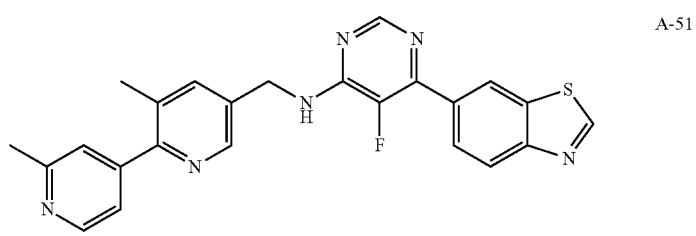
A-51
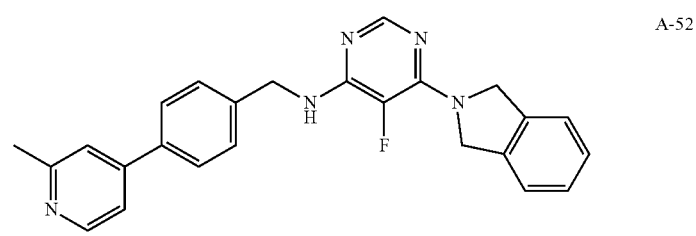
A-52
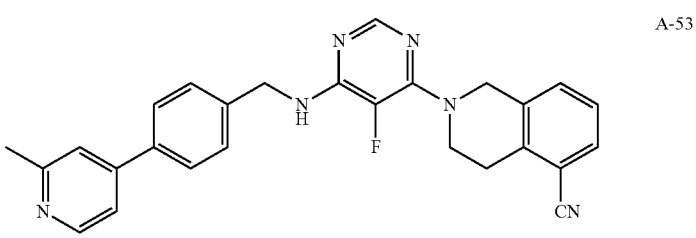
A-53
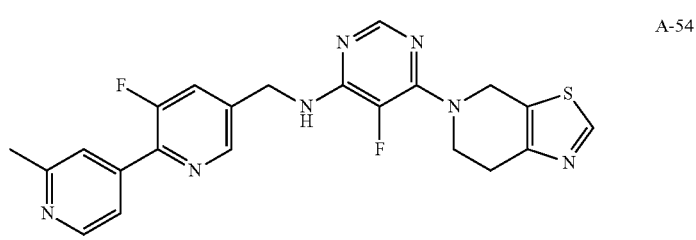
A-54

TABLE 1-continued
Compounds of Formula I
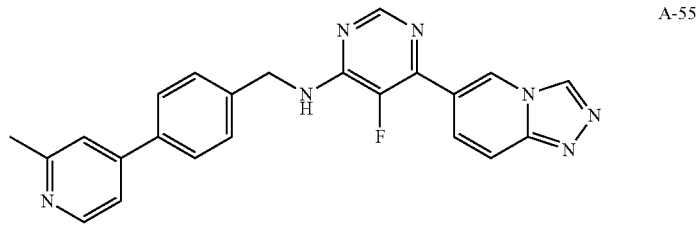
A-55
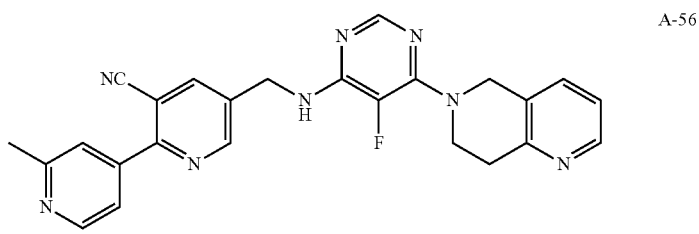
A-56
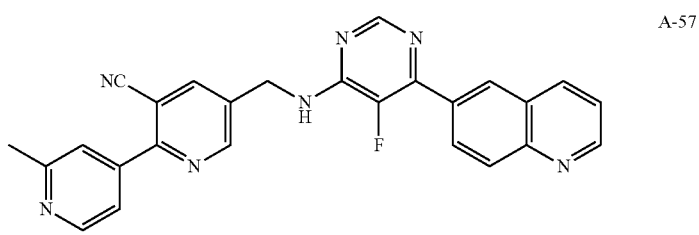
A-57
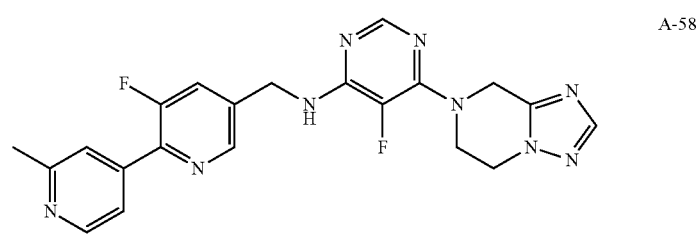
A-58
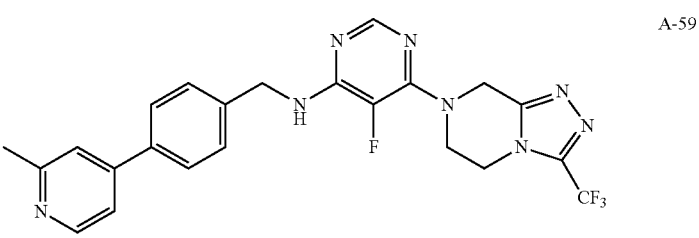
A-59
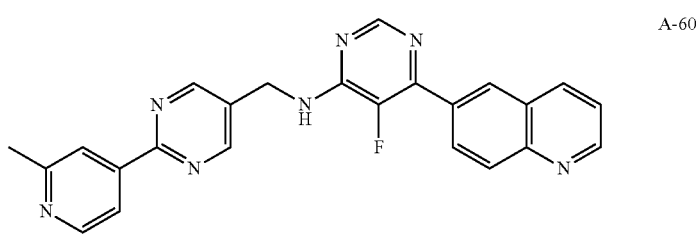
A-60

TABLE 1-continued

Compounds of Formula I

| | |
|---|---|
| (structure) | A-61 |
| (structure) | A-62 |
| (structure) | A-63 |
| (structure) | A-64 |
| (structure) | A-65 |
| (structure) | A-66 |
| (structure) | A-67 |

TABLE 1-continued
Compounds of Formula I
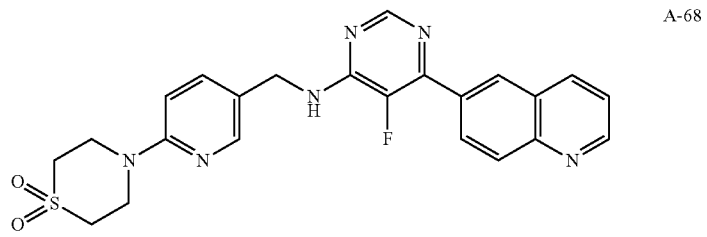
A-68
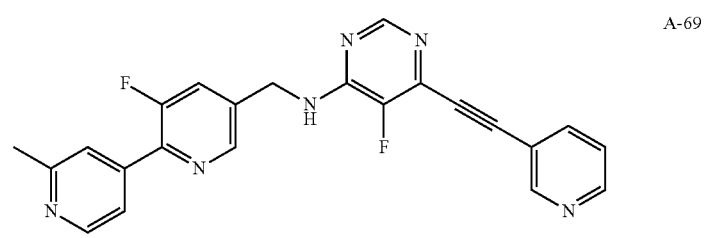
A-69
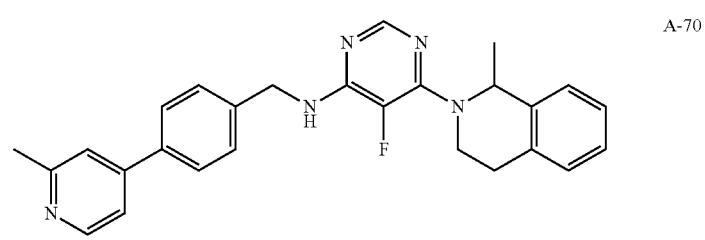
A-70
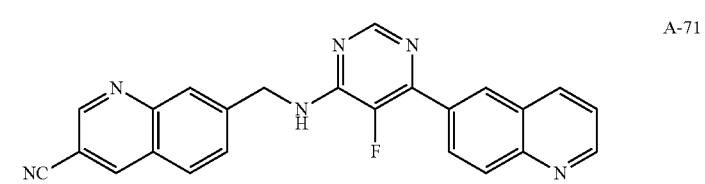
A-71
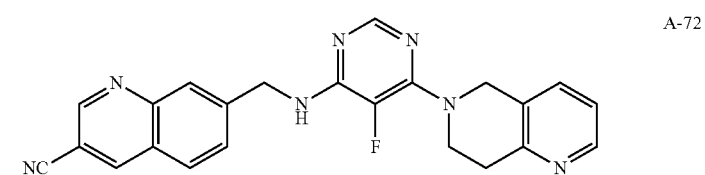
A-72
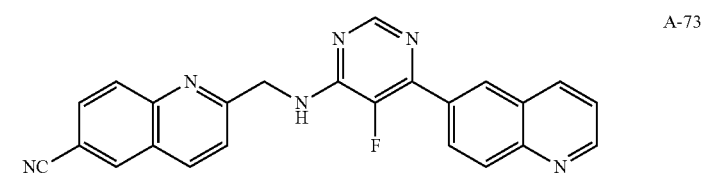
A-73
A-74

TABLE 1-continued
Compounds of Formula I
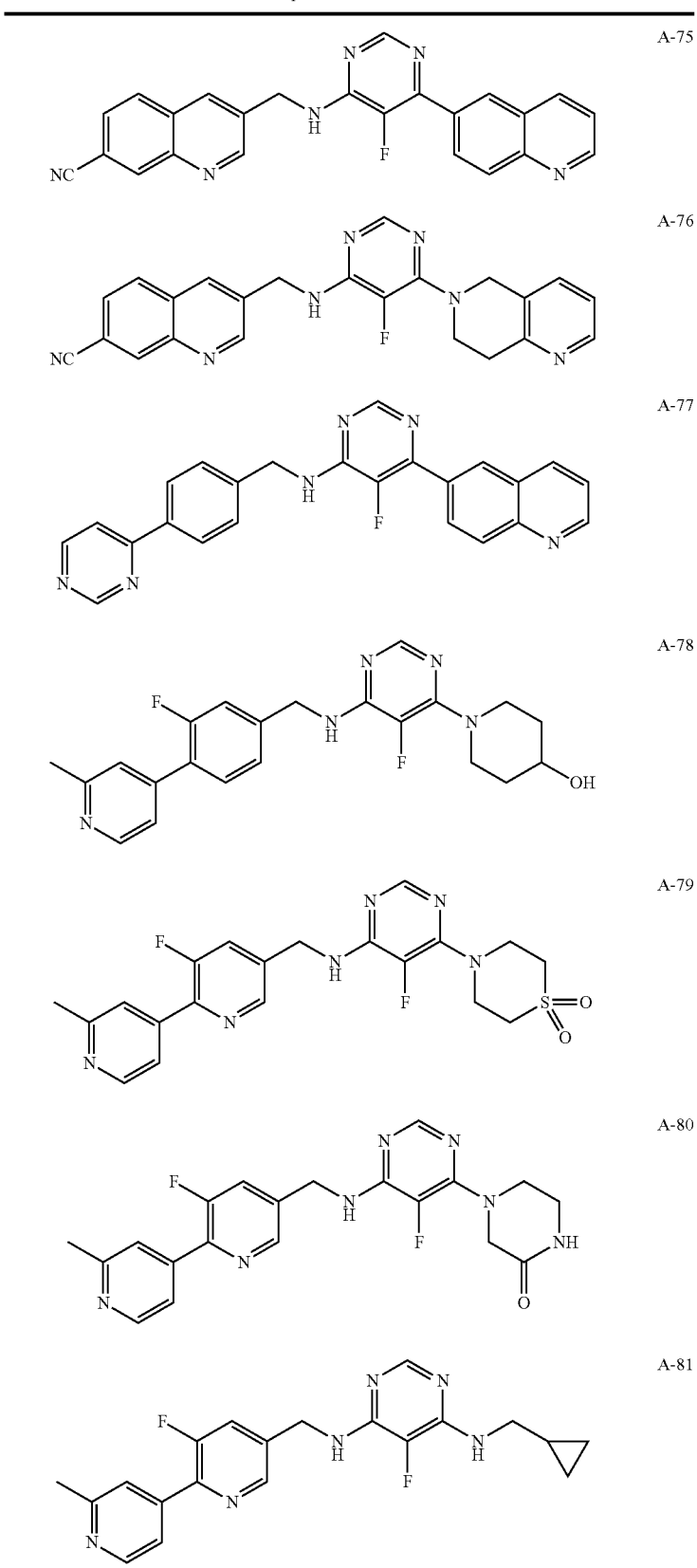
A-75
A-76
A-77
A-78
A-79
A-80
A-81

TABLE 1-continued

Compounds of Formula I

| | |
|---|---|
| (structure) | A-82 |
| (structure) | A-83 |
| (structure) | A-84 |
| (structure) | A-85 |
| (structure) | A-86 |
| (structure) | A-87 |

TABLE 1-continued
Compounds of Formula I
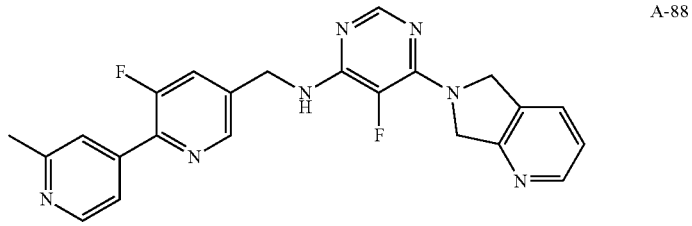
A-88
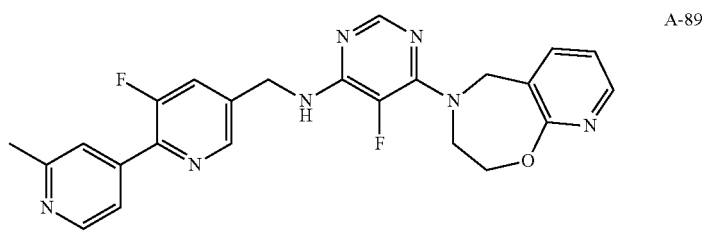
A-89
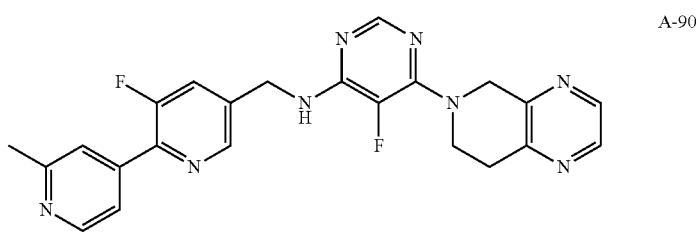
A-90
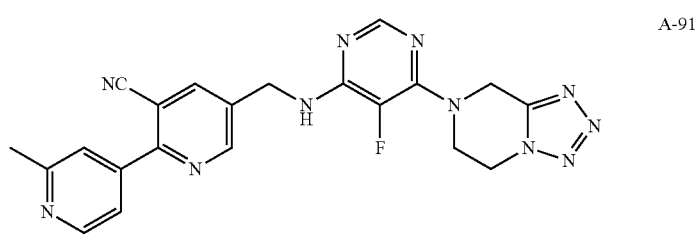
A-91
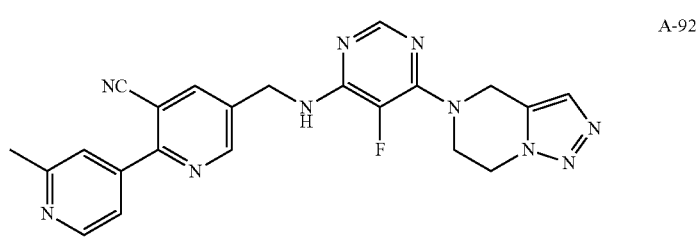
A-92
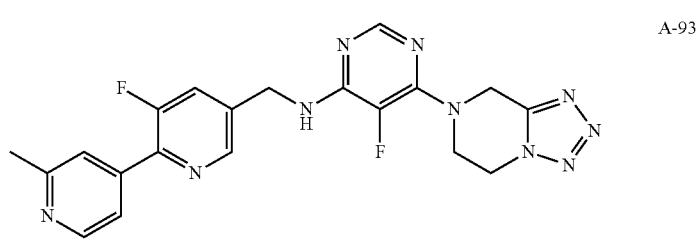
A-93

TABLE 1-continued

Compounds of Formula I

A-94

A-95

A-96

A-97

A-98

A-99

TABLE 1-continued
Compounds of Formula I
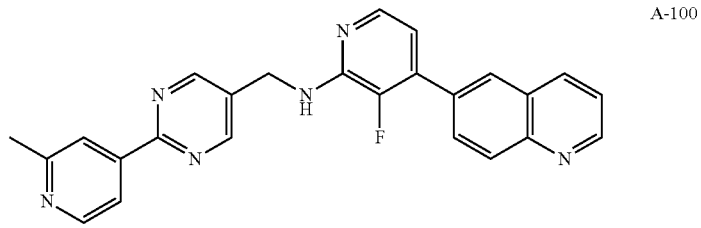
A-100
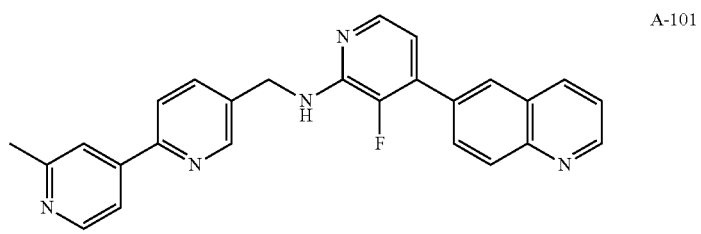
A-101
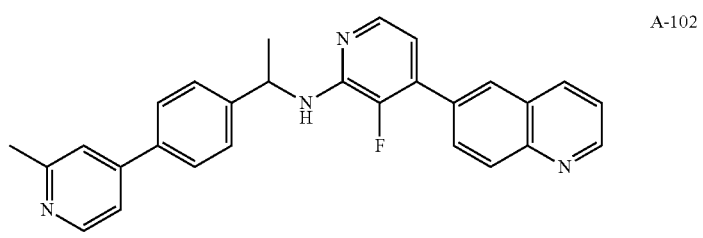
A-102
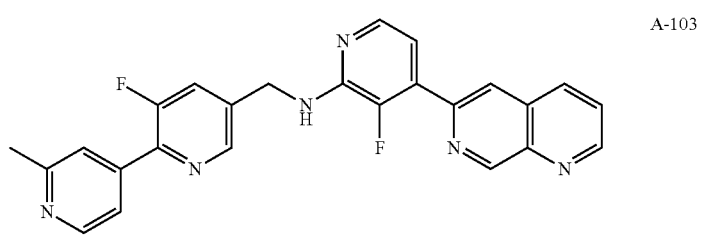
A-103
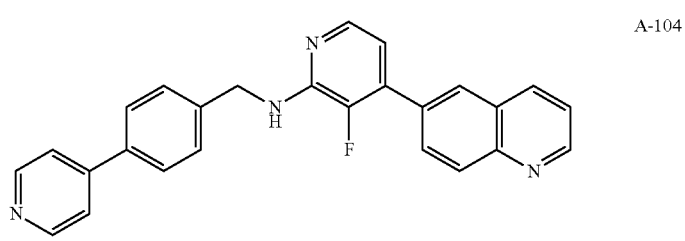
A-104
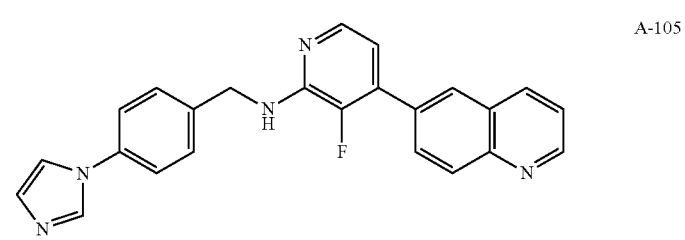
A-105

TABLE 1-continued

Compounds of Formula I

A-106

A-107

A-108

A-109

A-110

A-111

A-112

TABLE 1-continued
Compounds of Formula I
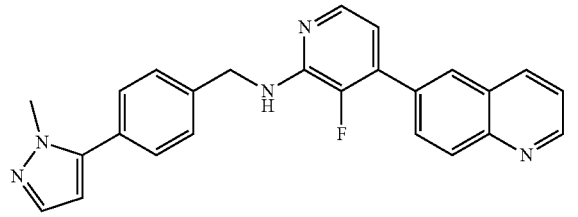 [SMILES: Cn1nccc1-c1ccc(CNc2nccc(-c3ccc4ncccc4c3)c2F)cc1] A-113
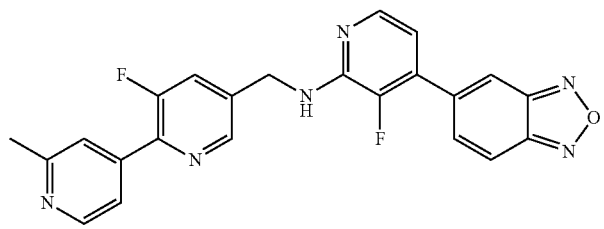 [SMILES: Cc1cc(-c2ncc(CNc3nccc(-c4ccc5nonc5c4)c3F)cc2F)ccn1] A-114
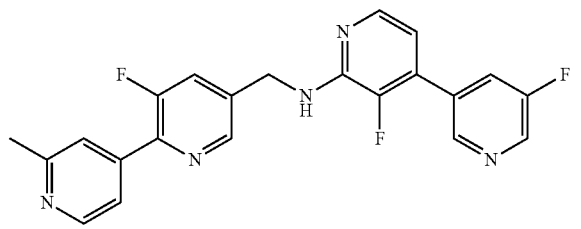 [SMILES: Cc1cc(-c2ncc(CNc3nccc(-c4cncc(F)c4)c3F)cc2F)ccn1] A-115
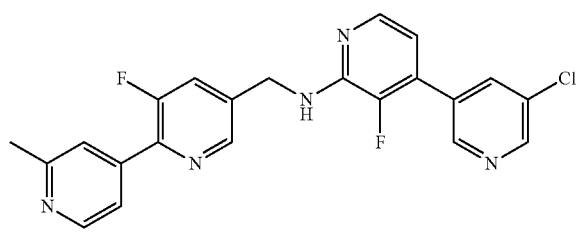 [SMILES: Cc1cc(-c2ncc(CNc3nccc(-c4cncc(Cl)c4)c3F)cc2F)ccn1] A-116
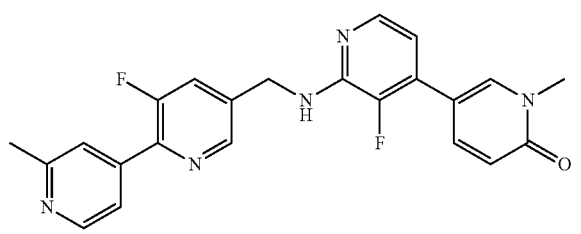 [SMILES: Cc1cc(-c2ncc(CNc3nccc(-c4ccc(=O)n(C)c4)c3F)cc2F)ccn1] A-117
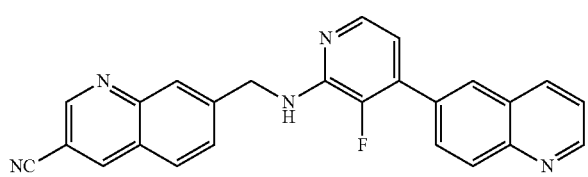 [SMILES: N#Cc1cnc2cc(CNc3nccc(-c4ccc5ncccc5c4)c3F)ccc2c1] A-118
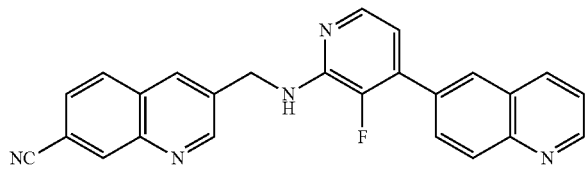 [SMILES: N#Cc1ccc2cc(CNc3nccc(-c4ccc5ncccc5c4)c3F)cnc2c1] A-119

TABLE 1-continued

Compounds of Formula I

A-120

A-121

A-122

A-123

A-124

A-125

A-126

TABLE 1-continued
Compounds of Formula I
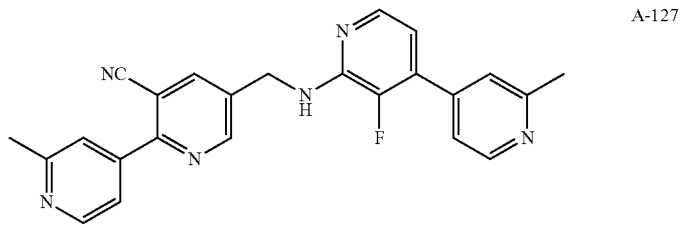
A-127
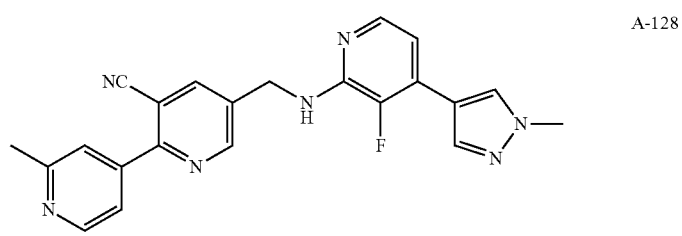
A-128
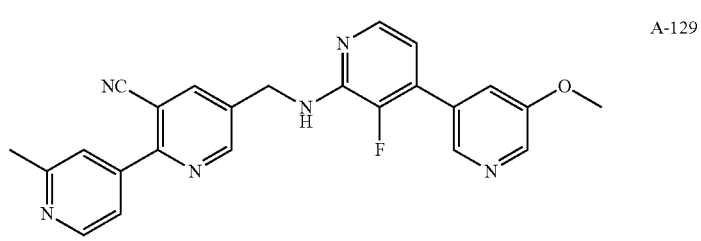
A-129
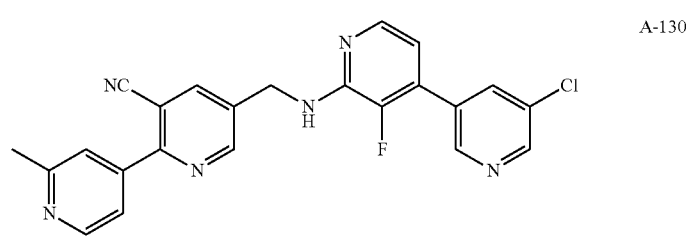
A-130
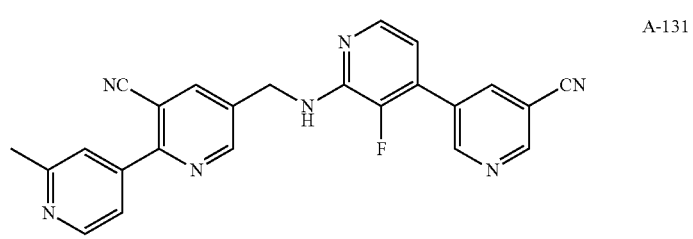
A-131
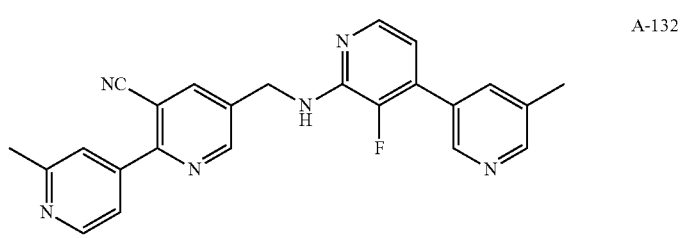
A-132

TABLE 1-continued
Compounds of Formula I
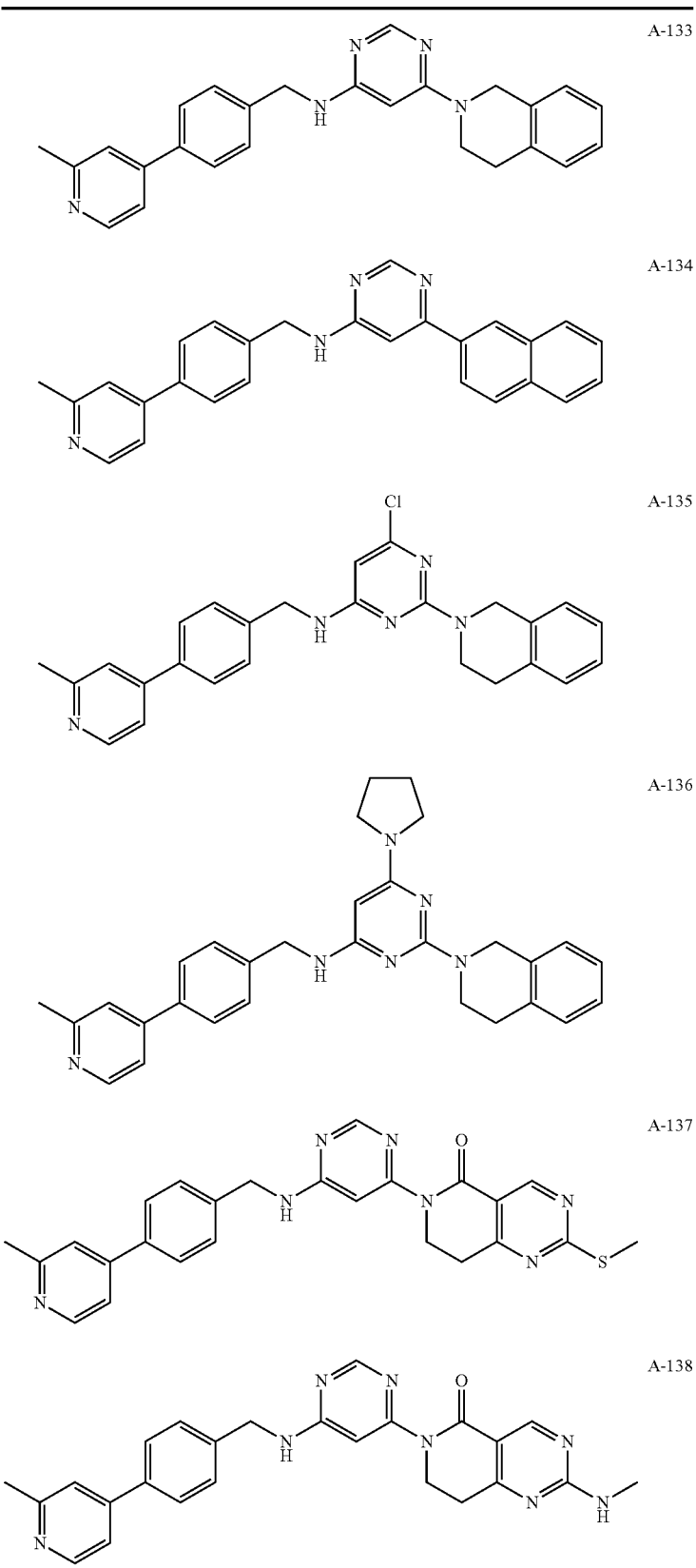

TABLE 1-continued
Compounds of Formula I
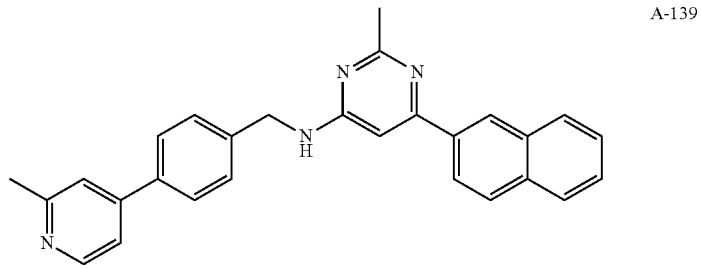
A-139
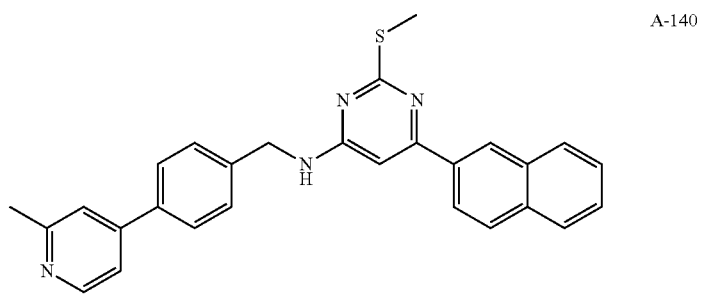
A-140
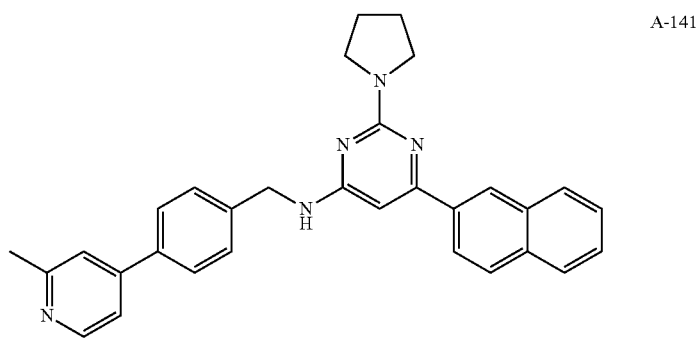
A-141
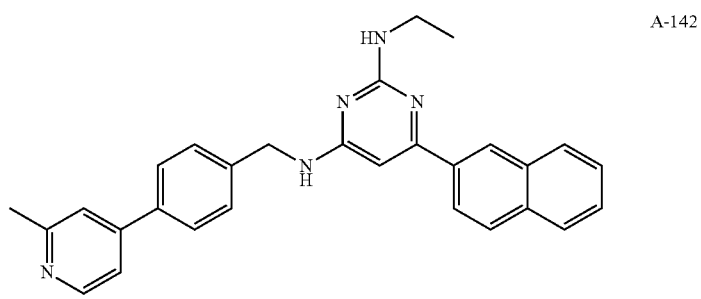
A-142
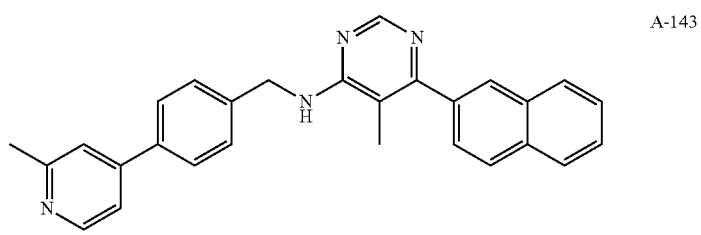
A-143

TABLE 1-continued
Compounds of Formula I
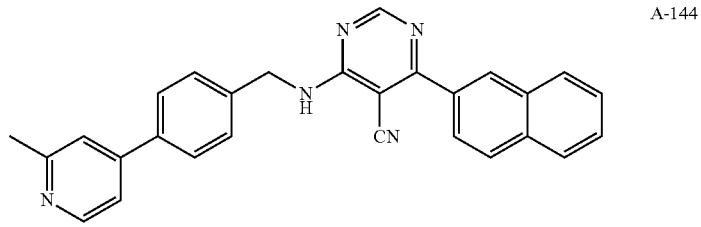
A-144
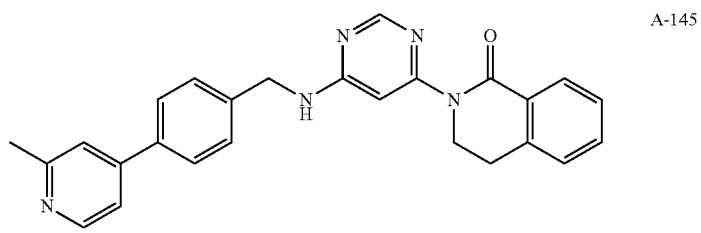
A-145
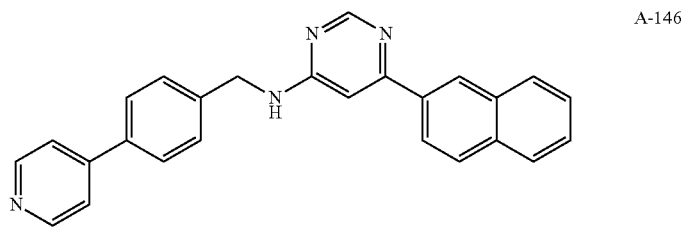
A-146
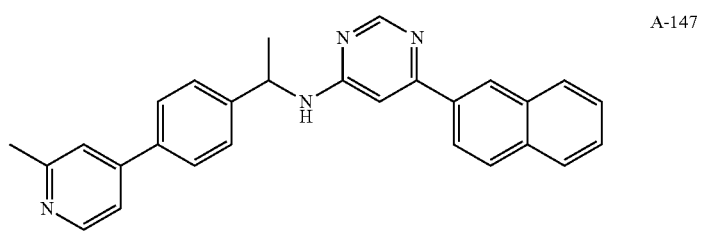
A-147
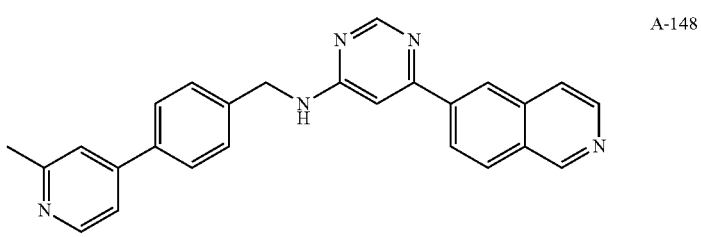
A-148
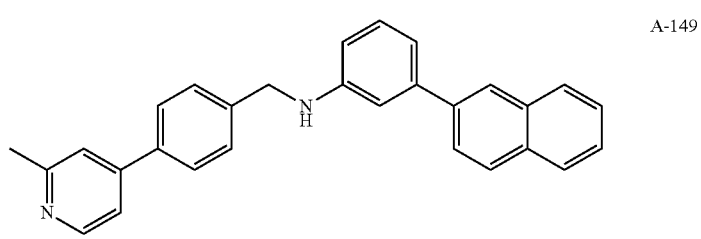
A-149

TABLE 1-continued
Compounds of Formula I
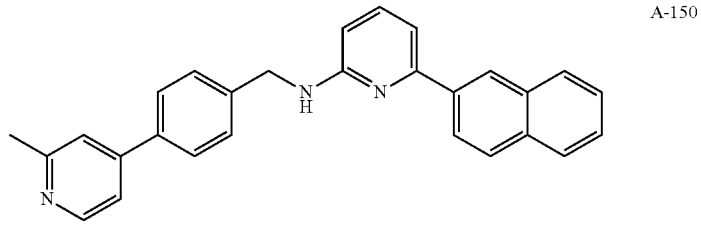
A-150
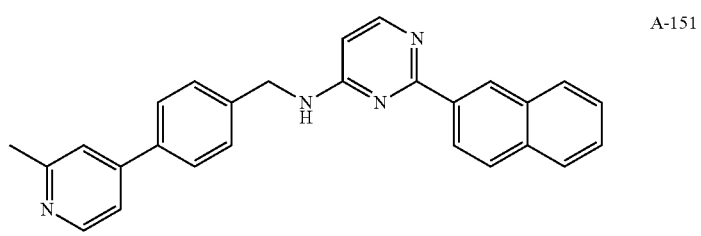
A-151
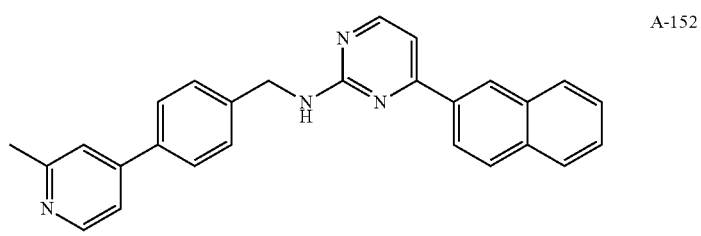
A-152
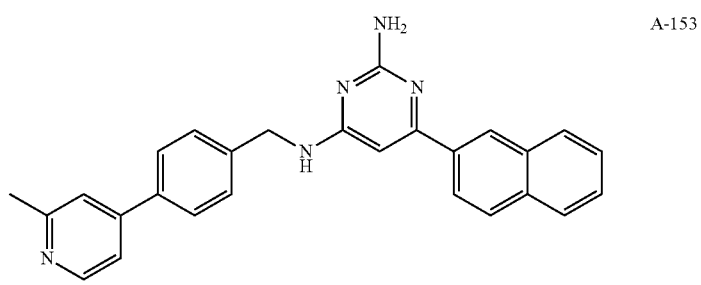
A-153
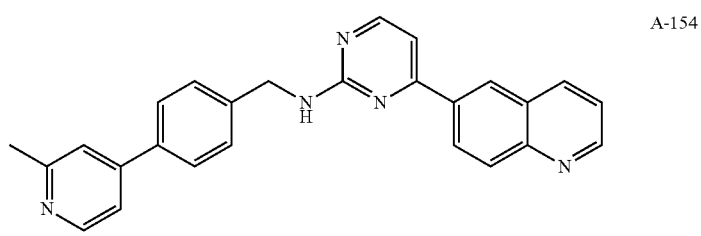
A-154
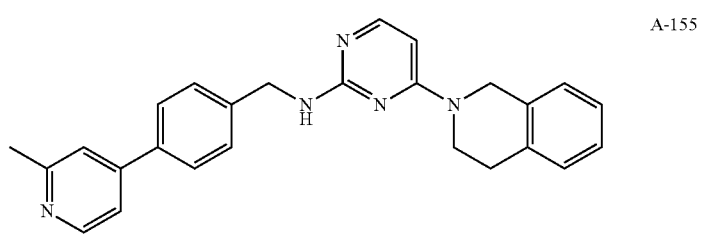
A-155

TABLE 1-continued
Compounds of Formula I
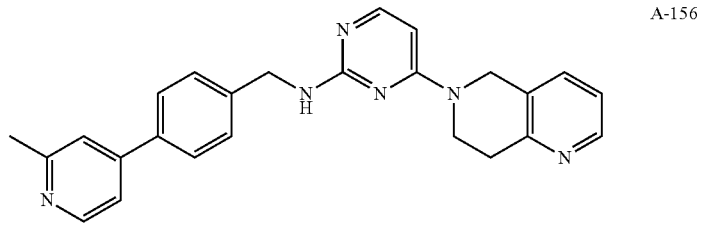
A-156
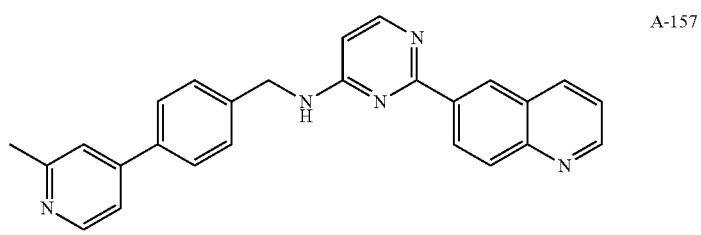
A-157
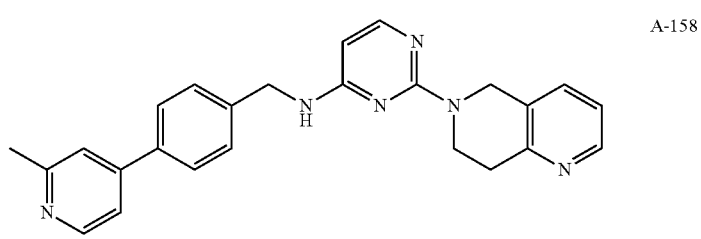
A-158
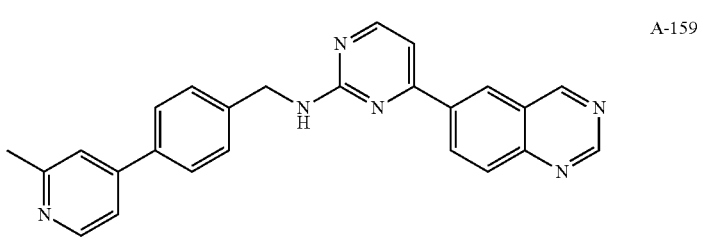
A-159
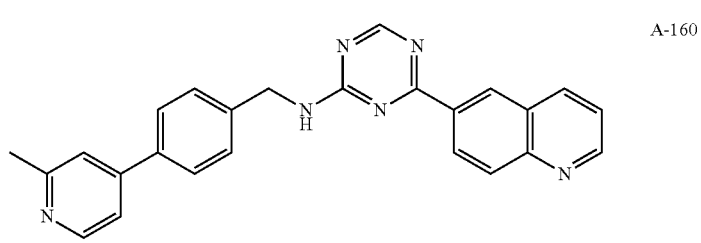
A-160
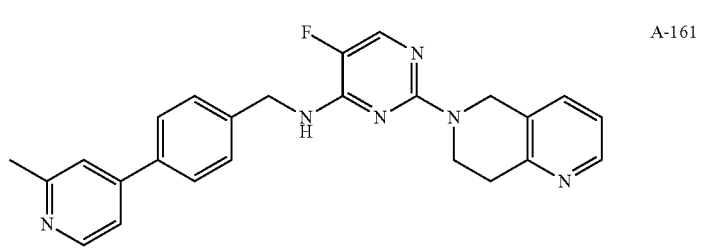
A-161

TABLE 1-continued
Compounds of Formula I
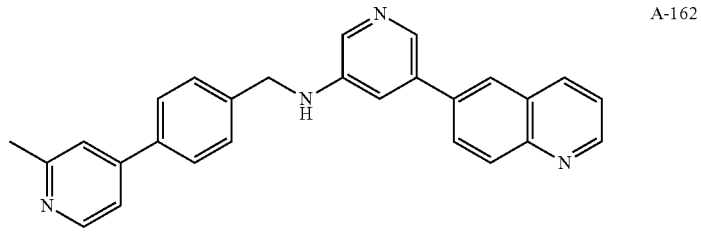
A-162
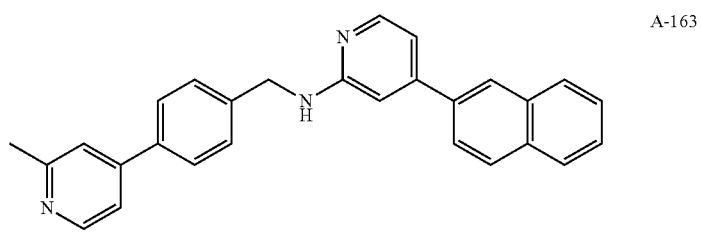
A-163
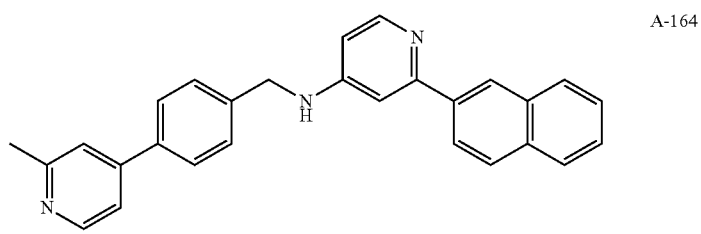
A-164
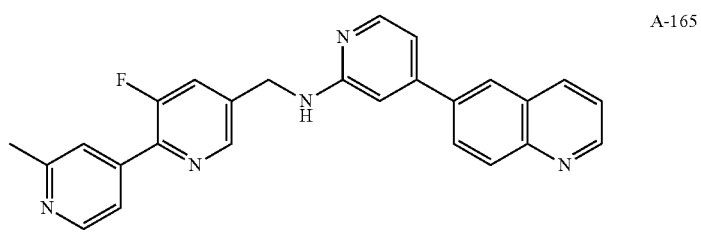
A-165
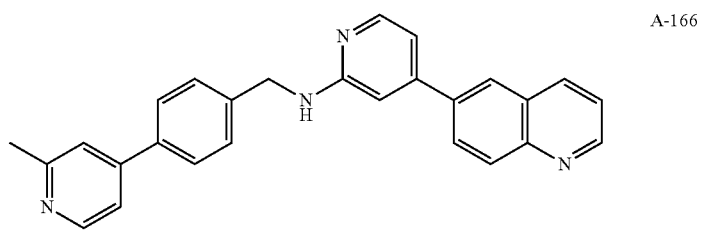
A-166
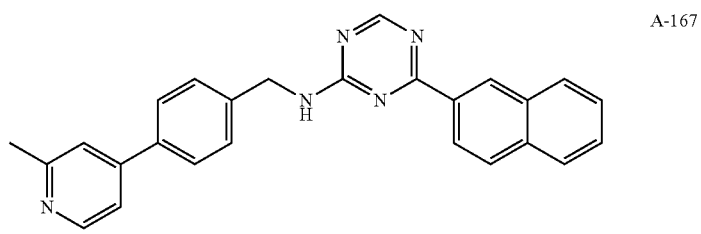
A-167

TABLE 1-continued
Compounds of Formula I
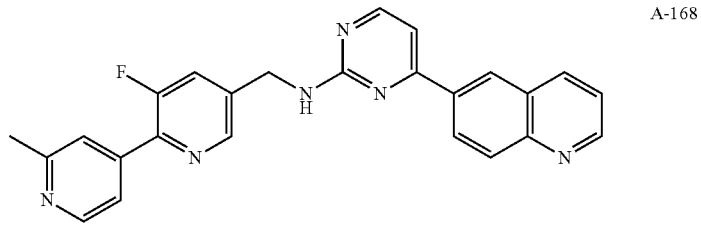
A-168
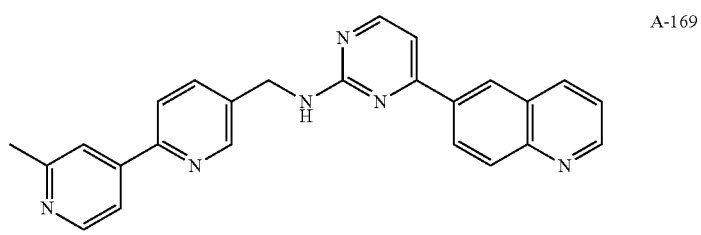
A-169
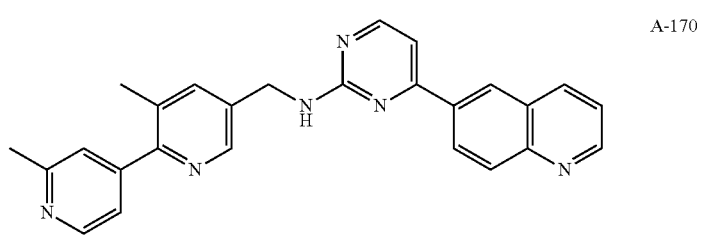
A-170
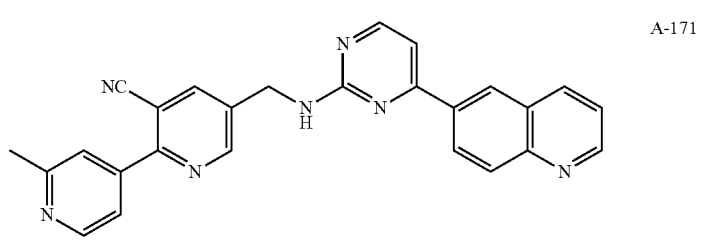
A-171
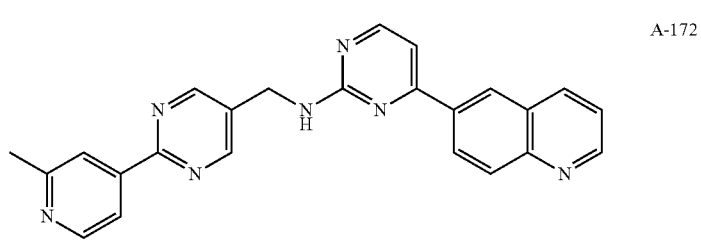
A-172
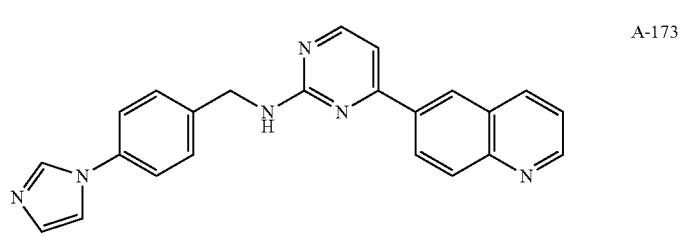
A-173

TABLE 1-continued

Compounds of Formula I

| | |
|---|---|
| (structure) | A-174 |
| (structure) | A-175 |
| (structure) | A-176 |
| (structure) | A-177 |
| (structure) | A-178 |
| (structure) | A-179 |
| (structure) | A-180 |

TABLE 1-continued
Compounds of Formula I
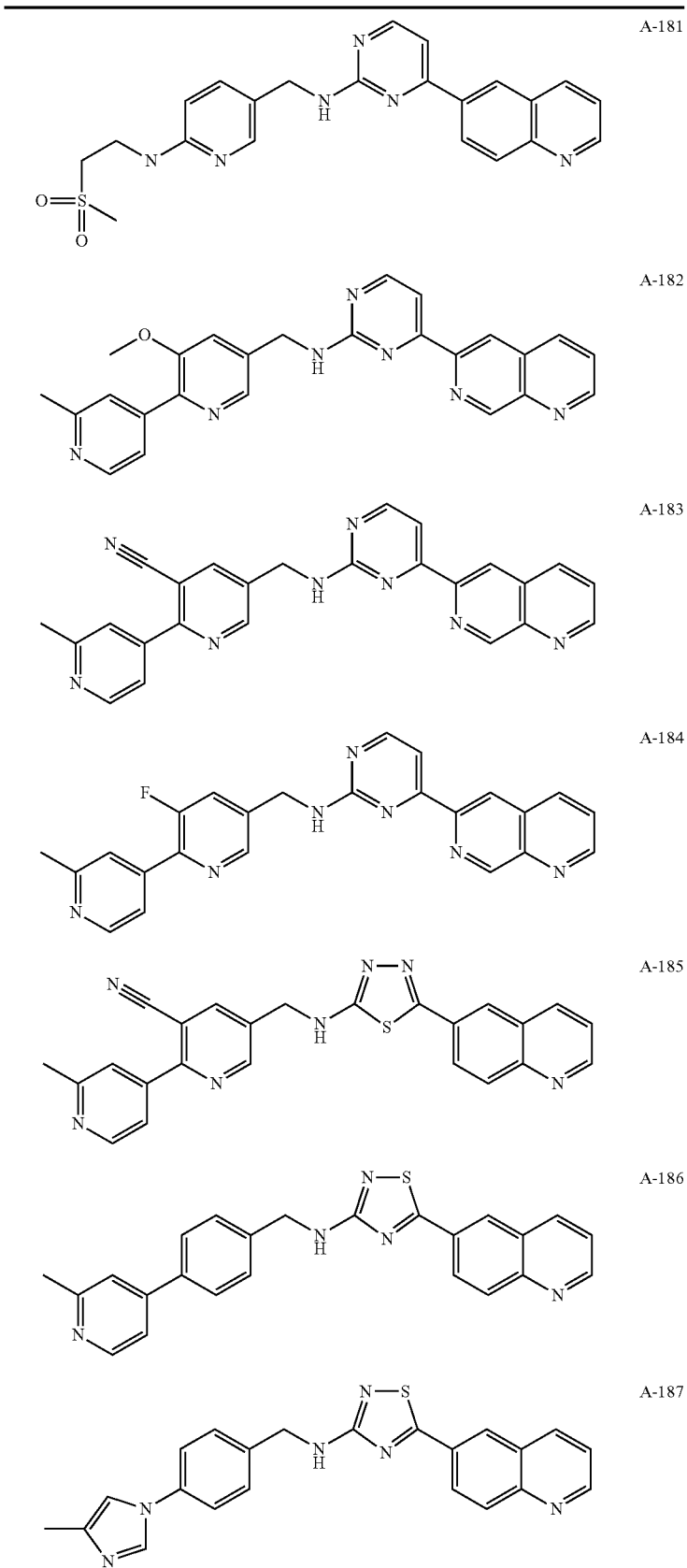
A-181
A-182
A-183
A-184
A-185
A-186
A-187

TABLE 1-continued
Compounds of Formula I
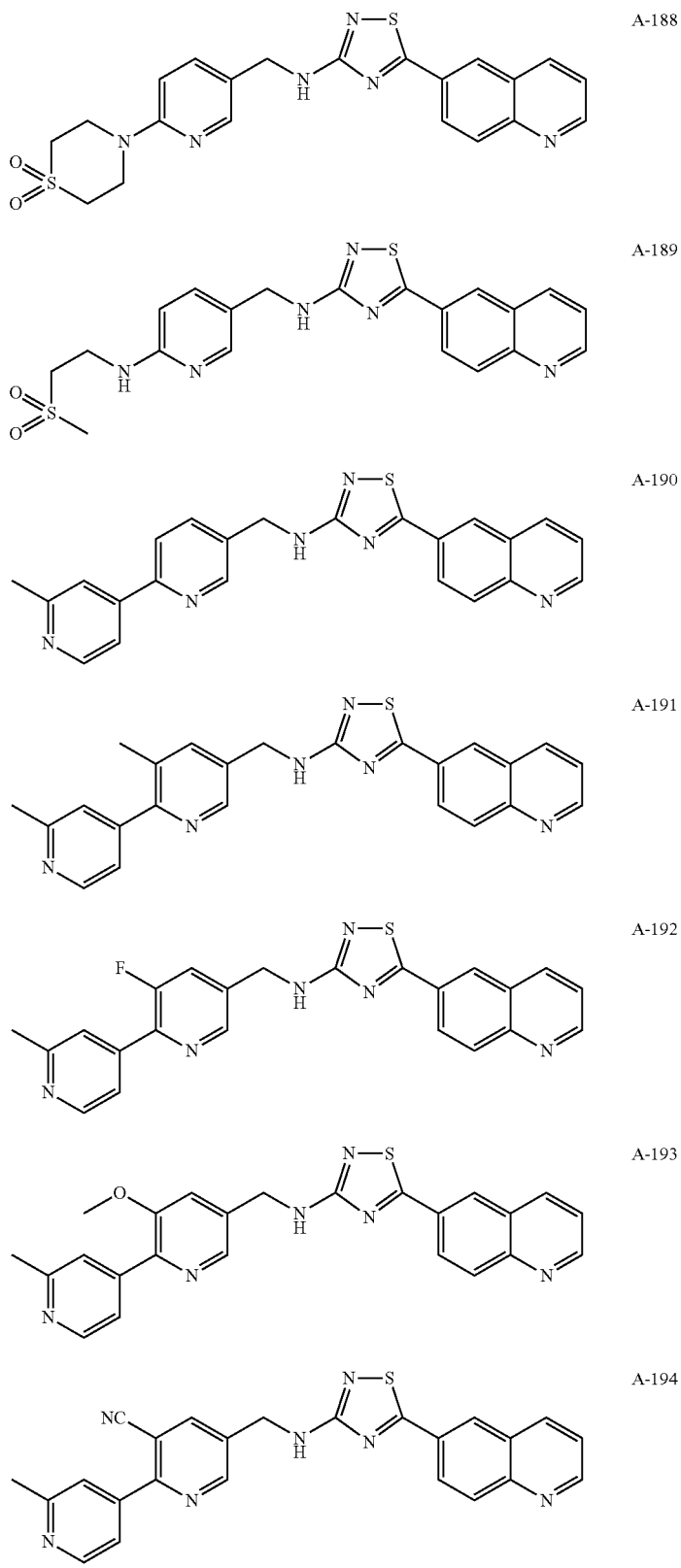
A-188
A-189
A-190
A-191
A-192
A-193
A-194

TABLE 1-continued
Compounds of Formula I
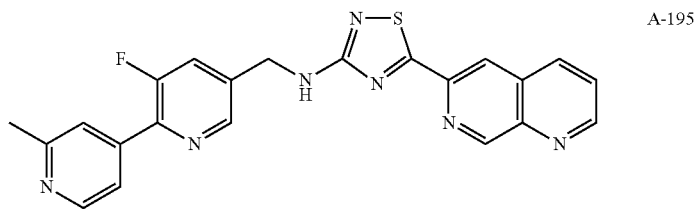
A-195
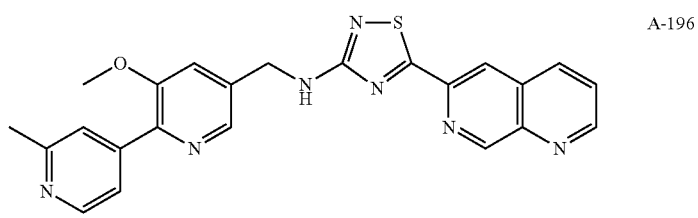
A-196
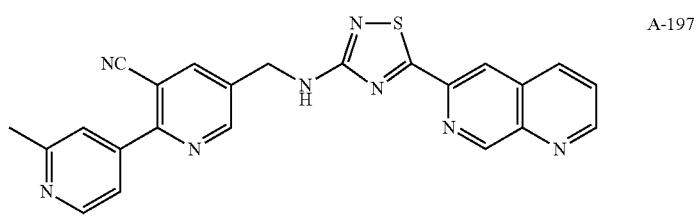
A-197
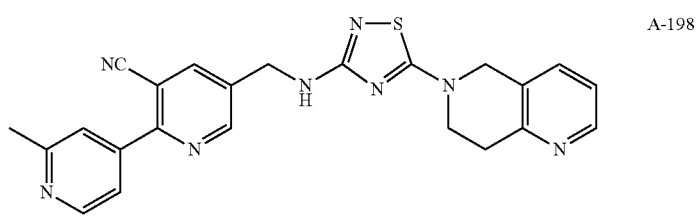
A-198
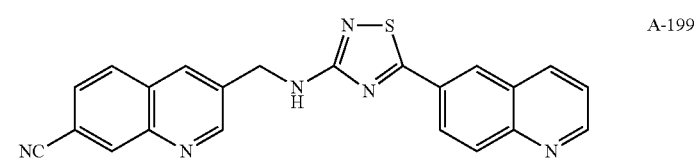
A-199
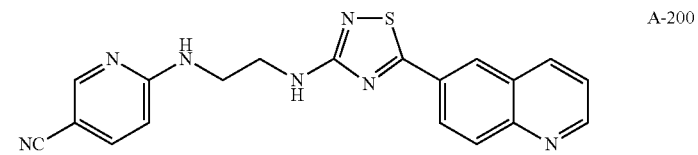
A-200
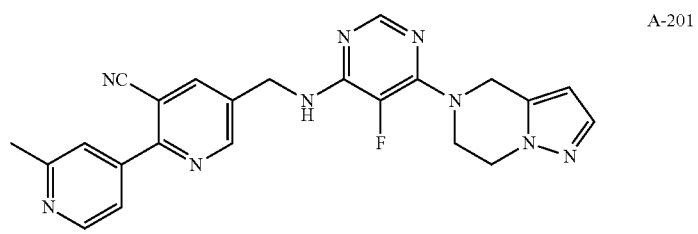
A-201

TABLE 1-continued

Compounds of Formula I

A-202

Figure 1:
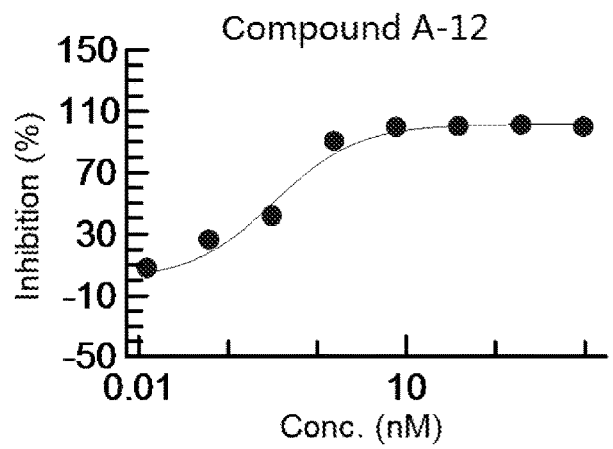
FIG. 1 depicts the IC50 curve of compound A-12 of the present invention in the primary assay.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

DETAILED DESCRIPTION OF THE INVENTION

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the term "alkyl" refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_{1-4}$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

"Alkenyl" refers to straight or branched chain alkene groups, which comprise at least one unsaturated carbon-carbon double bond. Alkenyl groups include $C_{2-8}$ alkenyl, $C_{2-6}$ alkenyl and $C_{2-4}$ alkenyl groups, which have from 2 to 8, 2 to 6 or 2 to 4 carbon atoms, respectively, including, for example, ethenyl, allyl or isopropenyl. "Alkynyl" refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{2-4}$ alkynyl groups, which have from 2 to 8, 2 to 6 or 2 to 4 carbon atoms, respectively.

A "cycloalkyl" is a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. Certain cycloalkyl groups are $C_{3-7}$ cycloalkyl, in which the cycloalkyl group contains a single ring having from 3 to 7 ring members, all of which are carbon. A "cycloalkenyl" is a group that comprises one or more unsaturated rings in which all ring members are carbon.

"Alkoxy" is meant an alkyl group as described above attached via an oxygen bridge. Alkoxy groups include $C_{1-6}$ alkoxy and $C_{1-4}$ groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_{1-6}$ alkyl)amino groups, in which each $C_{1-6}$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

"Halogen" means fluorine, chlorine, bromine, and iodine. A "haloalkyl" is an alkyl group that is substituted with 1 or more independently chosen halogens (e.g., "$C_{1-6}$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl;

mono-, di-, tri-, tetra- or penta-chloroethyl; and 1,2,2,2-tetrafluoro-1-trifluoromethyl-ethyl.

A "heteroaryl" is an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

A "substituent" and "substituted," as used herein, denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom.

The term "pharmaceutically acceptable" when used with reference to a compound of formula I is intended to refer to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of formula I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of formula I is used to treat a subject by administering the compound(s) as a pharmaceutical composition. To this end, the compound (s), in one embodiment, is combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of formula I, or a stereoisomer, tautomer, hydrate, solvate or pharmaceutically acceptable salt thereof, and at least one pharmaceutically acceptable excipient.

In some embodiments, the present invention provides methods for regulating the Wnt signaling pathway and/or treating a Wnt-mediated disorder in a mammal suffering therefrom. The method comprises administrating to a mammalian subject a therapeutically effective amount of at least one compound of formula I, or a pharmaceutical composition thereof, and optionally in combination with a second therapeutic agent. The method comprises treating or preventing disorder is a cell proliferative disorder selected from the group consisting of systemic sclerosis, skin fibrosis, idiopathic pulmonary fibrosis, renal fibrosis, liver fibrosis, drug-induced fibrosis, radiation-induced fibrosis, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomysarcoma, brain tumor, Wilm's tumor, basal cell carcinoma, melanoma, head and neck cancer, cervical cancer and prostate cancer.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: *The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H.A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Synthetic Methods

Methods of the present invention include the use of at least one compound of formula I, which inhibits hedgehog signaling in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of hedgehog proteins may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, N.Y. (1981), in The Peptides, Volume 3, E. Gross and J. Meienhofer editors, Academic Press, London and New York (1981).

All synthetic procedures described herein can be carried out under known reaction conditions, advantageously under those described herein, either in the absence or in the presence (usually) of solvents or diluents.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Protecting groups, their introduction and removal are described above.

General Method A:

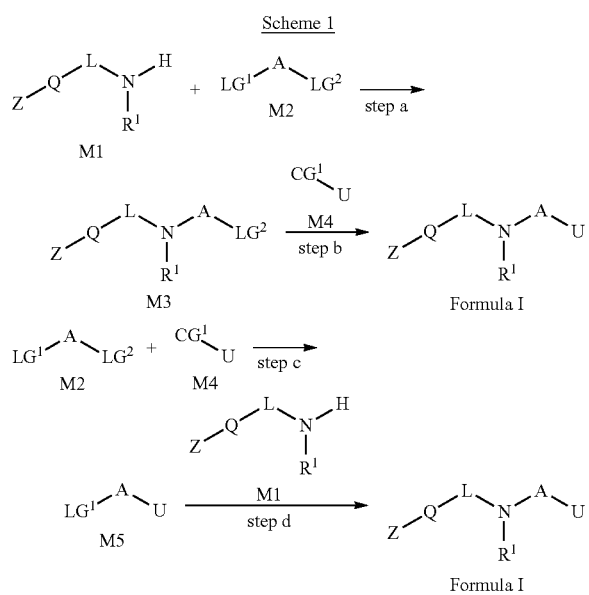

Scheme 1

Scheme 1 depicts a general synthetic route leading to the synthesis of compounds of Formula I. Compounds of Formula I can be assembled from three components: M1, M2, and M4. Component M1 can be formed from other precursors, as shown in examples vide infra. Component M2 has two leaving groups ($LG^1$ and $LG^2$) which can undergo reactions with an amino group in component M1 and a chemical group ($CG^1$) in component M4 to form compounds of Formula I. $LG^1$ and $LG^2$ can be selected from halide, $CH_3S(O)_2$—, triflate, tosylate, and mesylate. $CG^1$ can be selected from borate, organotin, alkyne, amino, and amide groups. Palladium catalyzed reactions of borate, organotin, alkyne, amide, or amino in $CG^1$, or treating amino group in $CG^1$ with a base can form a covalent bond between A and U in M. Further modifications of A or U may be needed to complete the syntheses of compounds of Formula I. Alternatively, $LG^2$ can be converted to borate and $CG^1$ can be selected from Br, I, and triflate so that a palladium catalyzed reaction may form the covalent bond between A and U. Further, M1 may only contains shorter tails, such as Q-L- or L- to start with, and Z or Z-Q may be added later to complete the synthesis of compounds of Formula I. Conditions for steps a and d can be: DIPEA, t-BuOH, 50-60° C., overnight; DIPEA, i-PrOH, 60-80° C. overnight; $Et_3N$, THF, rt, overnight; DIPEA, cyclohexanol, $ZnCl_2$, 120° C., 40 h; $K_2CO_3$, DMSO, 120-135° C., 10 h; $Pd(AcO)_2$, BINAP, t-BuONa, dioxane, 100° C., 12 h; and DIPEA, THF, 50° C., overnight. Conditions for steps b and c can be: DIPEA, NMP, 120-130° C., overnight; DIPEA, THF, reflux, overnight; DIPEA, t-BuOH, 50° C.; NMP, 130° C., 24 h; $Pd(PPh_3)_4$, $K_2CO_3$, dioxane/$H_2O$, 100-120° C., overnight; $Cs_2CO_3$, $Pd(PPh_3)_4$, dioxane/$H_2O$, 100° C., 12 h; $Pd(dppf)Cl_2$, dppf, $K_3PO_4$, dioxane, $H_2O$, 100° C., 12 h; $Pd(dppf)Cl_2$, dioxane/$H_2O$, 100° C., 10 h; and $Pd(PPh_3)_4$, xantphos, $Cs_2CO_3$, dioxane, reflux, overnight.

General Method B:

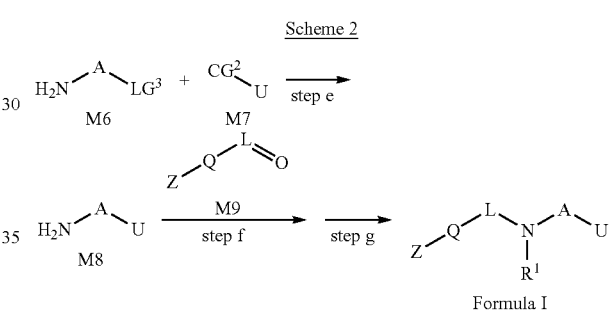

Scheme 2

Scheme 2 illustrates another general synthetic route leading the synthesis of compounds of Formula I. $LG^3$ can be selected from halide, triflate, tosylate, and mesylate, while $CG^2$ can be a borate group. Alternatively, $LG^3$ can be selected from halide, triflate, tosylate, and mesylate; and $CG^2$ can be a borate group. Palladium catalyzed reaction can lead to the covalent bond formation between A and U in M8. An ensuing reductive amination between M8 and M9 form the covalent bond between L and the amino group on A. Further alkylation of the amino group, if needed, may lead to compounds of Formula I. Step e can be $Na_2CO_3$, $Pd(PPh_3)_4$, EtOH, toluene, $H_2O$, 90° C., 12 h; and $K_2CO_3$, $Pd(PPh_3)_4$, dioxane/$H_2O$, 80° C., 10-12 h. Step f can be 1) EtOH, 90° C., 12 h, 2) $NaBH_4$; and TFA, $Et_3SiH$, MeCN, 80° C.

Method C:

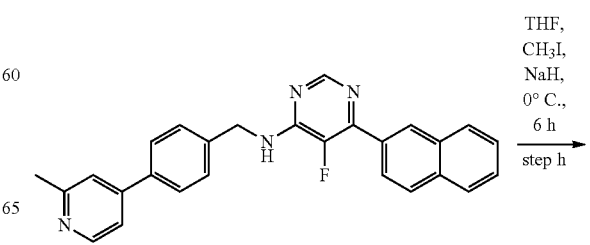

89 -continued
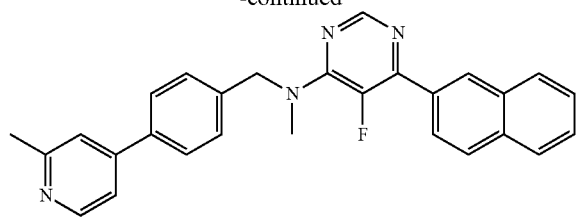
90 -continued
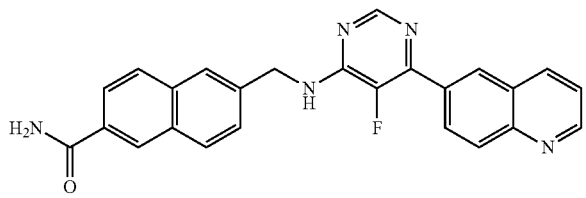
Method D:
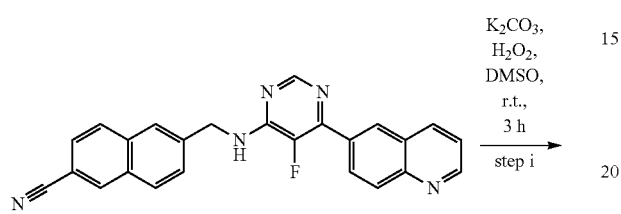
K₂CO₃, H₂O₂, DMSO, r.t., 3 h
step i
Method E:
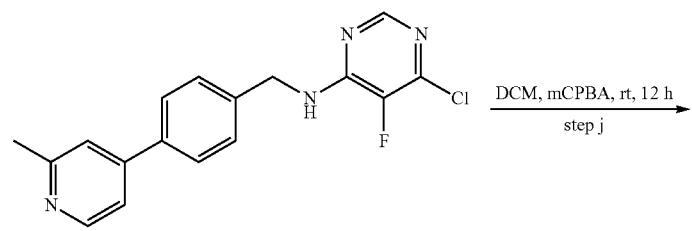
DCM, mCPBA, rt, 12 h
step j
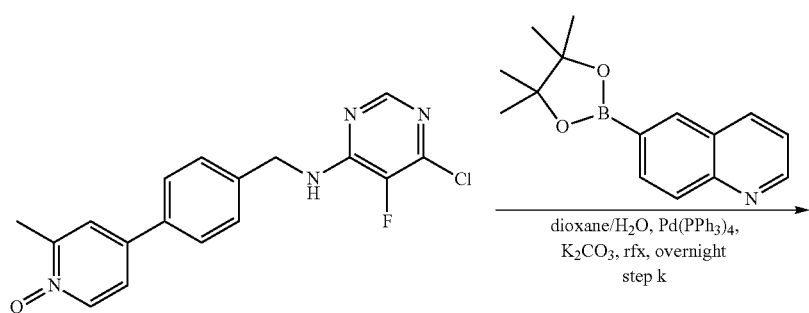
dioxane/H₂O, Pd(PPh₃)₄, K₂CO₃, rfx, overnight
step k
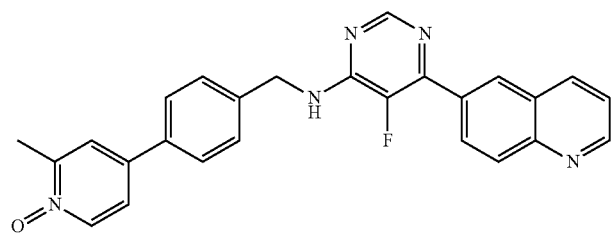

Method F:

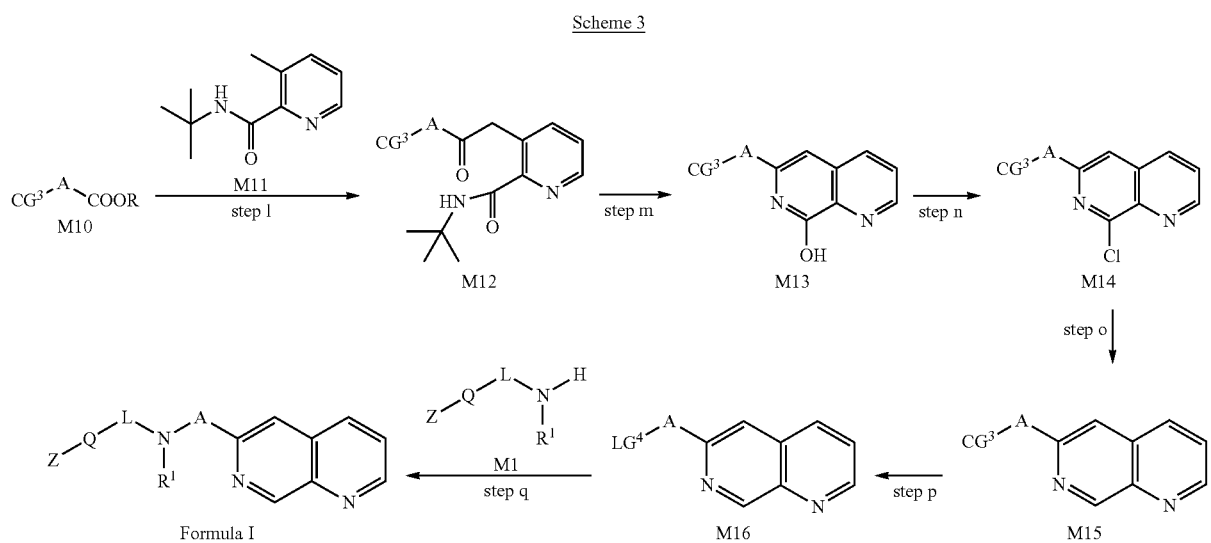

Scheme 3 depicts a general synthetic route leading to the synthesis of compounds of Formula I. Compounds of Formula I can be assembled from three components: M1, M10, and M11. Component M10 can be formed from other precursors, as shown in examples vide infra. Component M10 has a ester group (R=Me or Et) which can undergo reaction with the methyl group in component M11 to afford M12. Ring closure of M12 with loss of tert-butylamine afforded M13. The OH group of M13 was converted to hydrogen in two steps to give M14. The $CG^3$ group of M14 was converted to leaving group ($LG^4$) which can undergo reactions with an amino group in component M1 to form compounds of Formula I. $CG^3$ can be selected from $CH_3S$— and $CH_3O$— groups. $LG^4$ can be selected from $CH_3S(O)_2$— and HO— groups. Conditions for steps l can be: LDA, THF, —60° C., 1 h. Conditions for steps m can be: $NH_4OAc$, AcOH, 108° C., 8 h. Conditions for steps n can be: $POCl_3$, 100° C., 1 h. Conditions for steps o can be: $Pd(PPh_3)_4$, HCOOH, $Et_3N$, DMSO, 100° C., 1-3 h. Conditions for steps p can be: HBr, $H_2O$, 100° C., 1 h; and Oxone, THF, $H_2O$, r.t., 10 h. Conditions for steps q can be: PyBOP, DIPEA, DMF, r.t., 12 h; and DIPEA, NMP, 135° C., 16 h.

Method G:

Materials and Methods

All reagents and solvents were obtained commercially. When required, all reagents and solvents were purified by standard techniques: tetrahydrofuran was purified by distillation from sodium. All thin-layer chromatography (TLC, GF254) analyses and column purification (100-200 mesh) were performed on silica gel (Qingdao Haiyang Chemical Co. Ltd. or Yantai Chemical Co. Ltd.) and spots revealed by UV visualization at 254 nm and $I_2$ vapor or phosphomolybdic acid. All nuclear magnetic resonance spectra were recorded using a Varian unity INOVA 400NB spectrometer at 400 MHz or a Varian Vnmrs spectrometer at 300 MHz as indicated. LC-MS was run using an Agilent 1100 system using an Agela Durashell C18 3.5 μm 4.6×50 mm column Gradients were run using 0.1 $NH_4HCO_3$ aqueous solution and acetonitrile with gradient 5/95 to 95/5 in the run time indicated (for example, 5 min), flow rate at 1.8 mL/min.

SYNTHESIS

Example 1

Preparation of 5-fluoro-N-(4-(2-methylpyridin-4-yl)benzyl)-6-(naphthalen-2-yl)pyrimidin-4-amine (A-1)

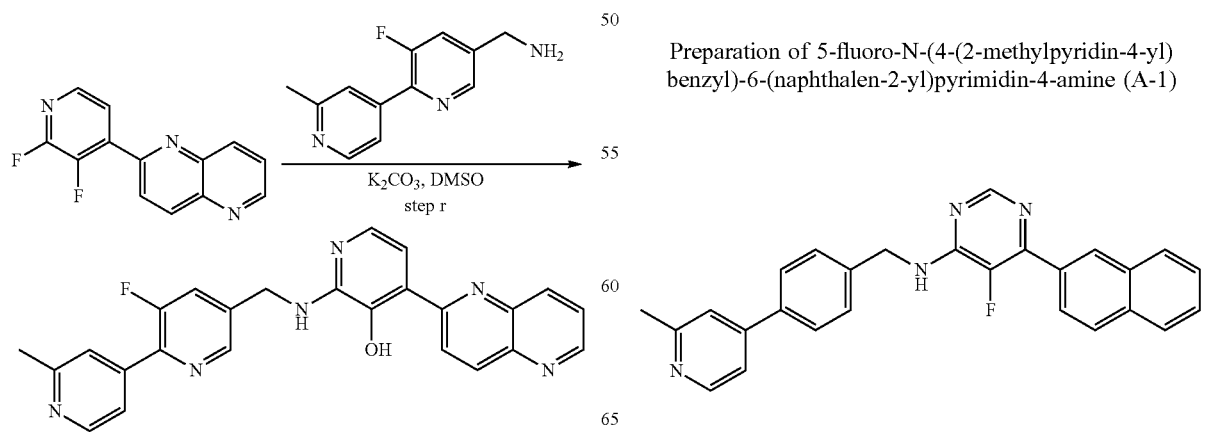

Method A-Step a: 6-chloro-5-fluoro-N-(4-(2-methylpyridin-4-yl)benzyl)pyrimidin-4-amine

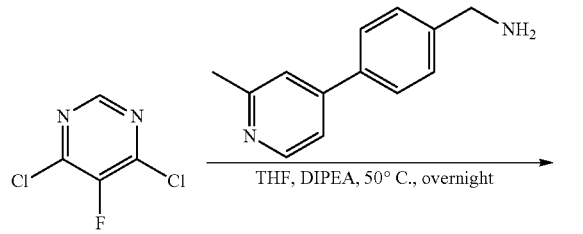

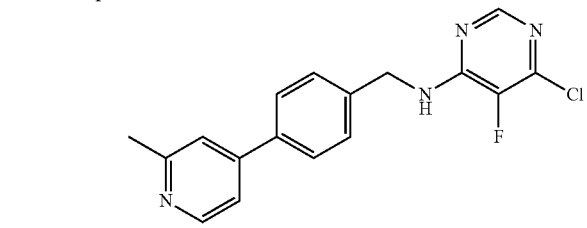

To a solution of (4-(2-methylpyridin-4-yl)phenyl)methanamine (100 mg, 0.51 mmol) in THF (10 mL), was added 4,6-dichloro-5-fluoropyrimidine (101 mg, 0.61 mmol) and N,N-diisopropylethylamine (260 mg, 2.0 mmol), and the reaction mixture was stirred at 50° C. overnight. After cooling to room temperature, the mixture was concentrated and the resulting residue was purified by silica gel column chromatography (CH$_2$Cl$_2$:MeOH=100:1) to give the title compound (140 mg, 84%) as a white solid. $^1$H NMR (400 MHz, CDCl$_3$) δ 8.54 (d, J=5.2 Hz, 1H), 8.23 (s, 1H), 7.62 (d, J=8.4 Hz, 2H), 7.45 (d, J=8.4 Hz, 2H), 7.36 (s, 1H), 7.30 (d, J=5.2 Hz, 1H), 5.60 (s, 1H), 4.79 (d, J=6.0 Hz, 2H), 2.62 (s, 3H).

Method A-Step b: 5-fluoro-N-(4-(2-methylpyridin-4-yl)benzyl)-6-(naphthalen-2-yl)pyrimidin-4-amine

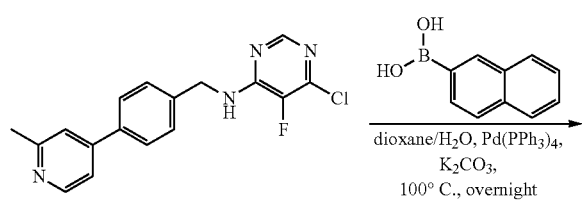

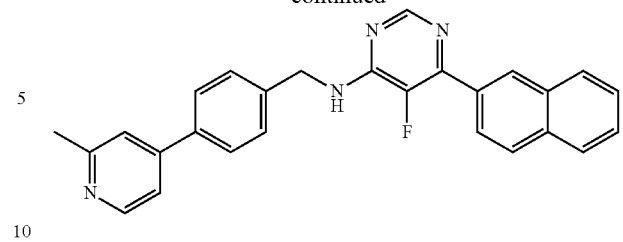

To a solution of 6-chloro-5-fluoro-N-(4-(2-methylpyridin-4-yl)benzyl)pyrimidin-4-amine (66 mg, 0.20 mmol), naphthalen-2-ylboronic acid (52 mg, 0.30 mmol) in dioxane (5 mL) and H$_2$O (1 mL), was added K$_2$CO$_3$ (116 mg, 0.84 mmol) and Pd(PPh$_3$)$_4$ (12 mg, 0.01 mmol). The mixture was stirred at 100° C. overnight under N$_2$ atmosphere. After cooling to room temperature, the mixture was filtered through Celite. The filtrate was diluted with EtOAc (15 mL), dried over Na$_2$SO$_4$, and concentrated. The resulting residue was purified by silica gel column chromatography (CH$_2$Cl$_2$:MeOH=200:1-50:1) to give the title compound (45 mg, 54%) as a white solid.

Example 2

Preparation of 5-fluoro-N-methyl-N-(4-(2-methylpyridin-4-yl)benzyl)-6-(naphthalen-2-yl)pyrimidin-4-amine (A-27)

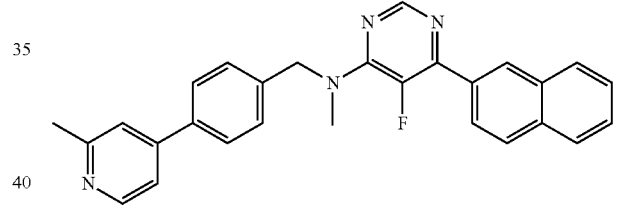

Method C-Step h: 5-fluoro-N-methyl-N-(4-(2-methylpyridin-4-yl)benzyl)-6-(naphthalen-2-yl) pyrimidin-4-amine

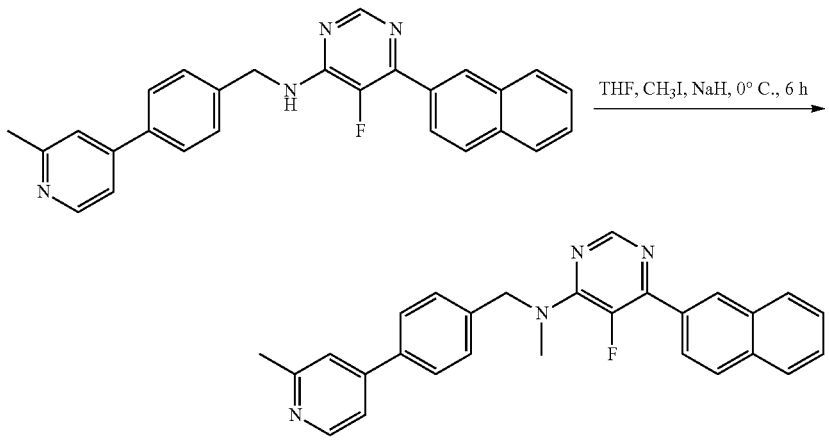

To a solution of 5-fluoro-N-(4-(2-methylpyridin-4-yl) benzyl)-6-(naphthalen-2-yl)pyrimidin-4-amine (30 mg, 0.07 mmol) in THF (3 mL) at 0° C., was added NaH (6 mg, 80%, 0.20 mmol). The mixture was stirred for 30 min before MeI (20 mg, 0.14 mmol) was added. After stirring for further 6 h, the mixture was concentrated and the resulting residue was purified by silica gel column chromatography (CH$_2$Cl$_2$: MeOH=100:1) to give the title compound (30 mg, 97%) as a pale yellow oil.

Example 3

Preparation of 6-((5-fluoro-6-(quinolin-6-yl)pyrimidin-4-ylamino)methyl)-2-naphthonitrile (A-42)

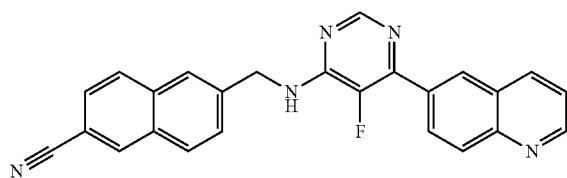 [SMILES: N#Cc1ccc2cc(CNc3ncnc(-c4ccc5ncccc5c4)c3F)ccc2c1]

Preparation of 6-(aminomethyl)-2-naphthonitrile

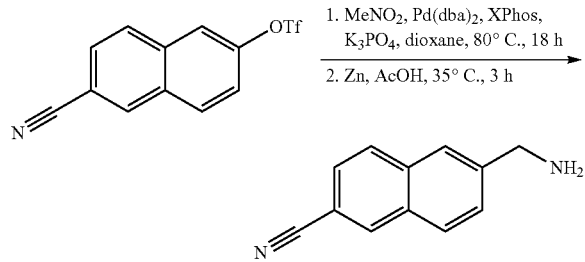

A mixture of 6-cyanonaphthalen-2-yl trifluoromethanesulfonate (1.35 g, 4.49 mmol), K$_3$PO$_4$ (1.27 g, 5.99 mmol), Pd(dba)$_2$ (114 mg, 0.20 mmol), and XPhos (143 mg, 0.30 mmol) in MeNO$_2$ (4 mL) and 1,4-dioxane (25 mL) was heated to 80° C. under N$_2$ atmosphere for 18 h. After cooling to room temperature, AcOH (8 mL) was added, followed by Zn power (2.93 g, 45 mmol). The mixture was stirred at 35° C. for another 3 h. After filtration, the filtrate was diluted with H$_2$O (30 mL) and washed with EtOAc (20 mL×2). The aqueous phase was treated with 1 N NaOH to adjust PH=10, and extracted with EtOAc (50 mL×3). The combined organic layers was washed with brine, dried over Na2SO4, and concentrated. The resulting residue was purified by silica gel column chromatography (petroleum ether: EtOAc=3:1-0:1) to give the title compound (280 mg, 34%) as a yellow solid.

Method A-Step a: 6-((6-chloro-5-fluoropyrimidin-4-ylamino)methyl)-2-naphthonitrile

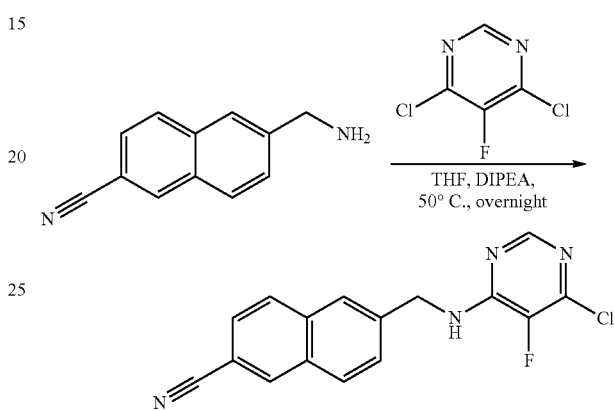

To a solution of 6-(aminomethyl)-2-naphthonitrile (182 mg, 1.0 mmol) in THF (1 mL), was added 4,6-dichloro-5-fluoropyrimidine (167 mg, 1.0 mmol) and N,N-diisopropylethylamine (260 mg, 2.0 mmol), and the reaction mixture was stirred at 50° C. overnight. After cooling to room temperature, the mixture was concentrated and the resulting residue was purified by silica gel column chromatography (petroleum ether:EtOAc=5:1-3:1) to give the title compound (120 mg, 38%) as a pale yellow solid.

Method A-Step b: 6-((5-fluoro-6-(quinolin-6-yl)pyrimidin-4-ylamino)methyl)-2-naphthonitrile

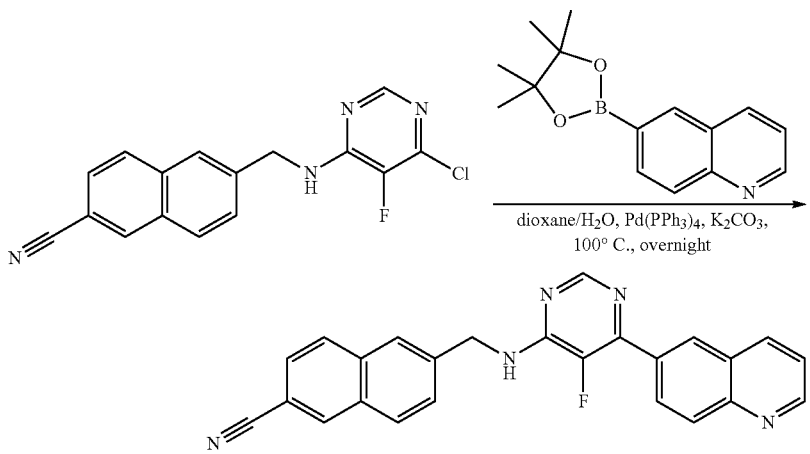

To a solution of 6-((6-chloro-5-fluoropyrimidin-4-ylamino)methyl)-2-naphthonitrile (53 mg, 0.17 mmol), 6-(4,4,5,5-tetramethyl-1,3,2-dioxaborolan-2-yl)quinoline (66 mg, 0.26 mmol) in dioxane (5 mL) and H$_2$O (1 mL), was added K₂CO₃ (96 mg, 0.69 mmol) and Pd(PPh₃)₄ (20 mg, 0.017 mmol). The mixture was stirred at 100° C. overnight under N₂ atmosphere. After cooling to room temperature, the mixture was filtered through Celite. The filtrate was diluted with EtOAc (15 mL), dried over Na₂SO₄, and concentrated. The resulting residue was purified by silica gel column chromatography (CH₂Cl₂:MeOH=100:1-50:1) to give the title compound (35 mg, 66%) as a pale yellow solid.

Example 4

Preparation of 6-((5-fluoro-6-(quinolin-6-yl)pyrimidin-4-ylamino)methyl)-2-naphthamide (A-43)

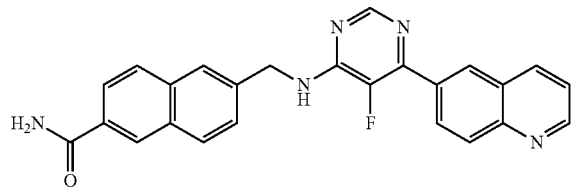 [SMILES: NC(=O)c1ccc2cc(CNc3ncnc(-c4ccc5ncccc5c4)c3F)ccc2c1]

Method D-Step is 6-((5-fluoro-6-(quinolin-6-yl)pyrimidin-4-ylamino)methyl)-2-naphthamide

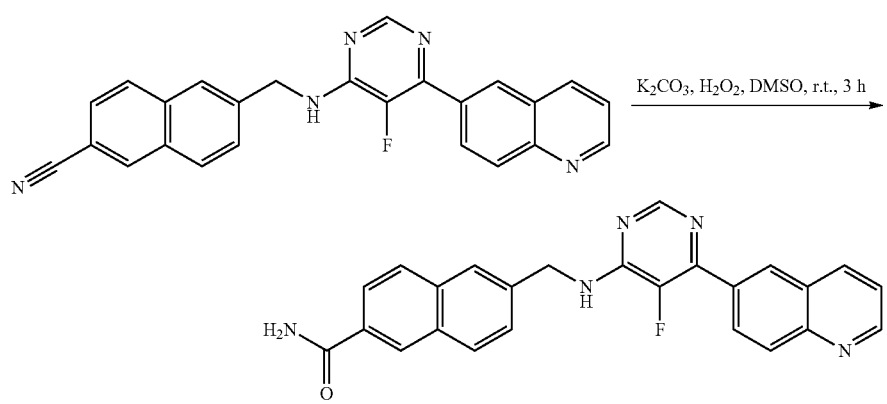

To a suspension of 6-((5-fluoro-6-(quinolin-6-yl)pyrimidin-4-ylamino)methyl)-2-naphthonitrile (17 mg, 0.04 mmol) and K₂CO₃ (2.8 mg, 0.02 mmol) in DMSO (1 mL), was added 30% H₂O₂ (6 mg, 0.05 mmol). The mixture was stirred at room temperature for 3 h, and then poured into H₂O (5 mL). The resulting precipitate was filtered, washed with water followed by hexane, and dried in vacuum to give the title compound (14 mg, 83%) as a pale yellow solid.

Example 5

Preparation of 6-(7,8-dihydro-1,6-naphthyridin-6(5H)-yl)-5-fluoro-N-((2-(2-methylpyridin-4-yl)pyrimidin-5-yl)methyl)pyrimidin-4-amine (A-61)

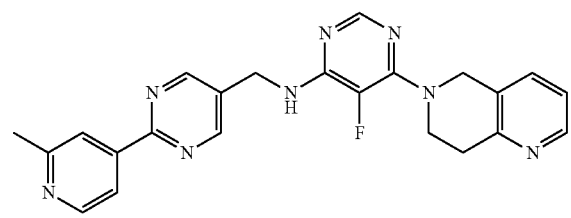 [SMILES: Cc1cc(-c2ncc(CNc3ncnc(N4CCc5ncccc5C4)c3F)cn2)ccn1]

Preparation of (2-(2-methylpyridin-4-yl)pyrimidin-5-yl)methanamine

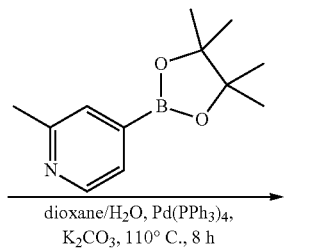

To a solution of (2-chloropyrimidin-5-yl)methanamine (1.0 g, 7.0 mmol) in dioxane (30 mL) and H₂O (6 mL) was added 2-methyl-4-(4,4,5,5-tetramethyl-1,3,2-dioxaborolan-2-yl)pyridine (45%, 3.7 g, 7.7 mmol), K₂CO₃ (2.9 g, 21 mmol) and Pd(PPh₃)₄ (809 mg, 0.7 mmol). The mixture was stirred at 100° C. under N₂ atmosphere for 8 h. After cooling to room temperature, the mixture was filtered through Celite. The filtrate was diluted with H₂O (10 mL), and extracted with EtOAc (50 mL×3). The combined organic layers was washed with brine (15 mL×3), dried over Na₂SO₄, and concentrated. The resulting residue was purified by silica gel column chromatography (petroleum ether:EtOAc=2:1-1:1) to give the title compound (1.3 g, 93%) as a gray solid.

Method A-Step a: 6-chloro-5-fluoro-N-((2-(2-methylpyridin-4-yl)pyrimidin-5-yl)methyl) pyrimidin-4-amine

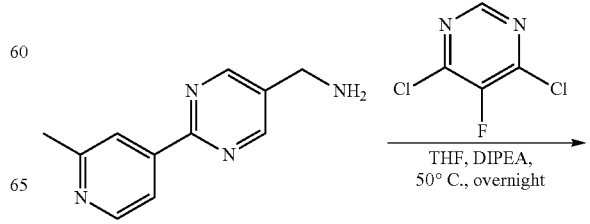

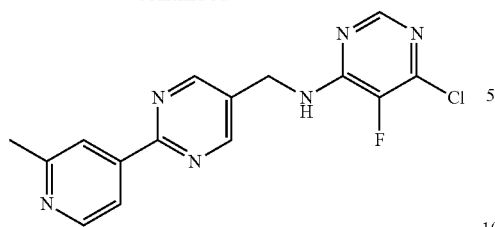

To a solution of (2-(2-methylpyridin-4-yl)pyrimidin-5-yl)methanamine (300 mg, 1.51 mmol) in THF (6 mL) was added 4,6-dichloro-5-fluoropyrimidine (278 mg, 1.51 mmol) and N,N-diisopropylethylamine (580 mg, 4.53 mmol), and the reaction mixture was stirred at 50° C. overnight. After cooling to room temperature, the mixture was concentrated and the resulting residue was purified by silica gel column chromatography (petroleum ether:EtOAc=1:1-0:1) to give the title compound (200 mg, 40%) as a yellow solid.

Method A-Step b: 6-(7,8-dihydro-1,6-naphthyridin-6(5H)-yl)-5-fluoro-N-((2-(2-methylpyridin-4-yl)pyrimidin-5-yl)methyl)pyrimidin-4-amine

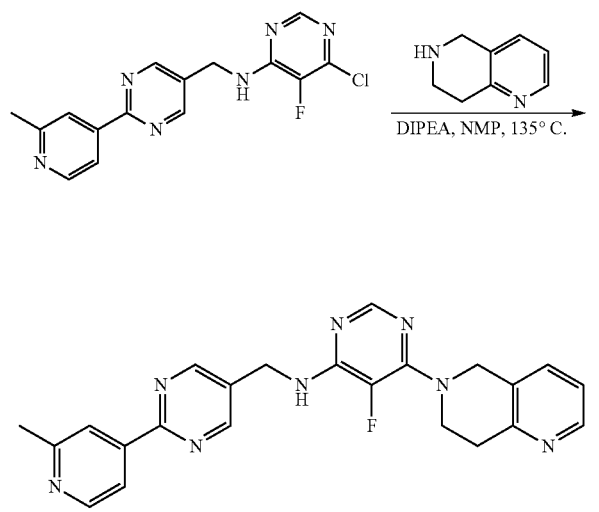

A mixture of 6-chloro-5-fluoro-N-((2-(2-methylpyridin-4-yl)pyrimidin-5-yl)methyl)pyrimidin-4-amine (80 mg, 0.24 mmol), 5,6,7,8-tetrahydro-1,6-naphthyridine (129 mg, 0.97 mmol) and N,N-diisopropylethylamine (467 mg, 3.6 mmol) in NMP (2 mL) was stirred at 135° C. for 8 h. After cooling to room temperature, the mixture was diluted with H₂O (5 mL), and extracted with EtOAc (5 mL×3). The combined organic layers was washed with brine (5 mL×3), dried over Na₂SO₄, and concentrated. The resulting residue was purified by silica gel column chromatography (petroleum ether:EtOAc=5:1-1:1) to give the title compound (30 mg, 50%) as a brown solid.

Example 6

Preparation of 4-(4-((5-fluoro-6-(quinolin-6-yl)pyrimidin-4-ylamino)methyl)phenyl)-2-methylpyridine 1-oxide (A-64)

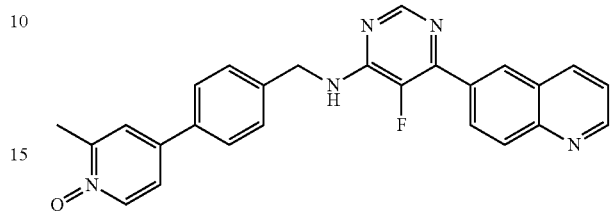

Method E-Step j: 4-(4-((6-chloro-5-fluoropyrimidin-4-ylamino)methyl)phenyl)-2-methylpyridine 1-oxide

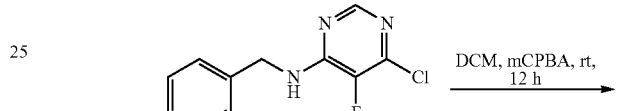

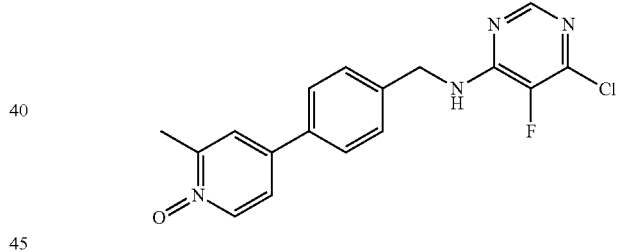

To a solution of 6-chloro-5-fluoro-N-(4-(2-methylpyridin-4-yl)benzyl)pyrimidin-4-amine (133 mg, 0.404 mmol) in CH₂Cl₂ (5 mL) at room temperature, was added m-CPBA (174 mg, 1.01 mmol). The mixture was stirred at room temperature overnight, and then diluted with CH₂Cl₂ (15 mL). A mixture of sat. Na₂S₂O₃ (5 mL) and sat. NaHCO₃ (5 mL) was added, and the mixture was stirred for another 30 min The organic layer was separated, washed with brine (5 mL), dried over Na₂SO₄, and concentrated. The resulting residue was purified by silica gel column chromatography (CH₂Cl₂:MeOH=100:1-50:1) to give the title compound (130 mg, 96%) as a white solid. ¹H NMR (400 MHz, CDCl₃) δ 8.25 (d, J=6.8 Hz, 1H), 8.22 (s, 1H), 7.54 (d, J=8.0 Hz, 2H), 7.43 (d, J=8.0 Hz, 3H), 7.35-7.29 (m, 1H), 5.91 (s, 1H), 4.79 (d, J=6.0 Hz, 2H), 2.57 (s, 3H).

Method E-Step k: 4-(4-((5-fluoro-6-(quinolin-6-yl)pyrimidin-4-ylamino)methyl)phenyl)-2-methylpyridine 1-oxide

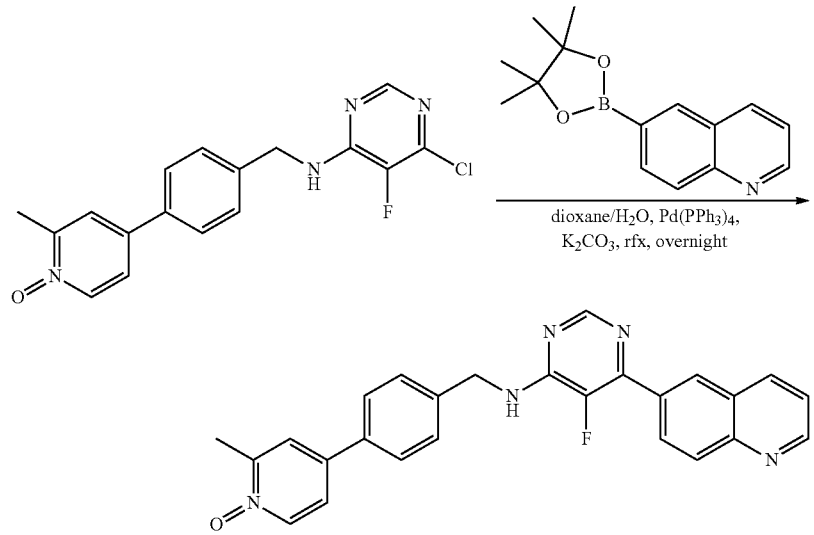

To a solution of 4-(4-((6-chloro-5-fluoropyrimidin-4-ylamino)methyl)phenyl)-2-methylpyridine 1-oxide (67 mg, 0.19 mmol), 6-(4,4,5,5-tetramethyl-1,3,2-dioxaborolan-2-yl)quinoline (74 mg, 0.29 mmol) in dioxane (5 mL) and H$_2$O (1 mL), was added K$_2$CO$_3$ (107 mg, 0.78 mmol) and Pd(PPh$_3$)$_4$ (22 mg, 0.02 mmol). The mixture was stirred at reflux overnight under N$_2$ atmosphere. After cooling to room temperature, the mixture was filtered through Celite. The filtrate was diluted with EtOAc (15 mL), dried over Na$_2$SO$_4$, and concentrated. The resulting residue was purified by silica gel column chromatography (CH$_2$Cl$_2$:MeOH=50:1-30:1) to give the title compound (65 mg, 77%) as a white solid.

Example 7

Preparation of 5-fluoro-N-((3-fluoro-2'-methyl-2,4'-bipyridin-5-yl)methyl)-6-(pyridin-3-ylethynyl)pyrimidin-4-amine (A-69)

Preparation of (3-fluoro-2'-methyl-2,4'-bipyridin-5-yl)methanamine

-continued

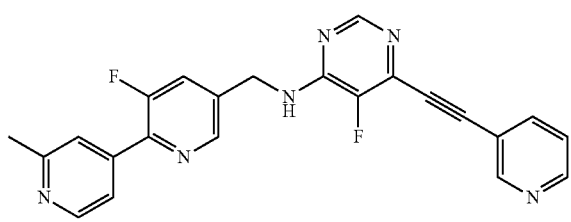 [SMILES: Cc1cc(-c2ncc(CNc3ncnc(C#Cc4cccnc4)c3F)cc2F)ccn1]

To a solution of (6-chloro-5-fluoropyridin-3-yl)methanamine (2.36 g, 14.6 mmol) in dioxane (50 mL) and H$_2$O (10 mL) was added 2-methyl-4-(4,4,5,5-tetramethyl-1,3,2-dioxaborolan-2-yl)pyridine (1.7 g, 16.1 mmol), K$_2$CO$_3$ (8.09 g, 58.6 mmol) and Pd(PPh$_3$)$_4$ (847 mg, 0.73 mmol). The mixture was stirred at 100° C. under N$_2$ atmosphere for 8 h. After cooling to room temperature, the mixture was filtered through Celite. The filtrate was diluted with H$_2$O (100 mL), and extracted with CH$_2$Cl$_2$ (100 mL×6). The combined organic layers was dried over Na$_2$SO$_4$ and concentrated. The resulting residue was purified by silica gel column chromatography (CH$_2$Cl$_2$:MeOH:NH$_4$OH=50:1:0.1-20:1:0.1) to give the title compound (2.5 g, 79%) as a brown solid. $^1$H NMR (400 MHz, CDCl$_3$) δ 8.61 (d, J=4.8 Hz, 1H), 8.50 (s, 1H), 7.77 (s, 1H), 7.69 (d, J=4.0 Hz, 1H), 7.58 (d, J=12.0 Hz, 1H), 4.01 (s, 2H), 2.65 (s, 3H).

Method A-Step a: 6-chloro-5-fluoro-N-((3-fluoro-2'-methyl-2,4'-bipyridin-5-yl)methyl)pyrimidin-4-amine

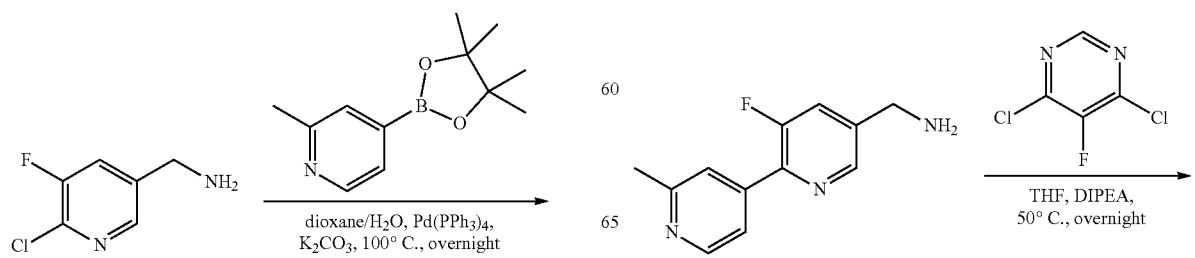

-continued

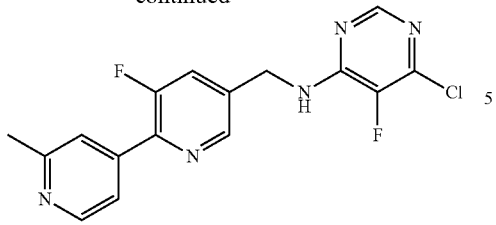

To a solution of (3-fluoro-2'-methyl-2,4'-bipyridin-5-yl)methanamine (200 mg, 0.92 mmol) in THF (10 mL), was added 4,6-dichloro-5-fluoropyrimidine (154 mg, 0.92 mmol) and N,N-diisopropylethylamine (357 mg, 2.77 mmol), and the reaction mixture was stirred at 50° C. overnight. After cooling to room temperature, the mixture was concentrated and the resulting residue was purified by silica gel column chromatography (CH$_2$Cl$_2$:MeOH=50:1) to give the title compound (200 mg, 62%) as a gray solid. $^1$H NMR (400 MHz, CDCl$_3$) δ 8.61 (d, J=4.8 Hz, 1H), 8.56 (s, 1H), 8.24 (s, 1H), 7.76 (s, 1H), 7.69 (s, 1H), 7.55 (d, J=11.6 Hz, 1H), 5.78 (s, 1H), 4.84 (d, J=6.0 Hz, 2H), 2.65 (s, 3H).

Method A-Step b: 5-fluoro-N-((3-fluoro-2'-methyl-2,4'-bipyridin-5-yl)methyl)-6-(pyridin-3-ylethynyl)pyrimidin-4-amine

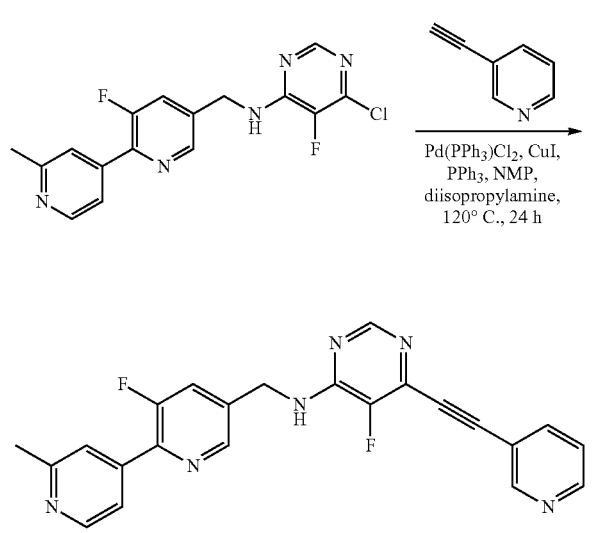

A mixture of 6-chloro-5-fluoro-N-((3-fluoro-2'-methyl-2,4'-bipyridin-5-yl)methyl)pyrimidin-4-amine (100 mg, 0.29 mmol), 3-ethynylpyridine (92 mg, 0.87 mmol), Pd(PPh$_3$)$_2$Cl$_2$ (9 mg, 0.012 mmol), PPh$_3$ (6.1 mg, 0.023 mmol), and CuI (0.55 mg, 0.023 mmol) in diisopropylanmine (2 mL) and NMP (2 mL) was heated at 100° C. under N$_2$ atmosphere for 24 h. After cooling to room temperature, the mixture was filtered through Celite. The filtrate was diluted with H$_2$O (10 mL), and extracted with EtOAc (10 mL×3). The combined organic layers was washed with brine (5 mL×2), dried over Na$_2$SO$_4$, and concentrated. The resulting residue was purified by silica gel column chromatography (petroleum ether:EtOAc=2:1-1:1) to give the title compound (17 mg, 14%) as a white solid.

Example 8

Preparation of 5-fluoro-N-((3-fluoro-2'-methyl-2,4'-bipyridin-5-yl)methyl)-6-(1,7-naphthyridin-6-yl)pyrimidin-4-amine (A-85)

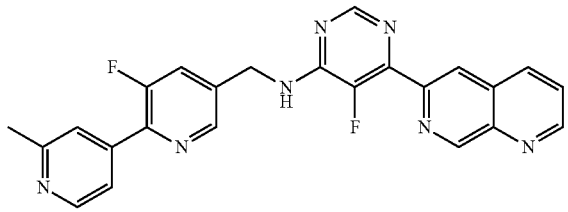 [SMILES: Cc1cc(-c2ncc(CNc3ncnc(-c4cc5cccnc5cn4)c3F)cc2F)ccn1]

Preparation of ethyl 5-fluoro-6-hydroxypyrimidine-4-carboxylate

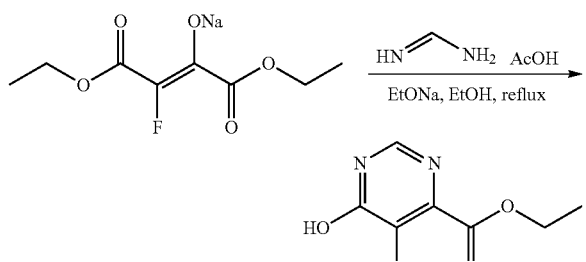

A solution of sodium (E)-1,4-diethoxy-3-fluoro-1,4-dioxobut-2-en-2-olate (45.6 g, 200 mmol), formamidine acetate (20.8 g, 200 mmol) and EtONa (13.6 g, 200 mmol) in anhydrous EtOH (200 mL) was heated at reflux overnight. After cooling to room temperature, the solvent was removed by vacuum. The residue was neutralized with 2 N HCl and extracted with ethyl acetate (100 mL×3). The combined organic layers was dried over Na$_2$SO$_4$, and concentrated to give the title compound (22 g, 59%) as a brown solid, which was used directly in the next step without further purification.

Preparation of ethyl 6-chloro-5-fluoropyrimidine-4-carboxylate

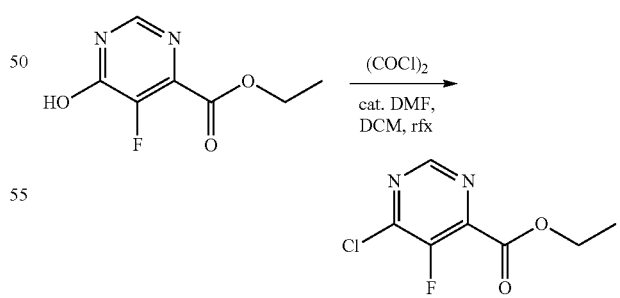

To a stirred solution of ethyl 5-fluoro-6-hydroxypyrimidine-4-carboxylate (21.0 g, 113 mmol) and DMF (0.5 mL) in CH$_2$Cl$_2$ (200 mL) at room temperature, was added (COCl)$_2$ (43.0 g, 339 mmol) dropwise. The reaction was heated at reflux overnight. After cooling to room temperature, the solvent was removed by vacuum. The residue was dissolved in ethyl acetate (300 mL) and washed with sat.

NaHCO₃ and brine successively. The organic layer was dried over Na₂SO₄, and concentrated. The resulting residue was purified by column chromatography (petroleum ether:ethyl acetate=10:1) to give the title compound (17.8 g, 77%) as a colerless oil. ¹H NMR (400 MHz, CDCl₃) δ 8.90 (s, 1H), 4.52 (q, J=7.1 Hz, 2H), 1.44 (t, J=7.2 Hz, 3H).

Preparation of ethyl 5-fluoro-6-methoxypyrimidine-4-carboxylate

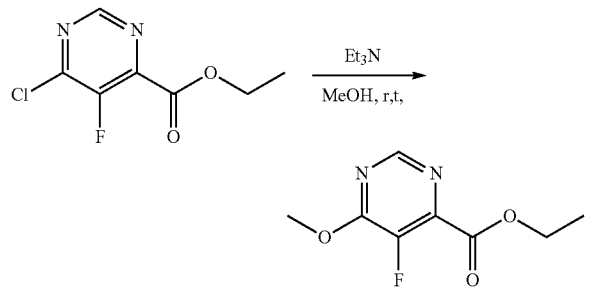

A mixture of ethyl 6-chloro-5-fluoropyrimidine-4-carboxylate (6.14 g, 30.0 mmol) and triethylamine (3.03 g, 30.0 mmol) in methanol (50 mL) was stirred at room temperature overnight. After concentration, the residue was purified by column chromatography (petroleum ether:ethyl acetate=10:1) to give the title compound (4.14 g, 74%) as a white solid. ¹H NMR (400 MHz, CDCl₃) δ 8.59 (s, 1H), 4.11 (s, 3H), 4.01 (s, 3H).

Method F-Step l: N-(tert-butyl)-3-(2-(5-fluoro-6-methoxypyrimidin-4-yl)-2-oxoethyl) picolinamide

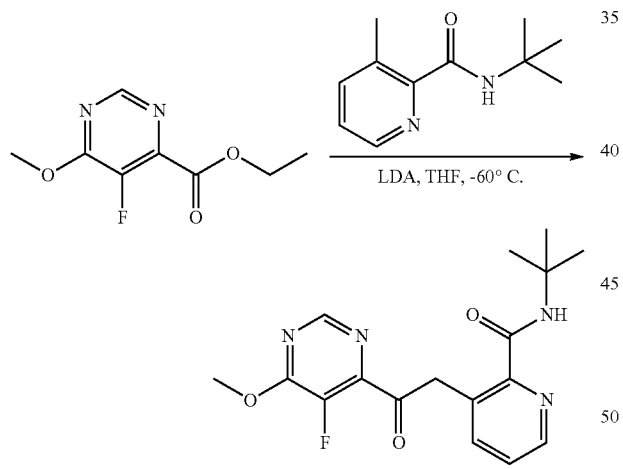

To a stirred solution of N-(tert-butyl)-3-methylpicolinamide (2.69 g, 14 mmol) in anhydrous tetrahydrofuran (50 mL) at −40° C., was added lithium diisopropylamide (2 M in THF, 28 mL, 56 mmol) dropwise. The mixture was stirred at this temperature for 30 min and then cooled to −60° C. Ethyl 5-fluoro-6-methoxypyrimidine-4-carboxylate (2.60 g, 14.0 mmol) in 5 mL anhydrous tetrahydrofuran was added and the reaction mixture was stirred at −60° C. for another 1 h. The reaction was quenched with sat. NH₄Cl (50 mL) and extracted with ethyl acetate (50 mL×3). The combined organic layers dried over Na₂SO₄, and concentrated. The resulting residue was purified by silica gel column chromatography (petroleum ether:ethyl acetate=3:1) to give the title compound (1.36 g, 28%) as a yellow solid. ¹H NMR (400 MHz, CDCl₃) δ 8.61 (s, 1H), 8.48 (d, J=4.4 Hz, 1H), 8.08 (s, 1H), 7.60 (d, J=7.6 Hz, 1H), 7.41-7.37 (m, 1H), 4.86 (s, 2H), 4.13 (s, 3H), 1.40 (s, 9H).

Method F-Step m: 6-(5-fluoro-6-methoxypyrimidin-4-yl)-1,7-naphthyridin-8-ol

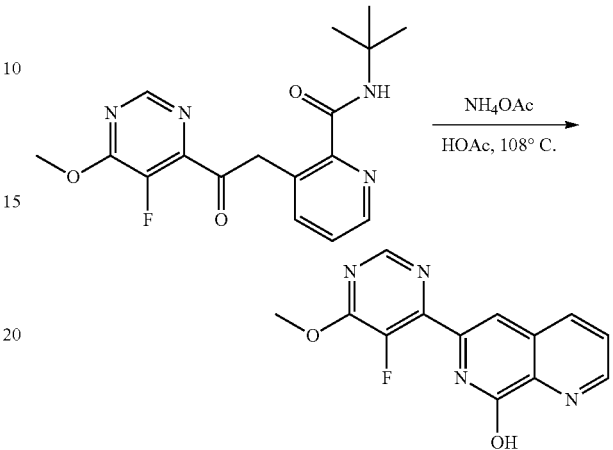

A mixture of N-(tert-butyl)-3-(2-(5-fluoro-6-methoxypyrimidin-4-yl)-2-oxoethyl)picolinamide (1.36 g, 3.93 mmol) and NH₄OAc (3.03 g, 39.3 mmol) in HOAc (20 mL) was heated to 108° C. for 8 h. After concentration, the resulting residue was dissolved in ethyl acetate (30 mL) and washed with sat. NaHCO₃ (5 mL). The organic layer was dried over Na₂SO₄ and concentrated to give the title compound (880 mg, 82%) as a yellow solid without further purification.

Method F-Step n: 8-chloro-6-(5-fluoro-6-methoxypyrimidin-4-yl)-1,7-naphthyridine

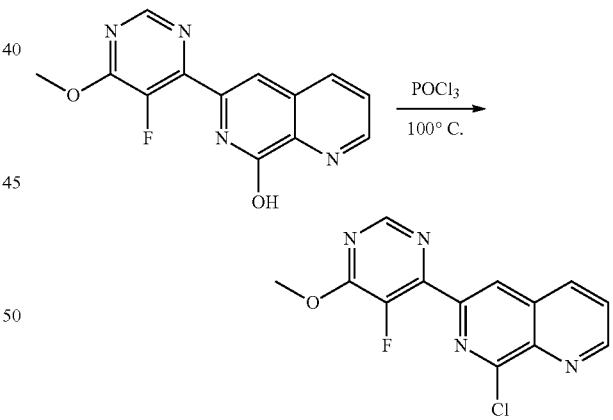

A mixture of 6-(5-fluoro-6-methoxypyrimidin-4-yl)-1,7-naphthyridin-8-ol (440 mg, 1.62 mmol) and triethylamine (327 mg, 3.24 mmol) in POCl₃ (7.5 mL) and toluene (2.5 mL) was heated to 100° C. for 1 h. After concentration, the residue was dissolved in ethyl acetate (20 mL) and washed with sat. NaHCO₃ (5 mL). The organic layer was dried over Na₂SO₄ and concentrated. The resulting residue was purified by column chromatography (petroleum ether:ethyl acetate=2:1) to give the title compound (440 mg, 100%) as a white solid. ¹H NMR (400 MHz, CDCl₃) δ 9.22 (s, 1H), 8.68 (s, 1H), 8.47 (s, 1H), 8.34 (d, J=8.2 Hz, 1H), 7.78-7.74 (m, 1H), 4.16 (s, 3H).

Method F-Step o: 6-(5-fluoro-6-methoxypyrimidin-4-yl)-1,7-naphthyridine

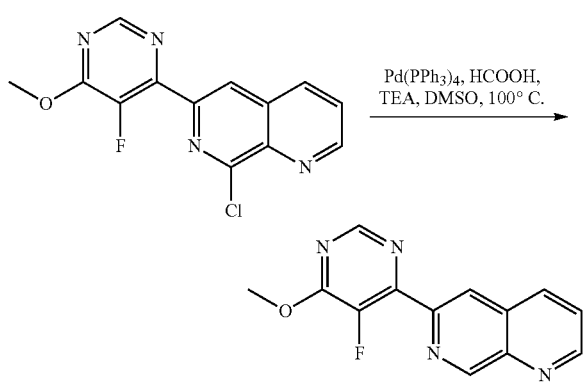

A mixture of 8-chloro-6-(5-fluoro-6-methoxypyrimidin-4-yl)-1,7-naphthyridine (440 mg, 1.62 mmol), triethylamine (924 mg, 9.15 mmol), formic acid (253 mg, 5.50 mmol) and Pd(PPh$_3$)$_4$ (200 mg, 0.173 mmol) in DMSO (10 mL) was stirred at 100° C. under N$_2$ atmosphere for 1 h. After cooling to room temperature, the mixture was diluted with ethyl acetate (40 mL) and filtered. The filtrate was washed with brine (10 mL×3), dried over Na$_2$SO$_4$, and concentrated. The residue was purified by column chromatography (petroleum ether:ethyl acetate=3:1) to give the title compound (400 mg, 96%) as a white solid. $^1$H NMR(400 MHz, CDCl$_3$) δ 9.70 (s, 1H), 9.12 (d, J=3.6 Hz, 1H), 8.70 (s, 1H), 8.52 (s, 1H), 8.30 (d, J=8.4 Hz, 1H), 7.56-7.53 (m, 1H), 4.16 (s, 3H).

Method F-Step p: 5-fluoro-6-(1,7-naphthyridin-6-yl)pyrimidin-4-ol

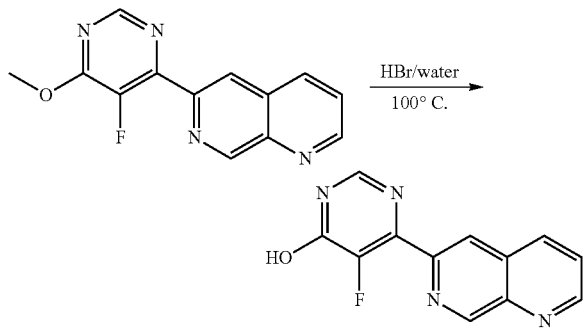

A mixture of 6-(5-fluoro-6-methoxypyrimidin-4-yl)-1,7-naphthyridine (400 mg, 1.56 mmol) in 37% HBr (10 mL) was heated at reflux for 1 h. After concentration, the resulting residue was suspended in isopropanol (10 mL). The precipitate was filtered and washed with ether (3 mL) to give the title compound (400 mg, quantitative) as a yellow solid.

Method F-Step q: 5-fluoro-N-((3-fluoro-2'-methyl-2,4'-bipyridin-5-yl)methyl)-6-(1,7-naphthyridin-6-yl)pyrimidin-4-amine

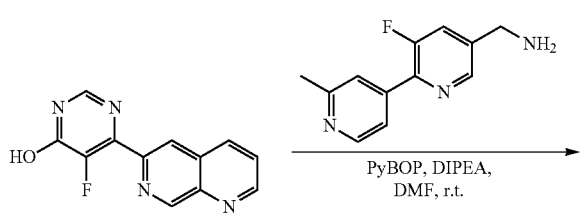

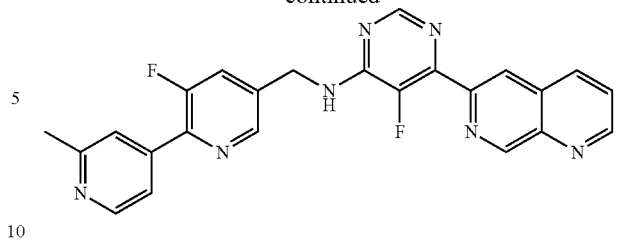

To a stirred solution of 5-fluoro-6-(1,7-naphthyridin-6-yl)pyrimidin-4-ol (25 mg, 0.1 mmol), (3-fluoro-2'-methyl-2,4'-bipyridin-5-yl)methanamine (22 mg, 0.1 mmol), and N,N-diisopropylethylamine (26 mg, 0.2 mmol) in N,N-Dimethylformamide (1 mL) at room temperature, was added PyBOP (78 mg, 0.15 mmol) in portions. The mixture was stirred at room temperature for 12 h and then diluted with ethyl acetate (5 mL). The organic phase was washed with brine (2 mL), dried over Na$_2$SO$_4$, and concentrated. The residue was purified by column chromatography (CH$_2$Cl$_2$: MeOH=100:4) to give the title compound (30 mg, 68%) as a white solid.

Example 9

Preparation of 5-((3-fluoro-4-(1,7-naphthyridin-6-yl)pyridin-2-ylamino)methyl)-2'-methyl-2,4'-bipyridine-3-carbonitrile (A-121)

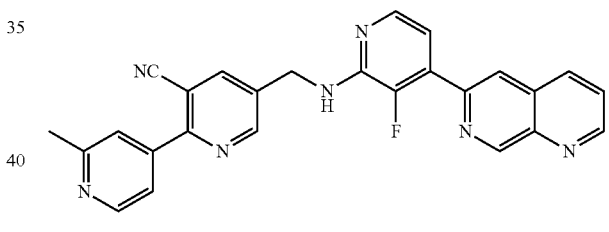

Preparation of 2-bromo-5-(bromomethyl)nicotinonitrile

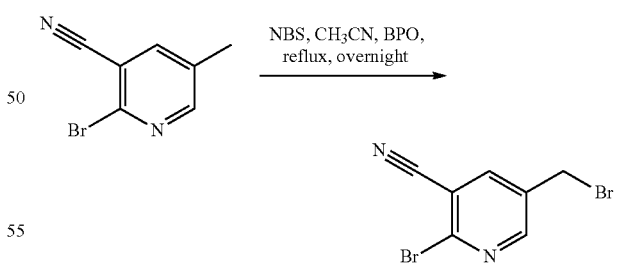

To a solution of 2-bromo-5-methylnicotinonitrile (5 g, 25.4 mmol) in MeCN (100 mL) was added NBS (6.8 g, 38 mmol) and BPO (100 mg, 0.41 mmol). The mixture was heated at reflux overnight, and then BPO (50 mg, 0.21 mmol) was added. The mixture was heated at reflux for another 12 h. After cooling to room temperature, the mixture was concentrated and purified by column chromatography (petroleum ether:ethyl acetate=100:1-50:1) to give the title compound (4.3 g, 61%) as a brown solid.

Preparation of 5-(aminomethyl)-2-bromonicotinonitrile

Method A-Step c: 6-(2,3-difluoropyridin-4-yl)-1,7-naphthyridine

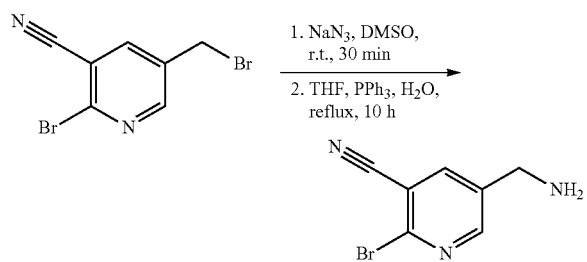

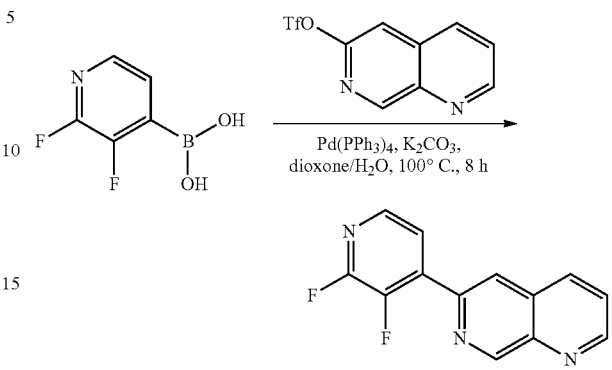

To a solution of 2-bromo-5-(bromomethyl)nicotinonitrile (2.3 g, 8.2 mmol) in DMSO (40 mL) in ice bath, was added NaN₃ (637 mg, 9.8 mmol). The mixture was stirred at room temperature for 30 min before H₂O (100 mL) was added. The mixture was extracted with EtOAc (100 mL×3). The combined organic layers was washed with brine (50 mL×3), dried over Na₂SO₄ and concentrated to give a white solid (940 mg). THF (15 mL) was added followed by PPh₃ (1.14 g, 4.34 mmol) and H₂O (3 mL) and the mixture was heated at reflux 10 h. After cooling to room temperature, the mixture was diluted with EtOAc (100 mL), and extracted with 0.2 N HCl (20 mL×2). The combined aqueous layers was washed with EtOAc (20 mL) before sat. Na₂CO₃ was added to adjust PH=9. The aqueous layer was extracted with CH₂Cl₂ (40 mL×5). The combined organic layers was washed with brine (20 mL), dried over Na₂SO₄ and concentrated to give a yellow solid (570 mg, 33%).

Preparation of 5-(aminomethyl)-2-bromonicotinonitrile

To a solution of 2,3-difluoropyridin-4-ylboronic acid (105 mg, 0.66 mmol) and 1,7-naphthyridin-6-yl trifluoromethanesulfonate (167 mg, 0.6 mmol) in dioxane (4 mL) and H₂O (1 mL), was added Pd(dppf)Cl₂ (39 mg, 0.048 mmol), dppf (26 mg, 0.048 mmol) and K₃PO₄ (254 mg, 1.2 mmol). The mixture was stirred at 100° C. under N₂ atmosphere for 8 h. After cooling to room temperature, the mixture was concentrated and purified by silica gel column chromatography (petroleum ether:EtOAc=1:1) to give the title compound (80 mg, 47%) as a white solid.

Method A-Step d: 5-((3-fluoro-4-(1,7-naphthyridin-6-yl)pyridin-2-ylamino)methyl)-2'-methyl-2,4'-bipyridine-3-carbonitrile

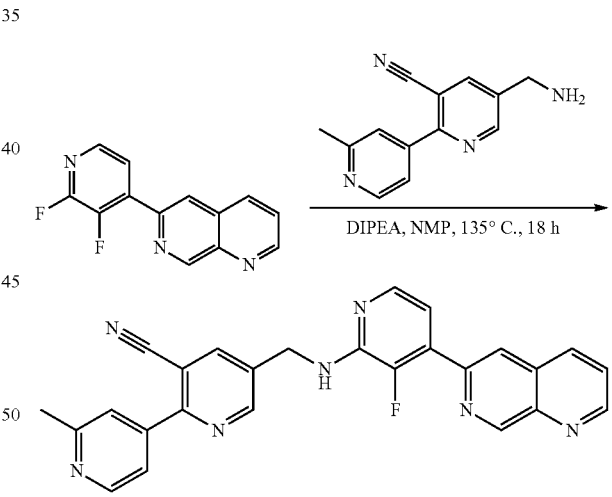

To a solution of (6-chloro-5-fluoropyridin-3-yl)methanamine (570 mg, 2.69 mmol) in dioxane (15 mL) and H₂O (3 mL) was added 2-methyl-4-(4,4,5,5-tetramethyl-1,3,2-dioxaborolan-2-yl)pyridine (1.43 g, 45%, 2.96 mmol), K₂CO₃ (1.12 g, 8.07 mmol) and Pd(PPh₃)₄ (310 mg, 0.27 mmol). The mixture was stirred at 100° C. under N₂ atmosphere for 8 h. After cooling to room temperature, the mixture was filtered through Celite. The filtrate was diluted with H₂O (10 mL), and extracted with EtOAc (50 mL×6). The combined organic layers was dried over Na₂SO₄ and concentrated. The resulting residue was purified by silica gel column chromatography (petroleum ether:ethyl acetate=2:1-1:1) to give the title compound (570 mg, 95%) as a gray solid.

To a solution of 5-(aminomethyl)-2'-methyl-2,4'-bipyridine-3-carbonitrile (89 mg, 0.4 mmol) and N,N-diisopropylethylamine (206 mg, 1.6 mmol) in NMP (1 mL), was added 6-(2,3-difluoropyridin-4-yl)-1,7-naphthyridine (49 mg, 0.2 mmol). The mixture was stirred at 135° C. under N₂ atmosphere for 18 h. After cooling to room temperature, the mixture was diluted with H₂O (10 mL), and extracted with EtOAc (20 mL×3). The combined organic layers was washed with brine (10 mL×3), dried over Na₂SO₄, and concentrated. The resulting residue was purified by silica gel column chromatography (CH₂Cl₂:MeOH=50:1) to give the title compound (42 mg, 48%) as a yellow solid.

Example 10

Preparation of 6-(6-(4-(2-methylpyridin-4-yl)benzylamino)pyrimidin-4-yl)-2-(methylthio)-7,8-dihydropyrido[4,3-d]pyrimidin-5(6H)-one (A-137)

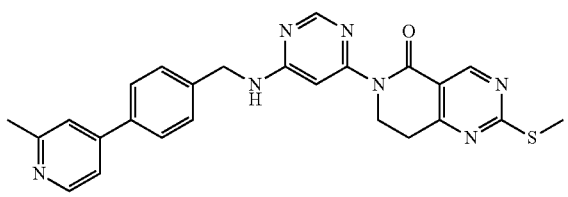

Method A-Step b: 6-(6-(4-(2-methylpyridin-4-yl)benzylamino)pyrimidin-4-yl)-2-(methylthio)-7,8-dihydropyrido[4,3-d]pyrimidin-5(6H)-one

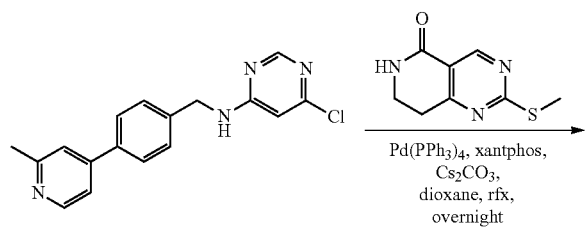

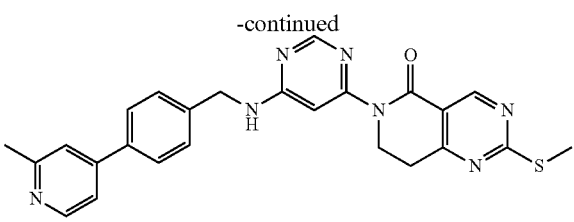

To a solution of 6-chloro-N-(4-(2-methylpyridin-4-yl)benzyl)pyrimidin-4-amine (400 mg, 1.29 mmol) and 2-(methylthio)-7,8-dihydropyrido[4,3-d]pyrimidin-5(6H)-one (305 mg, 1.55 mmol) in dioxane (10 mL) was added Pd(PPh$_3$)$_4$ (60 mg, 0.05 mmol), Xantphos (60 mg, 0.11 mmol) and Cs$_2$CO$_3$ (1.0 g, 3.23 mmol). The mixture was stirred at reflux overnight. After cooling to room temperature, the mixture was diluted with EtOAc (20 mL), and washed with H$_2$O (6 mL×3). The organic layer was dried over Na$_2$SO$_4$, and concentrated. The resulting residue was purified by silica gel column chromatography (petroleum ether:EtOAc=1:2) to give the title compound (180 mg, 31%) as a white solid.

Example 11

Preparation of 2-(methylamino)-6-(6-(4-(2-methylpyridin-4-yl)benzylamino)pyrimidin-4-yl)-7,8-dihydropyrido[4,3-d]pyrimidin-5(6H)-one (A-138)

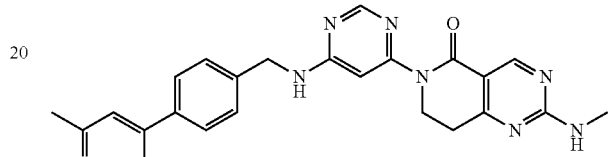

Preparation of 6-(6-(4-(2-methylpyridin-4-yl)benzylamino)pyrimidin-4-yl)-2-(methylthio)-7,8-dihydropyrido[4,3-d]pyrimidin-5(6H)-one

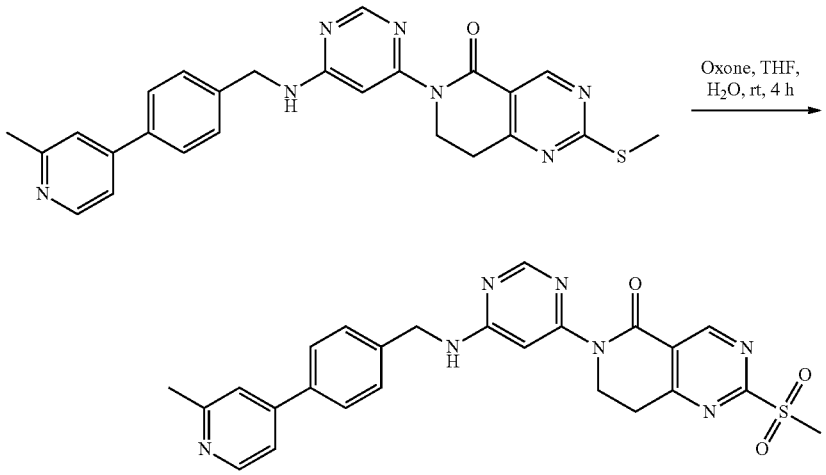

To a solution of 6-(6-(4-(2-methylpyridin-4-yl)benzylamino)pyrimidin-4-yl)-2-(methylthio)-7,8-dihydropyrido[4,3-d]pyrimidin-5(6H)-one (50 mg, 0.11 mmol) in THF (3 mL) and H$_2$O (1 mL) was added oxone (69 mg, 0.22 mmol), and the mixture was stirred at room temperature for 4 h. After concentration, the title compound (120 mg, crude) was obtained as a yellow solid, which was used directly in the next step without further purification.

Preparation of 2-(methylamino)-6-(6-(4-(2-methylpyridin-4-yl)benzylamino)pyrimidin-4-yl)-7,8-dihydropyrido[4,3-d]pyrimidin-5(6H)-one

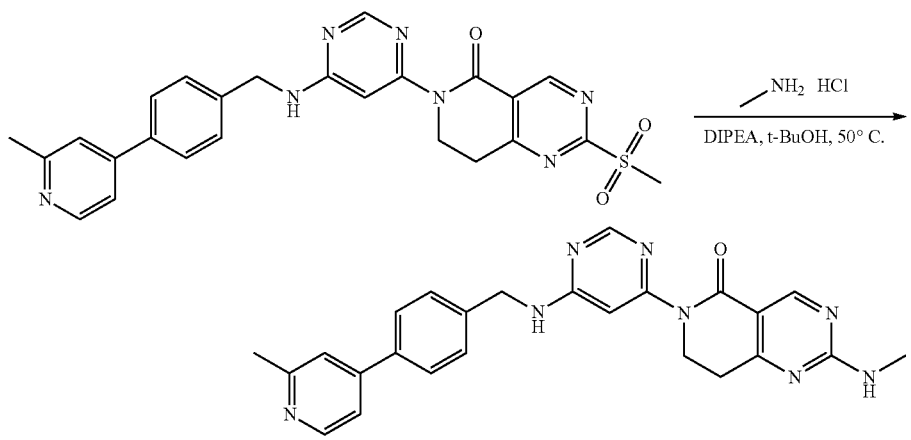

A mixture of 6-(6-(4-(2-methylpyridin-4-yl)benzylamino)pyrimidin-4-yl)-2-(methylthio)-7,8-dihydropyrido[4,3-d]pyrimidin-5(6H)-one (50 mg, 0.1 mmol), methanamine hydrochloride (68 mg, 1.0 mmol), and N,N-diisopropylethylamine (194 mg, 1.5 mmol) in t-BuOH (3 mL) was stirred at 120° C. overnight. After cooling to room temperature, the mixture was diluted with EtOAc (40 mL) and washed with H₂O (8 mL×3). The organic layer was dried over Na₂SO₄ and concentrated. The resulting residue was purified by silica gel column chromatography (CH₂Cl₂:MeOH=60:1) to give the title compound (31 mg, 68%) as a white solid.

Example 12

Preparation of N-(4-(2-methylpyridin-4-yl)benzyl)-4-(naphthalen-2-yl)pyridin-2-amine (A-163)

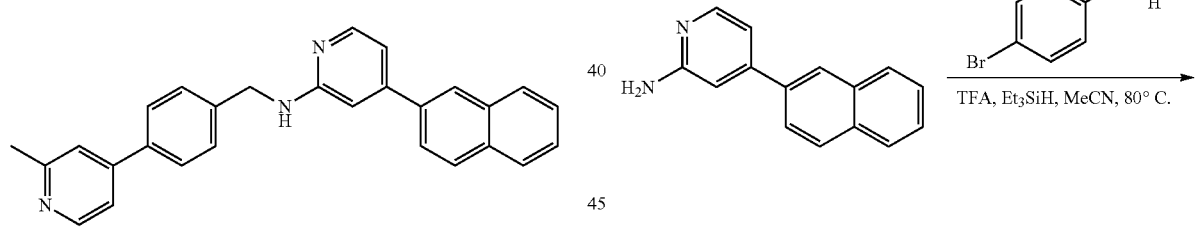

Method B-Step e: 4-(naphthalen-2-yl)pyridin-2-amine

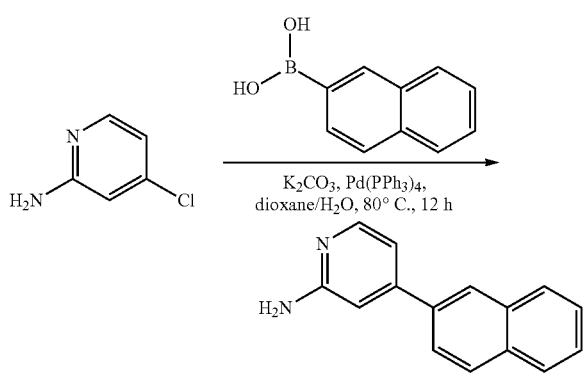

To a solution of naphthalen-2-ylboronic acid (206 mg, 1.20 mmol) and 4-chloropyridin-2-amine (128 mg, 1.00 mmol) in dioxane (16 mL) and H₂O (4 mL), was added Pd(PPh₃)₄ (115 mg, 0.10 mmol) and K₂CO₃ (276 mg, 2.00 mmol). The mixture was stirred at 80° C. under N₂ atmosphere for 12 h. After cooling to room temperature, the mixture was filtered through Celite. The filtrate was diluted with EtOAc (40 mL), washed with brine (20 mL), dried over Na₂SO₄, and concentrated. The resulting residue was purified by silica gel column chromatography (CH₂Cl₂:MeOH=100:3) to give the title compound (120 mg, 55%) as a yellow solid.

Method B-Step f: N-(4-bromobenzyl)-4-(naphthalen-2-yl)pyridin-2-amine

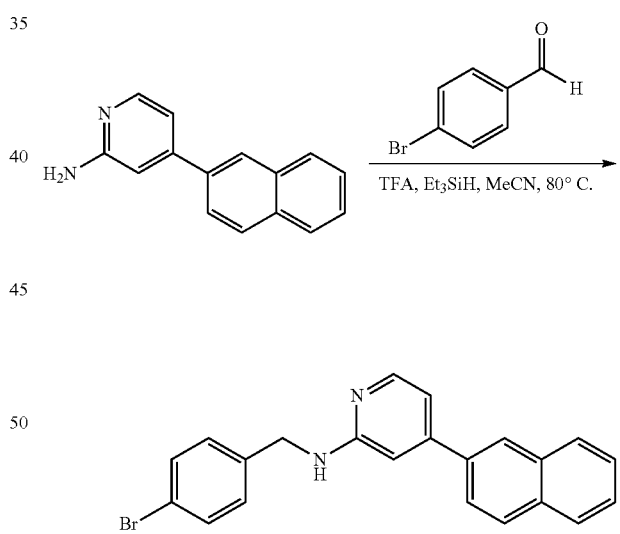

To a solution of 4-(naphthalen-2-yl)pyridin-2-amine (110 mg, 0.50 mmol) and 4-bromobenzaldehyde (95 mg, 0.50 mmol) in MeCN (10 mL), was added trifluoroacetic acid (574 mg, 5.00 mmol) and triethylsilane (580 mg, 5.00 mmol). The mixture was stirred at 80° C. for 12 h. After cooling to room temperature, the mixture was diluted with EtOAc (40 mL), washed with sat. NaHCO₃ (10 mL×3), dried over Na₂SO₄, and concentrated. The resulting residue was purified by silica gel column chromatography (petroleum ether:EtOAc=5:1) to give the title compound (80 mg, 41%) as a yellow solid.

Method B-Step g: N-(4-(2-methylpyridin-4-yl)benzyl)-4-(naphthalen-2-yl)pyridin-2-amine

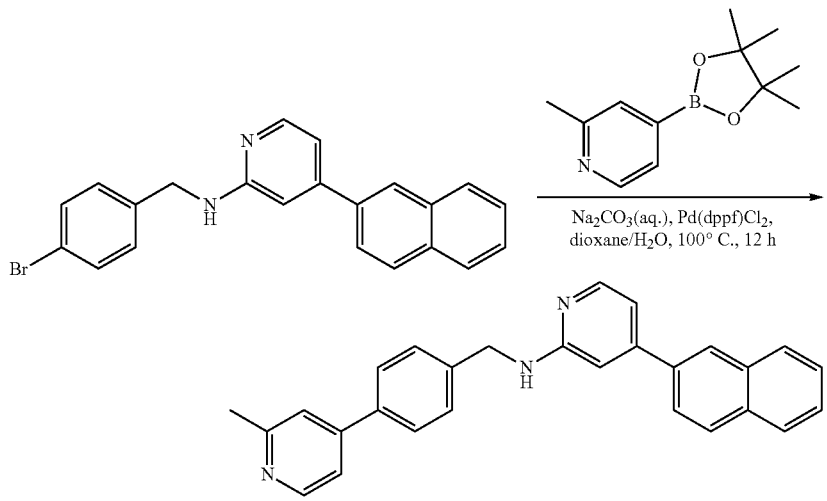

To a solution of N-(4-bromobenzyl)-4-(naphthalen-2-yl)pyridin-2-amine (130 mg, 0.33 mmol) and 2-methyl-4-(4,4,5,5-tetramethyl-1,3,2-dioxaborolan-2-yl)pyridine (27%, 406 mg, 0.50 mmol) in dioxane (20 mL), was added 1M aqueous Na$_2$CO$_3$ (1 mL) and Pd(dppf)Cl$_2$(28 mg, 0.034 mmol). The mixture was stirred at 100° C. under N$_2$ atmosphere for 12 h. After cooling to room temperature, the mixture was filtered through Celite. The filtrate was diluted with EtOAc (40 mL), washed with brine (10 mL×3), dried over Na$_2$SO$_4$, and concentrated. The resulting residue was purified by silica gel column chromatography (CH$_2$Cl$_2$:MeOH=100:3) to give the title compound (50 mg, 37%) as a yellow solid.

Example 13

Preparation of 7-((4-(quinolin-6-yl)pyrimidin-2-ylamino)methyl)quinoline-3-carbonitrile (A-179)

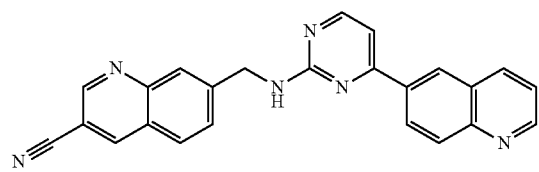 [SMILES: N#Cc1cnc2cc(CNc3nccc(-c4ccc5ncccc5c4)n3)ccc2c1]

Preparation of 7-(bromomethyl)quinoline-3-carbonitrile

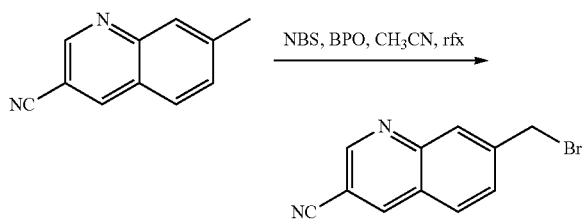

To a solution of 7-methylquinoline-3-carbonitrile (1.5 g, 8.9 mmol) in MeCN (50 mL) was added NBS (2.1 g, 11.8 mmol) and BPO (216 mg, 0.9 mmol). The mixture was heated at reflux overnight. After cooling to room temperature, H$_2$O (100 mL) and EtOAc (100 mL) was added. The aqueous layer was extracted with EtOAc (40 mL×3). The combined organic layers was dried over Na$_2$SO$_4$, and concentrated. The resulting residue was purified by silica gel column chromatography (CH$_2$Cl$_2$:petroleum ether=3:2) to give the title compound (743 g, 34%) as a white solid.

Preparation of 7-(azidomethyl)quinoline-3-carbonitrile

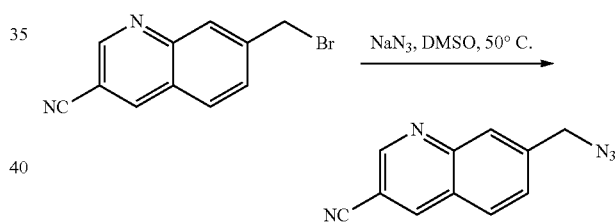

To a solution of 7-(bromomethyl)quinoline-3-carbonitrile (743 mg, 3 mmol) in DMSO (15 mL), was added NaN$_3$ (293 mg, 4.5 mmol). The mixture was stirred at 50° C. for 1 h. After cooling to room temperature, H$_2$O (75 mL) and EtOAc (75 mL) was added. The organic layer was dried over Na$_2$SO$_4$, and concentrated. The resulting residue was purified by silica gel column chromatography (petroleum ether:EtOAc=10:1-5:1) to give the title compound (392 mg, 62%) as a white solid.

Preparation of 7-(aminomethyl)quinoline-3-carbonitrile

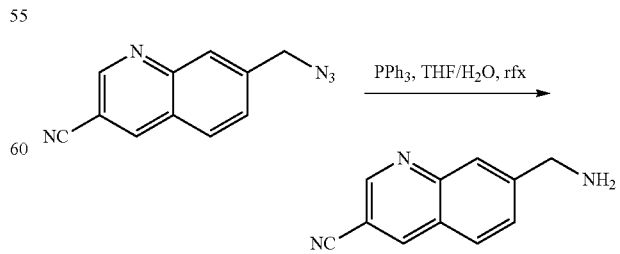

To a solution of 7-(azidomethyl)quinoline-3-carbonitrile (392 mg, 1.87 mmol) in THF (10 mL) was added PPh$_3$ (541 mg, 2.1 mmol). The mixture was heated at reflux for 5 min before H₂O (1 mL) was added. The mixture was heated at reflux for another 1 h. After cooling to room temperature, the mixture was diluted with EtOAc (100 mL), and extracted with 1 N HCl (100 mL). To the aqueous layer was added NH₄OH to adjust PH=8. The mixture was extracted with EtOAc (100 mL). The organic layer was dried over Na₂SO₄ and concentrated to give the title compound (340 mg, 99%) as a pale yellow solid.

Method A-Step c: 6-(2-(methylthio)pyrimidin-4-yl)quinoline

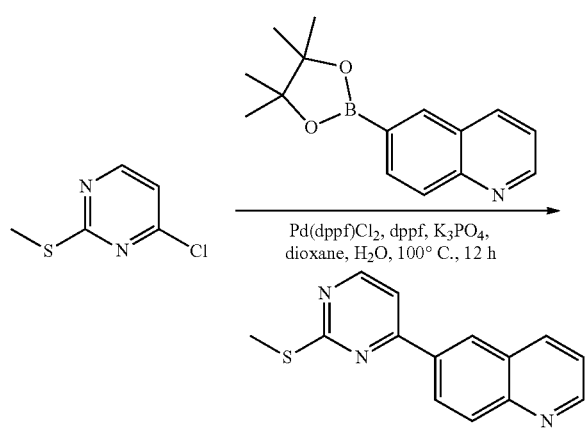

To a solution of 4-chloro-2-(methylthio)pyrimidine (1.6 g, 10 mmol) and 6-(4,4,5,5-tetramethyl-1,3,2-dioxaborolan-2-yl)quinoline (3.06 g, 12 mmol) in dioxane (50 mL) and H₂O (12.5 mL), was added Pd(dppf)Cl₂ (653 mg, 0.80 mmol), dppf (443 mg, 0.80 mmol) and K₃PO₄ (4.24 g, 20 mmol). The mixture was stirred at 100° C. under N₂ atmosphere for 12 h. After cooling to room temperature, the mixture was concentrated and purified by silica gel column chromatography (CH₂Cl₂:MeOH=25:1) to give the title compound (2.0 g, 80%) as a yellow solid.

Preparation of 6-(2-(methylsulfonyl)pyrimidin-4-yl)quinoline

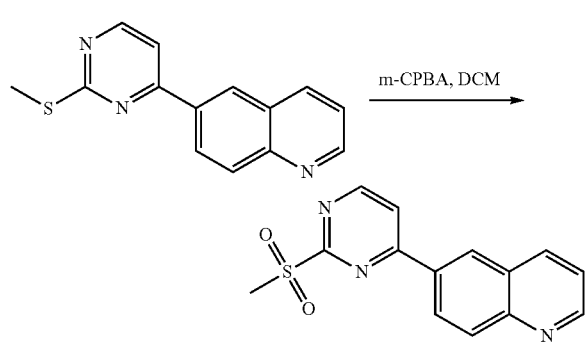

To a solution of 6-(2-(methylthio)pyrimidin-4-yl)quinoline (1.24 g, 4.9 mmol) in CH₂Cl₂ (50 mL) was added m-CPBA (1.79 g, 85%, 8.82 mmol). The mixture was stirred at room temperature for 2 h and sat. Na₂S₂O₃ (15 mL) and sat. NaHCO₃ (15 mL) was added to quench the reaction. The mixture was extracted with CH₂Cl₂ (100 mL×3), dried over Na₂SO₄, and concentrated to give the title compound (1.1 g, 78%) as a yellow solid.

Method A-Step d: N-((3-fluoro-2'-methyl-2,4'-bipyridin-5-yl)methyl)-4-(quinolin-6-yl)pyrimidin-2-amine

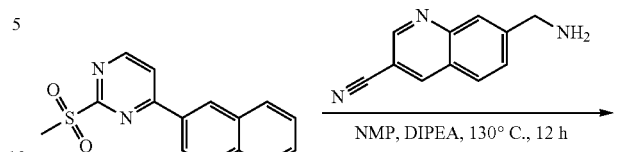

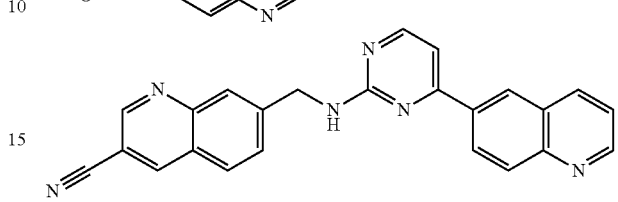

To a solution of 7-(aminomethyl)quinoline-3-carbonitrile (39 mg, 0.21 mmol) in NMP (1.5 mL) was added 6-(2-(methylsulfonyl)pyrimidin-4-yl)quinoline (50 mg, 0.18 mmol) and N,N-diisopropylethylamine (190 mg, 1.4 mmol). The mixture was stirred at 130° C. overnight. After cooling to room temperature, the mixture was diluted with H₂O (50 mL) and EtOAc (50 mL). The aqueous layer was separated and extracted with EtOAc (30 mL×3). The combined organic layers was dried over Na₂SO₄, and concentrated. The resulting residue was purified by silica gel column chromatography (CH₂Cl₂:MeOH=100:1-20:1) to give the title compound (25 mg, 36%) as a yellow solid.

Example 14

Preparation of 2-((3-fluoro-2'-methyl-2,4'-bipyridin-5-yl)methylamino)-4-(1,5-naphthyridin-2-yl)pyridin-3-ol (A-176)

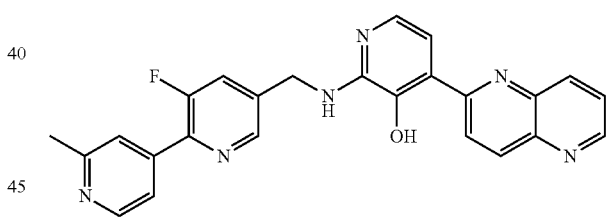

Method A-Step c: 2-(2,3-difluoropyridin-4-yl)-1,5-naphthyridine

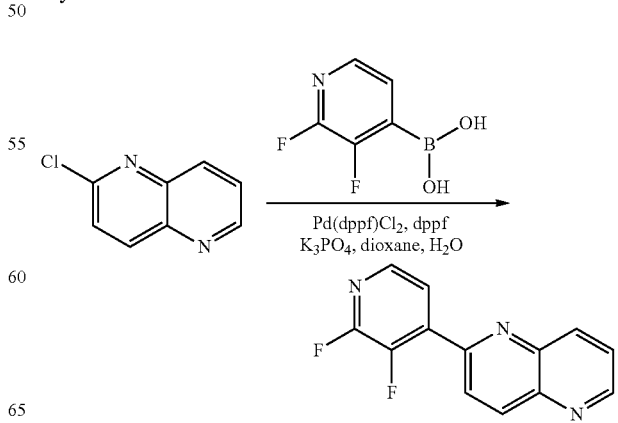

To a solution of 2,3-difluoropyridin-4-ylboronic acid (175 mg, 1.1 mmol) and 2-chloro-1,5-naphthyridine (164 mg, 1.0 mmol) in dioxane (4 mL) and H₂O (1 mL), was added Pd(dppf)Cl₂ (65 mg, 0.08 mmol), dppf (44 mg, 0.08 mmol) and K₃PO₄ (424 mg, 2.0 mmol). The mixture was stirred at 100° C. under N₂ atmosphere for 12 h. After cooling to room temperature, the mixture was concentrated and purified by silica gel column chromatography (petroleum ether:EtOAc=1:1) to give the title compound (130 mg, 53%) as a white solid.

Method G-Step r: 2-((3-fluoro-2'-methyl-2,4'-bipyridin-5-yl)methylamino)-4-(1,5-naphthyridin-2-yl)pyridin-3-ol

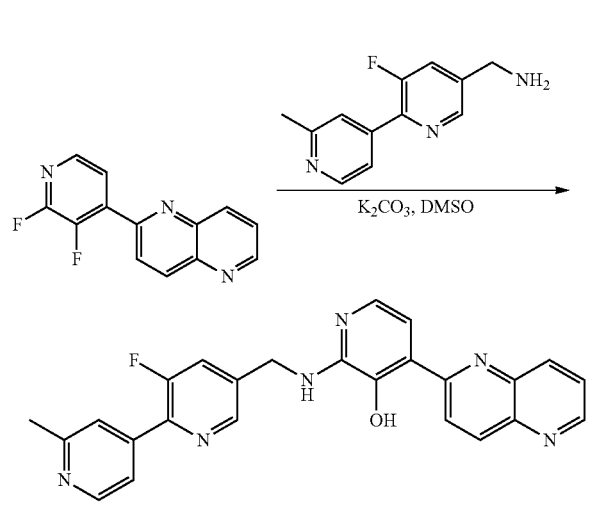

To a solution of 2-(2,3-difluoropyridin-4-yl)-1,5-naphthyridine (70 mg, 0.29 mmol) in DMSO (2 mL) was added (3-fluoro-2'-methyl-2,4'-bipyridin-5-yl)methanamine (93 mg, 0.43 mmol) and K₂CO₃ (80 mg, 0.58 mmol). The mixture was stirred at 135° C. for 18 h. After cooling to room temperature, the mixture was diluted with H₂O (30 mL), and extracted with EtOAc (30 mL×3). The combined organic layers was washed with brine (30 mL×3), dried over Na₂SO₄, and concentrated. The resulting residue was purified by silica gel column chromatography (CH₂Cl₂:MeOH=30:1) to give the title compound (10 mg, 8%) as a yellow solid.

Example 15

Preparation of 5-((4-(1,7-naphthyridin-6-yl)pyrimidin-2-ylamino)methyl)-2'-methyl-2,4'-bipyridine-3-carbonitrile (A-183)

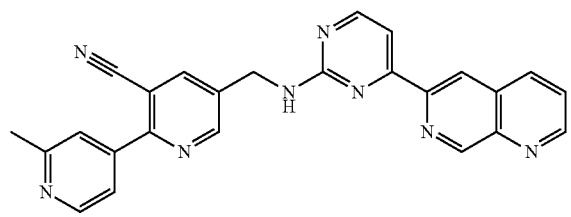 [SMILES: Cc1cc(-c2ncc(CNc3nccc(-c4cc5cccnc5cn4)n3)cc2C#N)ccn1]

Method F-Step 1: N-tert-butyl-3-(2-(2-(methylthio)pyrimidin-4-yl)-2-oxoethyl)picolinamide

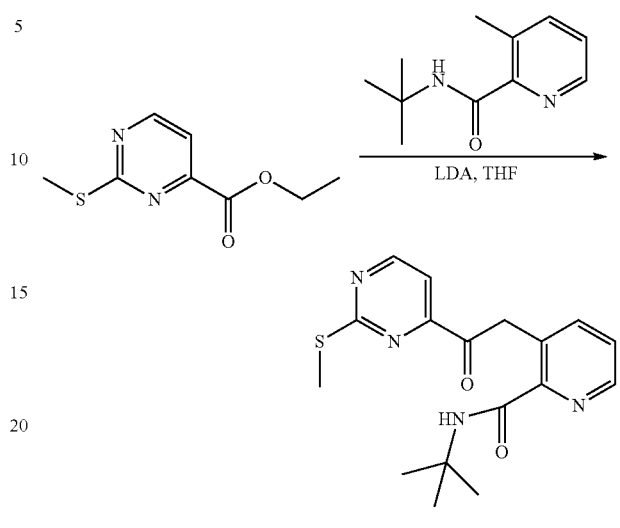

To a stirred solution of N-(tert-butyl)-3-methylpicolinamide (2.0 g, 10 mmol) in anhydrous tetrahydrofuran (100 mL) at −40° C., was added lithium diisopropylamide (2 M in THF, 12.5 mL, 25 mmol) dropwise. The mixture was stirred at this temperature for 30 min and then cooled to −60° C. Ethyl 2-(methylthio)pyrimidine-4-carboxylate (2.0 g, 10 mmol) in anhydrous THF (10 mL) was added and the reaction mixture was stirred at −60° C. for another 1 h. The reaction was quenched with sat. NH₄Cl (50 mL) and extracted with ethyl acetate (80 mL×3). The combined organic layers dried over Na₂SO₄, and concentrated. The resulting residue was purified by silica gel column chromatography (petroleum ether:ethyl acetate=5:1) to give the title compound (1.2 g, 35%) as a yellow solid.

Method F-Step m: 6-(2-(methylthio)pyrimidin-4-yl)-1,7-naphthyridin-8-ol

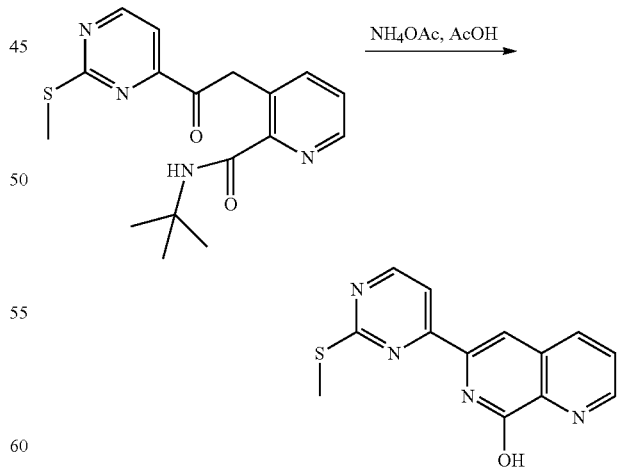

A mixture of N-tert-butyl-3-(2-(2-(methylthio)pyrimidin-4-yl)-2-oxoethyl)picolinamide (500 mg, 1.45 mmol) and NH₄OAc (1.11 g, 14.5 mmol) in HOAc (10 mL) was heated to 108° C. for 8 h. After concentration, the resulting residue was dissolved in ethyl acetate (30 mL) and washed with sat.

NaHCO₃ (5 mL). The organic layer was dried over Na₂SO₄ and concentrated to give the title compound (350 mg, 89%) as a yellow solid without further purification.

Method F-Step n: 8-chloro-6-(2-(methylthio)pyrimidin-4-yl)-1,7-naphthyridine

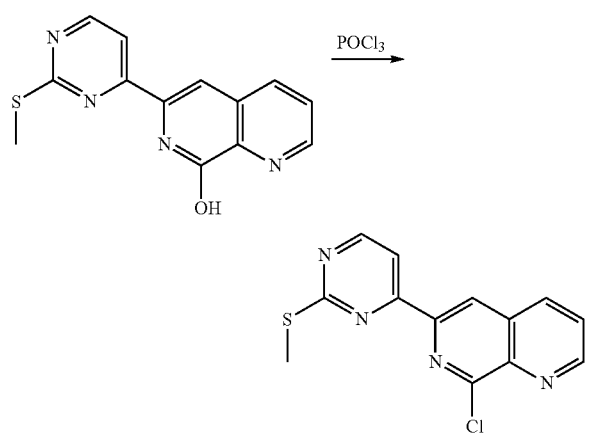

A solution of 6-(2-(methylthio)pyrimidin-4-yl)-1,7-naphthyridin-8-ol (350 mg, 1.3 mmol) in POCl₃ (6 mL) was heated to 100° C. for 1 h. After concentration, the residue was dissolved in ethyl acetate (20 mL) and washed with sat. NaHCO₃ (5 mL). The organic layer was dried over Na₂SO₄ and concentrated. The resulting residue was purified by column chromatography (petroleum ether:ethyl acetate=5:1) to give the title compound (350 mg, 93%) as a pale yellow solid.

Method F-Step o: 6-(2-(methylthio)pyrimidin-4-yl)-1,7-naphthyridine

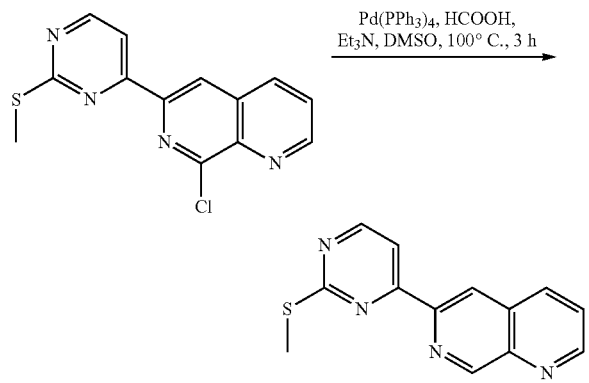

A mixture of 8-chloro-6-(2-(methylthio)pyrimidin-4-yl)-1,7-naphthyridine (350 mg, 1.2 mmol), triethylamine (924 mg, 9.15 mmol), formic acid (253 mg, 5.50 mmol) and Pd(PPh₃)₄ (138 mg, 0.12 mmol) in DMSO (5 mL) was stirred at 100° C. under N₂ atmosphere for 3 h. After cooling to room temperature, the mixture was diluted with ethyl acetate (40 mL) and filtered. The filtrate was washed with brine (10 mL×3), dried over Na₂SO₄, and concentrated. The residue was purified by column chromatography (petroleum ether:ethyl acetate=5:1) to give the title compound (180 mg, 59%) as a pale yellow solid.

Method F-Step p: 6-(2-(methylsulfonyl)pyrimidin-4-yl)-1,7-naphthyridine

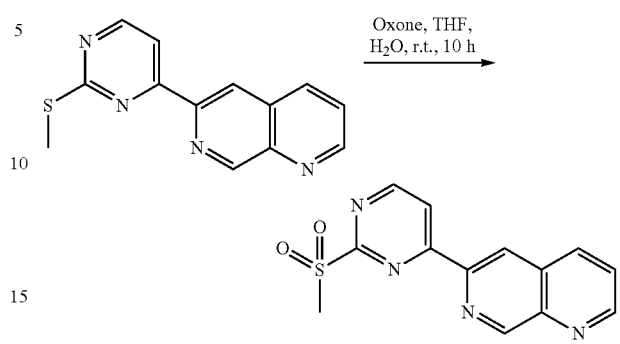

To a solution of 6-(2-(methylthio)pyrimidin-4-yl)-1,7-naphthyridine (180 mg, 0.71 mmol) in THF (5 mL) and H₂O (0.5 mL) was added oxone (497 mg, 1.56 mmol), and the mixture was stirred at room temperature for 10 h. After concentration, the title compound (680 mg, crude) was obtained as a yellow solid, which was used directly in the next step without further purification.

Method F-Step q: 5-((4-(1,7-naphthyridin-6-yl)pyrimidin-2-ylamino)methyl)-2'-methyl-2,4'-bipyridine-3-carbonitrile

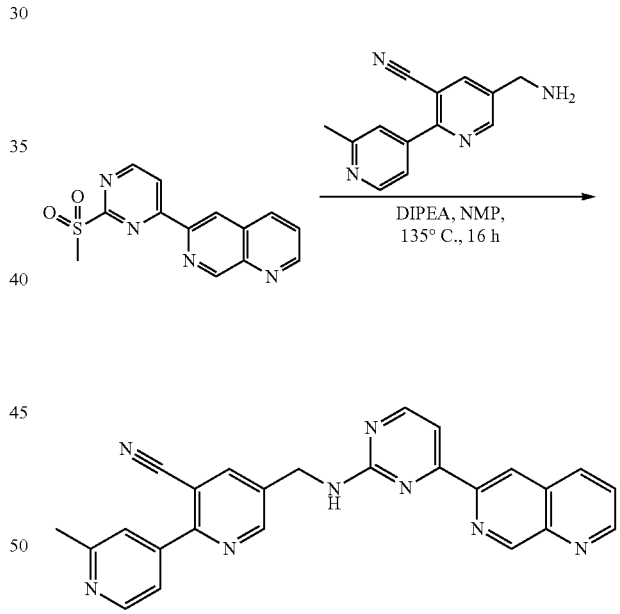

To a solution of 5-(aminomethyl)-2'-methyl-2,4'-bipyridine-3-carbonitrile (68 mg, 0.3 mmol) and N,N-diisopropylethylamine (194 mg, 1.5 mmol) in NMP (1 mL), was added 6-(2-(methylsulfonyl)pyrimidin-4-yl)-1,7-naphthyridine (140 mg, 30%, 0.15 mmol). The mixture was stirred at 135° C. under N₂ atmosphere for 16 h. After cooling to room temperature, the mixture was diluted with H₂O (10 mL), and extracted with EtOAc (20 mL×3). The combined organic layers was washed with brine (10 mL×3), dried over Na₂SO₄, and concentrated. The resulting residue was purified by silica gel column chromatography (CH₂Cl₂: MeOH=50:1) to give the title compound (12 mg, 19%) as a pale yellow solid.

Example 16

Preparation of 3-((5-(quinolin-6-yl)-1,2,4-thiadiazol-3-ylamino)methyl)quinoline-7-carbonitrile (A-199)

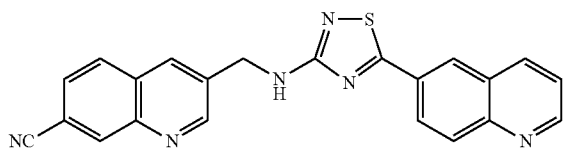 [SMILES: N#Cc1ccc2cc(CNc3nsc(-c4ccc5ncccc5c4)n3)cnc2c1]

Preparation of 3-(bromomethyl)quinoline-7-carbonitrile

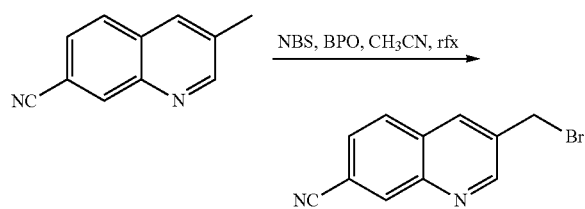

To a solution of 3-methylquinoline-7-carbonitrile (1.5 g, 8.9 mmol) in MeCN (80 mL) was added NBS (1.9 g, 10.7 mmol) and BPO (216 mg, 0.9 mmol). The mixture was heated at reflux overnight. After cooling to room temperature, $H_2O$ (100 mL) and EtOAc (100 mL) was added. The aqueous layer was extracted with EtOAc (40 mL×3). The combined organic layers was dried over $Na_2SO_4$, and concentrated. The resulting residue was purified by silica gel column chromatography ($CH_2Cl_2$:petroleum ether=8:1) to give the title compound (1.0 g, 45%) as a pale yellow solid.

Preparation of 3-(azidomethyl)quinoline-7-carbonitrile

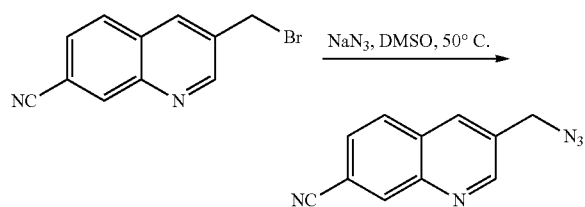

To a solution of 3-(bromomethyl)quinoline-7-carbonitrile (1 g, 4.1 mmol) in DMSO (20 mL), was added $NaN_3$ (395 mg, 6.2 mmol). The mixture was stirred at 50° C. for 1 h. After cooling to room temperature, $H_2O$ (100 mL) and EtOAc (100 mL) was added. The aqueous layer was extracted with EtOAc (40 mL×3). The combined organic layers was dried over $Na_2SO_4$, and concentrated. The resulting residue was purified by silica gel column chromatography (petroleum ether:EtOAc=10:1-5:1) to give the title compound (800 mg, 93%) as a yellow solid.

Preparation of 3-(aminomethyl)quinoline-7-carbonitrile

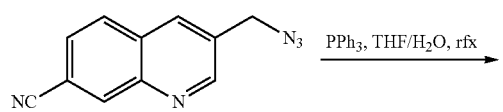

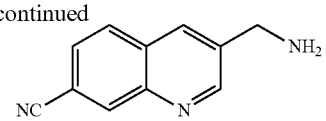

To a solution of 3-(azidomethyl)quinoline-7-carbonitrile (800 mg, 3.8 mmol) in THF (20 mL) was added $PPh_3$ (1.1 g, 4.2 mmol). The mixture was heated at reflux for 5 min before $H_2O$ (2 mL) was added. The mixture was heated at reflux for another 1 h. After cooling to room temperature, the mixture was diluted with EtOAc (100 mL), and extracted with 1 N HCl (100 mL). To the aqueous layer was added $NH_4OH$ to adjust PH=8. The mixture was extracted with EtOAc (30 mL×3). The combined organic layers was washed with brine (30 mL×3), dried over $Na_2SO_4$ and concentrated to give the title compound (400 mg, 56%) as a pale yellow solid.

Method A-Step c: 3-chloro-5-(quinolin-6-yl)-1,2,4-thiadiazole

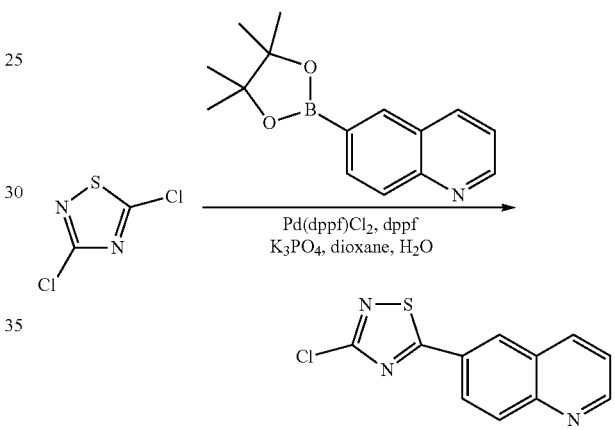

To a solution of 6-(4,4,5,5-tetramethyl-1,3,2-dioxaborolan-2-yl)quinoline (280 mg, 1.1 mmol) and 3,5-dichloro-1,2,4-thiadiazole (155 mg, 1.0 mmol) in dioxane (6 mL) and $H_2O$ (1.5 mL), was added $Pd(dppf)Cl_2$ (65 mg, 0.08 mmol), dppf (44 mg, 0.08 mmol) and $K_3PO_4$ (420 mg, 2.0 mmol). The mixture was stirred at 100° C. under $N_2$ atmosphere for 12 h. After cooling to room temperature, the mixture was concentrated and purified by silica gel column chromatography (petroleum ether:EtOAc=3:1) to give the title compound (200 mg, 81%) as a gray solid. $^1$H NMR (400 MHz, $CDCl_3$) δ 9.03 (d, J=3.2 Hz, 1H), 8.53 (s, 1H), 8.29 (d, J=8.0 Hz, 1H), 8.24 (d, J=8.8 Hz, 1H), 8.18 (d, J=8.8 Hz, 1H), 7.53 (dd, J=8.0, 4.0 Hz, 1H).

Method A-Step d: 3-((5-(quinolin-6-yl)-1,2,4-thiadiazol-3-ylamino)methyl)quinoline-7-carbonitrile

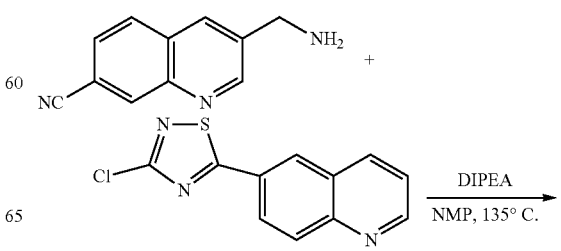

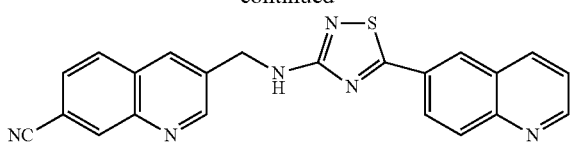

To a solution of 3-(aminomethyl)quinoline-7-carbonitrile (59 mg, 0.32 mmol) in NMP (1.5 mL) was added 3-chloro-5-(quinolin-6-yl)-1,2,4-thiadiazole (40 mg, 0.16 mmol) and N,N-diisopropylethylamine (165 mg, 1.28 mmol). The mixture was stirred at 135° C. for 40 h. After cooling to room temperature, the mixture was diluted with $H_2O$ (30 mL), and extracted with EtOAc (30 mL×3). The combined organic layers was washed with brine (30 mL×3), dried over $Na_2SO_4$, and concentrated. The resulting residue was purified by silica gel column chromatography ($CH_2Cl_2$:MeOH=30:1) to give the title compound (12 mg, 19%) as an orange solid.

Example 17

Preparation of N-((3-methoxy-2'-methyl-2,4'-bipyridin-5-yl)methyl)-5-(1,7-naphthyridin-6-yl)-1,2,4-thiadiazol-3-amine (A-196)

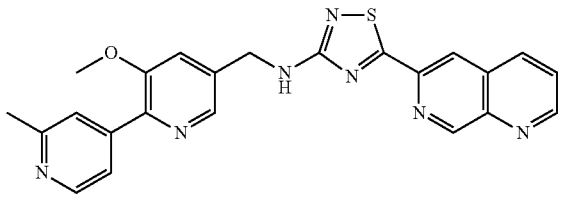 [SMILES: COc1cc(CNc2nsc(-c3cc4cccnc4cn3)n2)cnc1-c1ccnc(C)c1]

Preparation of (6-iodo-5-methoxypyridin-3-yl)methanol

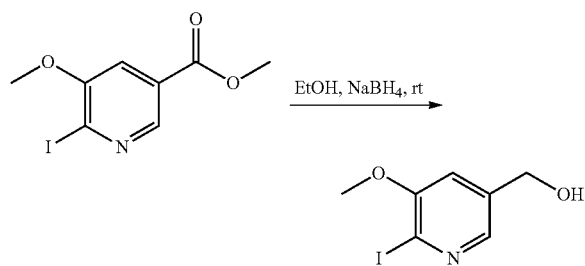

To a suspension of $NaBH_4$ (1.65 g, 43.3 mmol) in EtOH (100 mL) at 0° C. was added a solution of methyl 6-iodo-5-methoxynicotinate (2.54 g, 8.67 mmol) in EtOH (30 mL) dropwise. The mixture was stirred at room temperature for 20 h. After concentration, $H_2O$ (100 mL) was added and the mixture was extracted with $CH_2Cl_2$ (100 mL×3). The combined organic layers was dried over $Na_2SO_4$, and concentrated to give the title compound (2.0 g, 87%) as a colorless oil. $^1$HNMR (400 MHz, $CDCl_3$) δ 8.18 (d, J=2.0 Hz, 1H), 8.13 (s, 1H), 7.94 (s, 1H), 7.09 (s, 1H), 4.71 (s, 2H), 3.92 (s, 3H).

Preparation of 5-(azidomethyl)-2-iodo-3-methoxypyridine

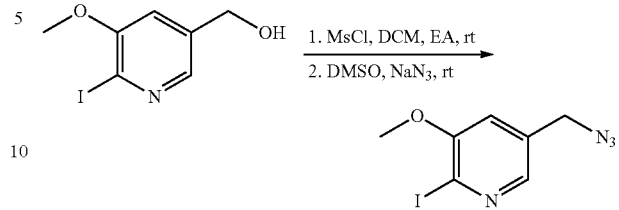

To a solution of (6-iodo-5-methoxypyridin-3-yl)methanol (2.0 g, 7.55 mmol) and $Et_3N$ (3.05 g, 30.2 mmol), was added MsCl (1.72 g, 15.1 mmol). The mixture was stirred at room temperature overnight and then washed with brine (50 mL×2). The combined organic layers was dried over $Na_2SO_4$, and concentrated. The resulting residue was dissolved in DMSO (40 mL), and $NaN_3$ (873 mg, 13.4 mmol) was added. After stirring at room temperature for 8 h, $H_2O$ (50 mL) was added and the mixture was extracted with EtOAc (50 mL×3). The combined organic layers was washed with brine (100 mL×3), dried over $Na_2SO_4$, and concentrated. The resulting residue was purified by silica gel column chromatography (petroleum ether:EtOAc=10:1) to give the title compound (1.35 g, 61%) as a yellow oil. $^1$H NMR (400 MHz, $CDCl_3$) δ 7.96 (d, J=1.6 Hz, 1H), 6.96 (d, J=1.6 Hz, 1H), 4.38 (s, 2H), 3.94 (s, 3H).

Preparation of (6-iodo-5-methoxypyridin-3-yl)methanamine

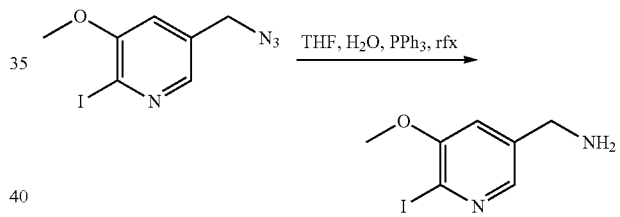

To a solution of 5-(azidomethyl)-2-iodo-3-methoxypyridine (1.35 g, 4.66 mmol) in THF (20 mL) was added $PPh_3$ (1.14 g, 4.34 mmol). The mixture was heated at reflux and $H_2O$ (3 mL) was added. The mixture was heated at reflux for 8 h. After cooling to room temperature, the mixture was diluted with EtOAc (40 mL), and extracted with 0.2 N HCl (50 mL). The aqueous layer was washed with EtOAc (50 mL) before NaOH was added to adjust PH=10. The aqueous layer was extracted with $CH_2Cl_2$ (50 mL×6). The combined organic layers was dried over $Na_2SO_4$ and concentrated to give the title compound (1.18 g, 96%) as a yellow solid. $^1$H NMR (400 MHz, $CDCl_3$) δ 7.95 (s, 1H), 7.07 (s, 1H), 3.92 (s, 3H), 3.89 (s, 2H).

Preparation of (3-methoxy-2'-methyl-2,4'-bipyridin-5-yl)methanamine

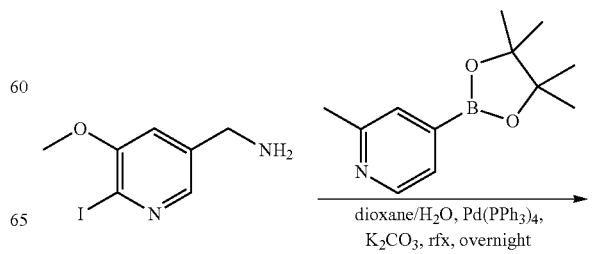

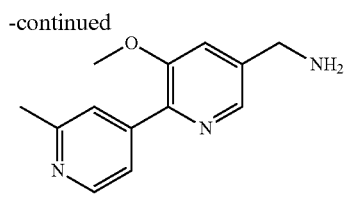

To a solution of (6-iodo-5-methoxypyridin-3-yl)methanamine (1.12 g, 4.24 mmol) in dioxane (20 mL) and H$_2$O (4 mL) was added 2-methyl-4-(4,4,5,5-tetramethyl-1,3,2-dioxaborolan-2-yl)pyridine (1.51 g, 50%, 5.52 mmol), K$_2$CO$_3$ (2.34 g, 17.0 mmol) and Pd(PPh$_3$)$_4$ (245 mg, 0.21 mmol). The mixture was stirred at reflux under N$_2$ atmosphere overnight. After cooling to room temperature, the mixture was filtered through Celite. The filtrate was diluted with EtOAc (100 mL). The organic layer was separated, dried over Na$_2$SO$_4$, and concentrated. The resulting residue was purified by silica gel column chromatography (CH$_2$Cl$_2$: MeOH=100:1-50:1) to give the title compound (730 mg, 75%) as a brown oil. $^1$H NMR (400 MHz, CDCl$_3$) δ 8.55 (d, J=5.2 Hz, 1H), 8.27 (s, 1H), 7.71 (s, 1H), 7.67 (d, J=5.2 Hz, 1H), 7.38 (s, 1H), 3.99 (s, 2H), 3.93 (s, 3H), 2.62 (s, 3H).

Preparation of 6-(trimethylstannyl)-1,7-naphthyridine

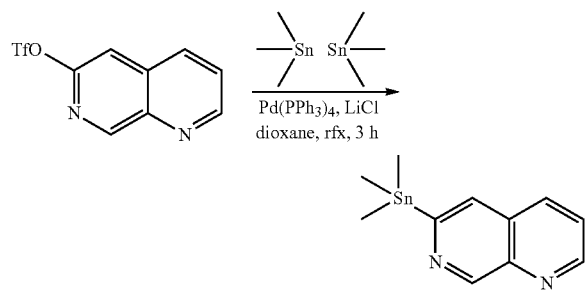

A mixture of 1,7-naphthyridin-6-yl trifluoromethanesulfonate (1.3 g, 4.76 mmol), 1,1,1,2,2,2-hexamethyldistannane (2.3 g, 7.0 mmol), LiCl (590 mg, 14.0 mmol), and Pd(PPh$_3$)$_4$ (270 mg, 0.23 mmol) in dioxane (20 mL) was heated at reflux under N$_2$ atmosphere for 3 h. After cooling to room temperature, the mixture was concentrated. The residue was dissolved in EtOAc (30 mL) and washed with brine (30 mL). The organic layer was dried over Na$_2$SO$_4$, and concentrated. The resulting residue was purified by silica gel column chromatography (petroleum ether:EtOAc=10:1) to give the title compound (600 mg, 43%) as an colorless oil.

Method A-Step c: 3-chloro-5-(1,7-naphthyridin-6-yl)-1,2,4-thiadiazole

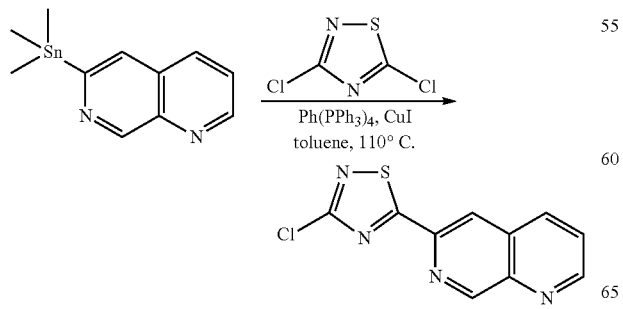

To a solution of 6-(trimethylstannyl)-1,7-naphthyridine (29 mg, 0.1 mmol) and 3,5-dichloro-1,2,4-thiadiazole (21 mg, 0.17 mmol) in toluene (1 mL) was added Pd(PPh$_3$)$_4$ (12 mg, 0.01 mmol) and CuI (2 mg, 0.01 mmol). The mixture was stirred at 110° C. under N$_2$ atmosphere overnight. After cooling to room temperature, the mixture was concentrated and purified by silica gel column chromatography (CH$_2$Cl$_2$: MeOH=80:1) to give the title compound (17 mg, 70%) as a white solid. $^1$H NMR (400 MHz, CDCl$_3$) δ 9.52 (s, 1H), 9.14 (d, J=3.6 Hz, 1H), 8.60 (s, 1H), 8.33 (d, J=8.4 Hz, 1H), 7.73 (dd, J=8.0, 4.0 Hz, 1H).

Method A-Step d: N-((3-methoxy-2'-methyl-2,4'-bipyridin-5-yl)methyl)-5-(1,7-naphthyridin-6-yl)-1,2,4-thiadiazol-3-amine

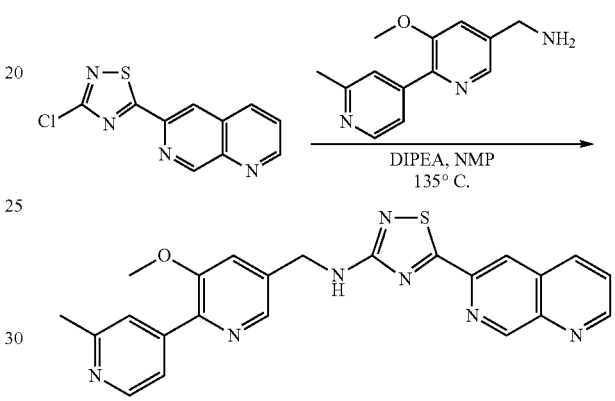

To a solution of (3-methoxy-2'-methyl-2,4'-bipyridin-5-yl)methanamine (37 mg, 0.16 mmol) in NMP (1.5 mL) was added 3-chloro-5-(1,7-naphthyridin-6-yl)-1,2,4-thiadiazole (20 mg, 0.08 mmol) and N,N-diisopropylethylamine (83 mg, 0.64 mmol). The mixture was stirred at 135° C. for 40 h. After cooling to room temperature, the mixture was diluted with H$_2$O (30 mL), and extracted with EtOAc (30 mL×3). The combined organic layers was washed with brine (30 mL×3), dried over Na$_2$SO$_4$, and concentrated. The resulting residue was purified by silica gel column chromatography (CH$_2$Cl$_2$:MeOH=30:1) to give the title compound (8 mg, 23%) as a pale yellow solid.

Example 18

Preparation of 5-((5-(7,8-dihydro-1,6-naphthyridin-6(5H)-yl)-1,2,4-thiadiazol-3-ylamino)methyl)-2'-methyl-2,4'-bipyridine-3-carbonitrile (A-198)

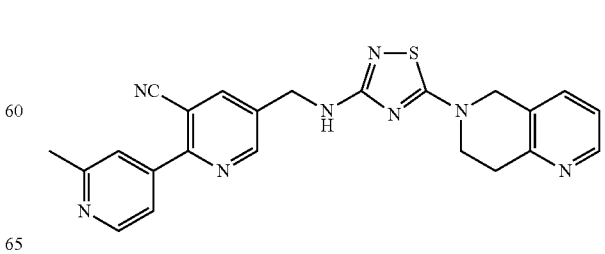

Method A-Step c: 3-chloro-5-(7,8-dihydro-1,6-naphthyridin-6(5H)-yl)-1,2,4-thiadiazole

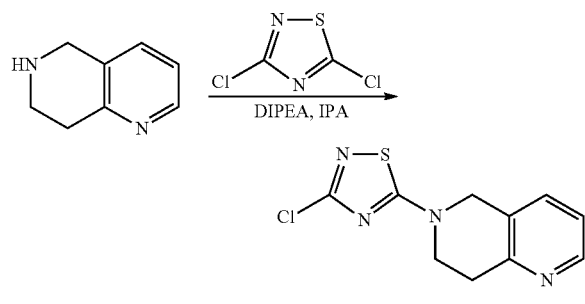

To a solution of 3,5-dichloro-1,2,4-thiadiazole (155 mg, 1.0 mmol) in i-PrOH (10 mL) was added 5,6,7,8-tetrahydro-1,6-naphthyridine (134 mg, 1.0 mmol) and N,N-diisopropylethylamine (645 mg, 5.0 mmol), and the mixture was stirred at room temperature overnight. The mixture was diluted with $H_2O$ (30 mL), and extracted with EtOAc (30 mL×3). The combined organic layers was washed with brine (30 mL×3), dried over $Na_2SO_4$, and concentrated. The resulting residue was purified by silica gel column chromatography (petroleum ether:EtOAc=2:1) to give the title compound (180 mg, 71%) as a gray solid.

Method A-Step d: 5-((5-(7,8-dihydro-1,6-naphthyridin-6(5H)-yl)-1,2,4-thiadiazol-3-ylamino) methyl)-2'-methyl-2,4'-bipyridine-3-carbonitrile

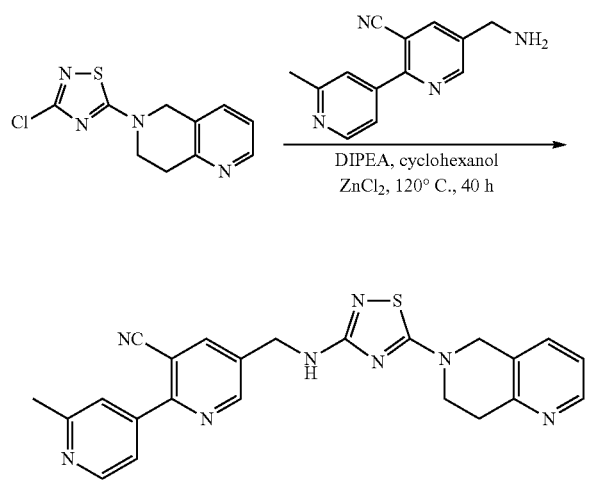

To a solution of 5-(aminomethyl)-2'-methyl-2,4'-bipyridine-3-carbonitrile (185 mg, 0.83 mmol) and N,N-diisopropylethylamine (213 mg, 1.65 mmol) in cyclohexanol (3 mL) in sealed tube was added 3-chloro-5-(7,8-dihydro-1,6-naphthyridin-6(5H)-yl)-1,2,4-thiadiazole (140 mg, 0.55 mmol) and $ZnCl_2$ (83 mg, 0.61 mmol). The mixture was stirred at 120° C. for 40 h. After cooling to room temperature, the mixture was purified by silica gel column chromatography (petroleum ether:EtOAc=5:1-$CH_2Cl_2$:MeOH=30:1) to give the title compound (12 mg, 5%) as a yellow solid.

Example 19

Preparation of 4-(7,8-dihydro-1,6-naphthyridin-6(5H)-yl)-3-fluoro-N-((3-fluoro-2'-methyl-2,4'-bipyridin-5-yl)methyl)pyridin-2-amine (A-202)

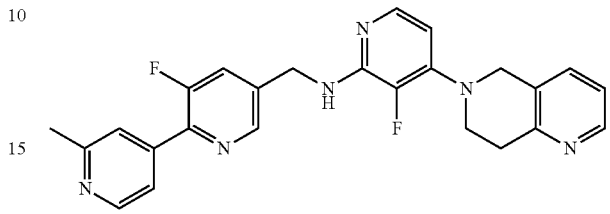

Method A-Step c: 6-(2,3-difluoropyridin-4-yl)-5,6,7,8-tetrahydro-1,6-naphthyridine

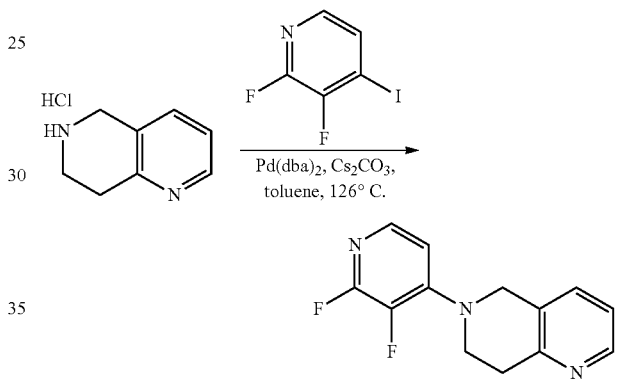

A mixture of 5,6,7,8-tetrahydro-1,6-naphthyridine hydrochloride (1.7 g, 10 mmol), 2,3-difluoro-4-iodopyridine (4.8 g, 20 mmol), $Cs_2CO_3$ (16.3 g, 50 mmol), $Pd_2(dba)_3$ (460 mg, 0.5 mmol) in toluene (20 mL) was heated at reflux under $N_2$ atmosphere for 12 h. After cooling to room temperature, the mixture was filtered through Celite and concentrated. The resulting residue was purified by silica gel column chromatography (petroleum ether:EtOAc=4:1-1:1) to give the title compound (2.3 g, 88%) as a yellow solid. $^1H$ NMR (400 MHz, $CDCl_3$) δ 8.48 (d, J=4.2 Hz, 1H), 7.72 (d, J=5.6 Hz, 1H), 7.45 (d, J=7.6 Hz, 1H), 7.17 (m, 1H), 6.69 (m, 1H), 4.57 (s, 2H), 3.81 (m, 2H), 3.18 (m, 2H).

Method A-Step d: 4-(7, 8-dihydro-1, 6-naphthyridin-6(5H)-yl)-3-fluoro-N-((3-fluoro-2'-methyl-2,4'-bipyridin-5-yl)methyl)pyridin-2-amine

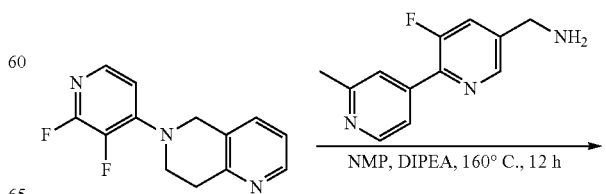

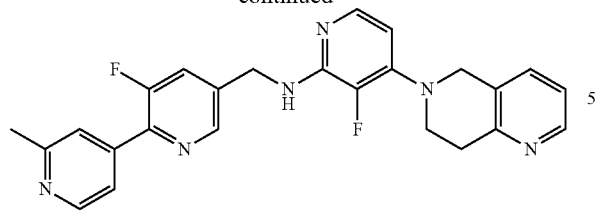

To a solution of 6-(2,3-difluoropyridin-4-yl)-5,6,7,8-tetrahydro-1,6-naphthyridine (50 mg, 0.21 mmol) and (3-fluoro-2'-methyl-2,4'-bipyridin-5-yl)methanamine (66 mg, 0.3 mmol) in NMP (1 mL), was added $K_2CO_3$ (131 mg, 1.0 mmol). The mixture was stirred at 160° C. for 12 h. After cooling to room temperature, the mixture was diluted with $H_2O$ (5 mL), and extracted with EtOAc (10 mL×3). The combined organic layers was washed with brine (10 mL×3), dried over $Na_2SO_4$, and concentrated. The resulting residue was purified by silica gel column chromatography (petroleum ether:EtOAc=1:1-0:1) to give the title compound (4 mg, 5%) as a yellow solid.

Table 2 shows a selection of compounds prepared according to the methods discussed above in detail and indicated in the Third column of the table:

TABLE 2

Selected compounds (A-1 to A-202) of the present invention.

| Compd NO. | Structure | Method | ¹HNMR | ESI-MS (m/z): [M + 1]⁺ |
|---|---|---|---|---|
| A-1 | 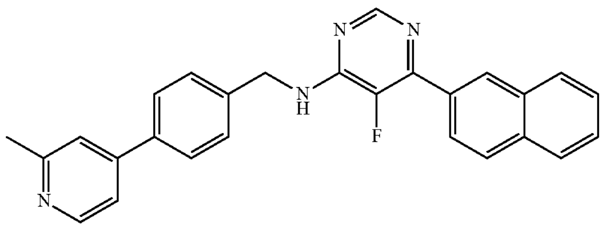 [SMILES: Cc1cc(-c2ccc(CNc3ncnc(-c4ccc5ccccc5c4)c3F)cc2)ccn1] | A | ¹H NMR (400 MHz, CDCl₃) δ 8.55 (d, J = 5.0 Hz, 3H), 8.13 (d, J = 8.8 Hz, 1H), 7.95 (d, J = 8.8 Hz, 2H), 7.89(d, J = 7.2 Hz, 1H), 7.64(d, J = 8.0 Hz, 2H), 7.58-7.51(m, 4H), 7.38(s, 1H), 7.32(d, J = 4.0 Hz, 1H), 5.59(s, 1H), 4.86(d, J = 6.0 Hz, 2H), 2.63(s, 3H). | 421.0 |
| A-2 | 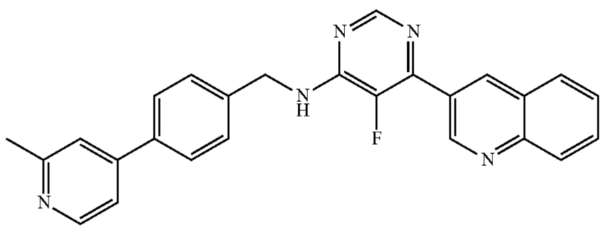 [SMILES: Cc1cc(-c2ccc(CNc3ncnc(-c4cnc5ccccc5c4)c3F)cc2)ccn1] | A | ¹HNMR(400 MHz, CDCl₃)δ9.55(s, 1H), 8.86(s, 1H), 8.57(d, J = 2.0 Hz, 1H), 8.55(d, J = 5.2 Hz, 1H), 8.17(d, J = 8.8 Hz, 1H), 7.95(d, J = 8.0 Hz, 1H), 7.804(d, J = 7.8 Hz, 1H), 7.66-7.60(m, 3H), 7.52(d, J = 8.4 Hz, 2H), 7.37(s, 1H), 7.31(d, J = 4.0 Hz, 1H), 5.68(s, 1H), 4.87(d, J = 6.0 Hz, 2H), 2.63(s, 3H). | 422.0 |
| A-3 | 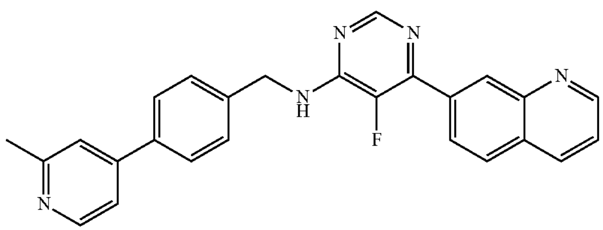 [SMILES: Cc1cc(-c2ccc(CNc3ncnc(-c4ccc5cccnc5c4)c3F)cc2)ccn1] | A | ¹HNMR(400 MHz, CDCl₃)δ8.99-8.98(m, 1H), 8.78(s, 1H), 8.59-8.51(m, 2H), 8.26(d, J = 8.4 Hz, 1H), 8.21(d, J = 8.4 Hz, 1H), 7.95(d, J = 8.4 Hz, 1H), 7.64(d, J = 8.4 Hz, 2H), 7.52(d, J = 8.4 Hz, 2H), 7.48-7.45(m, 1H), 7.37(s, 1H), 7.32(d, J = 4.8 Hz, 1H), 5.70(s, 1H), 4.86(d, J = 6.0 Hz, 2H), 2.63(s, 3H). | 422.0 |

TABLE 2-continued

Selected compounds (A-1 to A-202) of the present invention.

| Compd NO. | Structure | Method | $^1$HNMR | ESI-MS (m/z): [M + 1]$^+$ |
|---|---|---|---|---|
| A-4 | 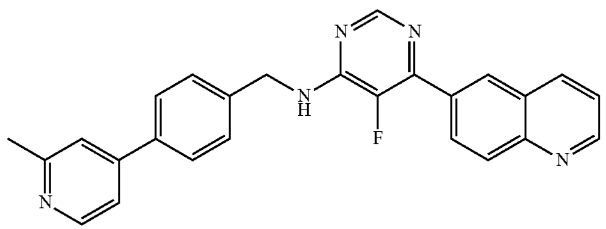 [SMILES: Cc1cc(-c2ccc(CNc3ncnc(-c4ccc5ncccc5c4)c3F)cc2)ccn1] | A | $^1$HNMR (400 MHz, CDCl$_3$) δ8.99-8.98(m, 1H), 8.55-8.54(m, 3H), 8.38(d, J = 9.2 Hz, 1H), 8.27(d, J = 8.0 Hz, 1H), 8.21(d, J = 8.8 Hz, 1H), 7.65(d, J = 8.0 Hz, 2H), 7.52(d, J = 8.0 Hz, 2H), 7.48-7.45(m, 1H), 7.37(s, 1H), 7.31(d, J = 5.2 Hz, 1H), 5.65(s, 1H), 4.87(d, J = 5.6 Hz, 2H), 2.63(s, 3H). | 422.0 |
| A-5 | 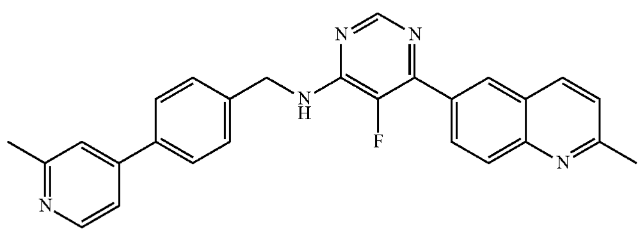 | A | $^1$HNMR(400 MHz, CDCl$_3$) δ8.55-8.54(m, 2H), 8.51(s, 1H), 8.34(d, J = 9.2 Hz, 1H), 8.15(d, J = 8.8 Hz, 1H), 8.11(d, J = 8.8 Hz, 1H), 7.64(d, J = 8.0 Hz, 2H), 7.51(d, J = 7.6 Hz, 2H), 7.37(s, 1H), 7.34(d, J = 8.4 Hz, 1H), 7.31(d, J = 4.8 Hz, 1H), 5.62(s, 1H), 4.86(d, J = 6.0 Hz, 2H), 2.78(s, 3H), 2.63(s, 3H). | 436.0 |
| A-6 | 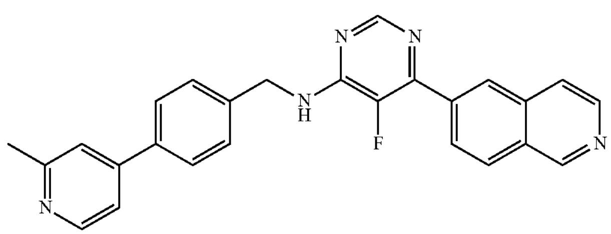 [SMILES: Cc1cc(-c2ccc(CNc3ncnc(-c4ccc5cnccc5c4)c3F)cc2)ccn1] | A | $^1$HNMR(400 MHz, CDCl$_3$) δ9.32(s, 1H), 8.60(d, J = 5.6 Hz, 1H), 8.57(d, J = 2.0 Hz, 1H), 8.55(d, J = 5.6 Hz, 1H), 8.52(s, 1H), 8.25(d, J = 8.4 Hz, 1H), 8.10(d, J = 8.8 Hz, 1H), 7.76(d, J = 5.6 Hz, 1H), 7.65(d, J = 8.0 Hz, 2H), 7.52(d, J = 8.0 Hz, 2H), 7.37(s, 1H), 7.32(d, J = 5.2 Hz, 1H), 5.65(s, 1H), 4.87(d, J = 6.0 Hz, 2H), 2.63(s, 3H). | 422.0 |
| A-7 | 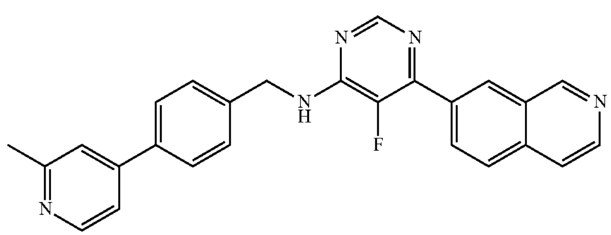 [SMILES: Cc1cc(-c2ccc(CNc3ncnc(-c4ccc5ccncc5c4)c3F)cc2)ccn1] | A | $^1$HNMR(400 MHz, CDCl$_3$) δ9.37(s, 1H), 8.70(s, 1H), 8.60(d, J = 5.6 Hz, 1H), 8.56(s, 2H), 8.38(d, J = 8.8 Hz, 1H), 7.95(d, J = 8.4 Hz, 1H), 7.71(d, J = 5.6 Hz, 1H), 7.66(d, J = 8.0 Hz, 2H), 7.53(d, J = 8.0 Hz, 2H), 7.41(s, 1H), 7.36(d, J = 5.6 Hz, 1H), 5.64(s, 1H), 4.88(d, J = 6.0 Hz, 2H), 2.66(s, 3H). | 422.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-8 | 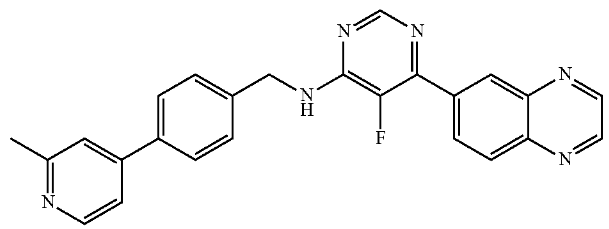 | A | ¹HNMR(400 MHz, CDCl₃)δ8.91(d, J = 2.8 Hz, 2H), 8.79(s, 1H), 8.57(s, 1H), 8.55(d, J = 5.2 Hz, 1H), 8.49(d, J = 8.4 Hz, 1H), 8.23(d, J = 8.8 Hz, 1H), 7.65(d, J = 8.0 Hz, 2H), 7.52(d, J = 8.0 Hz, 2H), 7.37(s, 1H), 7.31(d, J = 4.8 Hz, 1H), 5.68(s, 1H), 4.87(d, J = 5.6 Hz, 2H), 2.63(s, 3H). | 423.0 |
| A-9 | 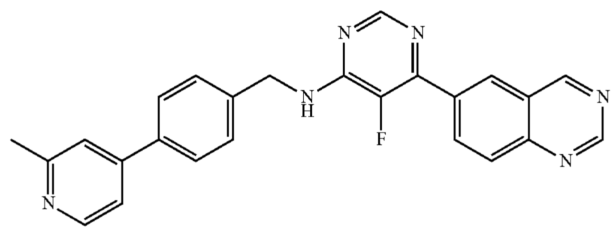 [SMILES: Cc1cc(-c2ccc(CNc3ncnc(-c4ccc5ncncc5c4)c3F)cc2)ccn1] | A | ¹HNMR(400 MHz, CDCl₃)δ9.51(s, 1H), 9.40(s, 1H), 8.67(s, 1H), 8.62(d, J = 8.4 Hz, 1H), 8.56-8.54(m, 2H), 8.17(d, J = 8.4 Hz, 1H), 7.65(d, J = 8.0 Hz, 2H), 7.52(d, J = 8.0 Hz, 2H), 7.38(s, 1H), 7.32(d, J = 5.2 Hz, 1H), 5.69(s, 1H), 4.88(d, J = 5.6 Hz, 2H), 2.64(s, 3H). | 423.0 |
| A-10 | 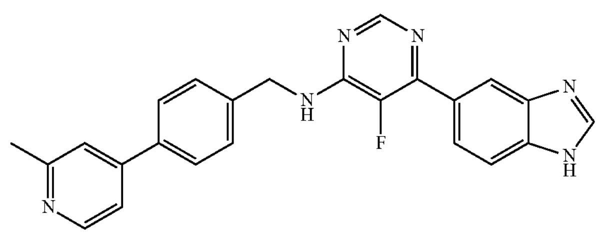 [SMILES: Cc1cc(-c2ccc(CNc3ncnc(-c4ccc5[nH]cnc5c4)c3F)cc2)ccn1] | A | ¹HNMR(400 MHz, DMSO)δ8.49(d, J = 5.2 Hz, 1H), 8.42-8.34(m, 2H), 8.33(s, 1H), 8.23(s, 1H), 7.88(d, J = 9.2 Hz, 1H), 7.76(d, J = 8.4 Hz, 2H), 7.71(d, J = 8.4 Hz, 1H), 7.59(s, 1H), 7.51(d, J = 7.6 Hz, 3H), 4.71(d, J = 6.0 Hz, 2H), 2.53(s, 3H). | |
| A-11 | 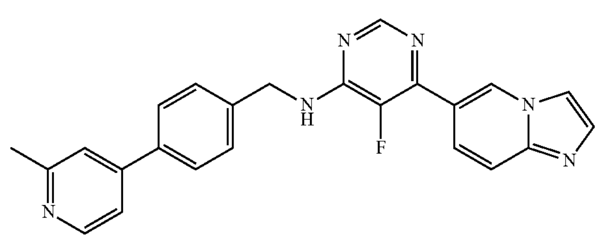 [SMILES: Cc1cc(-c2ccc(CNc3ncnc(-c4ccc5nccn5c4)c3F)cc2)ccn1] | A | ¹HNMR(400 MHz, CDCl₃)δ9.00(s, 1H), 8.55(d, J = 4.8 Hz, 1H), 8.46(s, 1H), 7.97(s, 2H), 7.76(s, 1H), 7.69(s, 1H), 7.63(d, J = 7.6 Hz, 2H), 7.51(d, J = 8.0 Hz, 2H), 7.36(s, 1H), 7.31(d, J = 4.8 Hz, 1H), 5.77(s, 1H), 4.85(d, J = 5.6 Hz, 2H), 2.63(s, 3H). | 411.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-12 | 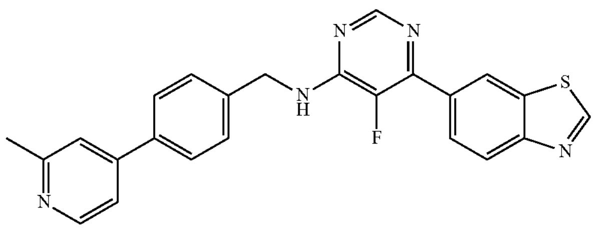 [SMILES: Cc1cc(-c2ccc(CNc3ncnc(-c4ccc5ncsc5c4)c3F)cc2)ccn1] | A | ¹HNMR(400 MHz, CDCl₃) δ 9.10 (s, 1H), 8.70 (s, 1H), 8.55-8.52 (m, 2H), 8.27-8.17 (m, 2H), 7.64 (d, J = 8.4 Hz, 2H), 7.51(d, J = 8.0 Hz, 2H), 7.37(s, 1H), 7.31(d, J = 5.2 Hz, 1H), 5.63(s, 1H), 4.86(d, J = 5.6 Hz, 2H), 2.63(s, 3H). | 427.9 |
| A-13 | 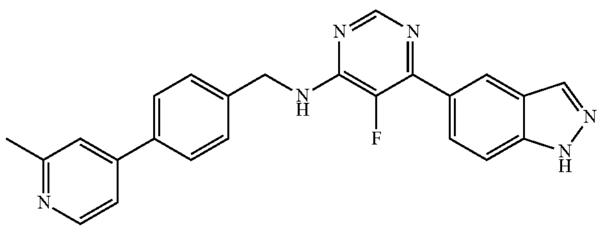 [SMILES: Cc1cc(-c2ccc(CNc3ncnc(-c4ccc5[nH]ncc5c4)c3F)cc2)ccn1] | A | ¹HNMR(400 MHz, DMSO)δ13.28(s, 1H), 8.47(d, J = 5.2 Hz, 1H), 8.43(s, 1H), 8.39(t, J = 6.0 Hz, 1H), 8.33(d, J = 2.0 Hz, 1H), 8.22(s, 1H), 8.01(d, J = 9.2 Hz, 1H), 7.75(d, J = 8.0 Hz, 2H), 7.66(d, J = 8.8 Hz, 1H), 7.56(s, 1H), 7.50-7.47(m, 3H), 4.71(d, J = 6.0 Hz, 2H), 2.52(s, 3H). | 411.0 |
| A-14 | 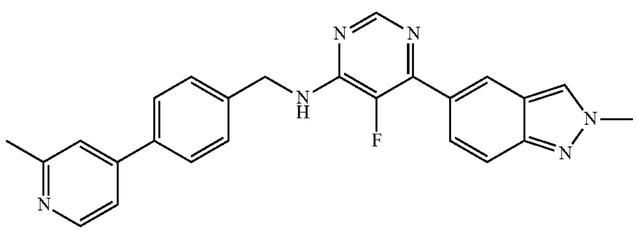 | A | ¹HNMR(400 MHz, CDCl₃)δ8.54(d, J = 5.2 Hz, 1H), 8.50(s, 1H), 8.40(s, 1H), 8.01(s, 1H), 7.96(d, J = 9.2 Hz, 1H), 7.78(d, J = 9.2 Hz, 1H), 7.63(d, J = 8.0 Hz, 2H), 7.50(d, J = 8.0 Hz, 2H), 7.36(s, 1H), 7.31(d, J = 5.2 Hz, 1H), 5.56(s, 1H), 4.84(d, J = 5.6 Hz, 2H), 4.25(s, 3H), 2.62(s, 3H). | 425.0 |
| A-15 | 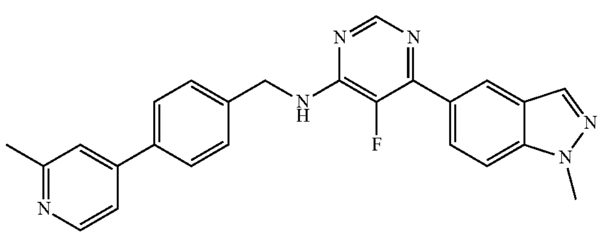 [SMILES: Cc1cc(-c2ccc(CNc3ncnc(-c4ccc5c(cnn5C)c4)c3F)cc2)ccn1] | A | ¹HNMR(400 MHz, CDCl₃)δ8.55(d, J = 5.2 Hz, 1H), 8.51(d, J = 1.6 Hz, 1H), 8.46(s, 1H), 8.12(d, J = 9.2 Hz, 1H), 8.08(s, 1H), 7.64(d, J = 8.4 Hz, 2H), 7.54-7.47(m, 3H), 7.37(s, 1H), 7.31(d, J = 5.2 Hz, 1H), 5.57(s, 1H), 4.85(d, J = 6.0 Hz, 2H), 4.12(s, 3H), 2.63(s, 3H). | 425.0 |

TABLE 2-continued

Selected compounds (A-1 to A-202) of the present invention.

| Compd NO. | Structure | Method | $^1$HNMR | ESI-MS (m/z): [M + 1]$^+$ |
|---|---|---|---|---|
| A-16 | 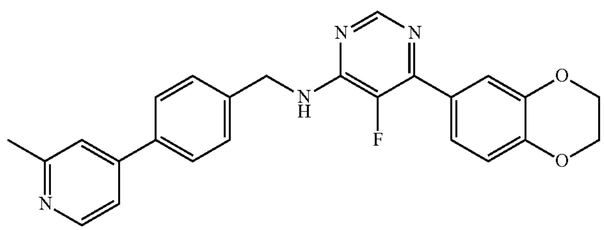 [SMILES: Cc1cc(-c2ccc(CNc3ncnc(-c4ccc5c(c4)OCCO5)c3F)cc2)ccn1] | A | $^1$HNMR(400 MHz, CDCl$_3$)δ8.54(d, J = 4.8 Hz, 1H), 8.45(s, 1H), 7.63(d, J = 8.0 Hz, 3H), 7.58(d, J = 8.8 Hz, 1H), 7.49(d, J = 8.0 Hz, 2H), 7.37(s, 1H), 7.31(d, J = 5.2 Hz, 1H), 6.96(d, J = 8.8 Hz, 1H), 5.52(s, 1H), 4.82(d, J = 5.8 Hz, 2H), 4.31(d, J = 2.4 Hz, 4H), 2.62(s, 3H). | 429.0 |
| A-17 | 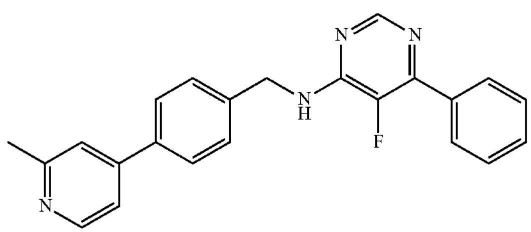 [SMILES: Cc1cc(-c2ccc(CNc3ncnc(-c4ccccc4)c3F)cc2)ccn1] | A | $^1$HNMR(400 MHz, CDCl$_3$)δ8.54(d, J = 5.2 Hz, 1H), 8.50(d, J = 1.6 Hz, 1H), 8.01(d, J = 7.6 Hz, 2H), 7.63(d, J = 8.0 Hz, 2H), 7.51-7.48(m, 5H), 7.36(s, 1H), 7.31(d, J = 4.8 Hz, 1H), 5.54(s, 1H), 4.84(d, J = 5.8 Hz, 2H), 2.62(s, 3H). | 371.0 |
| A-18 | 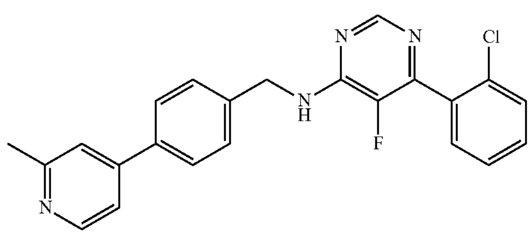 [SMILES: Cc1cc(-c2ccc(CNc3ncnc(-c4ccccc4Cl)c3F)cc2)ccn1] | A | $^1$HNMR(400 MHz, CDCl$_3$)δ8.54(d, J = 5.2 Hz, 1H), 8.50(d, J = 1.6 Hz, 1H), 8.01(d, J = 7.6 Hz, 2H), 7.63(d, J = 8.4 Hz, 2H), 7.51-7.48(m, 4H), 7.36(s, 1H), 7.31(d, J = 5.2 Hz, 1H), 5.55(s, 1H), 4.84(d, J = 5.6 Hz, 2H), 2.63(s, 3H). | |
| A-19 | 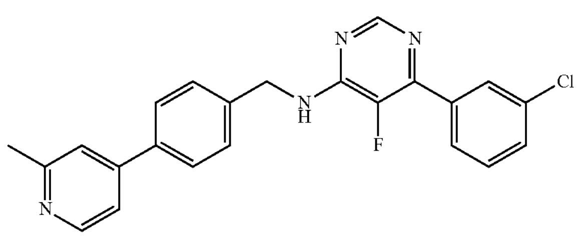 [SMILES: Cc1cc(-c2ccc(CNc3ncnc(-c4cccc(Cl)c4)c3F)cc2)ccn1] | A | $^1$HNMR(400 MHz, CDCl$_3$)δ8.54(d, J = 4.8 Hz, 1H), 8.49(d, J = 1.6 Hz, 1H), 8.04(s, 1H), 7.91(d, J = 7.2 Hz, 1H), 7.63(d, J = 8.0 Hz, 2H), 7.49(d, J = 8.0 Hz, 2H), 7.47-7.39(m, 2H), 7.36(s, 1H), 7.30(d, J = 5.2 Hz, 1H), 5.59(s, 1H), 4.83(d, J = 6.0 Hz, 2H), 2.62(s, 3H). | 405.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-20 | 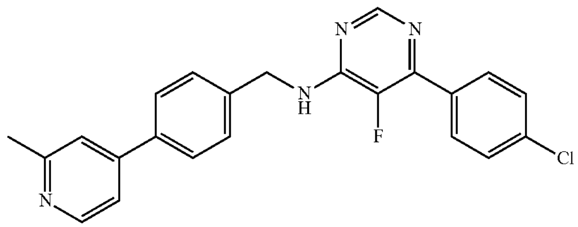 [SMILES: Cc1cc(-c2ccc(CNc3ncnc(-c4ccc(Cl)cc4)c3F)cc2)ccn1] | A | ¹HNMR(400 MHz, CDCl₃)δ8.54(d, J = 5.2 Hz, 1H), 8.48(d, J = 1.6 Hz, 1H), 7.99(d, J = 8.0 Hz, 2H), 7.63(d, J = 8.0 Hz, 2H), 7.50-7.45(m, 4H), 7.36(s, 1H), 7.30(d, J = 4.4 Hz, 1H), 5.54(s, 1H), 4.83(d, J = 6.0 Hz, 2H), 2.62(s, 3H). | 405.0 |
| A-21 | 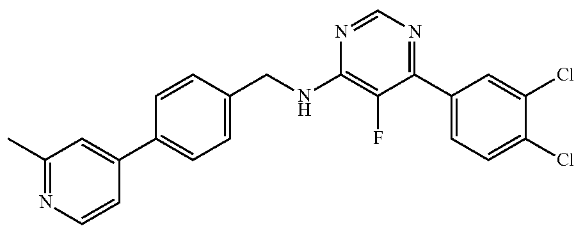 [SMILES: Cc1cc(-c2ccc(CNc3ncnc(-c4ccc(Cl)c(Cl)c4)c3F)cc2)ccn1] | A | ¹HNMR(400 MHz, CDCl₃)δ8.55(d, J = 4.8 Hz, 1H), 8.48(s, 1H), 8.18(s, 1H), 7.90(d, J = 8.4 Hz, 1H), 7.63(d, J = 8.4 Hz, 2H), 7.56(d, J = 8.4 Hz, 1H), 7.49(d, J = 8.0 Hz, 2H), 7.36(s, 1H), 7.30(d, J = 4.8 Hz, 1H), 5.58(s, 1H), 4.83(d, J = 5.6 Hz, 2H), 2.63(s, 3H). | 438.9 |
| A-22 | 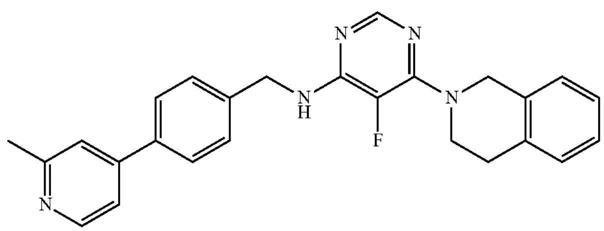 [SMILES: Cc1cc(-c2ccc(CNc3ncnc(N4CCc5ccccc5C4)c3F)cc2)ccn1] | A | ¹HNMR(400 MHz, CDCl₃)δ8.53(d, J = 5.2 Hz, 1H), 8.06(s, 1H), 7.60(d, J = 8.0 Hz, 2H), 7.45(d, J = 8.0 Hz, 2H), 7.35(s, 1H), 7.29(d, J = 5.2 Hz, 1H), 7.22-7.12(m, 4H), 5.10(s, 1H), 4.85(s, 2H), 4.74(d, J = 6.0 Hz, 2H), 3.94(m, J = 5.8 Hz, 2H), 2.97(t, J = 5.8 Hz, 2H), 2.62(s, 3H). | 444.0 |
| A-23 | 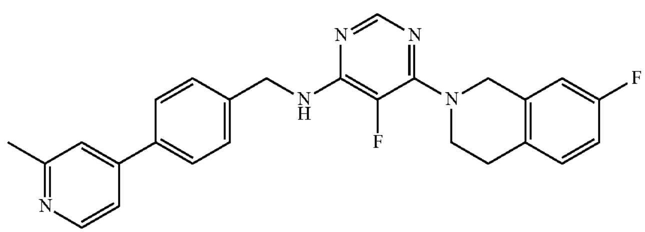 [SMILES: Cc1cc(-c2ccc(CNc3ncnc(N4CCc5ccc(F)cc5C4)c3F)cc2)ccn1] | A | ¹HNMR(400 MHz, CDCl₃)δ8.53(d, J = 4.8 Hz, 1H), 8.05(s, 1H), 7.60(d, J = 7.6 Hz, 2H), 7.45(d, J = 7.6 Hz, 2H), 7.35(s, 1H), 7.30(d, J = 4.8 Hz, 1H), 7.20-7.08(m, 1H), 6.91(m, 2H), 5.10(s, 1H), 4.85(s, 2H), 4.74(d, J = 8 Hz, 2H), 3.94(m, 2H), 2.93(m, 2H), 2.62(s, 3H). | 444.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-24 | 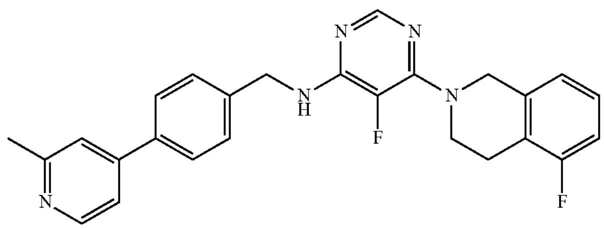 [SMILES: Cc1cc(-c2ccc(CNc3ncnc(N4CCc5c(F)cccc5C4)c3F)cc2)ccn1] | A | ¹HNMR(400 MHz, CDCl₃) δ8.53(d, J = 4.8 Hz, 1H), 8.04(s, 1H), 7.60(d, J = 8 Hz, 2H), 7.45(d, J = 8 Hz, 2H), 7.36(s, 1H), 7.31(d, J = 4.8 Hz, 1H), 7.12-7.07(m, 1H), 6.87(m, 2H), 5.09(s, 1H), 4.81(s, 2H), 4.74(d, J = 6 Hz, 2H), 3.92(m, 2H), 2.92(m, 2H), 2.62(s, 3H). | 444.0 |
| A-25 | 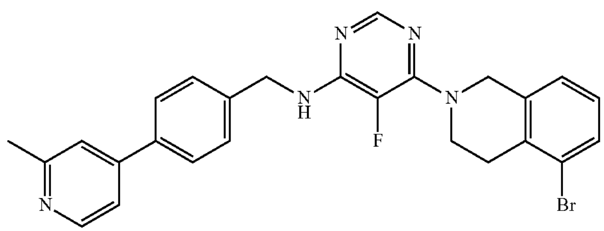 | A | ¹HNMR(400 MHz, CDCl₃) δ8.53(d, J = 4.8 Hz, 1H), 8.05(s, 1H), 7.60(d, J = 8.0 Hz, 2H), 7.45(d, J = 8.0 Hz, 3H), 7.36(s, 1H), 7.30(d, J = 4.8 Hz, 1H), 7.09(m, 2H), 5.09(s, 1H), 4.83(s, 2H), 4.74(d, J = 6 Hz, 2H), 3.95(m, 2H), 2.96(m, 2H), 2.62(s, 3H). | 503.9 |
| A-26 | 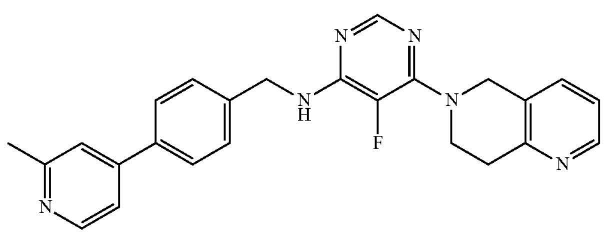 | A | ¹HNMR(400 MHz, CDCl₃) δ8.53(d, J = 5.2 Hz, 1H), 8.44(d, J = 4.4 Hz, 1H), 8.06(s, 1H), 7.60(d, J = 8.0 Hz, 2H), 7.46(d, J = 7.6 Hz, 3H), 7.36(s, 1H), 7.30(d, J = 5.2 Hz, 1H), 7.16-7.13(m, 1H), 5.13(s, 1H), 4.85(s, 2H), 4.75(d, J = 5.6 Hz, 2H), 4.03(t, J = 6.0 Hz, 2H), 3.14(t, J = 5.8 Hz, 2H), 2.62(s, 3H). | 427.0 |
| A-27 | 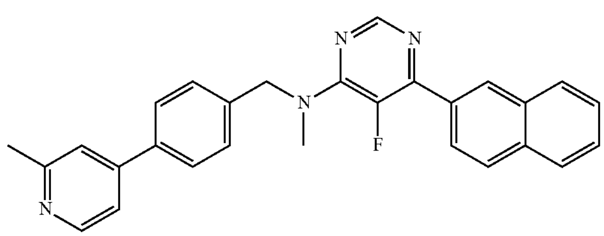 [SMILES: Cc1cc(-c2ccc(CN(C)c3ncnc(-c4ccc5ccccc5c4)c3F)cc2)ccn1] | C | ¹HNMR(400 MHz, CDCl₃) δ8.54-8.53(m, 2H), 8.48(s, 1H), 8.06(d, J = 8.4 Hz, 1H), 7.93(d, J = 8.4 Hz, 2H), 7.87(d, J = 7.6 Hz, 1H), 7.62(d, J = 8.0 Hz, 2H), 7.58-7.48(m, 2H), 7.43(d, J = 8.0 Hz, 2H), 7.36(s, 1H), 7.30(d, J = 4.8 Hz, 1H), 4.98(s, 2H), 3.32(d, J = 3.6 Hz, 3H), 2.62(s, 3H). | 435.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-28 | 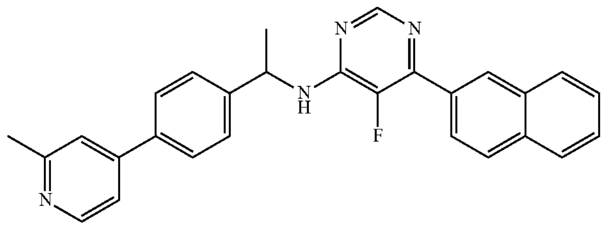 [SMILES: Cc1cc(-c2ccc(C(C)Nc3ncnc(-c4ccc5ccccc5c4)c3F)cc2)ccn1] | A | ¹HNMR(400 MHz, DMSO)δ8.54(s, 1H), 8.48(d, J = 5.2 Hz, 1H), 8.37-8.28(m, 2H), 8.08-8.06(m, 3H), 7.98(d, J = 8.0 Hz, 1H), 7.75(d, J = 8.4 Hz, 2H), 7.64-7.55(m, 5H), 7.48(d, J = 5.2 Hz, 1H), 5.46-5.39(m, 1H), 2.52(s, 3H), 1.59(d, J = 6.8 Hz, 3H). | 435.0 |
| A-29 | 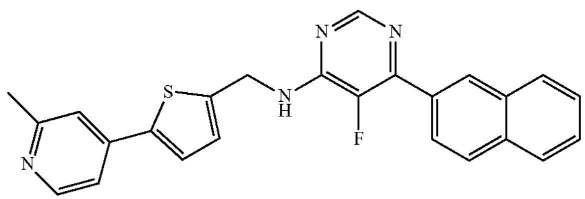 [SMILES: Cc1cc(-c2ccc(CNc3ncnc(-c4ccc5ccccc5c4)c3F)s2)ccn1] | A | ¹HNMR(400 MHz, CDCl₃)δ8.59(s, 1H), 8.55(s, 1H), 8.46(d, J = 5.2 Hz, 1H), 8.12(d, J = 8.8 Hz, 1H), 7.95(d, J = 8.8 Hz, 2H), 7.88(d, J = 8.0 Hz, 1H), 7.59-7.50(m, 2H), 7.36(d, J = 3.6 Hz, 1H), 7.30(s, 1H), 7.25(d, J = 3.6 Hz, 1H), 7.10(d, J = 3.6 Hz, 1H), 5.63(s, 1H), 4.98(d, J = 6.0 Hz, 2H), 2.58(s, 3H). | 427.0 |
| A-30 | 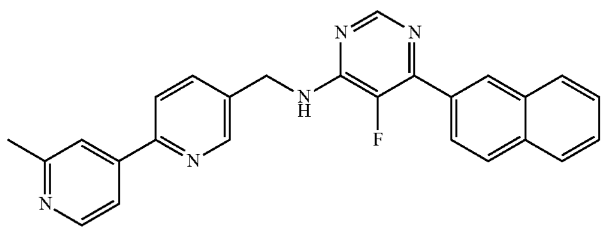 | A | ¹HNMR(400 MHz, CDCl₃)δ8.79(s, 1H), 8.60(d, J = 5.2 Hz, 1H), 8.55(s, 2H), 8.12(d, J = 8.4 Hz, 1H), 7.95(d, J = 8.8 Hz, 2H), 7.89-7.86(m, 2H), 7.82-7.76(m, 2H), 7.66(d, J = 4.8 Hz, 1H), 7.58-7.51(m, 2H), 5.69(s, 1H), 4.88(d, J = 6.0 Hz, 2H), 2.65(s, 3H). | 422.0 |
| A-31 | 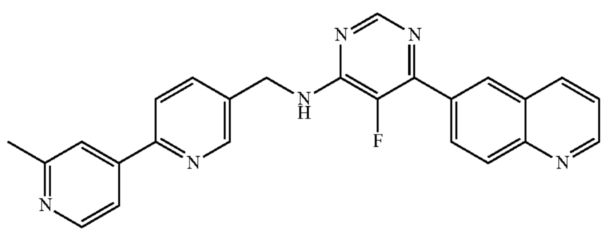 [SMILES: Cc1cc(-c2ccc(CNc3ncnc(-c4ccc5ncccc5c4)c3F)cn2)ccn1] | A | ¹HNMR(400 MHz, CDCl₃)δ8.99-8.98(m, 1H), 8.80(d, J = 1.6 Hz, 1H), 8.61(d, J = 5.2 Hz, 1H), 8.55(d, J = 1.6 Hz, 2H), 8.37(d, J = 8.8 Hz, 1H), 8.28(d, J = 7.6 Hz, 1H), 8.21(d, J = 8.8 Hz, 1H), 7.90-7.87(m, 1H), 7.80(d, J = 8.0 Hz, 2H), 7.66(d, J = 4.4 Hz, 1H), 7.49-7.46(m, 1H), 5.73(s, 1H), 4.89(d, J = 6.0 Hz, 2H), 2.65(s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-32 | 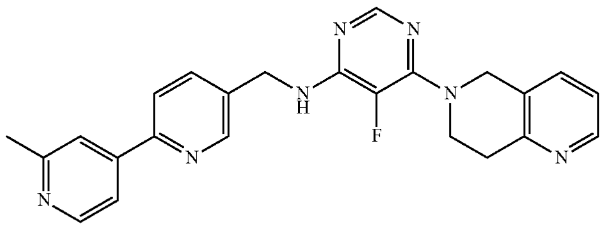 | A | ¹HNMR(400 MHz, CDCl₃)δ8.72(s, 1H), 8.59(d, J = 5.2 Hz, 1H), 8.44(d, J = 4.4 Hz, 1H), 8.04(s, 1H), 7.84-7.71(m, 3H), 7.65(d, J = 5.2 Hz, 1H), 7.46(s, 1H), 7.6 Hz, 1H), 7.16-7.13(m, 1H), 5.19(s, 1H), 4.85(s, 2H), 4.78(d, J = 6.0 Hz, 2H), 4.03(t, J = 5.8 Hz, 2H), 3.14(t, J = 5.6 Hz, 2H), 2.65(s, 3H). | 428.0 |
| A-33 | 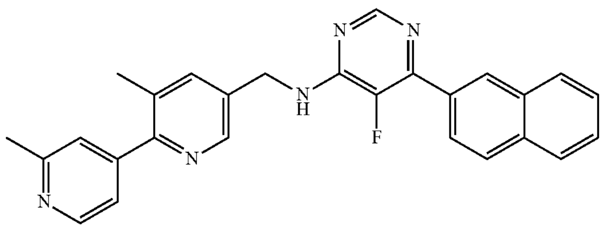 [SMILES: Cc1cc(-c2ncc(CNc3ncnc(-c4ccc5ccccc5c4)c3F)cc2C)ccn1] | A | ¹HNMR(400 MHz, CDCl₃)δ8.60-8.58(m, 2H), 8.56(s, 2H), 8.13(d, J = 8.4 Hz, 1H), 7.96(d, J = 8.0 Hz, 2H), 7.89(d, J = 7.6 Hz, 1H), 7.67(s, 1H), 7.59-7.50(m, 2H), 7.34(s, 1H), 7.24(d, J = 8.4 Hz, 1H), 5.63(s, 1H), 4.85(d, J = 5.6 Hz, 2H), 2.63(s, 3H), 2.38(s, 3H). | 436.0 |
| A-34 | 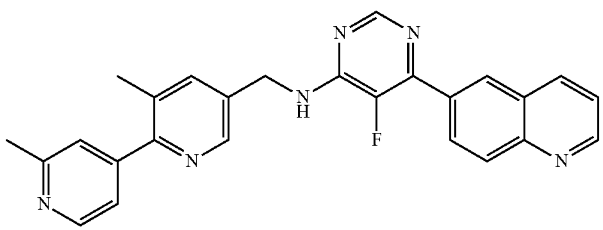 | A | ¹HNMR (400 MHz, CDCl₃) δ 8.99(d, J = 3.6 Hz, 1H), 8.63-8.57(m, 2H), 8.56(s, 2H), 8.38(d, J = 8.8 Hz, 1H), 8.28(d, J = 8.4 Hz, 1H), 8.22(d, J = 9.2 Hz, 1H), 7.68(s, 1H), 7.49-7.46(m, 1H), 7.33(s, 1H), 7.25(d, J = 5.2 Hz, 1H), 5.69(s, 1H), 4.86(d, J = 6.0 Hz, 2H), 2.63(s, 3H), 2.39(s, 3H). | 437.0 |
| A-35 | 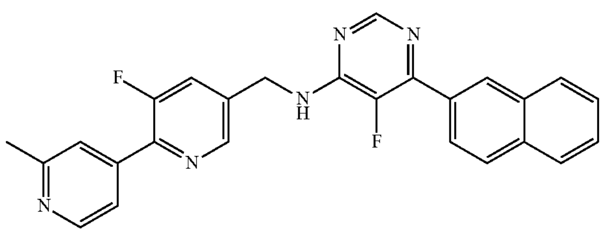 | A | ¹HNMR (400 MHz, CDCl₃) δ 8.61(s, 2H), 8.58-8.52 (m, 2H), 8.12 (d, J = 8.4 Hz, 1H), 7.96(d, J = 8.4 Hz, 2H), 7.89(d, J = 7.2 Hz, 1H), 7.77(s, 1H), 7.69(s, 1H), 7.61(d, J = 11.2 Hz, 1H), 7.59-7.51(m, 2H), 5.73(s, 1H), 4.90(d, J = 6.0 Hz, 2H), 2.65(s, 3H). | 440.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-36 | 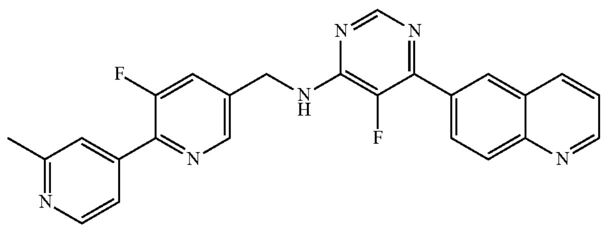 | A | ¹HNMR(400 MHz, DMSO)δ8.98(d, J = 4.0 Hz, 1H), 8.63(d, J = 4.4 Hz, 2H), 8.58-8.53(m, 3H), 8.42(s, 1H), 8.33(d, J = 8.8 Hz, 1H), 8.15(d, J = 8.8 Hz, 1H), 7.87(d, J = 12.4 Hz, 1H), 7.74(s, 1H), 7.67(d, J = 5.2 Hz, 1H), 7.63-7.60(m, 1H), 4.79(d, J = 6.0 Hz, 2H), 2.55(s, 3H). | |
| A-37 | 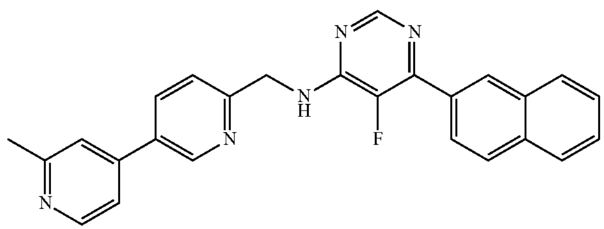 [SMILES: Cc1cc(-c2ccc(CNc3ncnc(-c4ccc5ccccc5c4)c3F)nc2)ccn1] | A | ¹HNMR(400 MHz, CDCl₃)δ8.87(s, 1H), 8.61(d, J = 5.2 Hz, 1H), 8.58(s, 1H), 8.54(s, 1H), 8.15(d, J = 8.8 Hz, 1H), 7.97-7.93(m, 3H), 7.89(d, J = 7.6 Hz, 1H), 7.59-7.51(m, 2H), 7.49(d, J = 8.4 Hz, 1H), 7.38(s, 1H), 7.33(d, J = 5.2 Hz, 1H), 6.60(s, 1H), 4.95(d, J = 5.2 Hz, 2H), 2.66(s, 3H). | 422.0 |
| A-38 | 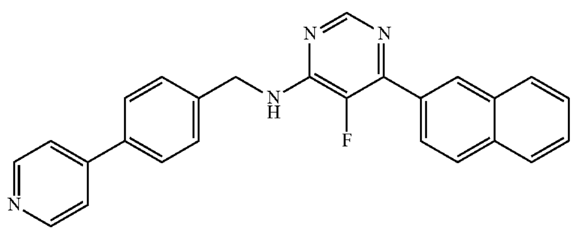 [SMILES: Fc1c(NCc2ccc(-c3ccncc3)cc2)ncnc1-c1ccc2ccccc2c1] | A | ¹HNMR(400 MHz, CDCl₃)δ8.68(brs, 2H), 8.55(s, 2H), 8.13(d, J = 8.8 Hz, 1H), 7.95(d, J = 8.8 Hz, 2H), 7.88(d, J = 7.2 Hz, 1H), 7.66(d, J = 8.4 Hz, 2H), 7.57-7.53(m, 6H), 5.63(s, 1H), 4.87(d, J = 5.6 Hz, 2H). | 407.0 |
| A-39 | 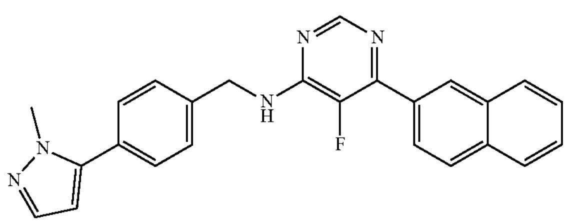 [SMILES: Cn1nccc1-c1ccc(CNc2ncnc(-c3ccc4ccccc4c3)c2F)cc1] | A | ¹HNMR(400 MHz, CDCl₃)δ8.55(s, 2H), 8.13(d, J = 8.8 Hz, 1H), 7.95(d, J = 8.4 Hz, 2H), 7.88(d, J = 7.2 Hz, 1H), 7.59-7.46(m, 5H), 7.43(d, J = 8.0 Hz, 2H), 6.31(s, 1H), 5.60(s, 1H), 4.86(d, J = 6.0 Hz, 2H), 3.90(s, 3H). | 410.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-40 | 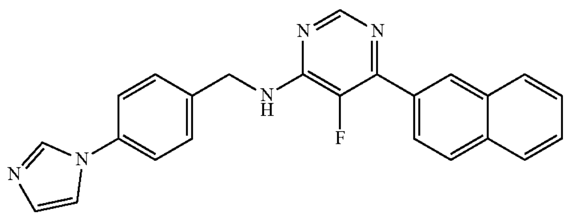 [SMILES: Fc1c(NCc2ccc(-n3ccnc3)cc2)ncnc1-c1ccc2ccccc2c1] | A | ¹HNMR(400 MHz, CDCl₃)δ8.55(s, 1H), 8.54(s, 1H), 8.12(d, J = 8.8 Hz, 1H), 7.95(d, J = 8.4 Hz, 2H), 7.89(d, J = 7.6 Hz, 1H), 7.86(s, 1H), 7.56-7.52(m, 4H), 7.40(d, J = 8.0 Hz, 2H), 7.29(s, 1H), 7.22(s, 1H), 5.64(s, 1H), 4.85(d, J = 6.0 Hz, 2H). | 396.0 |
| A-41 | 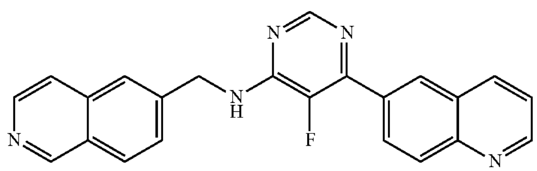 [SMILES: Fc1c(NCc2ccc3cnccc3c2)ncnc1-c1ccc2ncccc2c1] | A | ¹HNMR(400 MHz, CDCl₃)δ9.26(s, 1H), 8.99(d, J = 4.0 Hz, 1H), 8.57-8.54(m, 3H), 8.39(d, J = 8.8 Hz, 1H), 8.28(d, J = 8.4 Hz, 1H), 8.22(d, J = 8.8 Hz, 1H), 8.00(d, J = 8.4 Hz, 1H), 7.82(s, 1H), 7.65(d, J = 6.8 Hz, 2H), 7.49-7.46(m, 1H), 5.77(s, 1H), 5.02(d, J = 6.0 Hz, 2H). | 382.0 |
| A-42 | 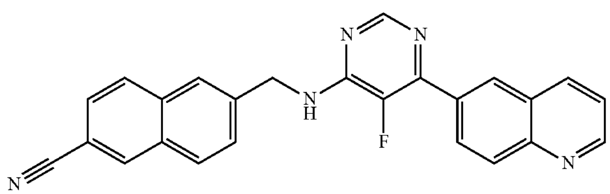 [SMILES: N#Cc1ccc2cc(CNc3ncnc(-c4ccc5ncccc5c4)c3F)ccc2c1] | A | ¹HNMR(400 MHz, CDCl₃)δ8.99(d, J = 4.4 Hz, 1H), 8.67-8.59(m, 2H), 8.58-8.53(m, 2H), 8.39(s, 1H), 8.34(d, J = 8.8 Hz, 1H), 8.16(d, J = 8.8 Hz, 1H), 8.10(d, J = 8.8 Hz, 1H), 8.05(d, J = 8.8 Hz, 1H), 7.98(s, 1H), 7.77(d, J = 8.4 Hz, 1H), 7.72(d, J = 8.4 Hz, 1H), 7.62(dd, J = 8.4, 4.4 Hz, 1H), 4.89(d, J = 6.0 Hz, 2H). | |
| A-43 | 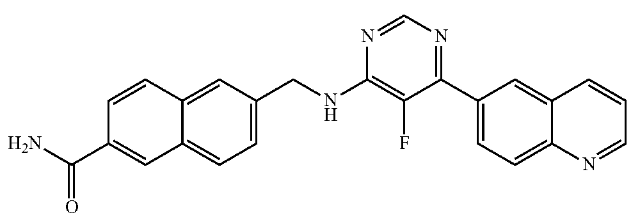 [SMILES: NC(=O)c1ccc2cc(CNc3ncnc(-c4ccc5ncccc5c4)c3F)ccc2c1] | D | ¹HNMR(400 MHz, CDCl₃)δ8.96(d, J = 2.8 Hz, 1H), 8.63-8.55(m, 2H), 8.53(d, J = 8.4 Hz, 1H), 8.43(s, 1H), 8.37(s, 1H), 8.32(d, J = 8.8 Hz, 1H), 8.18-8.12(m, 2H), 7.98(d, J = 8.4 Hz, 1H), 7.97-7.91(m, 2H), 7.89(s, 1H), 7.65-7.58(m, 1H), 7.42(s, 1H), 4.86(d, J = 6.0 Hz, 2H). | 424.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-44 | 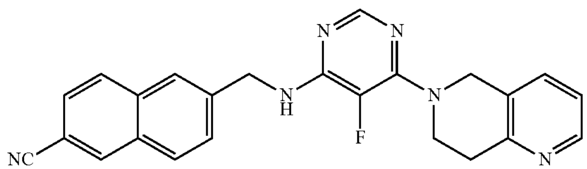 [SMILES: N#Cc1ccc2cc(CNc3ncnc(N4CCc5ncccc5C4)c3F)ccc2c1] | A | ¹H NMR (400 MHz, CDCl₃) δ 8.45 (d, J = 3.6 Hz, 1H), 8.22 (s, 1H), 8.05 (s, 1H), 7.88 (d, J = 8.4 Hz, 2H), 7.82 (s, 1H), 7.60 (m, 2H), 7.47 (d, J = 7.6 Hz, 1H), 7.20 (m, 1H), 5.24 (s, 1H), 4.91 (d, J = 6.0 Hz, 2H), 4.87 (s, 2H), 4.05 (m, 2H), 3.15 (m, 2H). | |
| A-45 | 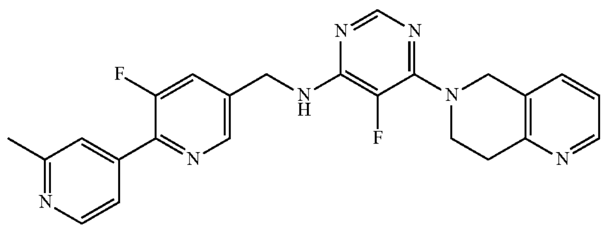 | A | ¹H NMR (400 MHz, CDCl₃) δ 8.59 (s, 1H), 8.53 (s, 1H), 8.44 (s, 1H), 8.02 (s, 1H), 7.75 (s, 1H), 7.67 (s, 1H), 7.54 (d, J = 11.6 Hz, 1H), 7.46 (d, J = 7.6 Hz, 1H), 7.14 (s, 1H), 5.27 (s, 1H), 4.85 (s, 2H), 4.79 (d, J = 5.6 Hz, 2H), 4.03 (d, J = 5.6 Hz, 2H), 3.14 (s, 2H), 2.88 (s, 1H), 2.64 (s, 3H). | |
| A-46 | 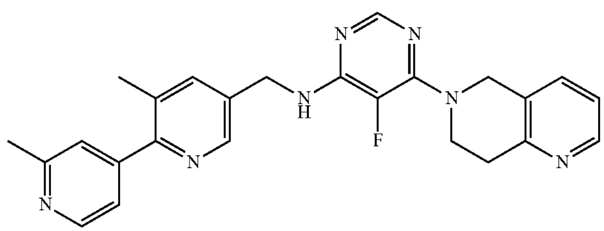 [SMILES: Cc1cc(-c2ncc(CNc3ncnc(N4CCc5ncccc5C4)c3F)cc2C)ccn1] | A | ¹H NMR (400 MHz, CDCl₃) δ 8.53 (s, 2H), 8.45 (s, 1H), 8.05 (s, 1H), 7.61 (s, 1H), 7.46 (d, J = 7.6 Hz, 1H), 7.33 (s, 1H), 7.24 (s, 1H), 7.15 (s, 1H), 5.24 (s, 1H), 4.86 (s, 2H), 4.74 (d, J = 5.6 Hz, 2H), 4.04 (t, J = 5.2 Hz, 2H), 3.14 (s, 2H), 2.62 (s, 3H), 2.35 (s, 3H). | |
| A-47 | 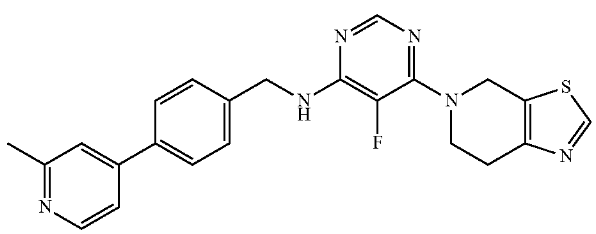 [SMILES: Cc1cc(-c2ccc(CNc3ncnc(N4CCc5ncsc5C4)c3F)cc2)ccn1] | A | ¹H NMR (400 MHz, CDCl₃) δ 8.68 (s, 1H), 8.53 (d, J = 5.2 Hz, 1H), 8.04 (s, 1H), 7.60 (d, J = 7.8 Hz, 2H), 7.45 (d, J = 7.2 Hz, 2H), 7.36 (s, 1H), 7.30 (d, J = 4.8 Hz, 1H), 5.13 (s, 1H), 4.94 (s, 2H), 4.75 (d, J = 5.6 Hz, 2H), 4.02 (d, J = 5.2 Hz, 2H), 3.07 (s, 2H), 2.62 (s, 3H). | 433.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-48 | 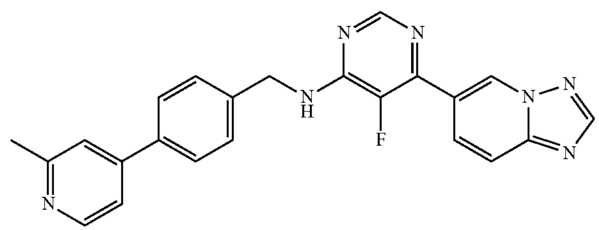 [SMILES: Cc1cc(-c2ccc(CNc3ncnc(-c4ccc5ncnn5c4)c3F)cc2)ccn1] | A | ¹H NMR (400 MHz, CDCl₃) δ 9.39 (s, 1H), 8.53 (d, J = 15.6 Hz, 2H), 8.42 (s, 1H), 8.33 (d, J = 9.4 Hz, 1H), 7.86 (d, J = 9.4 Hz, 1H), 7.64 (d, J = 6.4 Hz, 2H), 7.51 (d, J = 7.6 Hz, 2H), 7.37 (s, 1H), 7.31 (s, 1H), 5.67 (s, 1H), 4.86 (s, 2H), 2.63 (s, 3H). | 451.0 |
| A-49 | 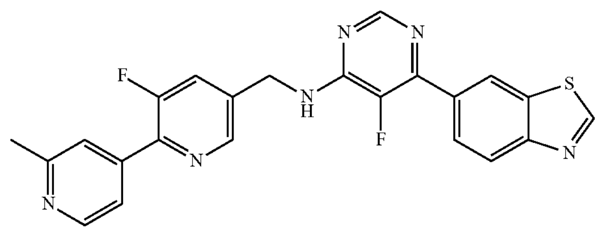 | A | ¹H NMR (400 MHz, CDCl₃) δ 9.11 (s, 1H), 8.70 (s, 1H), 8.62 (d, J = 5.2 Hz, 2H), 8.52 (s, 1H), 8.22 (m, 2H), 7.77 (s, 1H), 7.69 (d, J = 4.8 Hz, 1H), 7.61 (d, J = 11.2 Hz, 1H), 5.74 (s, 1H), 4.90 (d, J = 6.0 Hz, 2H), 2.65 (s, 3H). | |
| A-50 | 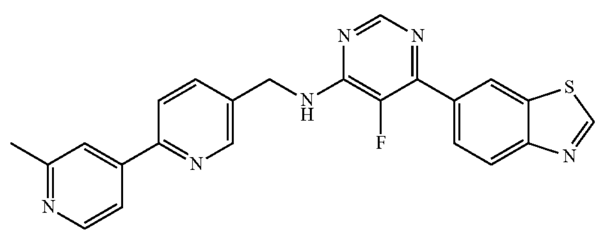 [SMILES: Cc1cc(-c2ccc(CNc3ncnc(-c4ccc5ncsc5c4)c3F)cn2)ccn1] | A | ¹H NMR (400 MHz, CDCl₃) δ 9.10 (s, 1H), 8.79 (s, 1H), 8.70 (s, 1H), 8.60 (d, J = 5.2 Hz, 1H), 8.52 (s, 1H), 8.22 (m, 2H), 7.90 (m, 1H), 7.79 (d, J = 7.8 Hz, 2H), 7.66 (d, J = 4.8 Hz, 1H), 5.69 (s, 1H), 4.88 (d, J = 6.0 Hz, 2H), 2.65 (s, 3H). | |
| A-51 | 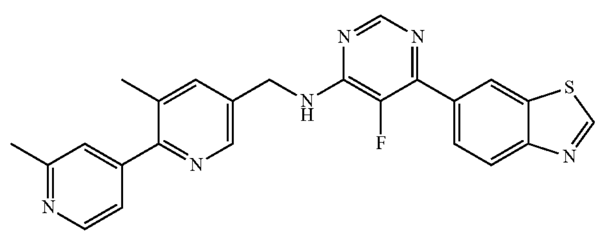 [SMILES: Cc1cc(-c2ncc(CNc3ncnc(-c4ccc5ncsc5c4)c3F)cc2C)ccn1] | A | ¹H NMR (400 MHz, CDCl₃) δ 9.10 (s, 1H), 8.70 (s, 1H), 8.59 (d, J = 5.6 Hz, 2H), 8.53 (s, 1H), 8.22 (q, J = 8.4 Hz, 2H), 7.67 (s, 1H), 7.33 (s, 1H), 7.23 (s, 1H), 5.64 (s, 1H), 4.85 (d, J = 5.6 Hz, 2H), 2.63 (s, 3H), 2.38 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-52 | 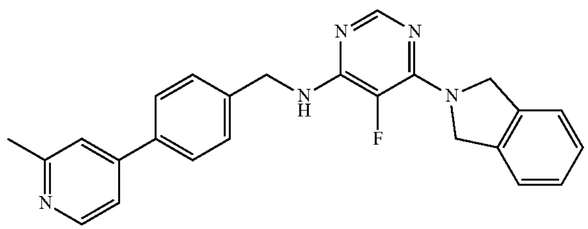 [SMILES: Cc1cc(-c2ccc(CNc3ncnc(N4Cc5ccccc5C4)c3F)cc2)ccn1] | A | ¹H NMR (400 MHz, CDCl₃) δ 8.53 (d, J = 5.2 Hz, 1H), 8.08 (s, 1H), 7.61 (d, J = 7.9 Hz, 2H), 7.48 (d, J = 8 Hz, 2H), 7.36 (s, 1H), 7.31 (s, 5H), 5.03 (d, J = 2.4 Hz, 5H), 4.85 (m, 1H), 4.77 (d, J = 6 Hz, 2H), 4.60 (m, 1H), 2.62 (s, 3H). | 412.0 |
| A-53 | 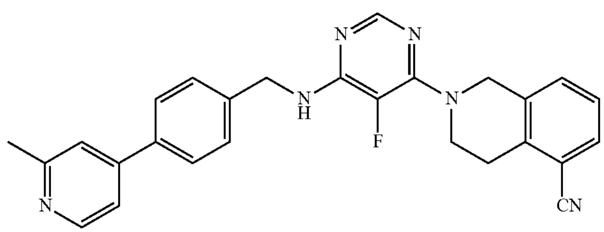 [SMILES: Cc1cc(-c2ccc(CNc3ncnc(N4CCc5c(C#N)cccc5C4)c3F)cc2)ccn1] | A | ¹H NMR (400 MHz, CDCl₃) δ 8.53 (d, J = 5.2 Hz, 1H), 8.05 (s, 1H), 7.60 (d, J = 8.0 Hz, 2H), 7.53 (d, J = 7.6 Hz, 1H), 7.45 (d, J = 8.0 Hz, 2H), 7.40 (m, 2H), 7.30 (d, J = 6.8 Hz, 2H), 5.13 (s, 1H), 4.86 (s, 2H), 4.75 (d, J = 6 Hz, 2H), 3.99 (t, J = 5.8 Hz, 2H), 3.16 (t, J = 5.8 Hz, 2H), 2.62 (s, 3H). | |
| A-54 | 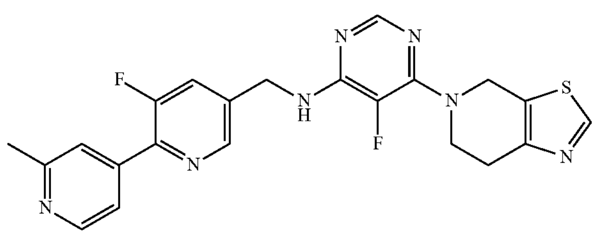 [SMILES: Cc1cc(-c2ncc(CNc3ncnc(N4CCc5ncsc5C4)c3F)cc2F)ccn1] | A | ¹H NMR (400 MHz, CDCl₃) δ 8.68 (s, 1H), 8.60 (d, J = 5.2 Hz, 1H), 8.54 (s, 1H), 8.02 (s, 1H), 7.76 (s, 1H), 7.67 (d, J = 4.8 Hz, 1H), 7.54 (d, J = 11.6 Hz, 1H), 5.23 (s, 1H), 4.95 (s, 2H), 4.79 (d, J = 6 Hz, 2H), 4.03 (t, J = 5.6 Hz, 2H), 3.07 (s, 2H), 2.64 (s, 3H). | |
| A-55 | 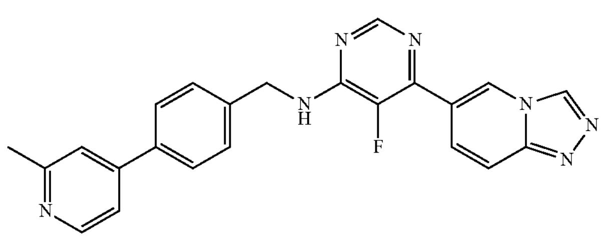 [SMILES: Cc1cc(-c2ccc(CNc3ncnc(-c4ccc5nncn5c4)c3F)cc2)ccn1] | A | ¹H NMR (400 MHz, CDCl₃) δ 8.96 (s, 1H), 8.91 (s, 1H), 8.55 (d, J = 5.2 Hz, 1H), 8.49 (s, 1H), 8.03 (d, J = 9.6 Hz, 1H), 7.87 (d, J = 9.6 Hz, 1H), 7.64 (d, J = 8.0 Hz, 2H), 7.50 (d, J = 8.0 Hz, 2H), 7.36 (s, 1H), 7.31 (d, J = 5.2 Hz, 1H), 5.69 (s, 1H), 4.85 (d, J = 5.8 Hz, 2H), 2.63 (s, 3H). | 412.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-56 | 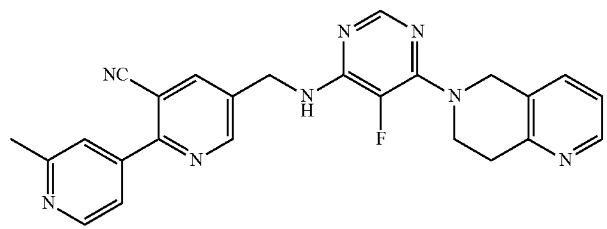 | A | ¹H NMR (400 MHz, CDCl₃) δ 8.89 (s, 1H), 8.67 (d, J = 5.2 Hz, 1H), 8.45 (d, J = 4.4 Hz, 1H), 8.10 (s, 1H), 8.02 (s, 1H), 7.67 (s, 1H), 7.62 (d, J = 5.0 Hz, 1H), 7.46 (d, J = 8 Hz, 1H), 7.15 (m, 1H), 5.28 (s, 1H), 4.87 (s, 2H), 4.81 (d, J = 6.2 Hz, 2H), 4.06 (t, J = 5.8 Hz, 2H), 3.15 (m, 2H), 2.67 (s, 3H). | |
| A-57 | 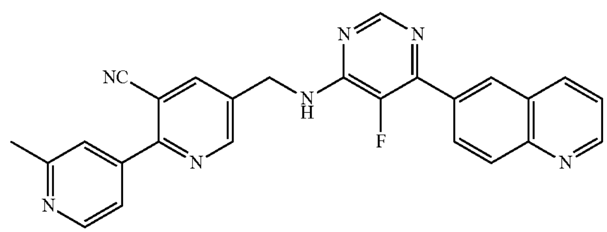 [SMILES: Cc1cc(-c2ncc(CNc3ncnc(-c4ccc5ncccc5c4)c3F)cc2C#N)ccn1] | A | ¹H NMR (400 MHz, CDCl₃) δ 9.0 (m, 2H), 8.69 (d, J = 5.2 Hz, 1H), 8.55 (d, J = 11.2 Hz, 2H), 8.38 (d, J = 9.0 Hz, 1H), 8.29 (d, J = 8.2 Hz, 1H), 8.23 (d, J = 9 Hz, 1H), 8.18 (s, 1H), 7.70 (s, 1H), 7.66 (d, J = 4.6 Hz, 1H), 7.48 (dd, J = 8.2, 4.2 Hz, 1H), 5.86 (s, 1H), 5.3 (m, 1H), 4.93 (d, J = 6 Hz, 2H), 2.68 (s, 3H). | |
| A-58 | 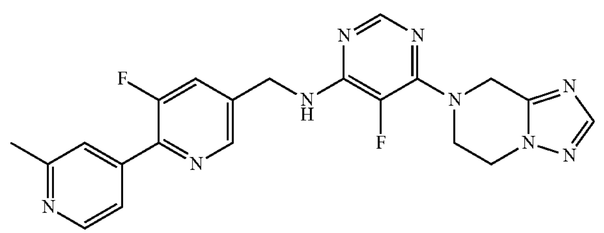 [SMILES: Cc1cc(-c2ncc(CNc3ncnc(N4CCn5ncnc5C4)c3F)cc2F)ccn1] | A | ¹H NMR (400 MHz, CDCl₃) δ 8.61 (d, J = 5.2 Hz, 1H), 8.54 (s, 1H), 8.05 (s, 1H), 7.92 (s, 1H), 7.75 (s, 1H), 7.67 (d, J = 4.8 Hz, 1H), 7.54 (d, J = 12.0 Hz, 1H), 5.35 (s, 1H), 5.01 (s, 2H), 4.80 (d, J = 6.2 Hz, 2H), 4.33 (m, 2H), 4.21 (m, 2H), 2.64 (s, 3H). | 436.0 |
| A-59 | 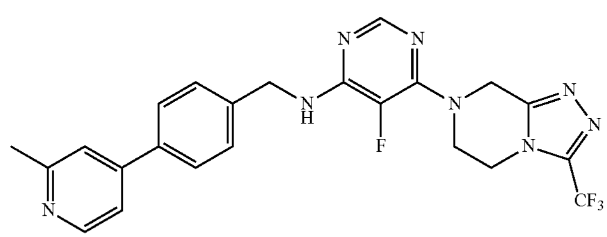 [SMILES: Cc1cc(-c2ccc(CNc3ncnc(N4CCn5c(nnc5C(F)(F)F)C4)c3F)cc2)ccn1] | A | ¹H NMR (400 MHz, CDCl₃) δ 8.53 (d, J = 4.6 Hz, 1H), 8.07 (s, 1H), 7.9 (m, 1H), 7.61 (d, J = 7.6 Hz, 2H), 7.45 (d, J = 7.8 Hz, 2H), 7.35 (s, 1H), 7.28 (s, 1H), 5.24 (s, 1H), 5.12 (s, 2H), 4.76 (d, J = 5.6 Hz, 2H), 4.28 (s, 2H), 4.15 (s, 2H), 2.62 (s, 3H). | 485.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-60 | 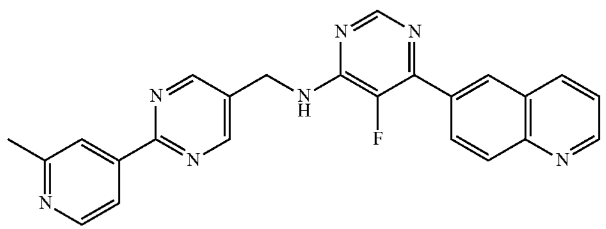 | A | ¹H NMR (400 MHz, CDCl₃) δ 9.0 (m, 3H), 8.61 (d, J = 5.2 Hz, 2H), 8.54 (d, J = 7.8 Hz, 2H), 8.43 (s, 1H), 8.32 (d, J = 8.6 Hz, 1H), 8.15 (m, 2H), 8.04 (d, J = 5.2 Hz, 1H), 7.61 (m, 1H), 4.76 (d, J = 5.6 Hz, 2H), 2.57 (s, 3H). | 424.0 |
| A-61 | 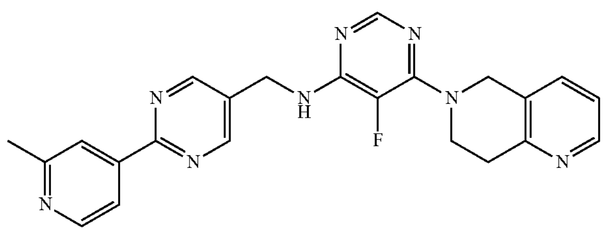 | A | ¹H NMR (400 MHz, CDCl₃) δ 8.87 (s, 2H), 8.64 (d, J = 5.2 Hz, 1H), 8.44 (d, J = 4 Hz, 1H), 8.14 (s, 1H), 8.06 (d, J = 4.8 Hz, 1H), 8.03 (d, J = 5.1 Hz, 1H), 7.45 (d, J = 7.6 Hz, 1H), 7.16 (m, 1H), 5.23 (s, 1H), 4.85 (s, 2H), 4.76 (d, J = 6 Hz, 2H), 4.03 (m, 2H), 3.13 (m, 2H), 2.66 (s, 3H). | 430.9 |
| A-62 | 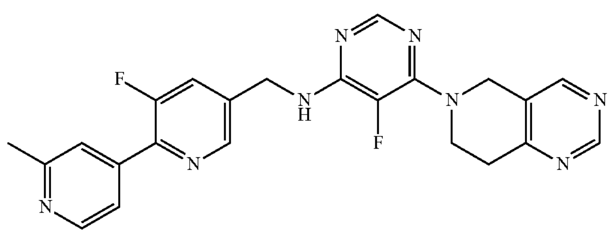 [SMILES: Cc1cc(-c2ncc(CNc3ncnc(N4CCc5ncncc5C4)c3F)cc2F)ccn1] | A | ¹H NMR (400 MHz, CDCl₃) δ 9.02 (s, 1H), 8.61 (d, J = 5.2 Hz, 1H), 8.53 (d, J = 7.8 Hz, 2H), 8.04 (s, 1H), 7.76 (s, 1H), 7.68 (d, J = 4.8 Hz, 1H), 7.54 (d, J = 11.0 Hz, 1H), 5.26 (s, 1H), 4.87 (s, 2H), 4.80 (d, J = 6.2 Hz, 2H), 4.04 (t, J = 5.9 Hz, 2H), 3.10 (t, J = 5.8 Hz, 2H), 2.64 (s, 3H) | 447.0 |
| A-63 | 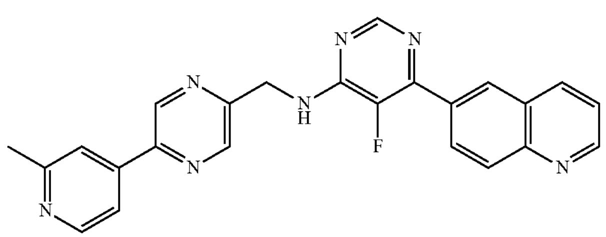 [SMILES: Cc1cc(-c2cnc(CNc3ncnc(-c4ccc5ncccc5c4)c3F)cn2)ccn1] | A | ¹H NMR (400 MHz, CDCl₃) δ 9.05 (s, 1H), 8.99 (d, J = 3.6 Hz, 1H), 8.82 (s, 1H), 8.66 (d, J = 5.2 Hz, 1H), 8.56 (d, J = 9.6 Hz, 2H), 8.39 (d, J = 8.8 Hz, 1H), 8.28 (d, J = 8.0 Hz, 1H), 8.22 (d, J = 9.2 Hz, 1H), 7.81 (s, 1H), 7.71 (d, J = 5.2 Hz, 1H), 7.47 (dd, J = 8.2, 4.2 Hz, 1H), 6.39 (s, 1H), 5.01 (d, J = 5.2 Hz, 2H), 2.68 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-64 | 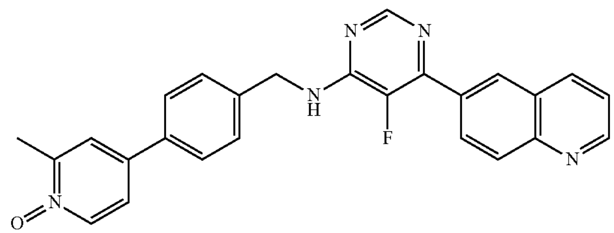 [SMILES: Cc1cc(-c2ccc(CNc3ncnc(-c4ccc5ncccc5c4)c3F)cc2)cc[n+]1[O-]] | E | ¹H NMR (400 MHz, CDCl₃) δ 8.25 (d, J = 6.8 Hz, 1H), 8.22 (s, 1H), 7.54 (d, J = 8.0 Hz, 2H), 7.43 (d, J = 8.0 Hz, 3H), 7.35-7.29 (m, 1H), 5.91 (s, 1H), 4.79 (d, J = 6.0 Hz, 2H), 2.57 (s, 3H). | |
| A-65 | 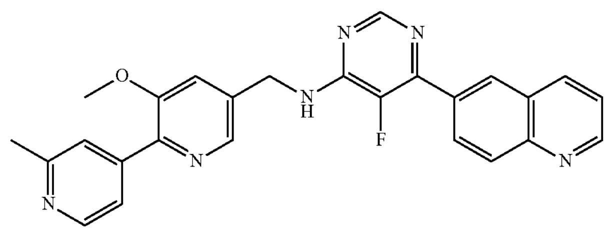 [SMILES: COc1cc(CNc2ncnc(-c3ccc4ncccc4c3)c2F)cnc1-c1ccnc(C)c1] | A | ¹H NMR (400 MHz, CDCl₃) δ 8.99 (d, J = 4.0 Hz, 1H), 8.57 (s, 1H), 8.56 (s, 2H), 8.38 (d, J = 9.6 Hz, 2H), 8.28 (d, J = 8.4 Hz, 1H), 8.22 (d, J = 8.8 Hz, 1H), 7.73 (s, 1H), 7.68 (d, J = 5.2 Hz, 1H), 7.47 (dd, J = 8.2, 4.2 Hz, 1H), 7.43 (s, 1H), 5.74 (s, 1H), 4.88 (d, J = 6.0 Hz, 2H), 3.92 (s, 3H), 2.63 (s, 3H). | 452.9 |
| A-66 | 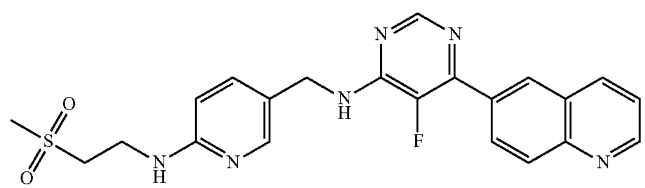 [SMILES: CS(=O)(=O)CCNc1ccc(CNc2ncnc(-c3ccc4ncccc4c3)c2F)cn1] | A | ¹H NMR (400 MHz, CDCl₃) δ 8.98 (d, J = 3.2 Hz, 1H), 8.53 (s, 2H), 8.35 (d, J = 8.8 Hz, 1H), 8.27 (d, J = 8.4 Hz, 1H), 8.20(d, J = 8.8 Hz, 1H), 8.16 (s, 1H), 7.52(d, J = 8.4 Hz, 1H), 7.46 (dd, J = 8.2, 4.2 Hz, 1H), 6.49 (d, J = 5.6 Hz, 2H), 5.46 (s, 1H), 5.04 (s, 1H), 4.65 (d, J = 5.6 Hz, 2H), 3.98-3.94 (m, 2H), 3.39 (t, J = 5.8 Hz, 2H), 2.96 (s, 3H). | |
| A-67 | 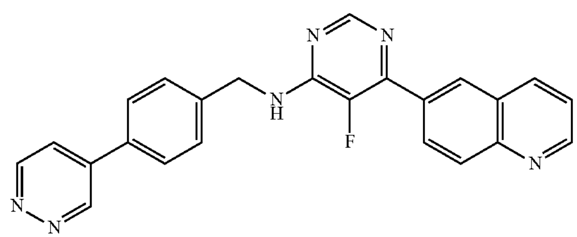 [SMILES: Fc1c(NCc2ccc(-c3ccnnc3)cc2)ncnc1-c1ccc2ncccc2c1] | A | ¹H NMR (400 MHz, CDCl₃) δ 9.47 (s, 1H), 9.24 (d, J = 5.2 Hz, 1H), 8.99 (d, J = 3.2 Hz, 1H), 8.56 (d, J = 4.0 Hz, 2H), 8.38 (d, J = 8.8 Hz, 1H), 8.28 (d, J = 8.0 Hz, 2H), 8.22 (d, J = 8.8 Hz, 1H), 7.70 (d, J = 8.0 Hz, 2H), 7.65 (d, J = 5.2 Hz, 1H), 7.59 (d, J = 7.6 Hz, 2H), 7.48 (dd, J = 8.2, 4.2 Hz, 1H), 5.70 (s, 1H), 4.90 (d, J = 6.0 Hz, 2H). | 409.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-68 | 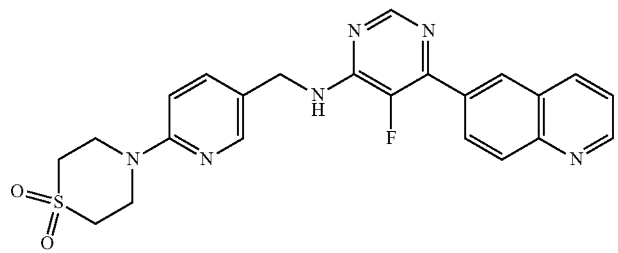 [SMILES: O=S1(=O)CCN(c2ccc(CNc3ncnc(-c4ccc5ncccc5c4)c3F)cn2)CC1] | A | ¹H NMR (400 MHz, CDCl₃) δ 8.98 (d, J = 3.2 Hz, 1H), 8.54 (d, J = 3.2 Hz, 2H), 8.35 (d, J = 8.8 Hz, 1H), 8.27 (d, J = 7.8 Hz, 2H), 8.20 (d, J = 8.8 Hz, 1H), 7.66 (d, J = 8.8 Hz, 1H), 7.47 (dd, J = 8.2, 4.2 Hz, 1H), 6.76 (d, J = 8.4 Hz, 1H), 5.51 (s, 1H), 4.70 (d, J = 5.6 Hz, 2H), 4.18 (s, 4H), 3.05 (s, 4H). | |
| A-69 | 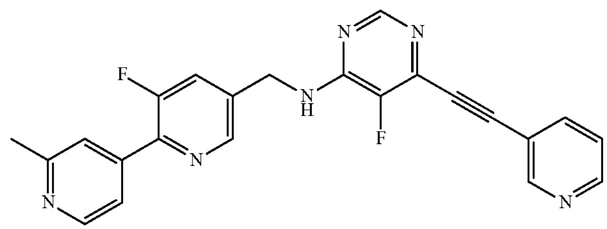 [SMILES: Cc1cc(-c2ncc(CNc3ncnc(C#Cc4cccnc4)c3F)cc2F)ccn1] | A | ¹H NMR (400 MHz, DMSO) δ 8.83 (s, 1H), 8.67 (m, 2H), 8.60(m, 2H), 8.29 (s, 1H), 8.08 (d, J = 7.8 Hz, 1H), 7.85 (d, J = 12.2 Hz, 1H), 7.76 (s, 1H), 7.68 (d, J = 4.6 Hz, 1H), 7.53 (m, 1H), 4.75 (d, J = 5.6 Hz, 2H), 2.56 (s, 3H). | 414.9 |
| A-70 | 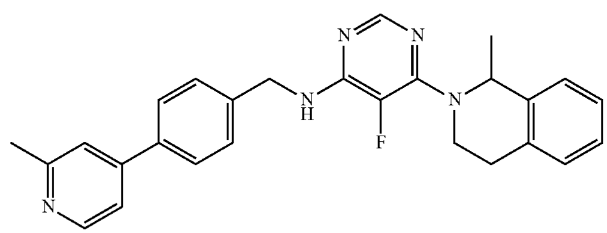 | A | ¹H NMR (400 MHz, CDCl₃) δ 8.53 (d, J = 5.2 Hz, 1H), 8.23 (s, 1H), 8.04 (s, 1H), 7.60 (d, J = 8.2 Hz, 2H), 7.52 (m, 1H), 7.45 (d, J = 8.0 Hz, 2H), 7.35 (s, 1H), 7.30 (d, J = 4.8 Hz, 1H), 7.17 (m, 4H), 5.54 (m, 1H), 5.04 (s, 1H), 4.74 (d, J = 5.6 Hz, 2H), 4.48 (d, J = 10.2 Hz, 1H), 3.48 (m, 1H), 3.16 (m, 1H), 2.80 (d, J = 16.2 Hz, 1H), 2.62 (s, 3H), 1.58 (s, 3H). | |
| A-71 | 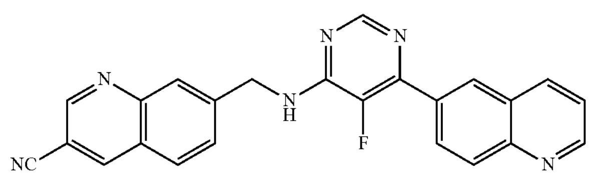 [SMILES: N#Cc1cnc2cc(CNc3ncnc(-c4ccc5ncccc5c4)c3F)ccc2c1] | A | ¹H NMR (400 MHz, DMSO-d₆) δ 9.14 (d, J = 2.0 Hz, 1H), 9.06 (s, 1H), 8.99 (d, J = 2.8 Hz, 1H), 8.68 (t, J = 5.4 Hz, 1H), 8.65 (s, 1H), 8.55 (d, J = 8.4 Hz, 1H), 8.39 (s, 1H), 8.34 (d, J = 9.2 Hz, 1H), 8.16 (d, J = 8.8 Hz, 1H), 8.09 (d, J = 8.8 Hz, 1H), 8.04 (s, 1H), 7.81 (d, J = 8.4 Hz, 1H), 7.62 (dd, J = 8.4, 4.4 Hz, 1H), 4.94 (d, J = 6.0 Hz, 2H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-72 | 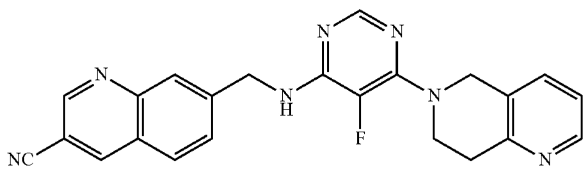 [SMILES: N#Cc1cnc2cc(CNc3ncnc(N4CCc5ncccc5C4)c3F)ccc2c1] | A | ¹H NMR (400 MHz, CDCl₃) δ 9.02 (d, J = 2.0 Hz, 1H), 8.52 (s, 1H), 8.45 (d, J = 4.8 Hz, 1H), 8.08 (s, 1H), 8.02 (s, 1H), 7.87 (d, J = 8.4 Hz, 1H), 7.68 (d, J = 8.4 Hz, 1H), 7.47 (d, J = 7.6 Hz, 1H), 7.15 (dd, J = 8.0, 4.8 Hz, 1H), 5.30 (s, 1H), 4.98 (d, J = 6.0 Hz, 2H), 4.87 (s, 2H), 4.05 (t, J = 5.8 Hz, 2H), 3.15 (t, J = 6.0 Hz, 2H). | |
| A-73 | 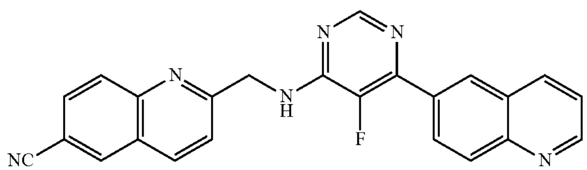 [SMILES: N#Cc1ccc2nc(CNc3ncnc(-c4ccc5ncccc5c4)c3F)ccc2c1] | A | ¹H NMR (400 MHz, DMSO-d₆) δ 8.99 (d, J = 2.4 Hz, 1H), 8.68-8.62 (m, 3H), 8.56 (d, J = 8.4 Hz, 1H), 8.46 (d, J = 8.8 Hz, 1H), 8.36 (s, 1H), 8.34 (s, 1H), 8.15 (dd, J = 14.8, 8.8 Hz, 2H), 8.05 (d, J = 8.8 Hz, 1H), 7.72 (d, J = 8.8 Hz, 1H), 7.62 (dd, J = 8.4, 4.0 Hz, 1H), 4.98 (d, J = 6.0 Hz, 2H). | 447.0 |
| A-74 | 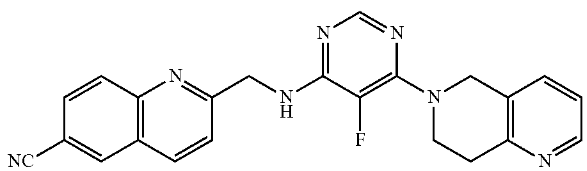 [SMILES: N#Cc1ccc2nc(CNc3ncnc(N4CCc5ncccc5C4)c3F)ccc2c1] | A | ¹H NMR (400 MHz, CDCl₃) δ 8.45 (d, J = 4.8 Hz, 1H), 8.24 (s, 1H), 8.19 (d, J = 8.8 Hz, 2H), 8.06 (s, 1H), 7.90 (d, J = 2.0 Hz, 1H), 7.54 (d, J = 8.8 Hz, 1H), 7.47 (d, J = 7.6 Hz, 1H), 7.19-7.12 (m, 1H), 6.38 (s, 1H), 4.99 (d, J = 4.8 Hz, 2H), 4.88 (s, 2H), 4.07 (t, J = 5.8 Hz, 2H), 3.16 (t, J = 6.0 Hz, 2H). | |
| A-75 | 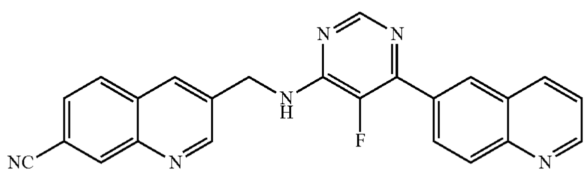 [SMILES: N#Cc1ccc2cc(CNc3ncnc(-c4ccc5ncccc5c4)c3F)cnc2c1] | A | ¹H NMR (400 MHz, CDCl₃) δ 9.11 (d, J = 2.2 Hz, 1H), 8.99 (d, J = 4.2 Hz, 1H), 8.55 (d, J = 8.6 Hz, 2H), 8.49 (s, 1H), 8.38 (d, J = 9.0 Hz, 1H), 8.28 (d, J = 8.3 Hz, 1H), 8.23 (m, 2H), 7.93 (d, J = 8.4 Hz, 1H), 7.72 (d, J = 8.4 Hz, 1H), 7.48 (m, 1H), 5.81 (s, 1H), 5.05 (d, J = 6.1 Hz, -2H). | |
| A-76 | 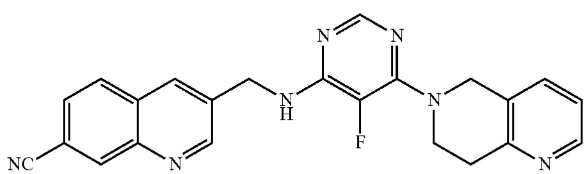 [SMILES: N#Cc1ccc2cc(CNc3ncnc(N4CCc5ncccc5C4)c3F)cnc2c1] | A | ¹H NMR (400 MHz, CDCl₃) δ 9.04 (s, 1H), 8.45 (d, J = 6.8 Hz, 2H), 8.14 (s, 1H), 8.02 (s, 1H), 7.88 (s, 1H), 7.69 (d, J = 8.2 Hz, 1H), 7.46 (d, J = 7.2 Hz, 1H), 7.15 (s, 1H), 5.30 (s, 2H), 4.94 (d, J = 6.2 Hz, 2H), 4.86 (s, 2H), 4.05 (m, 2H), 3.14 (m, 2H). | 412.0 |

TABLE 2-continued

Selected compounds (A-1 to A-202) of the present invention.

| Compd NO. | Structure | Method | $^1$HNMR | ESI-MS (m/z): [M + 1]$^+$ |
|---|---|---|---|---|
| A-77 | 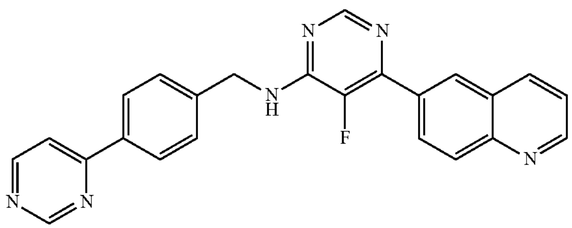 [SMILES: Fc1c(NCc2ccc(-c3ccncn3)cc2)ncnc1-c1ccc2ncccc2c1] | A | $^1$H NMR (400 MHz, CDCl$_3$) δ 9.28 (s, 1H), 8.99 (d, J = 3.2 Hz, 1H), 8.78 (d, J = 5.2 Hz, 1H), 8.56 (s, 2H), 8.38 (d, J = 8.8 Hz, 1H), 8.28 (d, J = 8.4 Hz, 1H), 8.22 (d, J = 8.8 Hz, 1H), 8.12 (d, J = 8.0 Hz, 2H), 7.73 (d, J = 5.2 Hz, 1H), 7.56 (d, J = 8.0 Hz, 2H), 7.50-7.44 (m, 1H), 5.67 (s, 1H), 4.89 (d, J = 5.6 Hz, 2H). | 409.0 |
| A-78 | 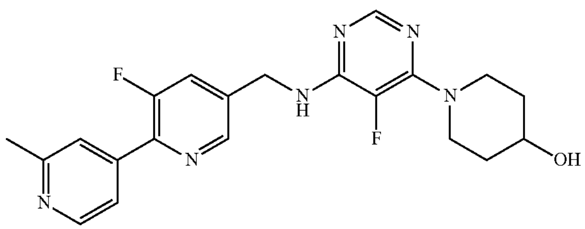 [SMILES: Cc1cc(-c2ncc(CNc3ncnc(N4CCC(O)CC4)c3F)cc2F)ccn1] | A | $^1$H NMR (400 MHz, CDCl$_3$) δ 8.61 (d, J = 5.2 Hz, 1H), 8.54 (s, 1H), 8.00 (s, 1H), 7.76 (s, 1H), 7.68 (d, J = 4.8 Hz, 1H), 7.55 (d, J = 11.6 Hz, 1H), 5.18 (s, 1H), 4.79 (d, J = 6.0 Hz, 2H), 4.18-4.10 (m, 2H), 3.99-3.90 (m, 1H), 3.34-3.24 (m, 2H), 2.64 (s, 3H), 2.02-1.94 (m, 2H), 1.66-1.58 (m, 2H). | |
| A-79 | 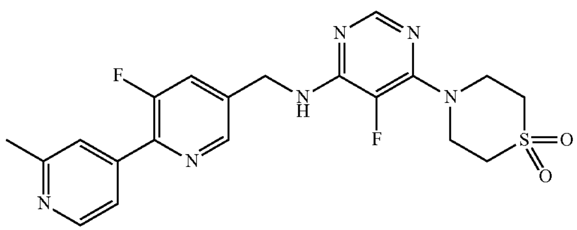 [SMILES: Cc1cc(-c2ncc(CNc3ncnc(N4CCS(=O)(=O)CC4)c3F)cc2F)ccn1] | A | $^1$H NMR (400 MHz, CDCl$_3$) δ 8.62 (d, J = 5.2 Hz, 1H), 8.55 (s, 1H), 8.04 (s, 1H), 7.76 (s, 1H), 7.68 (d, J = 4.4 Hz, 1H), 7.55 (d, J = 11.2 Hz, 1H), 5.34 (s, 1H), 4.81 (d, J = 6.0 Hz, 2H), 4.20 (s, 4H), 3.12 (s, 4H), 2.65 (s, 3H). | |
| A-80 | 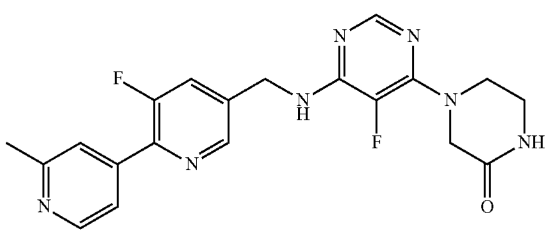 [SMILES: Cc1cc(-c2ncc(CNc3ncnc(N4CCNC(=O)C4)c3F)cc2F)ccn1] | A | $^1$H NMR (400 MHz, DMSO) δ 8.59-8.54 (m, 2H), 8.07 (s, 1H), 7.90 (s, 1H), 7.80-7.72 (m, 3H), 7.65 (d, J = 4.4 Hz, 1H), 4.66 (d, J = 5.6 Hz, 2H), 4.10 (s, 2H), 3.76 (s, 2H), 3.26 (s, 2H), 2.55 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-81 | 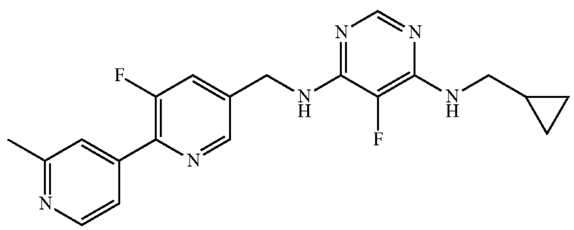 [SMILES: Cc1cc(-c2ncc(CNc3ncnc(NCC4CC4)c3F)cc2F)ccn1] | A | ¹H NMR (400 MHz, CDCl₃) δ 8.61 (d, J = 5.2 Hz, 1H), 8.54 (s, 1H), 8.01 (s, 1H), 7.76 (s, 1H), 7.68 (d, J = 4.8 Hz, 1H), 7.55 (d, J = 11.6 Hz, 1H), 5.01 (s, 1H), 4.79 (d, J = 6.0 Hz, 2H), 4.76 (s, 1H), 3.33 (t, J = 6.2 Hz, 2H), 2.65 (s, 3H), 1.13-1.02 (m, 1H), 0.56 (d, J = 7.6 Hz, 2H), 0.27 (d, J = 4.8 Hz, 2H). | |
| A-82 | 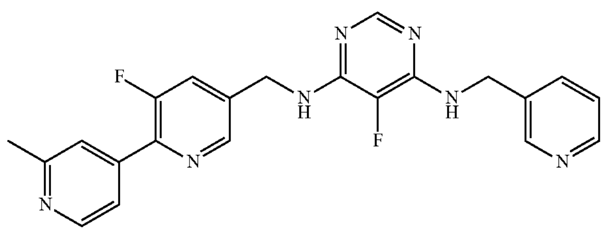 [SMILES: Cc1cc(-c2ncc(CNc3ncnc(NCc4cccnc4)c3F)cc2F)ccn1] | A | ¹H NMR (400 MHz, DMSO) δ 8.56 (d, J = 5.2 Hz, 1H), 8.54 (s, 1H), 8.51 (s, 1H), 8.41 (d, J = 4.0 Hz, 1H), 7.80 (s, 1H), 7.78-7.71 (m, 2H), 7.69 (d, J = 8.0 Hz, 1H), 7.65 (d, J = 4.8 Hz, 1H), 7.58-7.51 (m, 2H), 7.34-7.29 (m, 1H), 4.62 (d, J = 6.0 Hz, 2H), 4.54 (d, J = 6.0 Hz, 2H), 2.54 (s, 3H). | 420.0 |
| A-83 | 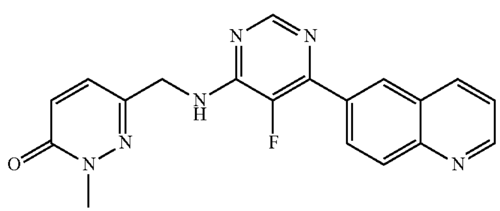 [SMILES: Cn1nc(CNc2ncnc(-c3ccc4ncccc4c3)c2F)ccc1=O] | A | ¹H NMR (400 MHz, DMSO) δ 8.98 (d, J = 3.2 Hz, 1H), 8.63 (s, 1H), 8.55 (d, J = 8.0 Hz, 1H), 8.43 (s, 2H), 8.32 (d, J = 8.8 Hz, 1H), 8.15 (d, J = 8.8 Hz, 1H), 7.64-7.59 (m, 1H), 7.49 (d, J = 9.6 Hz, 1H), 6.93 (d, J = 9.6 Hz, 1H), 4.58 (d, J = 6.0 Hz, 2H), 3.63 (s, 3H). | |
| A-84 | 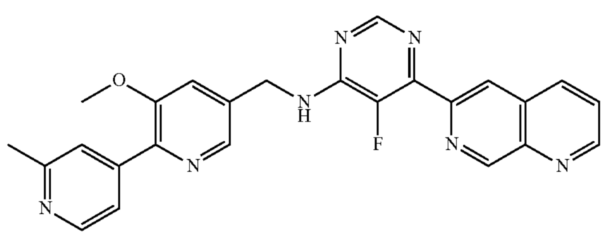 [SMILES: COc1cc(CNc2ncnc(-c3cc4cccnc4cn3)c2F)cnc1-c1ccnc(C)c1] | F | ¹H NMR (400 MHz, DMSO-d₆) δ 9.52 (s, 1H), 9.14 (d, J = 2.8 Hz, 1H), 8.67 (s, 1H), 8.63 (d, J = 8.4 Hz, 1H), 8.54 (s, 1H), 8.50 (d, J = 5.2 Hz, 1H), 8.43 (s, 1H), 8.36 (s, 1H), 7.87-7.84 (m, 1H), 7.75 (s, 1H), 7.69 (d, J = 4.9 Hz, 1H), 7.67 (s, 1H), 4.77 (d, J = 5.6 Hz, 2H), 3.89 (s, 3H), 2.52 (s, 3H). | 454.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-85 | 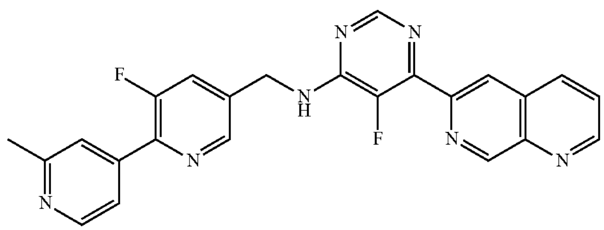 | F | ¹H NMR (400 MHz, CDCl₃) δ 9.68 (s, 1H), 9.12 (d, J = 3.2 Hz, 1H), 8.63-8.61 (m, 2H), 8.56 (d, J = 9.6 Hz, 2H), 8.30 (d, J = 8.4 Hz, 1H), 7.78 (s, 1H), 7.71-7.67 (m, 2H), 7.61 (d, J = 11.6 Hz, 1H), 5.87 (br s, 1H), 4.93 (d, J = 6.0 Hz, 2H), 2.66 (s, 3H). | 441.9 |
| A-86 | 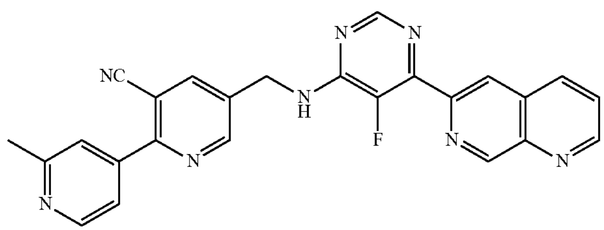 [SMILES: Cc1cc(-c2ncc(CNc3ncnc(-c4cc5cccnc5cn4)c3F)cc2C#N)ccn1] | F | ¹H NMR (400 MHz, CDCl₃) δ 9.67 (s, 1H), 9.12 (d, J = 2.8 Hz, 1H), 8.97 (s, 1H), 8.68 (d, J = 5.2 Hz, 1H), 8.56 (s, 2H), 8.30 (d, J = 8.4 Hz, 1H), 8.17 (s, 1H), 7.71-7.67 (m, 2H), 7.64 (d, J = 4.8 Hz, 1H), 5.94 (br s, 1H), 4.94 (d, J = 6.0 Hz, 2H), 2.67 (s, 3H). | 449.0 |
| A-87 | 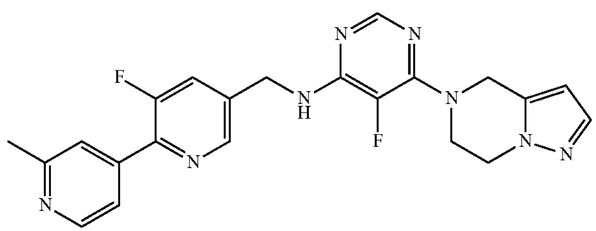 [SMILES: Cc1cc(-c2ncc(CNc3ncnc(N4CCn5nccc5C4)c3F)cc2F)ccn1] | A | ¹H NMR (400 MHz, CDCl₃) δ 8.60 (d, J = 5.2 Hz, 1H), 8.54 (s, 1H), 8.04 (s, 1H), 7.75 (s, 1H), 7.67 (d, J = 4.8 Hz, 1H), 7.54 (d, J = 11.6 Hz, 1H), 7.49 (s, 1H), 6.09 (s, 1H), 5.27 (s, 1H), 4.92 (s, 2H), 4.80 (d, J = 6.2 Hz, 2H), 4.31 (t, J = 5.2 Hz, 2H), 4.16 (t, J = 5.2 Hz, 2H), 2.64 (s, 3H). | 435.0 |
| A-88 | 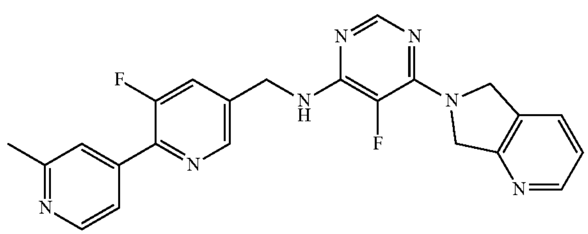 [SMILES: Cc1cc(-c2ncc(CNc3ncnc(N4Cc5cccnc5C4)c3F)cc2F)ccn1] | A | ¹H NMR (400 MHz, CDCl₃) δ 8.61 (d, J = 5.2 Hz, 1H), 8.58-8.50 (m, 2H), 8.07 (s, 1H), 7.76 (s, 1H), 7.66 (dd, J = 12.4, 6.0 Hz, 2H), 7.57 (d, J = 11.6 Hz, 1H), 7.22 (s, 1H), 5.19 (s, 1H), 5.06 (d, J = 8.2 Hz, 4H), 4.82 (d, J = 6.0 Hz, 2H), 2.64 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-89 | 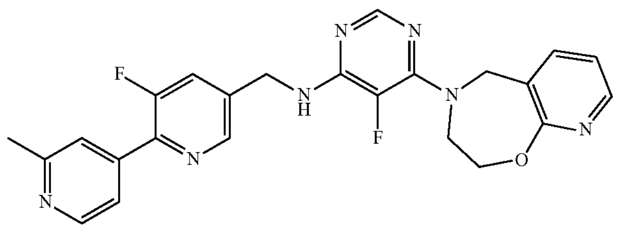 [SMILES: Cc1cc(-c2ncc(CNc3ncnc(N4CCOc5ncccc5C4)c3F)cc2F)ccn1] | A | ¹H NMR (400 MHz, CDCl₃) δ 8.60 (d, J = 5.2 Hz, 1H), 8.51 (s, 1H), 8.18 (d, J = 3.8 Hz, 1H), 7.95 (s, 1H), 7.74 (s, 1H), 7.68 (d, J = 9.0 Hz, 2H), 7.52 (d, J = 11.6 Hz, 1H), 7.08-6.92 (m, 1H), 5.15 (s, 1H), 4.79 (s, 2H), 4.75 (d, J = 6.2 Hz, 2H), 4.32 (d, J = 4.0 Hz, 2H), 4.21 (d, J = 3.8 Hz, 2H), 2.64 (s, 3H). | |
| A-90 | 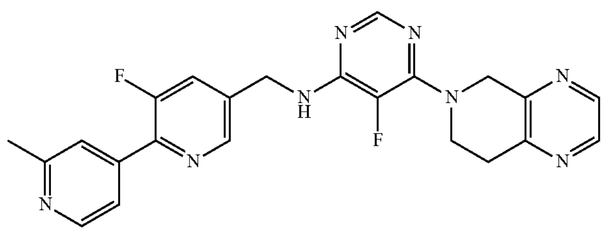 [SMILES: Cc1cc(-c2ncc(CNc3ncnc(N4CCc5nccnc5C4)c3F)cc2F)ccn1] | A | ¹H NMR (400 MHz, CDCl₃) δ 8.59 (d, J = 5.2 Hz, 1H), 8.53 (s, 1H), 8.41 (s, 2H), 8.21 (s, 1H), 8.04 (s, 1H), 7.75 (s, 1H), 7.67 (d, J = 4.8 Hz, 1H), 7.54 (d, J = 11.6 Hz, 1H), 5.30 (s, 1H), 4.98 (s, 2H), 4.79 (d, J = 6.2 Hz, 2H), 4.09 (t, J = 5.6 Hz, 2H), 3.17 (t, J = 5.6 Hz, 2H), 2.63 (s, 3H). | |
| A-91 | 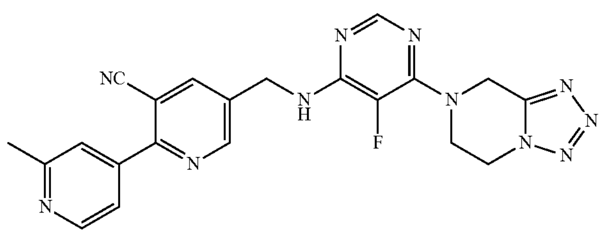 [SMILES: Cc1cc(-c2ncc(CNc3ncnc(N4CCn5nnnc5C4)c3F)cc2C#N)ccn1] | A | ¹H NMR (400 MHz, DMSO) δ 8.92 (s, 1H), 8.63 (d, J = 5.0 Hz, 1H), 8.34 (s, 1H), 7.95 (s, 2H), 7.67 (s, 1H), 7.61 (d, J = 4.8 Hz, 1H), 5.10 (s, 2H), 4.69 (d, J = 5.8 Hz, 2H), 4.53 (s, 2H), 4.15 (d, J = 4.8 Hz, 2H), 2.56 (s, 3H). | |
| A-92 | 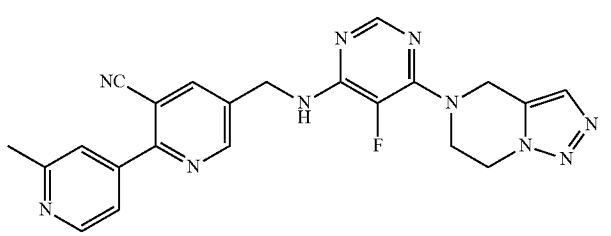 [SMILES: Cc1cc(-c2ncc(CNc3ncnc(N4CCn5nncc5C4)c3F)cc2C#N)ccn1] | A | ¹H NMR (400 MHz, DMSO) δ 8.92 (s, 1H), 8.63 (d, J = 4.6 Hz, 1H), 8.35 (s, 1H), 7.94 (s, 1H), 7.88 (s, 1H), 7.64 (m, 3H), 4.93 (s, 2H), 4.69 (d, J = 5.6 Hz, 2H), 4.47 (s, 2H), 4.10 (s, 2H), 2.56 (s, 3H) | |

TABLE 2-continued

Selected compounds (A-1 to A-202) of the present invention.

| Compd NO. | Structure | Method | 1HNMR | ESI-MS (m/z): [M + 1]+ |
|---|---|---|---|---|
| A-93 | 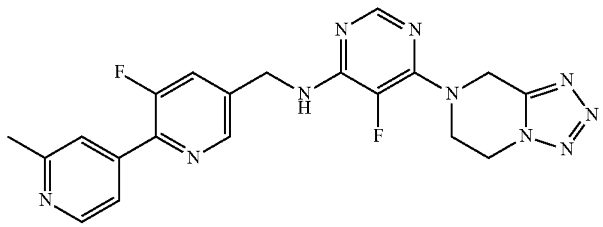 [SMILES: Cc1cc(-c2ncc(CNc3ncnc(N4CCn5nnnc5C4)c3F)cc2F)ccn1] | A | 1H NMR (400 MHz, CDCl3) δ 8.60 (d, J = 5.2 Hz, 1H), 8.55 (s, 1H), 8.06 (s, 1H), 7.75 (s, 1H), 7.67 (d, J = 4.6 Hz, 1H), 7.54 (d, J = 11.6 Hz, 1H), 5.52 (s, 1H), 5.18 (s, 2H), 4.81 (d, J = 6.2 Hz, 2H), 4.58 (m, 2H), 4.22 (m, 2H), 2.64 (s, 3H). | |
| A-94 | 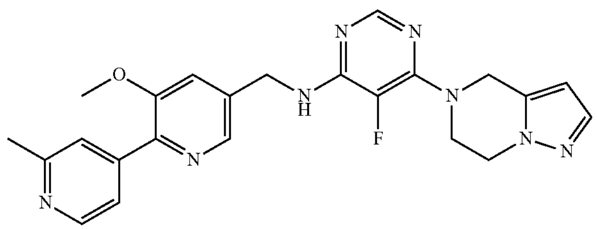 [SMILES: COc1cc(CNc2ncnc(N3CCn4nccc4C3)c2F)cnc1-c1ccnc(C)c1] | A | 1H NMR (400 MHz, CDCl3) δ 8.55 (d, J = 5.2 Hz, 1H), 8.31 (s, 1H), 8.06 (s, 1H), 7.70 (s, 1H), 7.65 (d, J = 4.8 Hz, 1H), 7.49 (s, 1H), 7.36 (s, 1H), 6.09 (s, 1H), 5.21 (s, 1H), 4.92 (s, 2H), 4.77 (d, J = 6.0 Hz, 2H), 4.31 (m, 2H), 4.16 (m, 2H), 3.88 (s, 3H), 2.62 (s, 3H). | |
| A-95 | 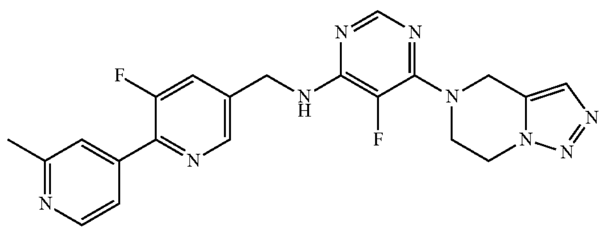 [SMILES: Cc1cc(-c2ncc(CNc3ncnc(N4CCn5nncc5C4)c3F)cc2F)ccn1] | A | 1H NMR (400 MHz, DMSO) δ 8.92 (s, 1H), 8.63 (d, J = 4.8 Hz, 1H), 8.35 (s, 1H), 7.94 (s, 1H), 7.88 (s, 1H), 7.64 (m, 3H), 4.93 (s, 2H), 4.69 (d, J = 5.6 Hz, 2H), 4.47 (s, 2H), 4.10 (s, 2H), 2.56 (s, 3H). | |
| A-96 | 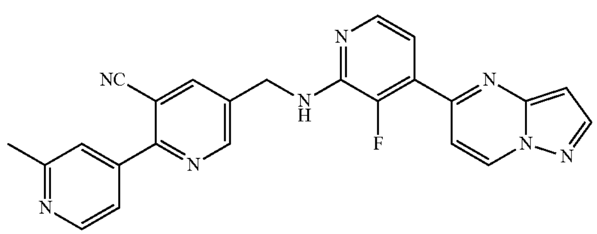 [SMILES: Cc1cc(-c2ncc(CNc3nccc(-c4ccn5nccc5n4)c3F)cc2C#N)ccn1] | A | 1H NMR (400 MHz, DMSO) δ 9.25 (d, J = 7.2 Hz, 1H), 8.85 (s, 1H), 8.63 (d, J = 5.0 Hz, 1H), 8.42-8.20 (m, 3H), 7.65 (m-4H), 7.53 (d, J = 7.2 Hz, 1H), 6.81 (s, 1H), 4.68 (s, 2H), 2.57 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-97 | 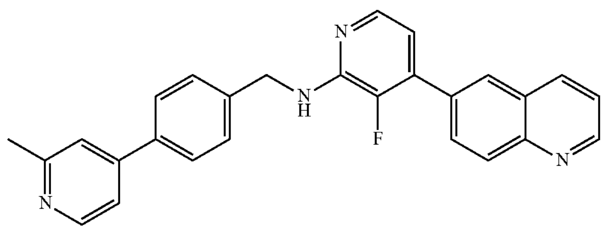 [SMILES: Cc1cc(-c2ccc(CNc3nccc(-c4ccc5ncccc5c4)c3F)cc2)ccn1] | A | ¹H NMR (400 MHz, CDCl₃) δ 8.98 (s, 1H), 8.54 (s, 1H), 8.22 (m, 2H), 8.06 (s, 1H), 8.02 (d, J = 5.2 Hz, 1H), 7.94 (d, J = 8.8 Hz, 1H), 7.63 (d, J = 7.8 Hz, 2H), 7.53 (d, J = 7.8 Hz, 2H), 7.47 (m, 4.0 Hz, 1H), 7.38 (s, 1H), 7.32 (s, 1H), 6.79 (m, 1H), 5.14 (s, 1H), 4.83 (d, J = 5.6 Hz, 2H), 2.63 (s, 3H). | |
| A-98 | 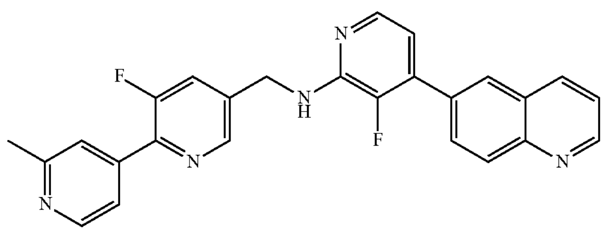 [SMILES: Cc1cc(-c2ncc(CNc3nccc(-c4ccc5ncccc5c4)c3F)cc2F)ccn1] | A | ¹H NMR (400 MHz, CDCl₃) δ 8.98 (d, J = 3.2 Hz, 1H), 8.62 (s, 2H), 8.22 (m, 2H), 8.06 (s, 1H), 8.00 (d, J = 5.2 Hz, 1H), 7.93 (d, J = 8.8 Hz, 1H), 7.78 (s, 1H), 7.70 (d, J = 5.0 Hz, 1H), 7.62 (d, J = 12 Hz, 1H), 7.48 (m, 4.2 Hz, 1H), 6.83 (m, 1H), 5.28 (s, 1H), 4.88 (d, J = 6.0 Hz, 2H), 2.65 (s, 3H). | 429.9 |
| A-99 | 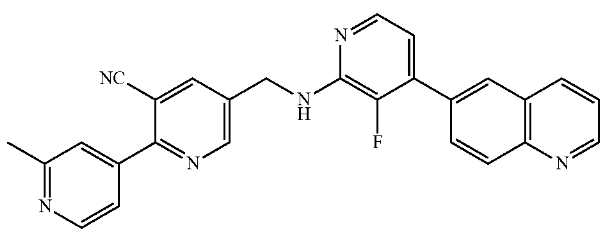 | A | ¹H NMR (400 MHz, CDCl₃) δ 8.97 (d, J = 9.6 Hz, 2H), 8.68 (d, J = 5.2 Hz, 1H), 8.22 (m, 3H), 8.07 (s, 1H), 7.98 (d, J = 5.2 Hz, 1H), 7.93 (d, J = 8.4 Hz, 1H), 7.69 (s, 1H), 7.64 (d, J = 4 Hz, 1H), 7.48 (m, 1H), 6.86 (m, 1H), 5.35 (s, 1H), 4.89 (d, J = 6.2 Hz, 2H), 2.67 (s, 3H). | |
| A-100 | 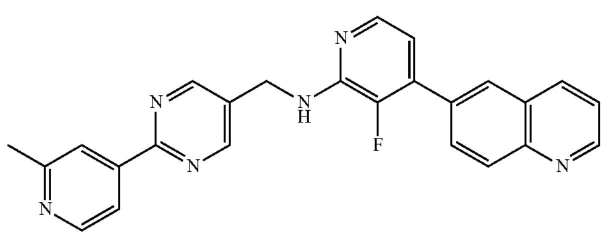 [SMILES: Cc1cc(-c2ncc(CNc3nccc(-c4ccc5ncccc5c4)c3F)cn2)ccn1] | A | ¹H NMR (400 MHz, CDCl₃) δ 8.98 (d, J = 2.6 Hz, 1H), 8.94 (s, 2H), 8.65 (d, J = 5.2 Hz, 1H), 8.20 (m, 3H), 8.07 (d, J = 17.8 Hz, 2H), 7.99 (d, J = 5.2 Hz, 1H), 7.92 (d, J = 8.4 Hz, 1H), 7.47 (m, 1H), 6.83 (m, 1H), 5.28 (s, 1H), 4.84 (d, J = 6.0 Hz, 2H), 2.68 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-101 | 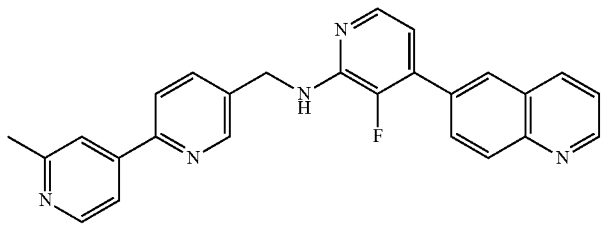 [SMILES: Cc1cc(-c2ccc(CNc3nccc(-c4ccc5ncccc5c4)c3F)cn2)ccn1] | A | ¹H NMR (400 MHz, CDCl₃) δ 8.98 (d, J = 4 Hz, 1H), 8.80 (s, 1H), 8.60 (d, J = 5.2 Hz, 1H), 8.22 (m, 2H), 8.06 (s, 1H), 8.00 (d, J = 5.2 Hz, 1H), 7.91 (m, 2H), 7.84-7.74 (m, 2H), 7.68 (d, J = 5.0 Hz, 1H), 7.47 (m, 1H), 6.81 (m, 1H), 5.21 (s, 1H), 4.86 (m, 2H), 2.66 (s, 3H). | |
| A-102 | 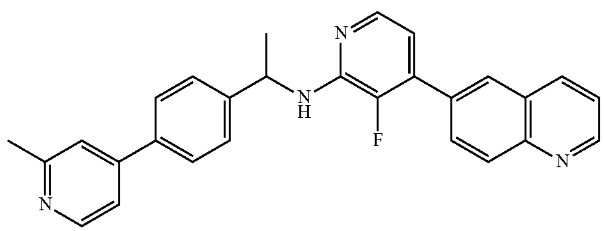 [SMILES: Cc1cc(-c2ccc(C(C)Nc3nccc(-c4ccc5ncccc5c4)c3F)cc2)ccn1] | A | ¹H NMR (400 MHz, CDCl₃) δ 8.97 (d, J = 2.8 Hz, 1H), 8.53 (d, J = 5.2 Hz, 1H), 8.27-8.15 (m, 2H), 8.04 (s, 1H), 7.95-7.89 (m, 2H), 7.62 (d, J = 8.0 Hz, 2H), 7.55 (d, J = 8.0 Hz, 2H), 7.47 (dd, J = 8.4, 4.4 Hz, 1H), 7.37 (s, 1H), 7.31 (d, J = 4.4 Hz, 1H), 6.76-6.70 (m, 1H), 5.48-5.39 (m, 1H), 5.06 (d, J = 5.6 Hz, 1H), 2.62 (s, 3H), 1.67 (d, J = 6.8 Hz, 3H). | 435.0 |
| A-103 | 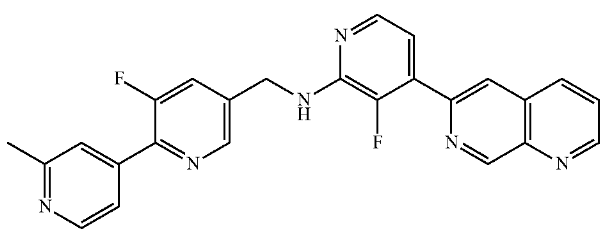 [SMILES: Cc1cc(-c2ncc(CNc3nccc(-c4cc5cccnc5cn4)c3F)cc2F)ccn1] | A | ¹H NMR (400 MHz, CDCl₃) δ 9.64 (s, 1H), 9.09 (d, J = 2.4 Hz, 1H), 8.61 (d, J = 4.8 Hz, 2H), 8.26 (d, J = 9.2 Hz, 2H), 8.05 (d, J = 5.2 Hz, 1H), 7.78 (s, 1H), 7.72-7.65 (m, 2H), 7.62 (d, J = 11.6 Hz, 1H), 7.41 (t, J = 5.2 Hz, 1H), 5.28 (s, 1H), 4.89 (d, J = 6.0 Hz, 2H), 2.65 (s, 3H). | 441.0 |
| A-104 | 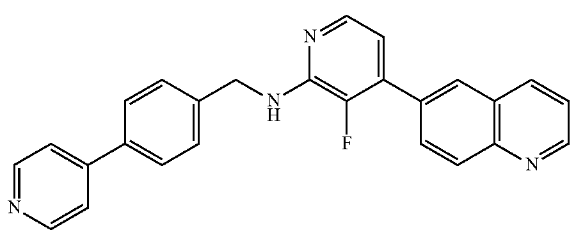 [SMILES: Fc1c(-c2ccc3ncccc3c2)ccnc1NCc1ccc(-c2ccncc2)cc1] | A | ¹H NMR (400 MHz, CDCl₃) δ 8.98 (d, J = 2.8 Hz, 1H), 8.66 (d, J = 6.0 Hz, 2H), 8.26-8.17 (m, 2H), 8.06 (s, 1H), 8.02 (d, J = 5.2 Hz, 1H), 7.94 (d, J = 8.8 Hz, 1H), 7.65 (d, J = 8.0 Hz, 2H), 7.58-7.50 (m, 4H), 7.47 (dd, J = 8.4, 4.4 Hz, 1H), 6.81-6.77 (m, 1H), 5.15 (s, 1H), 4.83 (d, J = 6.0 Hz, 2H). | 407.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-105 | 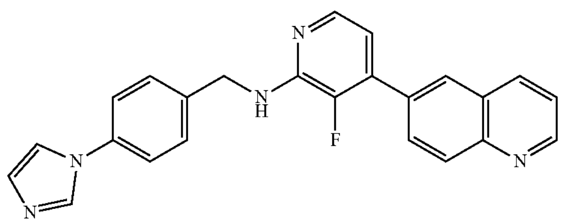 [SMILES: Fc1c(-c2ccc3ncccc3c2)ccnc1NCc1ccc(-n2ccnc2)cc1] | A | ¹H NMR (400 MHz, CDCl₃) δ 8.98 (d, J = 3.2 Hz, 1H), 8.26-8.18 (m, 2H), 8.06 (s, 2H), 8.00 (d, J = 5.2 Hz, 1H), 7.93 (d, J = 8.8 Hz, 1H), 7.55 (d, J = 8.0 Hz, 2H), 7.47 (dd, J = 8.0, 4.0 Hz, 1H), 7.39 (d, J = 8.4 Hz, 2H), 7.29 (d, J = 10.0 Hz, 2H), 6.83-6.77 (m, 1H), 5.19 (s, 1H), 4.83 (d, J = 6.0 Hz, 2H). | |
| A-106 | 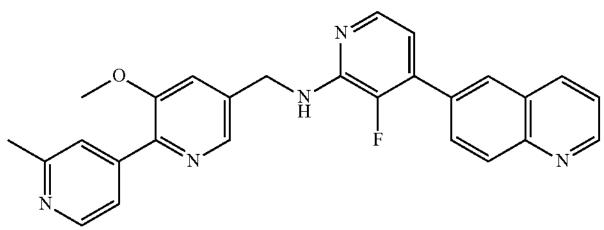 | A | ¹H NMR (400 MHz, CDCl₃) δ 8.98 (d, J = 3.6 Hz, 1H), 8.56 (d, J = 4.8 Hz, 1H), 8.39 (s, 1H), 8.26-8.18 (m, 2H), 8.06 (s, 1H), 8.02 (d, J = 5.2 Hz, 1H), 7.93 (d, J = 8.8 Hz, 1H), 7.72 (s, 1H), 7.67 (d, J = 4.8 Hz, 1H), 7.50-7.43 (m, 2H), 6.85-6.80 (m, 1H), 5.20 (s, 1H), 4.84 (d, J = 6.0 Hz, 2H), 3.90 (s, 3H), 2.62 (s, 3H). | 452.0 |
| A-107 | 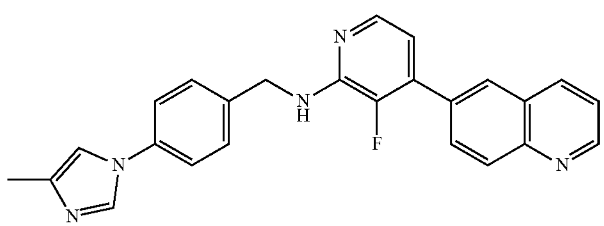 [SMILES: Cc1cn(-c2ccc(CNc3nccc(-c4ccc5ncccc5c4)c3F)cc2)cn1] | A | ¹H NMR (400 MHz, DMSO) δ 8.97 (d, J = 3.2 Hz, 1H), 8.48 (d, J = 8.0 Hz, 1H), 8.27 (s, 1H), 8.17-8.07 (m, 2H), 7.98 (d, J = 8.8 Hz, 1H), 7.90 (d, J = 5.2 Hz, 1H), 7.61 (dd, J = 8.0, 4.0 Hz, 1H), 7.53 (d, J = 8.4 Hz, 3H), 7.47 (d, J = 8.4 Hz, 2H), 7.41 (s, 1H), 6.83-6.77 (m, 1H), 4.65 (d, J = 5.6 Hz, 2H), 2.16 (s, 3H). | |
| A-108 | 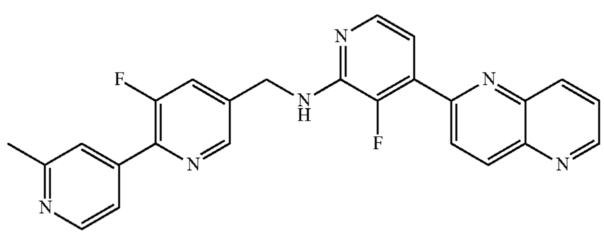 [SMILES: Cc1cc(-c2ncc(CNc3nccc(-c4ccc5ncccc5n4)c3F)cc2F)ccn1] | A | ¹H NMR (400 MHz, CDCl₃) δ 9.04 (s, 1H), 8.61 (s, 2H), 8.50 (dd, J = 13.2, 8.8 Hz, 2H), 8.13 (d, J = 8.4 Hz, 1H), 8.06 (d, J = 5.2 Hz, 1H), 7.81-7.67 (m, 3H), 7.61 (d, J = 11.6 Hz, 1H), 7.32-7.29 (m, 1H), 5.31 (s, 1H), 4.88 (d, J = 5.6 Hz, 2H), 2.64 (s, 3H). | 441.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-109 | 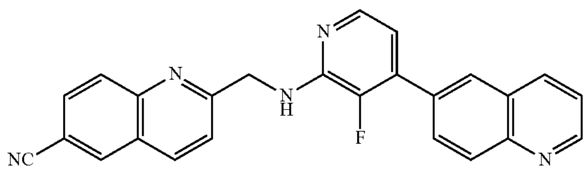 [SMILES: N#Cc1ccc2nc(CNc3nccc(-c4ccc5ncccc5c4)c3F)ccc2c1] | A | ¹H NMR (400 MHz, CDCl₃) δ 8.99 (d, J = 4.4 Hz, 1H), 8.19-8.25 (m, 5H), 8.11 (s, 1H), 8.02 (d, J = 5.2 Hz, 1H), 7.97 (d, J = 8.8 Hz, 1H), 7.88 (d, J = 8.8 Hz, 1H), 7.61 (d, J = 8.4 Hz, 1H), 7.52-7.45 (m, 1H), 6.82 (d, J = 5.2 Hz, 1H), 6.38 (s, 1H), 5.08 (d, J = 4.8 Hz, 2H). | |
| A-110 | 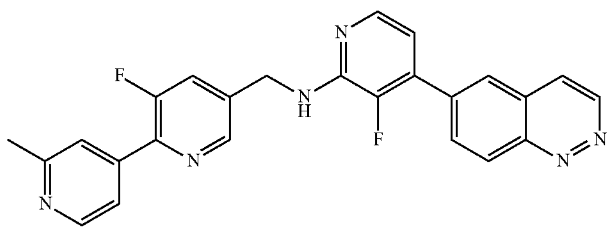 [SMILES: Cc1cc(-c2ncc(CNc3nccc(-c4ccc5nnccc5c4)c3F)cc2F)ccn1] | A | ¹H NMR (400 MHz, CDCl₃) δ 9.39 (d, J = 5.6 Hz, 1H), 8.65 (d, J = 8.8 Hz, 1H), 8.62 (s, 2H), 8.08-8.01 (m, 3H), 7.93 (d, J = 6.0 Hz, 1H), 7.78 (s, 1H), 7.70 (d, J = 4.0 Hz, 1H), 7.62 (d, J = 11.6 Hz, 1H), 6.84-6.79 (m, 1H), 5.33 (s, 1H), 4.88 (d, J = 6.0 Hz, 2H), 2.66 (s, 3H). | 441.0 |
| A-111 | 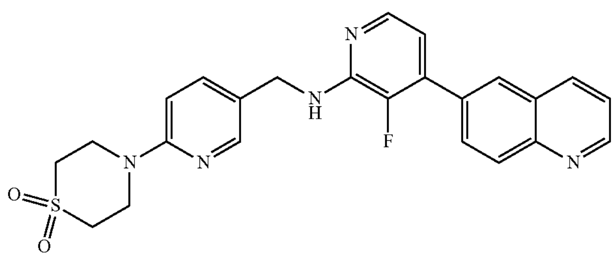 [SMILES: O=S1(=O)CCN(c2ccc(CNc3nccc(-c4ccc5ncccc5c4)c3F)cn2)CC1] | A | ¹H NMR (400 MHz, CDCl₃) δ 8.97 (d, J = 3.2 Hz, 1H), 8.28 (s, 1H), 8.24-8.16 (m, 2H), 8.04 (s, 1H), 8.01 (d, J = 5.2 Hz, 1H), 7.92 (d, J = 8.8 Hz, 1H), 7.66 (d, J = 7.2 Hz, 1H), 7.47 (dd, J = 8.4, 4.4 Hz, 1H), 6.82-6.72 (m, 2H), 5.01 (s, 1H), 4.66 (d, J = 5.6 Hz, 2H), 4.17 (s, 4H), 3.05 (s, 4H). | |
| A-112 | 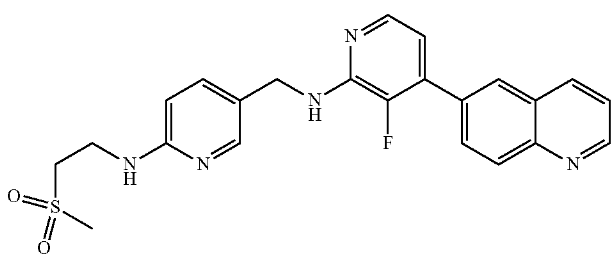 [SMILES: CS(=O)(=O)CCNc1ccc(CNc2nccc(-c3ccc4ncccc4c3)c2F)cn1] | A | ¹H NMR (400 MHz, CDCl₃) δ 8.97 (d, J = 3.2 Hz, 1H), 8.24-8.14 (m, 3H), 8.04 (s, 1H), 8.01 (d, J = 5.2 Hz, 1H), 7.91 (d, J = 8.8 Hz, 1H), 7.52 (d, J = 6.8 Hz, 1H), 7.46 (dd, J = 8.4, 4.0 Hz, 1H), 6.80-6.74 (m, 1H), 6.47 (d, J = 8.4 Hz, 1H), 4.94 (d, J = 6.0 Hz, 2H), 4.60 (d, J = 5.6 Hz, 2H), 3.95 (q, J = 6.0 Hz, 2H), 3.39 (t, J = 5.6 Hz, 2H), 2.95 (s, 3H). | 452.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-113 | 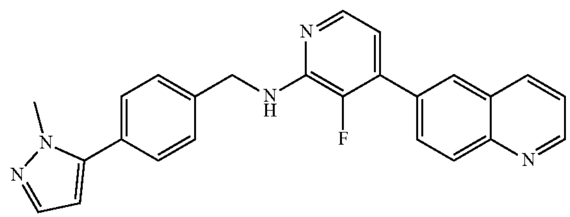 [SMILES: Cn1nccc1-c1ccc(CNc2nccc(-c3ccc4ncccc4c3)c2F)cc1] | A | ¹H NMR (400 MHz, CDCl₃) δ 8.98 (d, J = 3.2 Hz, 1H), 8.26-8.18 (m, 2H), 8.06 (s, 1H), 8.02 (d, J = 5.2 Hz, 1H), 7.94 (d, J = 8.8 Hz, 1H), 7.51 (d, J = 6.4 Hz, 3H), 7.47 (dd, J = 8.0, 4.0 Hz, 1H), 7.42 (d, J = 8.0 Hz, 2H), 6.82-6.77 (m, 1H), 6.31 (s, 1H), 5.15 (s, 1H), 4.83 (d, J = 5.6 Hz, 2H), 3.90 (s, 3H). | |
| A-114 | 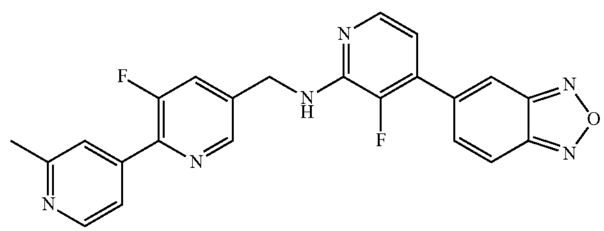 [SMILES: Cc1cc(-c2ncc(CNc3nccc(-c4ccc5nonc5c4)c3F)cc2F)ccn1] | A | ¹H NMR (400 MHz, CDCl₃) δ 8.61 (d, J = 5.2 Hz, 2H), 8.06 (s, 1H), 8.02 (d, J = 5.2 Hz, 1H), 7.96 (d, J = 9.2 Hz, 1H), 7.77 (s, 1H), 7.69 (d, J = 4.8 Hz, 1H), 7.61 (d, J = 10.8 Hz, 2H), 6.77-6.72 (m, 1H), 5.32 (s, 1H), 4.87 (d, J = 6.0 Hz, 2H), 2.65 (s, 3H). | |
| A-115 | 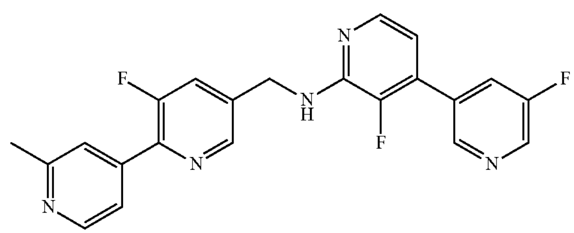 [SMILES: Cc1cc(-c2ncc(CNc3nccc(-c4cncc(F)c4)c3F)cc2F)ccn1] | A | ¹H NMR (400 MHz, CDCl₃) δ 8.67 (s, 1H), 8.61 (d, J = 6.0 Hz, 2H), 8.55 (s, 1H), 8.00 (d, J = 5.2 Hz, 1H), 7.77 (s, 1H), 7.69 (d, J = 4.0 Hz, 1H), 7.65 (d, J = 9.2 Hz, 1H), 7.60 (d, J = 11.6 Hz, 1H), 6.73-6.68 (m, 1H), 5.30 (s, 1H), 4.85 (d, J = 6.0 Hz, 2H), 2.65 (s, 3H). | |
| A-116 | 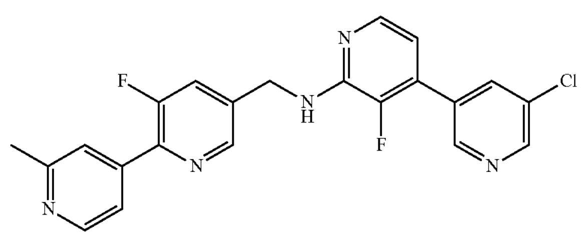 [SMILES: Cc1cc(-c2ncc(CNc3nccc(-c4cncc(Cl)c4)c3F)cc2F)ccn1] | A | ¹H NMR (400 MHz, CDCl₃) δ 8.71 (s, 1H), 8.65-8.57 (m, 3H), 7.99 (d, J = 5.2 Hz, 1H), 7.90 (s, 1H), 7.77 (s, 1H), 7.69 (d, J = 4.4 Hz, 1H), 7.59 (d, J = 11.6 Hz, 1H), 6.71-6.65 (m, 1H), 5.28 (s, 1H), 4.85 (d, J = 6.0 Hz, 2H), 2.65 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-117 | 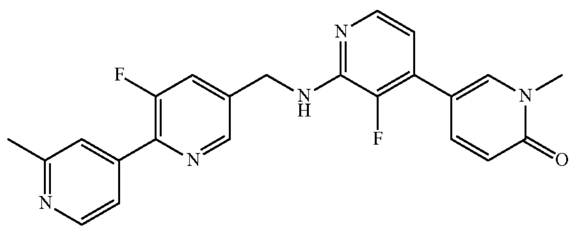 | A | ¹H NMR (400 MHz, CDCl₃) δ 8.61 (d, J = 5.2 Hz, 1H), 8.58 (s, 1H), 7.91 (d, J = 5.2 Hz, 1H), 7.77 (s, 1H), 7.68 (s, 2H), 7.62-7.55 (m, 2H), 6.68 (d, J = 9.6 Hz, 1H), 6.62-6.58 (m, 1H), 5.20 (s, 1H), 4.83 (d, J = 6.0 Hz, 2H), 3.63 (s, 3H), 2.65 (s, 3H). | |
| A-118 | | A | ¹H NMR (400 MHz, CDCl₃) δ 9.27 (d, J = 2.0 Hz, 1H), 8.98 (d, J = 4.0 Hz, 1H), 8.65 (d, J = 2.0 Hz, 1H), 8.21-8.26 (m, 2H), 8.16 (s, 1H), 8.08 (s, 1H), 7.99 (d, J = 5.2 Hz, 1H), 7.97-7.89 (m, 2H), 7.70 (d, J = 4.8 Hz, 1H), 7.46-7.49 (m, 1H), 6.80 (t, J = 6.8 Hz, 1H), 5.34 (s, 1H), 5.05 (d, J = 6.0 Hz, 2H). | |
| A-119 | 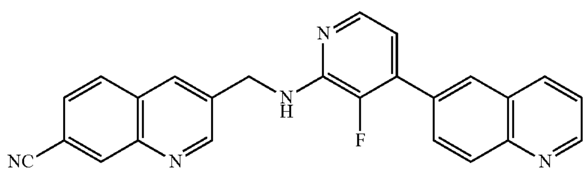 [SMILES: N#Cc1ccc2cc(CNc3nccc(-c4ccc5ncccc5c4)c3F)cnc2c1] | A | ¹H NMR (400 MHz, CDCl₃) δ 9.12 (s, 1H), 8.99 (d, J = 2.0 Hz 1H), 8.48 (s, 1H), 8.27-8.18 (m, 3H), 8.07 (s, 1H), 7.99 (d, J = 5.2 Hz, 1H), 7.92 (t, J = 8.6 Hz, 2H), 7.70 (d, J = 8.4 Hz, 1H), 7.5-7.46 (m, 1H), 6.83 (t, J = 5.2 Hz, 1H), 5.34 (s, 1H), 5.01 (d, J = 6.0 Hz, 3H). | |
| A-120 | 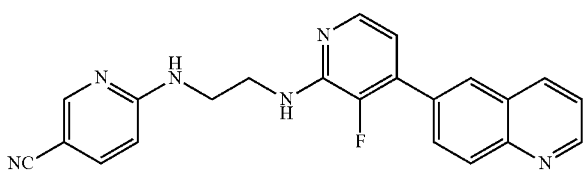 [SMILES: N#Cc1ccc(NCCNc2nccc(-c3ccc4ncccc4c3)c2F)nc1] | A | ¹H NMR (400 MHz, CDCl₃) δ 8.98 (d, J = 2.8 Hz, 1H), 8.39 (s, 1H), 8.24 (d, J = 8.4 Hz, 1H), 8.20 (d, J = 8.8 Hz, 1H), 8.04 (s, 1H), 8.00 (d, J = 5.2 Hz, 1H), 7.90 (d, J = 8.8 Hz, 1H), 7.53 (d, J = 8.8 Hz, 1H), 7.48 (dd, J = 8.2, 4.2 Hz, 1H), 6.79 (t, J = 5.2 Hz, 1H), 6.41 (d, J = 9.2 Hz, 1H), 6.30 (s, 1H), 5.35 (s, 1H), 3.84 (m, 2H), 3.69 (m, 2H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-121 | 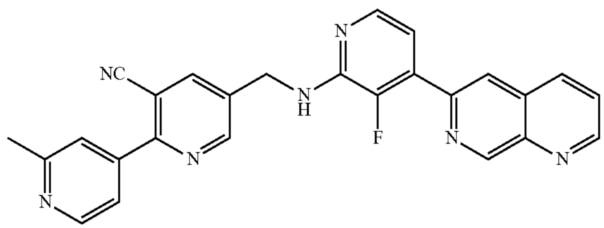 [SMILES: Cc1cc(-c2ncc(CNc3nccc(-c4cc5cccnc5cn4)c3F)cc2C#N)ccn1] | A | ¹H NMR (400 MHz, DMSO) δ 9.54 (s, 1H), 9.13 (d, J = 3.2 Hz, 1H), 8.99 (s, 1H), 8.64 (d, J = 4.8 Hz, 1H), 8.60 (d, J = 8.4 Hz, 1H), 8.47 (s, 1H), 8.43 (s, 1H), 7.95 (d, J = 5.2 Hz, 1H), 7.86 (dd, J = 8.4, 4.4 Hz, 1H), 7.69 (s, 1H), 7.64 (d, J = 5.2 Hz, 2H), 7.26-7.20 (m, 1H), 4.77 (d, J = 5.6 Hz, 2H), 2.57 (s, 3H). | 448.0 |
| A-122 | 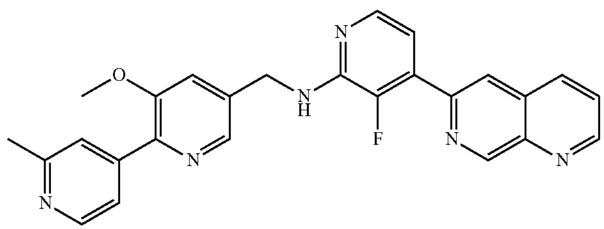 [SMILES: COc1cc(CNc2nccc(-c3cc4cccnc4cn3)c2F)cnc1-c1ccnc(C)c1] | A | ¹H NMR (400 MHz, DMSO) δ 9.54 (s, 1H), 9.13 (d, J = 3.6 Hz, 1H), 8.60 (d, J = 8.0 Hz, 1H), 8.47 (d, J = 7.2 Hz, 2H), 8.32 (s, 1H), 7.96 (d, J = 5.2 Hz, 1H), 7.86 (dd, J = 8.0, 4.0 Hz, 1H), 7.73 (s, 1H), 7.66 (s, 2H), 7.60-7.54 (m, 1H), 7.23-7.19 (m, 1H), 4.72 (d, J = 5.6 Hz, 2H), 3.88 (s, 3H), 2.51 (s, 3H). | 452.9 |
| A-123 | | A | ¹H NMR (400 MHz, DMSO) δ 9.30 (s, 1H), 8.61 (d, J = 6.0 Hz, 2H), 8.57 (d, J = 5.2 Hz, 1H), 7.99 (d, J = 9.2 Hz, 1H), 7.95-7.87 (m, 2H), 7.82 (d, J = 12.2 Hz, 1H), 7.74 (s, 1H), 7.66 (d, J = 5.2 Hz, 2H), 6.87 (t, J = 5.0 Hz, 1H), 4.72 (d, J = 5.8 Hz, 2H), 2.55 (s, 3H). | 430.0 |
| A-124 | | A | ¹H NMR (400 MHz, CDCl₃) δ 8.91 (s, 2H), 8.61 (d, J = 5.2 Hz, 2H), 8.36 (s, 1H), 8.22 (d, J = 8.8 Hz, 1H), 8.01 (t, J = 7.6 Hz, 2H), 7.77 (s, 1H), 7.69 (d, J = 4.8 Hz, 1H), 7.63 (d, J = 11.6 Hz, 1H), 6.85 (t, J = 5.2 Hz, 1H), 5.31 (s, 1H), 4.88 (d, J = 5.8 Hz, 2H), 2.65 (s, 3H). | 440.9 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-125 | 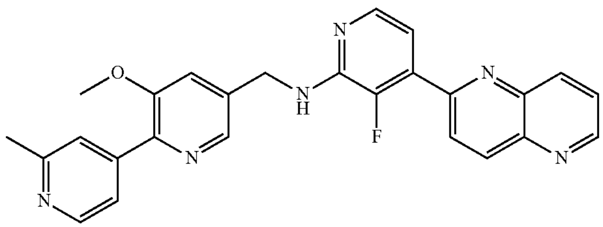 [SMILES: COc1cc(CNc2nccc(-c3ccc4ncccc4n3)c2F)cnc1-c1ccnc(C)c1] | A | ¹H NMR (400 MHz, CDCl₃) δ 9.02 (s, 1H), 8.51 (d, J = 10.3 Hz, 3H), 8.38 (s, 1H), 8.09 (d, J = 9.2 Hz, 2H), 7.69 (s, 3H), 7.44 (s, 1H), 7.26 (s, 1H), 5.28 (s, 1H), 4.83 (s, 2H), 3.88 (s, 3H), 2.62 (s, 3H). | 453.0 |
| A-126 | 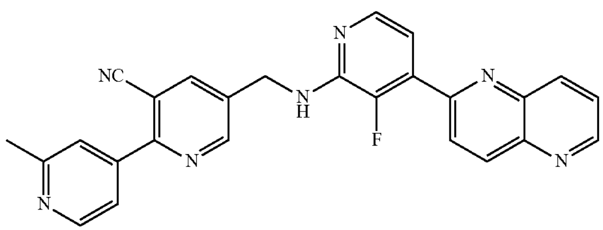 [SMILES: Cc1cc(-c2ncc(CNc3nccc(-c4ccc5ncccc5n4)c3F)cc2C#N)ccn1] | A | ¹H NMR (400 MHz, CDCl₃) δ 8.98 (d, J = 3.4 Hz, 1H), 8.91 (s, 1H), 8.62 (d, J = 5.2 Hz, 1H), 8.45 (m, 2H), 8.12 (s, 1H), 8.08 (d, J = 8.6 Hz, 1H), 7.99 (d, J = 5.2 Hz, 1H), 7.65 (m, 2H), 7.58 (d, J = 4.8 Hz, 1H), 7.28 (m, 1H), 5.33 (s, 1H), 4.84 (d, J = 6.0 Hz, 2H), 2.62 (s, 3H). | 447.9 |
| A-127 | 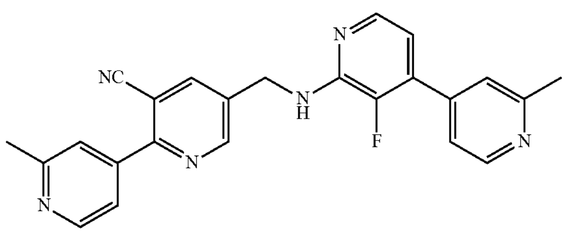 | A | ¹H NMR (400 MHz, CDCl₃) δ 8.94 (s, 1H), 8.68 (s, 1H), 8.61 (s, 1H), 8.16 (s, 1H), 7.96 (s, 1H), 7.68 (s, 1H), 7.64 (s, 1H), 7.35 (s, 1H), 7.29 (s, 1H), 6.73 (s, 1H), 5.34 (s, 1H), 4.87 (d, J = 4.4 Hz, 2H), 2.66 (d, J = 10.6 Hz, 6H). | 411.0 |
| A-128 | 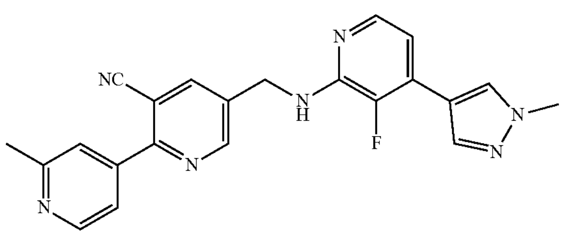 | A | ¹H NMR (400 MHz, CDCl₃) δ 8.93 (s, 1H), 8.67 (d, J = 5.2 Hz, 1H), 8.15 (s, 1H), 7.90 (s, 1H), 7.83 (d, J = 5.6 Hz, 2H), 7.67 (s, 1H), 7.63 (d, J = 4.8 Hz, 1H), 7.52 (s, 1H), 6.81 (t, J = 5.2 Hz, 1H), 5.23 (s, 1H), 4.84 (d, J = 6.0 Hz, 2H), 3.96 (d, J = 17.6 Hz, 3H), 2.66 (s, 3H). | |

TABLE 2-continued

Selected compounds (A-1 to A-202) of the present invention.

| Compd NO. | Structure | Method | $^1$HNMR | ESI-MS (m/z): [M + 1]$^+$ |
|---|---|---|---|---|
| A-129 | 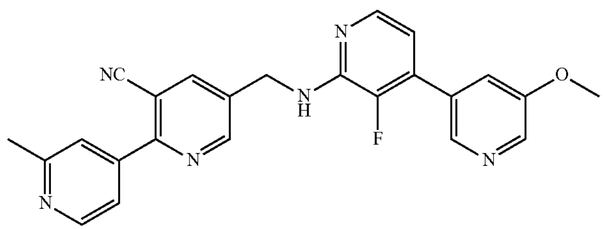 | A | $^1$H NMR (400 MHz, CDCl$_3$) δ 8.94 (s, 1H), 8.67 (d, J = 5.2 Hz, 1H), 8.44 (s, 1H), 8.38 (s, 1H), 8.16 (s, 1H), 7.96 (d, J = 5.2 Hz, 1H), 7.68 (s, 1H), 7.63 (d, J = 4.8 Hz, 1H), 7.40 (s, 1H), 6.74 (t, J = 5.0 Hz, 1H), 5.34 (s, 1H), 4.87 (d, J = 6 Hz, 2H), 3.93 (s, 3H), 2.67 (s, 3H). | 427.0 |
| A-130 | 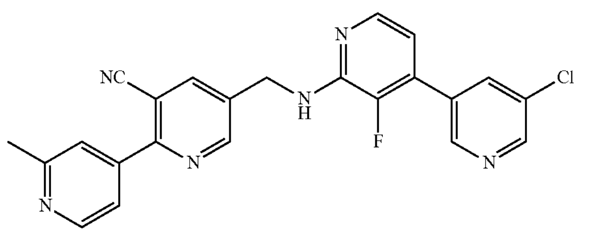 [SMILES: Cc1cc(-c2ncc(CNc3nccc(-c4cncc(Cl)c4)c3F)cc2C#N)ccn1] | A | $^1$H NMR (400 MHz, CDCl$_3$) δ 8.94 (s, 1H), 8.72 (s, 1H), 8.68 (d, J = 4.8 Hz, 1H), 8.64 (s, 1H), 8.15 (s, 1H), 7.98 (d, J = 5.0 Hz, 1H), 7.91 (s, 1H), 7.68 (s, 1H), 7.63 (d, J = 4.6 Hz, 1H), 6.72 (d, J = 4.8 Hz, 1H), 5.37 (s, 1H), 4.87 (d, J = 5.8 Hz, 2H), 2.67 (s, 3H). | |
| A-131 | 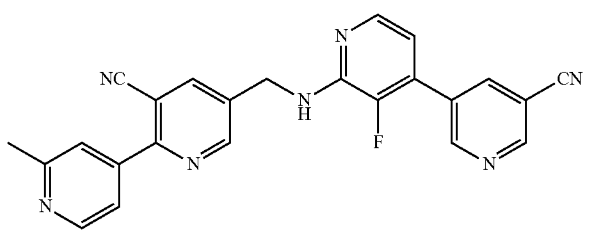 [SMILES: Cc1cc(-c2ncc(CNc3nccc(-c4cncc(C#N)c4)c3F)cc2C#N)ccn1] | A | $^1$H NMR (400 MHz, CDCl$_3$) δ 9.03 (s, 1H), 8.95 (s, 2H), 8.68 (d, J = 4.6 Hz, 1H), 8.17 (d, J = 14.4 Hz, 2H), 8.02 (d, J = 4.8 Hz, 1H), 7.69 (s, 1H), 7.64 (s, 1H), 6.72 (s, 1H), 5.41 (s, 1H), 4.88 (d, J = 5.8 Hz, 2H), 2.68 (s, 3H). | |
| A-132 | 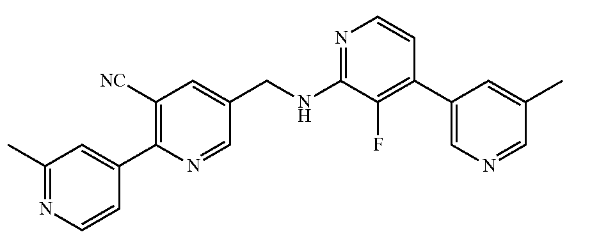 | A | $^1$H NMR (400 MHz, CDCl$_3$) δ 8.94 (s, 1H), 8.81-8.59 (m, 2H), 8.51 (s, 1H), 8.16 (s, 1H), 7.95 (d, J = 5.2 Hz, 1H), 7.69 (d, J = 10.2 Hz, 2H), 7.63 (d, J = 4.8 Hz, 1H), 6.73 (t, J = 5.2 Hz, 1H), 5.33 (s, 1H), 4.86 (d, J = 6.0 Hz, 2H), 2.67 (s, 3H), 2.43 (s, 3H). | 411.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-133 | 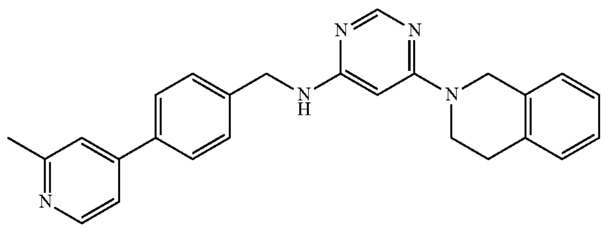 | A | ¹H NMR (400 MHz, CDCl₃) δ 8.53 (s, 1H), 8.22 (s, 1H), 7.61 (d, J = 7.2 Hz, 2H), 7.45 (d, J = 7.2 Hz, 2H), 7.36 (s, 1H), 7.30 (s, 1H), 7.17 (s, 4H), 5.44 (s, 1H), 5.20 (s, 1H), 4.64 (s, 2H), 4.56 (s, 2H), 3.77 (s, 2H), 2.91 (s, 2H), 2.61 (s, 3H). | 408.0 |
| A-134 | 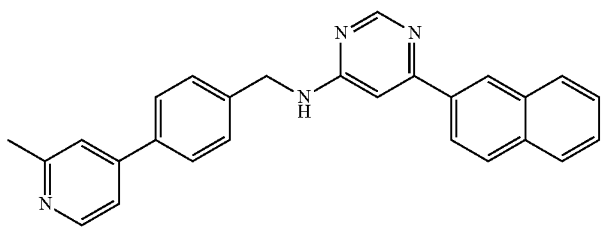 [SMILES: Cc1cc(-c2ccc(CNc3cc(-c4ccc5ccccc5c4)ncn3)cc2)ccn1] | A | ¹H NMR (400 MHz, CDCl₃) δ 8.76 (s, 1H), 8.54 (d, J = 5.2 Hz, 1H), 8.51 (s, 1H), 8.02 (d, J = 8.8 Hz, 1H), 7.93 (t, J = 8.0 Hz, 2H), 7.90-7.85 (m, 1H), 7.65 (s, 1H), 7.63 (s, 1H), 7.54 (t, J = 5.0 Hz, 1H), 7.51 (s, 2H), 7.49 (s, 1H), 7.37 (s, 1H), 7.31 (d, J = 5.2 Hz, 1H), 6.89 (s, 1H), 5.45 (s, 1H), 4.74 (d, J = 5.6 Hz, 2H), 2.62 (s, 3H). | 403.0 |
| A-135 | 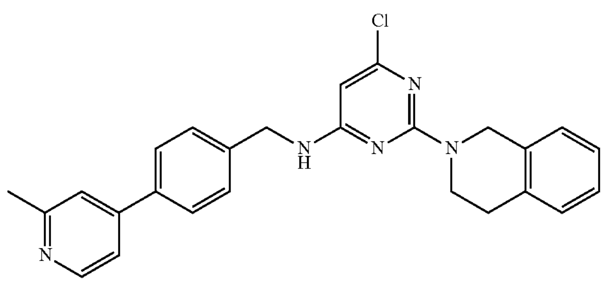 [SMILES: Cc1cc(-c2ccc(CNc3cc(Cl)nc(N4CCc5ccccc5C4)n3)cc2)ccn1] | A | ¹H NMR (400 MHz, CDCl₃) δ 8.54 (d, J = 5.2 Hz, 1H), 7.61 (d, J = 8.0 Hz, 2H), 7.44 (d, J = 8.0 Hz, 2H), 7.36 (s, 1H), 7.30 (d, J = 5.2 Hz, 1H), 7.16 (brs, 4H), 5.74 (s, 1H), 5.12 (brs, 1H), 4.85 (s, 2H), 4.61 (brs, 2H), 3.99 (t, J = 5.8 Hz, 2H), 2.88 (t, J = 5.4 Hz, 2H), 2.62 (s, 3H). | 442.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-136 | 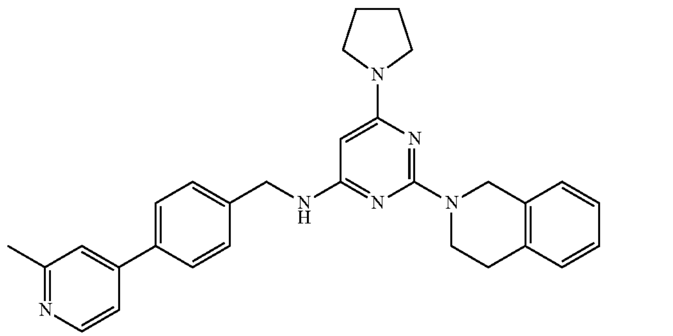 [SMILES: Cc1cc(-c2ccc(CNc3cc(N4CCCC4)nc(N4CCc5ccccc5C4)n3)cc2)ccn1] | A | ¹H NMR (400 MHz, CDCl₃) δ 8.53 (d, J = 5.2 Hz, 1H), 7.58 (d, J = 8.0 Hz, 2H), 7.46 (d, J = 8.0 Hz, 2H), 7.36 (s, 1H), 7.30 (d, J = 5.2 Hz, 1H), 7.18-7.10 (m, 4H), 4.88 (s, 2H), 4.76 (s, 2H), 4.53 (d, J = 5.6 Hz, 2H), 4.01 (t, J = 5.6 Hz, 2H), 3.41 (s, 4H), 2.87 (t, J = 5.6 Hz, 2H), 2.62 (s, 3H), 1.92 (s, 4H). | 477.1 |
| A-137 | 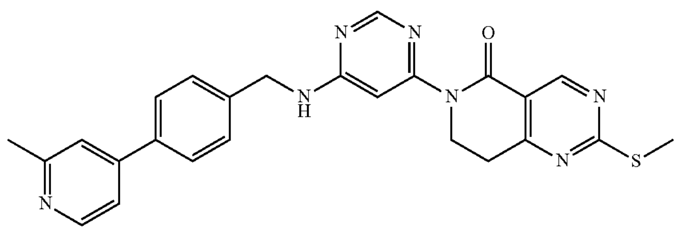 | A | ¹H NMR (400 MHz, CDCl₃) δ 9.09 (s, 1H), 8.54 (d, J = 5.2 Hz, 1H), 8.49 (s, 1H), 7.63 (d, J = 8.0 Hz, 2H), 7.47 (d, J = 8.0 Hz, 2H), 7.39 (s, 1H), 7.38 (s, 1H), 7.32 (d, J = 4.8 Hz, 1H), 5.36 (br s, 1H), 4.68 (s, 2H), 4.44 (t, J = 6.0 Hz, 2H), 3.15 (t, J = 6.8 Hz, 2H), 2.64 (s, 6H). | 470.0 |
| A-138 | 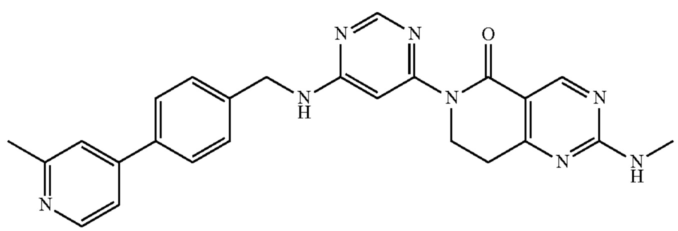 | A | ¹H NMR (400 MHz, CDCl₃) δ 8.98 (s, 0.4H), 8.84 (s, 0.6H), 8.60-8.55 (m, 1H), 8.46 (s, 1H), 7.61 (d, J = 8.0 Hz, 2H), 7.45 (d, J = 8.0 Hz, 2H), 7.40-7.30 (m, 2H), 7.27 (s, 1H), 5.73-5.51 (m, 1H), 5.38 (br s, 1H), 4.65 (s, 2H), 4.37 (s, 2H), 3.09 (s, 3H), 3.09-2.88 (m, 2H), 2.62 (s, 3H). | 453.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-139 | 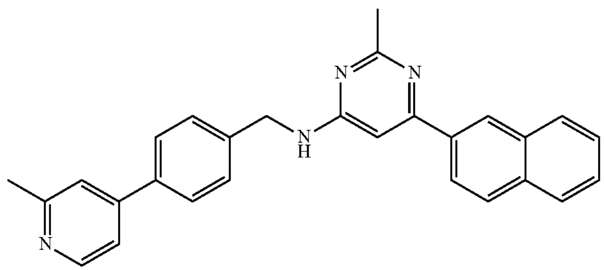 [SMILES: Cc1cc(-c2ccc(CNc3cc(-c4ccc5ccccc5c4)nc(C)n3)cc2)ccn1] | A | ¹H NMR (400 MHz, CDCl₃) δ 8.53 (d, J = 5.2 Hz, 1H), 8.47 (s, 1H), 8.00 (m, 1H), 7.89 (m, 3H), 7.63 (d, J = 8.4 Hz, 2H), 7.54-7.47 (m, 4H), 7.36 (s, 1H), 7.30 (d, J = 4.0 Hz, 1H), 6.67 (s, 1H), 5.49 (s, 1H), 4.70 (d, J = 6.0 Hz, 2H), 2.66 (s, 3H), 2.62 (s, 3H). | 417.0 |
| A-140 | 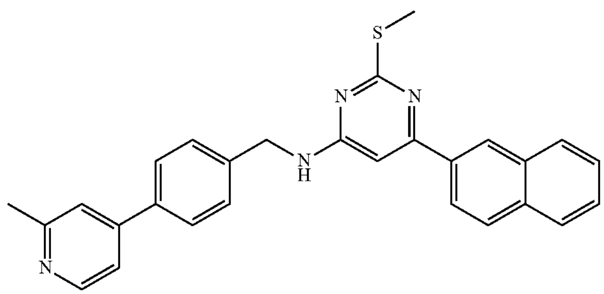 [SMILES: CSc1nc(NCc2ccc(-c3ccnc(C)c3)cc2)cc(-c2ccc3ccccc3c2)n1] | A | ¹H NMR (400 MHz, CDCl₃) δ 8.54 (d, J = 5.2 Hz, 1H), 8.50 (s, 1H), 8.05-8.03 (m, 1H), 7.96-7.82 (m, 3H), 7.62 (d, J = 8.4 Hz, 2H), 7.55-7.49 (m, 2H), 7.47 (d, J = 8.4 Hz, 2H), 7.36 (s, 1H), 7.30 (d, J = 4.0 Hz, 1H), 6.58 (s, 1H), 5.38 (s, 1H), 4.72 (d, J = 4.4 Hz, 2H), 2.63 (s, 3H), 2.62 (s, 3H). | 449.0 |
| A-141 | 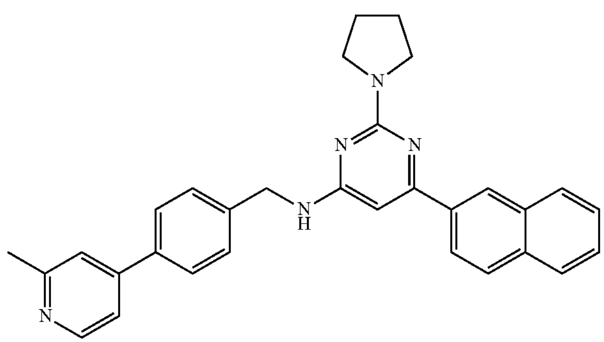 [SMILES: Cc1cc(-c2ccc(CNc3cc(-c4ccc5ccccc5c4)nc(N4CCCC4)n3)cc2)ccn1] | A | ¹H NMR (400 MHz, CDCl₃) δ 8.53 (d, J = 5.2 Hz, 1H), 8.48 (s, 1H), 8.09 (d, J = 8.4 Hz, 1H), 7.94-7.81 (m, 3H), 7.61 (d, J = 8.0 Hz, 2H), 7.51-7.47 (m, 4H), 7.36 (s, 1H), 7.30 (d, J = 5.2 Hz, 1H), 6.27 (s, 1H), 5.08 (s, 1H), 4.71 (d, J = 6.0 Hz, 2H), 3.69 (s, 4H), 2.62 (s, 3H), 1.99 (t, J = 6.5 Hz, 4H). | 472.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-142 | 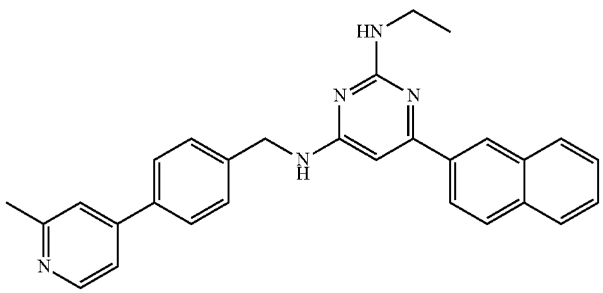 [SMILES: CCNc1nc(NCc2ccc(-c3ccnc(C)c3)cc2)cc(-c2ccc3ccccc3c2)n1] | A | ¹H NMR (400 MHz, CDCl₃) δ 8.54 (d, J = 4.8 Hz, 1H), 8.45 (s, 1H), 8.01 (d, J = 8.0 Hz, 1H), 7.95-7.82 (m, 3H), 7.62 (d, J = 8.4 Hz, 2H), 7.49 (d, J = 7.6 Hz, 4H), 7.37 (s, 1H), 7.31 (d, J = 5.2 Hz, 1H), 6.29 (s, 1H), 5.10 (s, 1H), 4.95 (s, 1H), 4.70 (d, J = 5.2 Hz, 2H), 3.54 (s, 2H), 2.62 (s, 3H), 1.26 (t, J = 7.0 Hz, 3H). | 446.1 |
| A-143 | 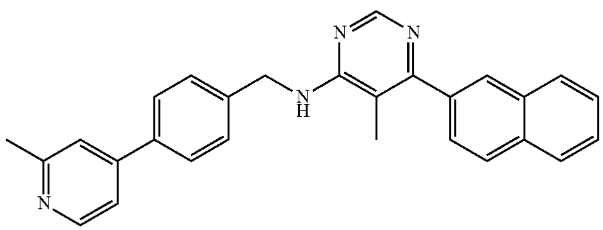 [SMILES: Cc1cc(-c2ccc(CNc3ncnc(-c4ccc5ccccc5c4)c3C)cc2)ccn1] | A | ¹H NMR (400 MHz, CDCl₃) δ 8.68 (s, 1H), 8.55 (d, J = 5.2 Hz, 1H), 7.99 (s, 1H), 7.96-7.86 (m, 3H), 7.64 (d, J = 8.0 Hz, 3H), 7.52 (t, J = 6.8 Hz, 4H), 7.37 (s, 1H), 7.31 (d, J = 4.8 Hz, 1H), 5.10 (s, 1H), 4.87 (d, J = 5.2 Hz, 2H), 2.63 (s, 3H), 2.18 (s, 3H). | 417.0 |
| A-144 | 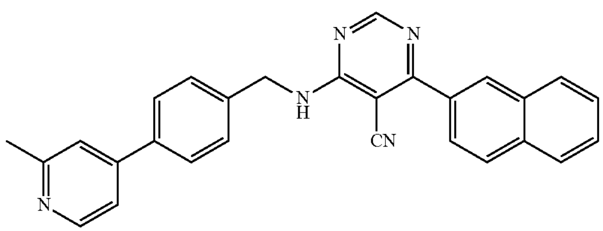 | A | ¹H NMR (400 MHz, CDCl₃) δ 8.84 (s, 1H), 8.56 (d, J = 5.2 Hz, 1H), 8.54 (s, 1H), 8.06 (d, J = 8.8 Hz, 1H), 7.99 (d, J = 8.8 Hz, 2H), 7.91 (d, J = 7.6 Hz, 1H), 7.65 (d, J = 8.0 Hz, 2H), 7.62-7.55 (m, 2H), 7.50 (d, J = 8.0 Hz, 2H), 7.37 (s, 1H), 7.31 (d, J = 4.0 Hz, 1H), 6.14 (s, 1H), 4.90(d, J = 5.6 Hz, 2H), 2.63 (s, 3H). | 428.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-145 | 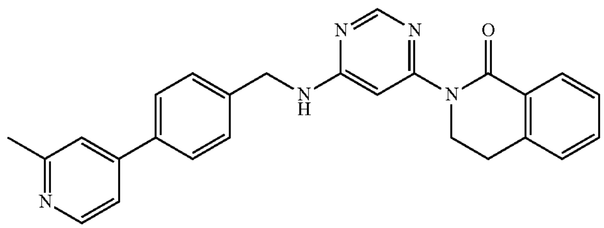 [SMILES: Cc1cc(-c2ccc(CNc3cc(N4CCc5ccccc5C4=O)ncn3)cc2)ccn1] | A | ¹H NMR (400 MHz, CDCl₃) δ 8.54 (d, J = 5.2 Hz, 1H), 8.48 (s, 1H), 8.14 (d, J = 7.6 Hz, 1H), 7.55-7.42 (m, 4H), 7.40 (d, J = 8.0 Hz, 1H), 7.36 (s, 1H), 7.31 (d, J = 9.2 Hz, 1H), 7.25 (s, 1H), 5.43 (br s, 1H), 4.66 (d, J = 5.6 Hz, 2H), 4.36 (d, J = 6.4 Hz, 2H), 3.07 (d, J = 6.4 Hz, 2H), 2.62 (s, 3H). | |
| A-146 | 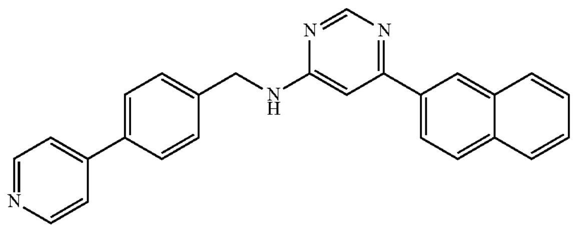 [SMILES: c1ccc2cc(-c3cc(NCc4ccc(-c5ccncc5)cc4)ncn3)ccc2c1] | A | ¹H NMR (400 MHz, CDCl₃) δ 8.65-8.58 (m, 3H), 8.57 (s, 1H), 8.20-7.95 (m, 5H), 7.79 (d, J = 8.0 Hz, 2H), 7.70 (d, J = 5.2 Hz, 2H), 7.57 (d, J = 9.2 Hz, 2H), 7.52 (d, J = 6.4 Hz, 1H), 7.19 (s, 1H), 4.69 (d, J = 6.0 Hz, 2H). | 389.0 |
| A-147 | 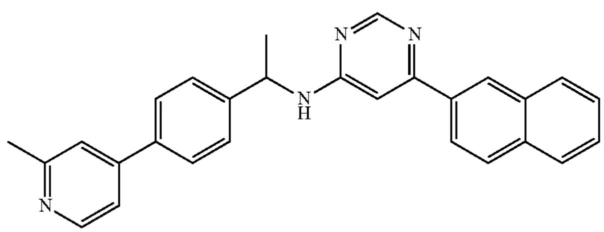 [SMILES: Cc1cc(-c2ccc(C(C)Nc3cc(-c4ccc5ccccc5c4)ncn3)cc2)ccn1] | A | ¹H NMR (400 MHz, CDCl₃) δ 8.71 (s, 1H), 8.53 (d, J = 5.2 Hz, 1H), 8.42 (s, 1H), 7.95-7.80 (m, 4H), 7.64 (d, J = 8.4 Hz, 2H), 7.54-7.50 (m, 4H), 7.35 (s, 1H), 7.29 (d, J = 5.2 Hz, 2H), 6.73 (s, 1H), 5.39 (br s, 1H), 5.08 (m, 1H) 2.61 (s, 3H), 1.67 (d, J = 6.8 Hz, 3H). | 417.0 |
| A-148 | 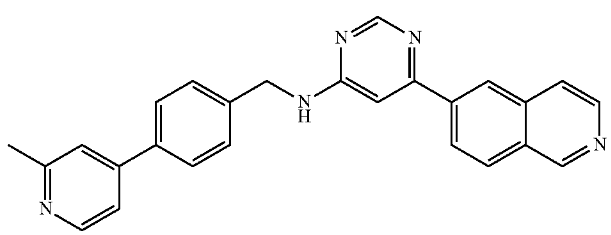 [SMILES: Cc1cc(-c2ccc(CNc3cc(-c4ccc5cnccc5c4)ncn3)cc2)ccn1] | A | ¹H NMR (400 MHz, CDCl₃) δ 9.30 (s, 1H), 8.77 (s, 1H), 8.57 (d, J = 6.0 Hz, 1H), 8.54 (d, J = 6.0 Hz, 1H), 8.47 (s, 1H), 8.13 (d, J = 8.0 Hz, 1H), 8.07 (d, J = 8.0 Hz, 1H), 7.75 (d, J = 6.0 Hz, 1H), 7.64 (d, J = 8.0 Hz, 2H), 7.50 (d, J = 8.0 Hz, 2H), 7.37 (s, 1H), 7.31 (d, J = 4.8 Hz, 1H), 6.90 (s, 1H), 5.30 (br s, 1H), 4.75 (s, 2H) 2.62 (s, 3H). | 404.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-149 | 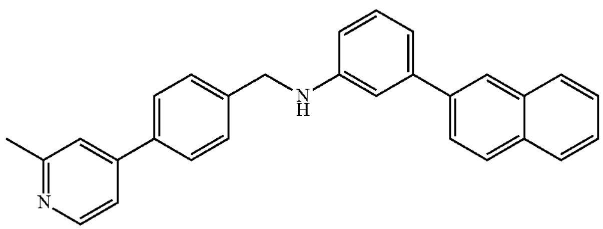 [SMILES: Cc1cc(-c2ccc(CNc3cccc(-c4ccc5ccccc5c4)c3)cc2)ccn1] | B | ¹H NMR (400 MHz, CDCl₃) δ 8.55 (d, J = 5.2 Hz, 1H), 7.99 (s, 1H), 7.91-7.83 (m, 3H), 7.71 (m, 1H), 7.64 (d, J = 8.0 Hz, 2H), 7.54 (d, J = 8.4 Hz, 2H), 7.51-7.44 (m, 2H), 7.39 (s, 1H), 7.31 (m, 2H), 7.10 (d, J = 7.6 Hz, 1H), 7.00 (s, 1H), 6.68 (m, 1H), 4.50 (s, 2H), 4.30 (s, 1H), 2.65 (s, 3H). | 401.1 |
| A-150 | 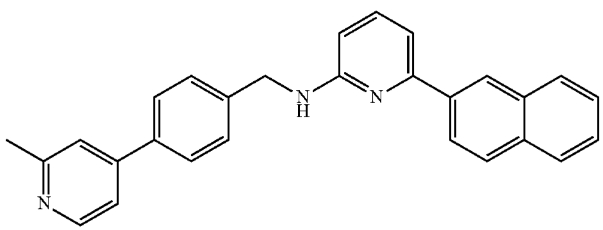 | A | ¹H NMR (400 MHz, CDCl₃) δ 8.54 (d, J = 5.2 Hz, 1H), 8.46 (s, 1H), 8.12 (d, J = 8.4 Hz, 1H), 7.90 (d, J = 8.4 Hz, 2H), 7.84 (s, 1H), 7.63 (d, J = 8.4 Hz, 2H), 7.55 (m, 3H), 7.51-7.45 (m, 2H), 7.38 (s, 1H), 7.33 (s, 1H), 7.24 (d, J = 8.0 Hz, 1H), 6.40 (d, J = 8.0 Hz, 1H), 4.72 (d, J = 5.6 Hz, 2H), 2.62 (s, 3H). | 402.0 |
| A-151 | 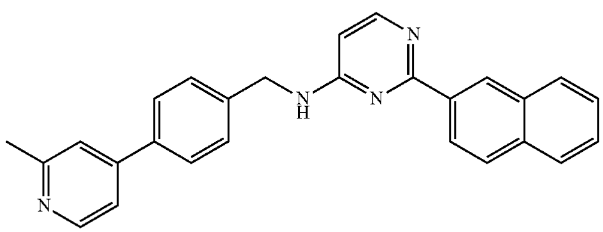 [SMILES: Cc1cc(-c2ccc(CNc3ccnc(-c4ccc5ccccc5c4)n3)cc2)ccn1] | A | ¹H NMR (400 MHz, CDCl₃) δ 8.91 (s, 1H), 8.55 (s, 1H), 8.49 (d, J = 8.2 Hz, 1H), 8.37 (s, 1H), 7.97 (d, J = 6.4 Hz, 1H), 7.89 (dd, J = 16.2, 7.8 Hz, 2H), 7.63 (d, J = 7.2 Hz, 2H), 7.52 (d, J = 6.2 Hz, 4H), 7.37 (s, 1H), 7.31 (s, 1H), 6.31 (d, J = 5.2 Hz, 1H), 5.43 (s, 1H), 4.78 (s, 2H), 2.62 (s, 3H), 1.74 (s, 1H), 1.24 (s, 1H). | 403.0 |
| A-152 | 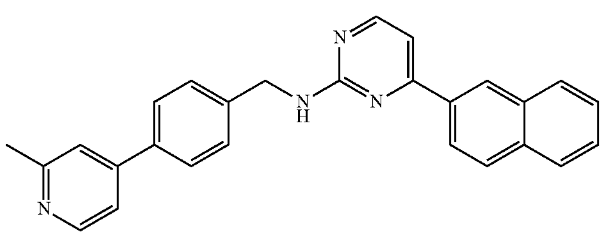 [SMILES: Cc1cc(-c2ccc(CNc3nccc(-c4ccc5ccccc5c4)n3)cc2)ccn1] | A | ¹H NMR (400 MHz, CDCl₃) δ 8.53 (s, 2H), 8.41 (s, 1H), 8.13 (d, J = 7.8 Hz, 1H), 7.94 (s, 2H), 7.87 (s, 1H), 7.62 (d, J = 6.4 Hz, 2H), 7.55 (d, J = 4.2 Hz, 1H), 7.37 (s, 1H), 7.31 (s, 1H), 7.18 (s, 1H), 5.67 (s, 1H), 4.85 (s, 2H), 2.62 (s, 3H). | 403.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-153 | 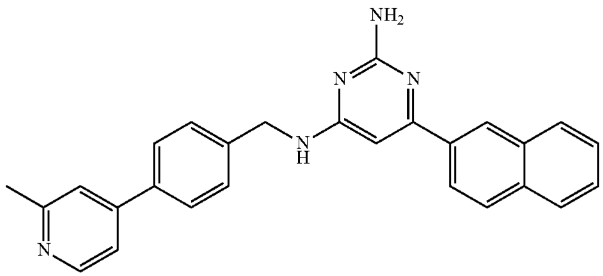 [SMILES: Cc1cc(-c2ccc(CNc3cc(-c4ccc5ccccc5c4)nc(N)n3)cc2)ccn1] | A | ¹H NMR (400 MHz, CDCl₃) δ 8.53 (d, J = 5.2 Hz, 1H), 8.42 (s, 1H), 7.96 (d, J = 8.8 Hz, 1H), 7.93-7.82 (m, 3H), 7.61 (d, J = 8.4 Hz, 2H), 7.53-7.48 (m, 2H), 7.46 (d, J = 8.4 Hz, 2H), 7.35 (s, 1H), 7.29 (d, J = 5.2 Hz, 1H), 6.34 (s, 1H), 5.25 (s, 1H), 4.94 (s, 2H), 4.67 (d, J = 5.6 Hz, 2H), 2.61 (s, 3H). | 418.0 |
| A-154 | 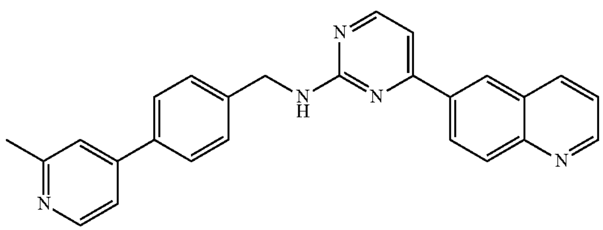 | A | ¹H NMR (400 MHz, CDCl₃) δ 8.96 (s, 1H), 8.52 (d, J = 8.8 Hz, 2H), 8.44 (d, J = 4.0 Hz, 1H), 8.36 (d, J = 8.8 Hz, 1H), 8.25 (d, J = 8.0 Hz, 1H), 8.19 (d, J = 8.8 Hz, 1H), 7.62 (d, J = 7.6 Hz, 2H), 7.54 (d, J = 7.6 Hz, 2H), 7.46 (dd, J = 7.6, 4.4 Hz, 1H), 7.36 (s, 1H), 7.30 (d, J = 4.4 Hz, 1H), 7.18 (d, J = 5.2 Hz, 1H), 5.65 (s, 1H), 4.84 (d, J = 5.2 Hz, 2H), 2.61 (s, 3H). | 404.0 |
| A-155 | 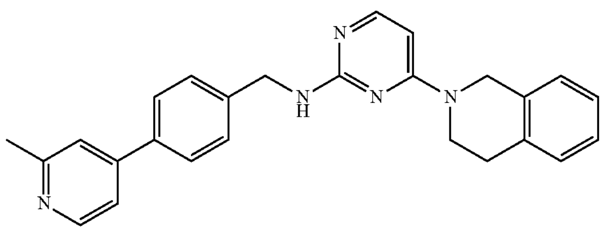 [SMILES: Cc1cc(-c2ccc(CNc3nccc(N4CCc5ccccc5C4)n3)cc2)ccn1] | A | ¹H NMR (400 MHz, CDCl₃) δ 8.52 (d, J = 5.2 Hz, 1H), 7.81 (d, J = 5.6 Hz, 1H), 7.59 (d, J = 8.0 Hz, 2H), 7.49 (d, J = 8.0 Hz, 2H), 7.35 (s, 1H), 7.30 (d, J = 4.8 Hz, 1H), 7.26 (s, 1H), 7.22-7.10 (m, 4H), 5.98 (d, J = 6.4 Hz, 1H), 4.69 (s, 2H), 4.68 (s, 2H), 3.80 (s, 2H), 2.91 (t, J = 5.6 Hz, 2H), 2.61 (s, 3H). | 408.1 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-156 | | A | ¹H NMR (400 MHz, CDCl₃) δ 8.53 (d, J = 5.2 Hz, 1H), 8.44 (d, J = 4.4 Hz, 1H), 7.89 (d, J = 4.4 Hz, 1H), 7.59 (d, J = 7.6 Hz, 2H), 7.48 (d, J = 8.0 Hz, 2H), 7.42 (d, J = 7.2 Hz, 1H), 7.35 (s, 1H), 7.29 (d, J = 4.8 Hz, 1H), 7.16–7.10 (m, 1H), 6.02 (d, J = 6.0 Hz, 1H), 4.72 (s, 2H), 4.68 (d, J = 5.6 Hz, 2H), 3.92 (t, J = 5.6 Hz, 2H), 3.09 (t, J = 5.6 Hz, 2H), 2.61 (s, 3H). | 409.0 |
| A-157 | 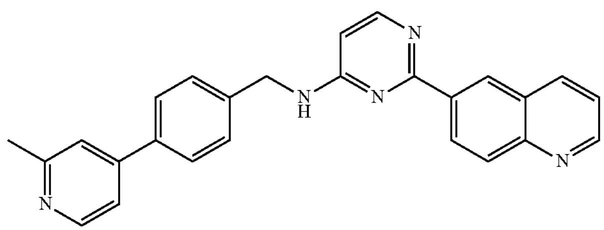 [SMILES: Cc1cc(-c2ccc(CNc3ccnc(-c4ccc5ncccc5c4)n3)cc2)ccn1] | A | ¹H NMR (400 MHz, CDCl₃) δ 8.94 (d, J = 4.0 Hz, 1H), 8.89 (s, 1H), 8.74 (d, J = 8.8 Hz, 1H), 8.54 (d, J = 4.8 Hz, 1H), 8.37 (d, J = 5.6 Hz, 1H), 8.27 (d, J = 8.0 Hz, 1H), 8.16 (d, J = 8.8 Hz, 1H), 7.64 (d, J = 7.6 Hz, 2H), 7.52 (d, J = 8.0 Hz, 2H), 7.43 (dd, J = 8.0, 4.4 Hz, 1H), 7.37 (s, 1H), 7.31 (d, J = 4.8 Hz, 1H), 6.34 (d, J = 5.6 Hz, 1H), 5.45 (s, 1H), 4.79 (s, 2H), 2.62 (s, 3H). | 404.0 |
| A-158 | 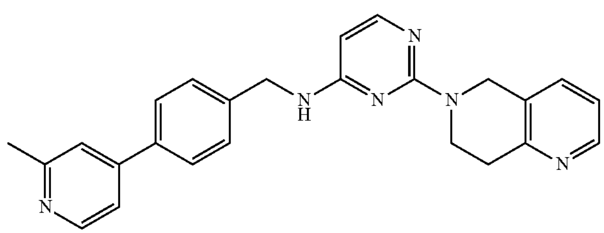 [SMILES: Cc1cc(-c2ccc(CNc3ccnc(N4CCc5ncccc5C4)n3)cc2)ccn1] | A | ¹H NMR (400 MHz, CDCl₃) δ 8.53 (d, J = 5.2 Hz, 1H), 8.41 (d, J = 4.0 Hz, 1H), 7.94 (d, J = 5.6 Hz, 1H), 7.60 (d, J = 8.0 Hz, 2H), 7.45 (d, J = 7.6 Hz, 3H), 7.36 (s, 1H), 7.30 (d, J = 5.2 Hz, 1H), 7.11 (dd, J = 7.2, 4.8 Hz, 1H), 5.76 (d, J = 6.0 Hz, 1H), 5.11 (s, 1H), 4.90 (s, 2H), 4.64 (d, J = 4.4 Hz, 2H), 4.13 (t, J = 6.0 Hz, 2H), 3.06 (t, J = 6.0 Hz, 2H), 2.62 (s, 3H). | 409.0 |
| A-159 | 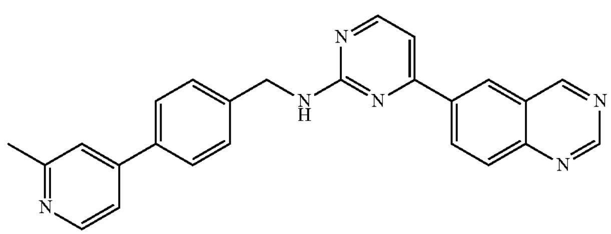 [SMILES: Cc1cc(-c2ccc(CNc3nccc(-c4ccc5ncncc5c4)n3)cc2)ccn1] | A | ¹H NMR (400 MHz, CDCl₃) δ 9.50 (s, 1H), 9.37 (s, 1H), 8.61 (s, 1H), 8.58 (d, J = 8.8 Hz, 1H), 8.53 (d, J = 4.8 Hz, 1H), 8.48 (d, J = 5.2 Hz, 1H), 8.14 (d, J = 8.8 Hz, 1H), 7.63 (d, J = 7.6 Hz, 2H), 7.54 (d, J = 8.0 Hz, 2H), 7.37 (s, 1H), 7.31 (d, J = 4.8 Hz, 1H), 7.18 (d, J = 4.8 Hz, 1H), 5.70 (s, 1H), 4.85 (d, J = 5.2 Hz, 2H), 2.62 (s, 3H). | 405.0 |

TABLE 2-continued

Selected compounds (A-1 to A-202) of the present invention.

| Compd NO. | Structure | Method | $^1$HNMR | ESI-MS (m/z): [M + 1]$^+$ |
|---|---|---|---|---|
| A-160 | 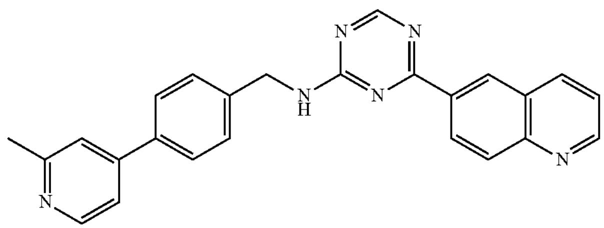 [SMILES: Cc1cc(-c2ccc(CNc3ncnc(-c4ccc5ncccc5c4)n3)cc2)ccn1] | A | $^1$H NMR (400 MHz, CDCl$_3$) δ 8.99 (s, 2H), 8.79 (s, 1H), 8.74 (d, J = 8.6 Hz, 1H), 8.67 (s, 1H), 8.55 (s, 1H), 8.30 (d, J = 6.8 Hz, 1H), 8.19 (d, J = 8.6 Hz, 1H), 7.63 (d, J = 6.4 Hz, 2H), 7.51 (dd, J = 15.4, 8.5 Hz, 3H), 7.37 (s, 1H), 7.32 (s, 1H), 6.18 (s, 1H), 6.05 (s, 1H), 4.92 (s, 1H), 4.83 (s, 1H), 2.62 (s, 3H). | 405.0 |
| A-161 | 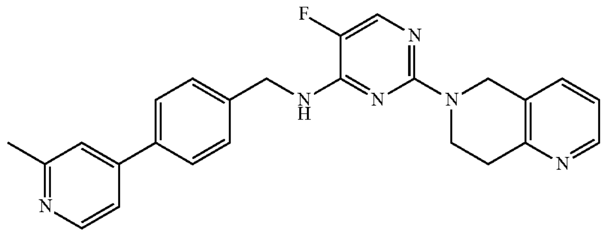 [SMILES: Cc1cc(-c2ccc(CNc3nc(N4CCc5ncccc5C4)ncc3F)cc2)ccn1] | A | $^1$H NMR (400 MHz, CDCl$_3$) δ 8.55 (d, J = 4.8 Hz, 1H), 8.41 (d, J = 4.0 Hz, 1H), 7.82 (d, J = 2.8 Hz, 1H), 7.62 (d, J = 8.4 Hz, 2H), 7.48 (d, J = 8.4 Hz, 2H), 7.45 (d, J = 8.0 Hz, 1H), 7.38 (s, 1H), 7.33 (d, J = 4.8 Hz, 1H), 7.11 (dd, J = 7.2, 4.4 Hz, 1H), 5.30 (s, 1H), 4.84 (s, 2H), 4.76 (d, J = 5.2 Hz, 2H), 4.08 (t, J = 5.6 Hz, 2H), 3.06 (t, J = 6.0 Hz, 2H), 2.64 (s, 3H). | 427.0 |
| A-162 | 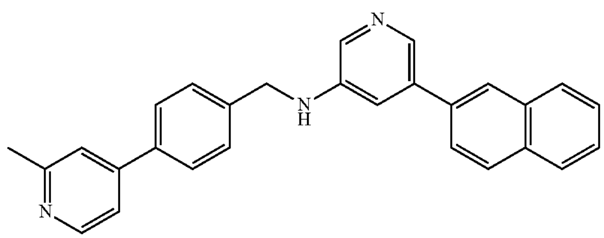 [SMILES: Cc1cc(-c2ccc(CNc3cncc(-c4ccc5ccccc5c4)c3)cc2)ccn1] | B | $^1$H NMR (400 MHz, DMSO) δ 8.46 (d, J = 5.2 Hz, 1H), 8.18 (d, J = 15.6 Hz, 2H), 8.07-7.89 (m, 5H), 7.77 (d, J = 8.0 Hz, 3H), 7.55 (m, 5H), 7.48 (d, J = 4.8 Hz, 1H), 7.30 (s, 1H), 6.74 (s, 1H), 4.50 (d, J = 5.6 Hz, 2H). | 402.0 |
| A-163 | 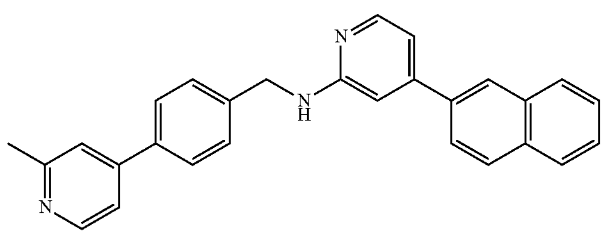 [SMILES: Cc1cc(-c2ccc(CNc3cc(-c4ccc5ccccc5c4)ccn3)cc2)ccn1] | B | $^1$H NMR (400 MHz, CDCl$_3$) δ 8.53 (d, J = 4.8 Hz, 1H), 8.18 (d, J = 4.8 Hz, 1H), 8.02 (s, 1H), 7.96-7.82 (m, 3H), 7.68-7.56 (m, 4H), 7.52 (d, J = 8.0 Hz, 5H), 7.37 (s, 1H), 7.31 (d, J = 4.4 Hz, 1H), 6.75 (s, 1H), 4.68 (d, J = 5.2 Hz, 2H), 2.62 (s, 3H). | |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-164 | 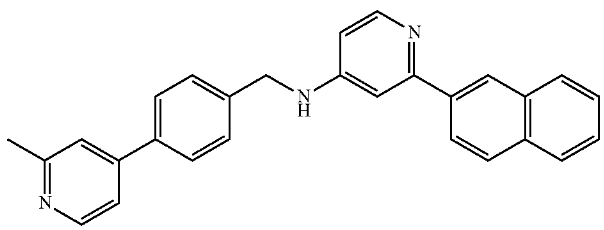 [SMILES: Cc1cc(-c2ccc(CNc3ccnc(-c4ccc5ccccc5c4)c3)cc2)ccn1] | B | ¹H NMR (400 MHz, CDCl₃) δ 8.54 (d, J = 5.2 Hz, 1H), 8.39 (s, 1H), 8.23 (d, J = 5.6 Hz, 1H), 7.97-7.78 (m, 4H), 7.63 (d, J = 8.0 Hz, 2H), 7.49 (d, J = 5.6 Hz, 4H), 7.35 (s, 1H), 7.29 (d, J = 5.6 Hz, 1H), 7.09 (s, 1H), 6.53 (s, 1H), 4.54 (d, J = 5.2 Hz, 2H), 2.62 (s, 3H). | 402.0 |
| A-165 | 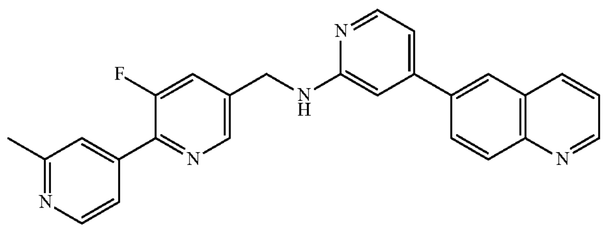 [SMILES: Cc1cc(-c2ncc(CNc3cc(-c4ccc5ncccc5c4)ccn3)cc2F)ccn1] | A | ¹H NMR (400 MHz, CDCl₃) δ 8.99 (s, 1H), 8.62 (s, 2H), 8.23 (t, J = 7.8 Hz, 2H), 8.16 (s, 1H), 8.03 (s, 1H), 7.90 (d, J = 9.2 Hz, 1H), 7.83 (s, 1H), 7.76 (s, 1H), 7.66 (d, J = 11.6 Hz, 1H), 7.50 (d, J = 4.2 Hz, 1H), 7.08 (s, 1H), 6.83 (s, 1H), 6.64 (s, 1H), 4.79 (s, 2H), 2.68 (s, 3H). | 454.0 |
| A-166 | 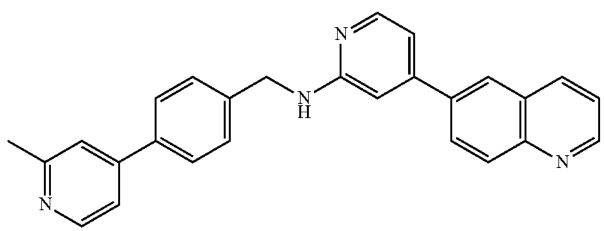 [SMILES: Cc1cc(-c2ccc(CNc3cc(-c4ccc5ncccc5c4)ccn3)cc2)ccn1] | A | ¹H NMR (400 MHz, CDCl₃) δ 9.00 (s, 1H), 8.55 (s, 1H), 8.21 (d, J = 8.4 Hz, 2H), 7.99 (s, 2H), 7.82 (d, J = 8.8 Hz, 1H), 7.66 (d, J = 7.6 Hz, 2H), 7.55 (d, J = 7.8 Hz, 2H), 7.52-7.46 (m, 1H), 7.40 (d, J = 15.8 Hz, 2H), 7.09 (s, 1H), 6.89 (s, 1H), 4.72 (s, 2H), 2.68 (s, 3H). | 404.0 |
| A-167 | 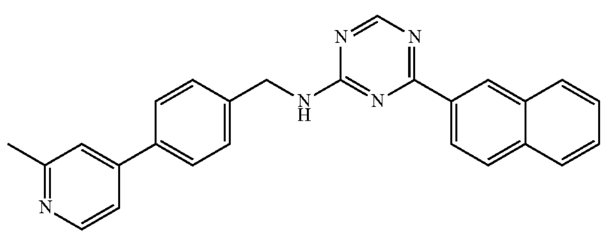 | A | ¹H NMR (400 MHz, CDCl₃) δ 8.99 (d, J = 10 Hz, 1H), 8.79 (s, 1H), 8.69 (s, 1H), 8.53 (s, 1H), 8.49 (d, J = 8.4 Hz, 1H), 8.44 (d, J = 8.8 Hz, 1H), 7.99 (d, J = 7.6 Hz, 1H), 7.91 (m, 2H), 7.64 (d, J = 7.6 Hz, 2H), 7.5 (m, 4H), 7.37 (s, 1H), 7.31 (d, J = 4.8 Hz, 1H), 5.91 (s, 1H), 4.93 (d, J = 5.6 Hz, 1H), 4.82 (d, J = 6 Hz, 1H), 2.62 (s, 3H). | 404.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-168 | 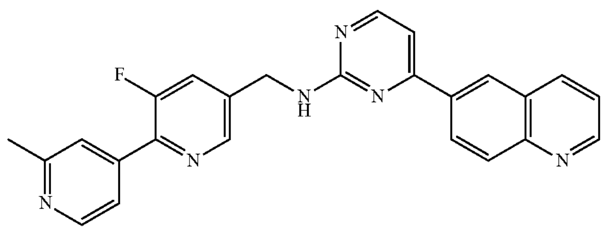 [SMILES: Cc1cc(-c2ncc(CNc3nccc(-c4ccc5ncccc5c4)n3)cc2F)ccn1] | A | ¹H NMR (400 MHz, DMSO) δ 8.96 (d, J = 2.8 Hz, 1H), 8.75 (s, 1H), 8.68 (s, 1H), 8.56 (d, J = 5.2 Hz, 1H), 8.50-8.44 (m, 3H), 8.11 (d, J = 8.8 Hz, 1H), 8.07-8.01 (m, 1H), 7.88 (s, 1H), 7.74 (s, 1H), 7.66 (d, J = 4.4 Hz, 1H), 7.61 (dd, J = 8.4, 4.0 Hz, 1H), 7.40 (d, J = 5.2 Hz, 1H), 4.74 (s, 2H), 2.53 (s, 3H). | 423.0 |
| A-169 | 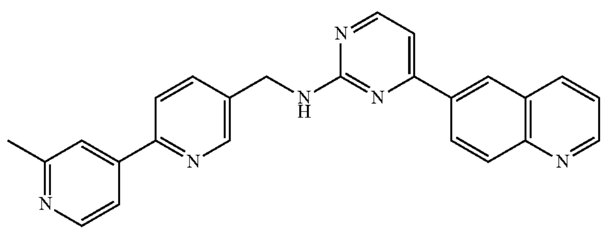 [SMILES: Cc1cc(-c2ccc(CNc3nccc(-c4ccc5ncccc5c4)n3)cn2)ccn1] | A | ¹H NMR (400 MHz, CDCl₃) δ 8.96 (d, J = 4.0 Hz, 1H), 8.79 (s, 1H), 8.73 (s, 1H), 8.52 (d, J = 5.2 Hz, 1H), 8.50-8.43 (m, 3H), 8.11 (d, J = 8.8 Hz, 1H), 8.08-7.89 (m, 4H), 7.82 (d, J = 4.8 Hz, 1H), 7.60 (dd, J = 8.4, 4.4 Hz, 1H), 7.37 (d, J = 5.2 Hz, 1H), 4.70 (s, 2H), 2.53 (s, 3H). | 405.0 |
| A-170 | 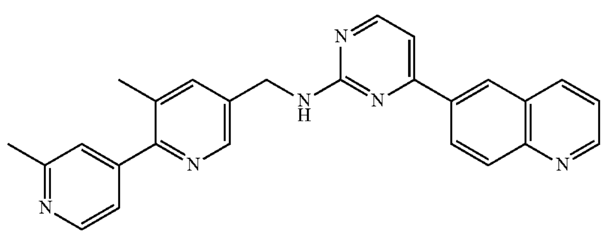 | A | ¹H NMR (400 MHz, DMSO) δ 8.96 (d, J = 2.4 Hz, 1H), 8.76 (s, 1H), 8.59 (s, 1H), 8.52-8.43 (m, 4H), 8.12 (d, J = 8.8 Hz, 1H), 8.04-7.97 (m, 1H), 7.79 (s, 1H), 7.61 (dd, J = 8.4, 4.4 Hz, 1H), 7.42 (s, 1H), 7.39-7.32 (m, 2H), 4.66 (s, 2H), 2.51 (s, 3H), 2.32 (s, 3H). | 419.0 |
| A-171 | 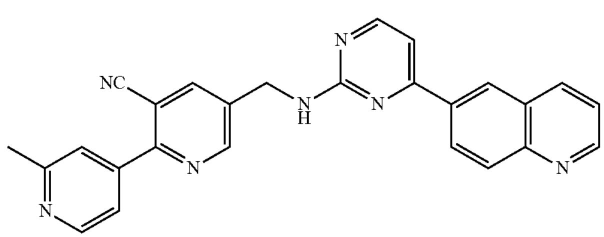 [SMILES: Cc1cc(-c2ncc(CNc3nccc(-c4ccc5ncccc5c4)n3)cc2C#N)ccn1] | A | ¹H NMR (400 MHz, DMSO) δ 9.04 (s, 1H), 8.96 (d, J = 3.6 Hz, 1H), 8.76 (s, 1H), 8.62 (d, J = 4.8 Hz, 1H), 8.56-8.39 (m, 4H), 8.12 (d, J = 8.8 Hz, 1H), 8.08-8.02 (m, 1H), 7.68 (s, 1H), 7.65-7.59 (m, 2H), 7.41 (d, J = 4.8 Hz, 1H), 4.75 (s, 2H), 2.55 (s, 3H). | 430.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-172 | (structure) | A | ¹H NMR (400 MHz, DMSO) δ 9.03 (s, 2H), 8.96 (d, J = 2.8 Hz, 1H), 8.76 (s, 1H), 8.60 (d, J = 5.2 Hz, 1H), 8.51-8.44 (m, 3H), 8.12 (d, J = 8.0 Hz, 2H), 8.06-8.00 (m, 2H), 7.61 (dd, J = 8.4, 4.4 Hz, 1H), 7.40 (d, J = 5.2 Hz, 1H), 4.71 (s, 2H), 2.56 (s, 3H). | 406.0 |
| A-173 | (structure) | A | ¹H NMR (400 MHz, CDCl₃) δ 8.97 (s, 1H), 8.51 (s, 1H), 8.44 (s, 1H), 8.36 (d, J = 8.8 Hz, 1H), 8.26 (d, J = 7.6 Hz, 1H), 8.19 (d, J = 8.8 Hz, 1H), 7.85 (s, 1H), 7.55 (d, J = 7.6 Hz, 2H), 7.46 (s, 1H), 7.38 (d, J = 7.2 Hz, 2H), 7.27 (s, 1H), 7.22-7.18 (m, 2H), 5.67 (s, 1H), 4.83 (d, J = 4.4 Hz, 2H). | 379.0 |
| A-174 | (structure) | A | ¹H NMR (400 MHz, CDCl₃) δ 9.04 (s, 1H), 8.97 (d, J = 2.8 Hz, 1H), 8.83 (s, 1H), 8.64 (d, J = 5.2 Hz, 1H), 8.50 (s, 1H), 8.45 (d, J = 4.8 Hz, 1H), 8.35 (dd, J = 8.8, 1.6 Hz, 1H), 8.27 (d, J = 8.4 Hz, 1H), 8.19 (d, J = 8.8 Hz, 1H), 7.79 (s, 1H), 7.70 (d, J = 4.8 Hz, 1H), 7.46 (dd, J = 8.0, 4.0 Hz, 1H), 7.21 (d, J = 5.2 Hz, 1H), 6.17 (t, J = 5.2 Hz, 1H), 5.00 (d, J = 5.6 Hz, 2H), 2.67 (s, 3H). | 406.0 |
| A-175 | (structure) | A | ¹H NMR (400 MHz, CDCl₃) δ 8.97 (d, J = 2.8 Hz, 1H), 8.55 (d, J = 4.4 Hz, 1H), 8.50 (s, 1H), 8.47-8.41 (m, 2H), 8.36 (d, J = 8.4 Hz, 1H), 8.26 (d, J = 8.4 Hz, 1H), 8.19 (d, J = 8.8 Hz, 1H), 7.82 (d, J = 10.8 Hz, 2H), 7.49-7.43 (m, 2H), 7.22 (d, J = 4.4 Hz, 1H), 5.73 (s, 1H), 4.86 (d, J = 4.8 Hz, 2H), 3.87 (s, 3H), 2.68 (s, 3H). | 435.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-176 | 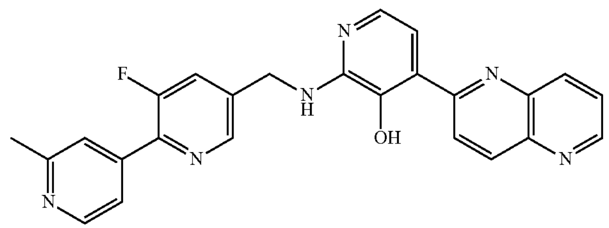 [SMILES: Cc1cc(-c2ncc(CNc3nccc(-c4ccc5ncccc5n4)c3O)cc2F)ccn1] | G | ¹H NMR (400 MHz, CDCl₃) δ 9.04 (d, J = 3.2 Hz, 1H), 8.65-8.55 (m, 3H), 8.38 (d, J = 8.4 Hz, 1H), 8.30 (d, J = 9.2 Hz, 1H), 7.79 (d, J = 6.0 Hz, 2H), 7.74 (dd, J = 8.4, 4.0 Hz, 1H), 7.69 (d, J = 4.4 Hz, 1H), 7.62 (d, J = 11.6 Hz, 1H), 7.14 (d, J = 5.6 Hz, 1H), 5.77 (t, J = 5.2 Hz, 1H), 4.89 (d, J = 6.0 Hz, 2H), 2.65 (s, 3H). | |
| A-177 | 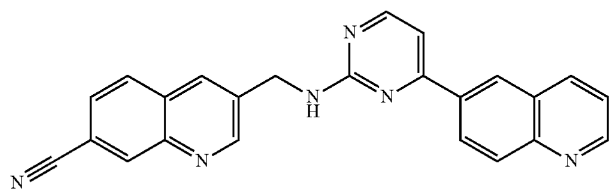 [SMILES: N#Cc1ccc2cc(CNc3nccc(-c4ccc5ncccc5c4)n3)cnc2c1] | A | ¹H NMR (400 MHz, CDCl₃) δ 9.14 (s, 1H), 8.97 (d, J = 4.0 Hz, 1H), 8.48 (d, J = 5.2 Hz, 1H), 8.45 (s, 1H), 8.32 (d, J = 9.2 Hz, 1H), 8.24 (d, J = 6.8 Hz, 2H), 8.18 (d, J = 8.8 Hz, 1H), 7.89 (d, J = 8.4 Hz, 1H), 7.68 (d, J = 8.4 Hz, 1H), 7.47 (m, 1H), 7.22 (d, J = 5.2 Hz, 1H), 5.85 (s, 1H), 5.02 (d, J = 6.4 Hz, 2H). | 389.1 |
| A-178 | 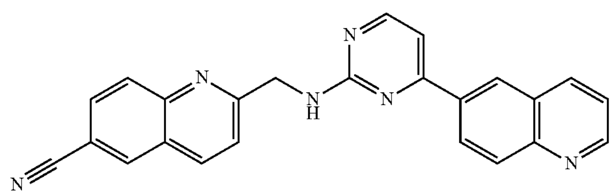 [SMILES: N#Cc1ccc2nc(CNc3nccc(-c4ccc5ncccc5c4)n3)ccc2c1] | A | ¹H NMR (400 MHz, CDCl₃) δ 8.97 (d, J = 3.2 Hz, 1H), 8.52 (s, 1H), 8.48 (d, J = 5.2 Hz, 1H), 8.39 (d, J = 8.8 Hz, 1H), 8.18-8.25 (m, 5H), 7.89 (d, J = 8.8 Hz, 1H), 7.63 (d, J = 8.4 Hz, 1H), 7.47 (dd, J = 8.0, 4.0 Hz, 1H), 7.21 (d, J = 4.8 Hz, 1H), 6.67 (s, 1H), 5.10 (d, J = 4.0 Hz, 2H). | 389.0 |
| A-179 | 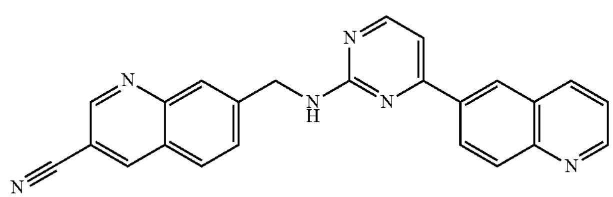 [SMILES: N#Cc1cnc2cc(CNc3nccc(-c4ccc5ncccc5c4)n3)ccc2c1] | A | ¹H NMR (400 MHz, CDCl₃) δ 9.03 (s, 1H), 8.96 (d, J = 2.8 Hz, 1H), 8.52 (s, 1H), 8.48 (s, 1H), 8.44 (d, J = 5.2 Hz, 1H), 8.32 (d, J = 8.8 Hz, 1H), 8.24(d, J = 8.0 Hz, 1H), 8.21 (s, 1H), 8.16 (d, J = 8.8 Hz, 1H), 7.89 (d, J = 8.4 Hz, 1H), 7.78 (d, J = 8.4 Hz, 1H), 7.47-7.44 (m, 1H), 7.20 (d, J = 4.8 Hz, 1H), 5.86 (s, 1H), 5.05 (d, J = 6.0 Hz, 2H). | 389.1 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-180 | 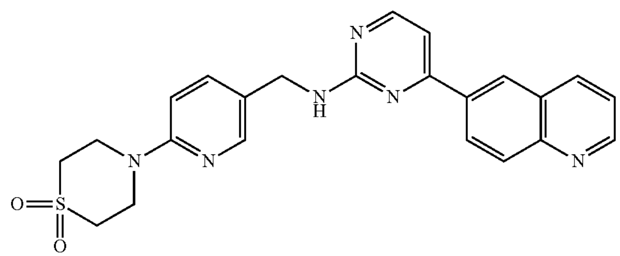 [SMILES: O=S1(=O)CCN(c2ccc(CNc3nccc(-c4ccc5ncccc5c4)n3)cn2)CC1] | A | ¹H NMR (400 MHz, DMSO) δ 8.96 (d, J = 3.2 Hz, 1H), 8.76 (s, 1H), 8.50 (d, J = 7.6 Hz, 2H), 8.43 (d, J = 4.4 Hz, 1H), 8.23 (s, 1H), 8.13 (d, J = 8.8 Hz, 1H), 7.86-7.78 (m, 1H), 7.67 (s, 1H), 7.61 (dd, J = 8.0, 4.0 Hz, 1H), 7.34 (d, J = 5.2 Hz, 1H), 6.99 (d, J = 8.8 Hz, 1H), 4.51 (s, 2H), 4.01 (s, 4H), 3.05 (s, 4H). | 447.0 |
| A-181 | 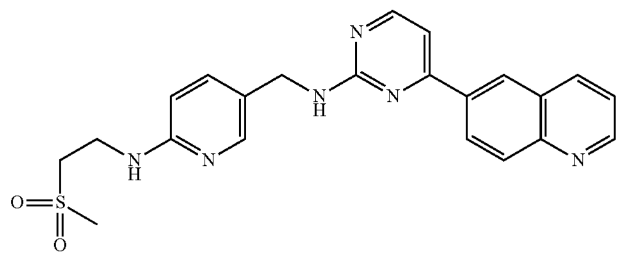 [SMILES: CS(=O)(=O)CCNc1ccc(CNc2nccc(-c3ccc4ncccc4c3)n2)cn1] | A | ¹H NMR (400 MHz, CDCl₃) δ 8.97 (d, J = 3.6 Hz, 1H), 8.52 (d, J = 5.2 Hz, 1H), 8.43 (d, J = 5.2 Hz, 1H), 8.37 (d, J = 8.8 Hz, 1H), 8.28 (d, J = 8.0 Hz, 1H), 8.21-8.16 (m, 2H), 7.53 (d, J = 8.0 Hz, 1H), 7.47 (dd, J = 8.2, 4.2 Hz, 1H), 7.17 (d, J = 5.2 Hz, 1H), 6.46 (d, J = 8.8 Hz, 1H), 5.48 (s, 1H), 4.93 (s, 1H), 4.63 (d, J = 5.6 Hz, 2H), 3.97-3.91 (m, 2H), 3.38 (t, J = 5.8 Hz, 2H), 2.94 (s, 3H). | |
| A182 | 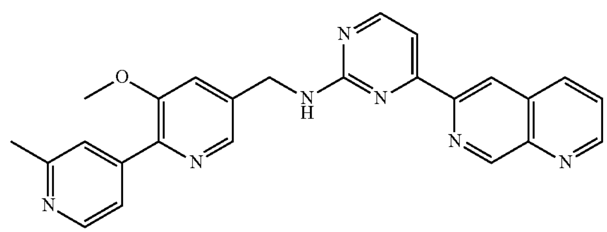 [SMILES: COc1cc(CNc2nccc(-c3cc4cccnc4cn3)n2)cnc1-c1ccnc(C)c1] | F | ¹H NMR (400 MHz, CDCl₃) δ 9.58 (s, 1H), 9.07 (s, 1H), 8.72 (s, 1H), 8.55 (d, J = 4.8 Hz, 2H), 8.44 (s, 1H), 8.28 (s, 1H), 7.83 (d, J = 3.6 Hz, 1H), 7.71 (s, 1H), 7.68-7.63 (m, 2H), 7.44 (s, 1H), 5.66 (s, 1H), 4.87 (d, J = 5.6 Hz, 2H), 3.86 (s, 3H), 2.62 (s, 3H). | 436.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-183 | 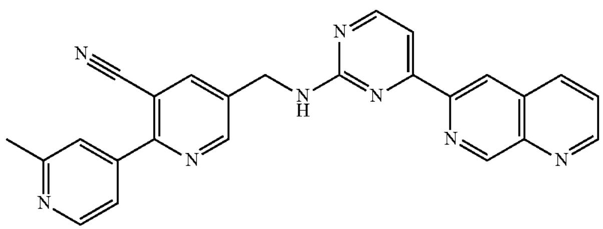 [SMILES: Cc1cc(-c2ncc(CNc3nccc(-c4cc5cccnc5cn4)n3)cc2C#N)ccn1] | F | ¹H NMR (400 MHz, CDCl₃) δ 9.57 (s, 1H), 9.07 (s, 1H), 8.67 (d, J = 8.4 Hz, 2H), 8.61 (d, J = 5.2 Hz, 1H), 8.54 (d, J = 5.2 Hz, 1H), 8.27 (d, J = 8.4 Hz, 1H), 7.85 (d, J = 5.2 Hz, 1H), 7.76 (s, 1H), 7.71-7.63 (m, 3H), 5.71 (s, 1H), 4.89 (d, J = 5.6 Hz, 2H), 2.64 (s, 3H). | |
| A184 | 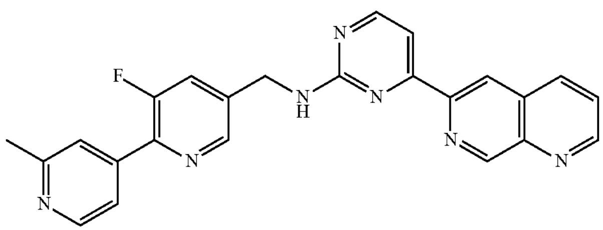 [SMILES: Cc1cc(-c2ncc(CNc3nccc(-c4cc5cccnc5cn4)n3)cc2F)ccn1] | F | ¹H NMR (400 MHz, CDCl₃) δ 9.58 (s, 1H), 9.09 (d, J = 3.2 Hz, 1H), 9.01 (s, 1H), 8.69-8.64 (m, 2H), 8.54 (d, J = 4.8 Hz, 1H), 8.29 (d, J = 8.4 Hz, 1H), 8.22 (s, 1H), 7.88 (d, J = 4.8 Hz, 1H), 7.70-7.60 (m, 3H), 5.77 (m, 1H), 4.90 (d, J = 6.0 Hz, 2H), 2.86 (s, 3H). | |
| A185 | 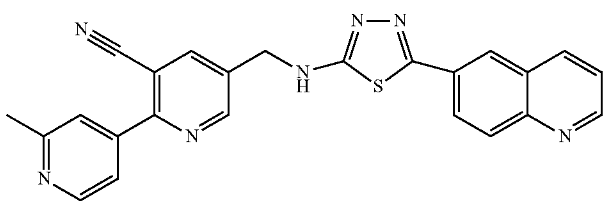 [SMILES: Cc1cc(-c2ncc(CNc3nnc(-c4ccc5ncccc5c4)s3)cc2C#N)ccn1] | A | ¹H NMR (400 MHz, CDCl₃) δ 8.99 (d, J = 3.2 Hz, 1H), 8.95 (d, J = 3.2 Hz, 1H), 8.68 (d, J = 5.2 Hz, 1H), 8.26 (s, 1H), 8.22-8.13 (m, 4H), 7.68 (s, 1H), 7.64 (d, J = 5.2 Hz, 1H), 7.46 (dd, J = 8.0, 4.4 Hz, 1H), 7.26 (s, 1H), 4.84 (s, 2H), 2.66 (s, 3H). | 436.0 |
| A-186 | 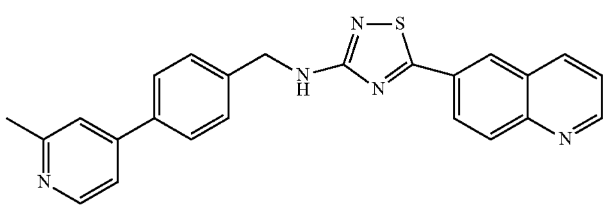 [SMILES: Cc1cc(-c2ccc(CNc3nsc(-c4ccc5ncccc5c4)n3)cc2)ccn1] | A | ¹H NMR (400 MHz, DMSO) δ 9.00 (d, J = 2.8 Hz, 1H), 8.62 (s, 1H), 8.57 (d, J = 8.4 Hz, 1H), 8.47 (d, J = 5.2 Hz, 1H), 8.30-8.25 (m, 1H), 8.22 (d, J = 8.4 Hz, 1H), 8.16 (d, J = 8.8 Hz, 1H), 7.76 (d, J = 8.0 Hz, 2H), 7.64 (dd, J = 8.4, 4.4 Hz, 1H), 7.57 (s, 1H), 7.52 (d, J = 8.0 Hz, 2H), 7.48 (d, J = 4.8 Hz, 1H), 4.61 (d, J = 6.0 Hz, 2H), 2.51 (s, 3H). | 410.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-187 | 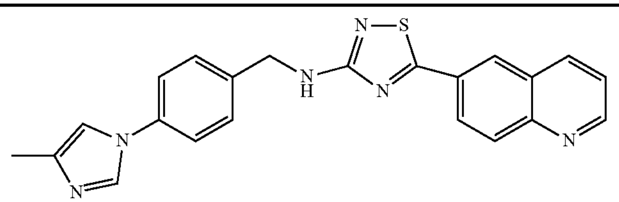 | A | ¹H NMR (400 MHz, DMSO) δ 9.00 (d, J = 3.2 Hz, 1H), 8.61 (s, 1H), 8.56 (d, J = 8.0 Hz, 1H), 8.29-8.24 (m, 1H), 8.23-8.14 (m, 3H), 7.64 (dd, J = 8.0, 4.0 Hz, 1H), 7.58 (d, J = 8.4 Hz, 2H), 7.51 (d, J = 8.8 Hz, 3H), 4.57 (d, J = 6.0 Hz, 2H), 2.19 (s, 3H). | |
| A-188 | 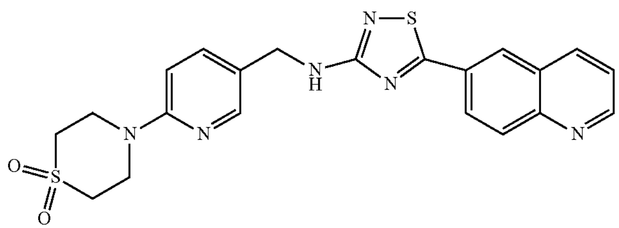 [SMILES: O=S1(=O)CCN(c2ccc(CNc3nsc(-c4ccc5ncccc5c4)n3)cn2)CC1] | A | ¹H NMR (400 MHz, DMSO) δ 9.00 (d, J = 2.8 Hz, 1H), 8.61 (s, 1H), 8.56 (d, J = 8.4 Hz, 1H), 8.23-8.07 (m, 4H), 7.68-7.61 (m, 2H), 7.00 (d, J = 8.8 Hz, 1H), 4.42 (d, J = 6.0 Hz, 2H), 4.03 (s, 4H), 3.06 (s, 4H). | |
| A-189 | 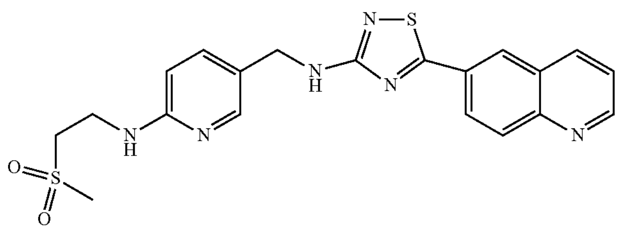 | A | ¹H NMR (400 MHz, DMSO) δ 9.00 (d, J = 3.2 Hz, 1H), 8.60 (s, 1H), 8.56 (d, J = 8.4 Hz, 1H), 8.21 (d, J = 9.6 Hz, 1H), 8.15 (d, J = 8.8 Hz, 1H), 8.04 (s, 2H), 7.64 (dd, J = 8.4, 4.4 Hz, 1H), 7.48 (d, J = 8.0 Hz, 1H), 6.74 (s, 1H), 6.50 (d, J = 8.4 Hz, 1H), 4.35 (d, J = 6.0 Hz, 2H), 3.69-3.61 (m, 2H), 3.32-3.30 (m, 2H), 2.99 (s, 3H). | |
| A-190 | 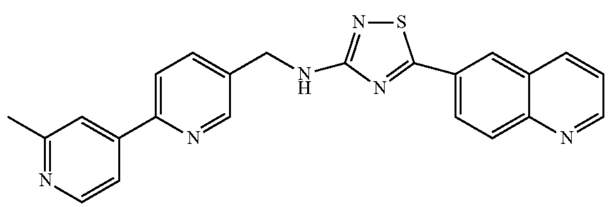 [SMILES: Cc1cc(-c2ccc(CNc3nsc(-c4ccc5ncccc5c4)n3)cn2)ccn1] | A | ¹H NMR (400 MHz, DMSO) δ 9.00 (d, J = 2.8 Hz, 1H), 8.76 (s, 1H), 8.62 (s, 1H), 8.59-8.51 (m, 2H), 8.34-8.29 (m, 1H), 8.22 (d, J = 8.8 Hz, 1H), 8.16 (d, J = 8.8 Hz, 1H), 8.07 (d, J = 8.0 Hz, 1H), 7.95 (d, J = 8.0 Hz, 1H), 7.92 (s, 1H), 7.82 (d, J = 5.2 Hz, 1H), 7.64 (dd, J = 8.0, 4.0 Hz, 1H), 4.63 (d, J = 6.0 Hz, 2H), 2.54 (s, 3H). | 411.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-191 | 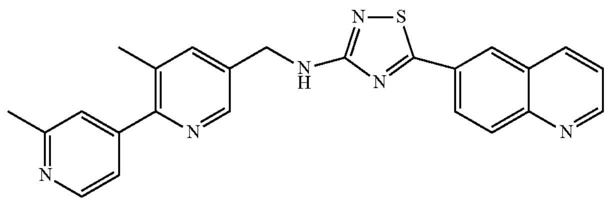 [SMILES: Cc1cc(-c2ncc(CNc3nsc(-c4ccc5ncccc5c4)n3)cc2C)ccn1] | A | ¹H NMR (400 MHz, CDCl₃) δ 9.00 (d, J = 2.8 Hz, 1H), 8.61 (s, 1H), 8.58 (d, J = 4.8 Hz, 1H), 8.40 (s, 1H), 8.26 (d, J = 8.0 Hz, 1H), 8.22-8.14 (m, 2H), 7.69 (s, 1H), 7.49 (dd, J = 8.0, 4.0 Hz, 1H), 7.33 (s, 1H), 7.24 (d, J = 5.6 Hz, 1H), 5.66 (s, 1H), 4.76 (d, J = 6.0 Hz, 2H), 2.62 (s, 3H), 2.37 (s, 3H). | 425.0 |
| A-192 | 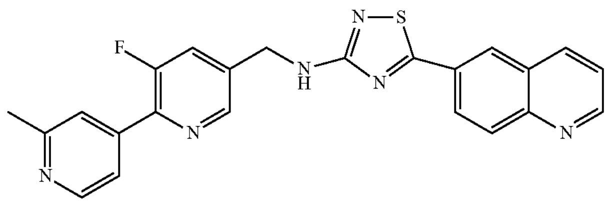 | A | ¹H NMR (400 MHz, DMSO) δ 9.00 (d, J = 2.8 Hz, 1H), 8.64 (d, J = 9.2 Hz, 2H), 8.60-8.54 (m, 2H), 8.38-8.32 (m, 1H), 8.22 (d, J = 8.8 Hz, 1H), 8.16 (d, J = 8.8 Hz, 1H), 7.88 (d, J = 12.0 Hz, 1H), 7.77 (s, 1H), 7.69 (d, J = 4.4 Hz, 1H), 7.64 (dd, J = 8.0, 4.0 Hz, 1H), 4.67 (d, J = 6.0 Hz, 2H), 2.55 (s, 3H). | 429.0 |
| A-193 | 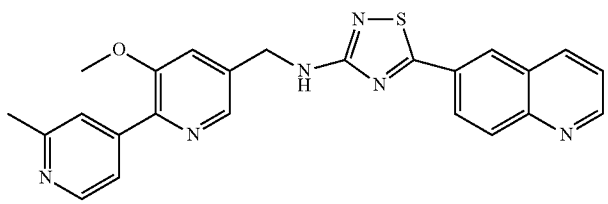 [SMILES: COc1cc(CNc2nsc(-c3ccc4ncccc4c3)n2)cnc1-c1ccnc(C)c1] | A | ¹H NMR (400 MHz, CDCl₃) δ 9.00 (d, J = 2.8 Hz, 1H), 8.55 (d, J = 4.8 Hz, 1H), 8.40 (s, 2H), 8.26 (d, J = 8.0 Hz, 1H), 8.22-8.14 (m, 2H), 7.73 (s, 1H), 7.69 (d, J = 4.4 Hz, 1H), 7.49 (dd, J = 8.0, 4.0 Hz, 1H), 7.45 (s, 1H), 5.70 (t, J = 5.6 Hz, 1H), 4.79 (d, J = 6.0 Hz, 2H), 3.90 (s, 3H), 2.63 (s, 3H). | 440.9 |
| A-194 | 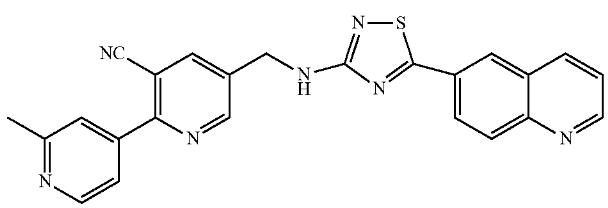 [SMILES: Cc1cc(-c2ncc(CNc3nsc(-c4ccc5ncccc5c4)n3)cc2C#N)ccn1] | A | ¹H NMR (400 MHz, CDCl₃) δ 9.00 (d, J = 3.2 Hz, 1H), 8.98 (s, 1H), 8.68 (d, J = 4.8 Hz, 1H), 8.39 (s, 1H), 8.27 (d, J = 8.4 Hz, 1H), 8.21 (d, J = 7.2 Hz, 2H), 8.15 (d, J = 8.8 Hz, 1H), 7.69 (d, J = 8.8 Hz, 1H), 7.64 (d, J = 4.8 Hz, 1H), 7.50 (dd, J = 8.0, 4.0 Hz, 1H), 5.83 (t, J = 5.6 Hz, 1H), 4.83 (d, J = 6.0 Hz, 2H), 2.67 (s, 3H). | 435.9 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-195 | 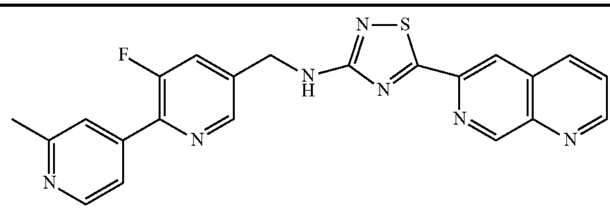 | A | ¹H NMR (400 MHz, DMSO) δ 9.47 (s, 1H), 9.15 (d, J = 3.2 Hz, 1H), 8.71 (d, J = 8.4 Hz, 1H), 8.64 (d, J = 8.4 Hz, 2H), 8.57 (d, J = 5.2 Hz, 1H), 8.28-8.22 (m, 1H), 7.92-7.84 (m, 2H), 7.75 (s, 1H), 7.67 (d, J = 4.4 Hz, 1H), 4.68 (d, J = 6.0 Hz, 2H), 2.55 (s, 3H). | 429.9 |
| A-196 | 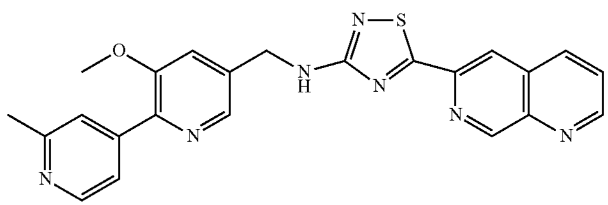 | A | ¹H NMR (400 MHz, DMSO) δ 9.47 (s, 1H), 9.15 (d, J = 3.2 Hz, 1H), 8.70 (d, J = 8.4 Hz, 1H), 8.64 (s, 1H), 8.48 (d, J = 4.8 Hz, 1H), 8.35 (s, 1H), 8.23-8.17 (m, 1H), 7.90 (dd, J = 8.4, 4.0 Hz, 1H), 7.73 (s, 1H), 7.68 (s, 1H), 7.67 (d, J = 6.0 Hz, 1H), 4.65 (d, J = 6.0 Hz, 2H), 3.89 (s, 3H), 2.51 (s, 3H). | 441.9 |
| A-197 | 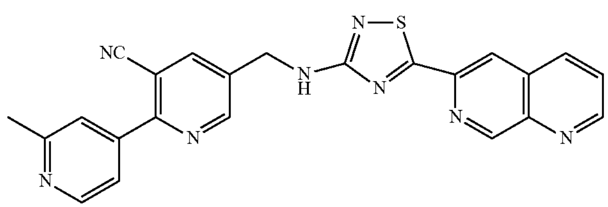 [SMILES: Cc1cc(-c2ncc(CNc3nsc(-c4cc5cccnc5cn4)n3)cc2F)ccn1] | A | ¹H NMR (400 MHz, DMSO) δ 9.47 (s, 1H), 9.16 (d, J = 3.2 Hz, 1H), 9.01 (s, 1H), 8.71 (d, J = 8.4 Hz, 1H), 8.64 (s, 2H), 8.46 (s, 1H), 8.29-8.23 (m, 1H), 7.90 (dd, J = 8.4, 4.0 Hz, 1H), 7.69 (s, 1H), 7.64 (d, J = 4.8 Hz, 1H), 4.69 (d, J = 6.0 Hz, 2H), 2.57 (s, 3H). | 437.0 |
| A-198 | 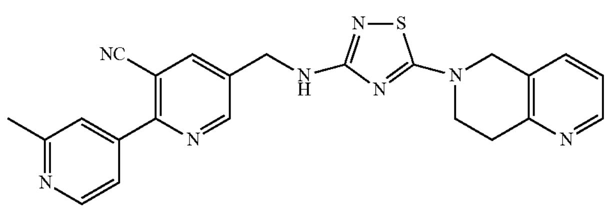 [SMILES: Cc1cc(-c2ncc(CNc3nsc(N4CCc5ncccc5C4)n3)cc2C#N)ccn1] | A | ¹H NMR (400 MHz, CDCl₃) δ 8.89 (s, 1H), 8.67 (d, J = 4.8 Hz, 1H), 8.48 (d, J = 4.4 Hz, 1H), 8.15 (s, 1H), 7.67 (s, 1H), 7.62 (d, J = 4.8 Hz, 1H), 7.48 (d, J = 7.6 Hz, 1H), 7.20 (dd, J = 6.8, 4.8 Hz, 1H), 5.33 (t, J = 5.6 Hz, 1H), 4.68 (d, J = 6.4 Hz, 2H), 4.65 (s, 2H), 3.80 (t, J = 4.8 Hz, 2H), 3.19 (t, J = 6.0 Hz, 2H), 2.67 (s, 3H). | 441.0 |

TABLE 2-continued

Selected compounds (A-1 to A-202) of the present invention.

| Compd NO. | Structure | Method | ¹HNMR | ESI-MS (m/z): [M + 1]⁺ |
|---|---|---|---|---|
| A-199 | 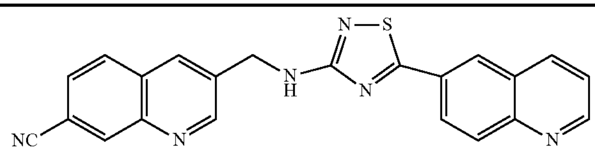 | A | ¹H NMR (400 MHz, DMSO) δ 9.12 (s, 1H), 9.00 (d, J = 3.2 Hz, 1H), 8.62 (s, 1H), 8.56 (d, J = 10.8 Hz, 2H), 8.45-8.39 (m, 2H), 8.21 (d, J = 8.0 Hz, 2H), 8.15 (d, J = 8.8 Hz, 1H), 7.90 (d, J = 8.4 Hz, 1H), 7.64 (dd, J = 8.0, 4.0 Hz, 1H), 4.79 (d, J = 5.6 Hz, 2H). | |
| A-200 | 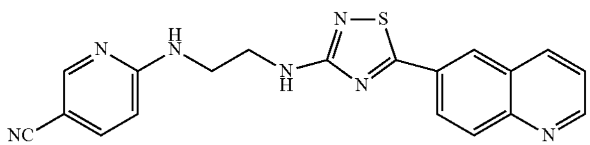 [SMILES: N#Cc1ccc(NCCNc2nsc(-c3ccc4ncccc4c3)n2)nc1] | A | ¹H NMR (400 MHz, DMSO) δ 9.00 (d, J = 2.8 Hz, 1H), 8.59 (s, 1H), 8.56 (d, J = 8.0 Hz, 1H), 8.41 (s, 1H), 8.21-8.12 (m, 2H), 7.78-7.60 (m, 4H), 6.57 (d, J = 8.8 Hz, 1H), 3.57 (s, 2H), 3.52 (t, J = 5.2 Hz, 2H). | |
| A-201 | 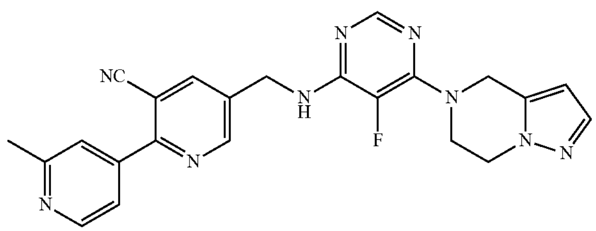 [SMILES: Cc1cc(-c2ncc(CNc3ncnc(N4CCn5nccc5C4)c3F)cc2C#N)ccn1] | A | ¹H NMR (400 MHz, CDCl₃) δ 8.89 (s, 1H), 8.67 (d, J = 5.0 Hz, 1H), 8.10 (s, 1H), 8.02 (s, 1H), 7.67 (s, 1H), 7.62 (d, J = 4.8 Hz, 1H), 7.50 (s, 1H), 6.10 (s, 1H), 5.34 (s, 1H), 4.94 (s, 2H), 4.81 (d, J = 6.2 Hz, 2H), 4.32 (m, 2H), 4.18 (m, 2H), 2.67 (s, 3H). | |
| A-202 | 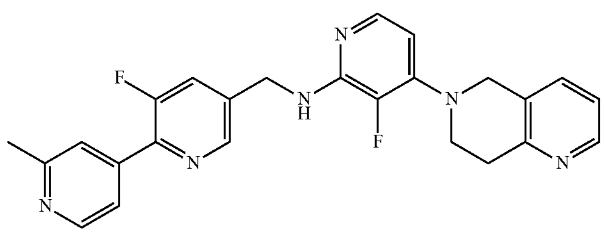 [SMILES: Cc1cc(-c2ncc(CNc3nccc(N4CCc5ncccc5C4)c3F)cc2F)ccn1] | A | ¹H NMR (400 MHz, CDCl₃) δ 8.59 (d, J = 5.0 Hz, 1H), 8.54 (s, 1H), 8.45 (d, J = 3.2 Hz, 1H), 7.75 (s, 1H), 7.71 (d, J = 5.6 Hz, 1H), 7.67 (d, J = 4.6 Hz, 1H), 7.55 (d, J = 11.8 Hz, 1H), 7.43 (d, J = 7.6 Hz, 1H), 7.18 (m, 1H), 6.30 (m, 1H), 5.02 (s, 1H), 4.78 (d, J = 5.8 Hz, 2H), 4.48 (s, 2H), 3.71 (m, 2H), 3.15 (m, 2H), 2.63 (s, 3H). | 445.0 |

Biological Activities:

The primary assay is based on Wnt pathway Super-top flash (STF) reporter gene assay:

HEK293 STF stable clones (HEK293 cells stably transfected with "Super-Top Flash" TCF-luciferase reporter plasmid) were kept in complete culture medium (DMEM with 4 mM L-Gln, 1.5 g/L sodium bicarbonate and 4.5 g/L glucose containing 6 µg/mL Blasticidin and 10% FBS). L Wnt3A cells (CRL-2647, ATCC) were kept in DMEM (Gibico) containing 10% FBS (Hyclone). HEK293 STF and L Wnt3A cells were harvested when 90% confluence and cell suspension was mixed with a fixed ratio of 1:1 (HEK293 STF: L Wnt3A). 100 µL/well of mixed cells suspension was added to the 96-well-plate with final cell concentration of 12,000 cells/well and then cultured for an additional 24 hours before adding compounds.

Compounds were diluted in DMSO in sequence and then diluted with DMEM medium. 20 µL medium containing compound was added to the cells according to the pre-setting dose. Cell plates were incubated at 37° C. for an additional 48 hours.

50 µL luciferase solution (Bright-Glo, Promega) was added to each well during the 48 h incubation. The plates were incubated at room temperature for 5 min under gentle shaking. Luminescence signaling was measured with a plate reader (PHERAstar FS, BMG). The $IC_{50}$ (potency) of compounds was calculated based on the inhibition of luminescence signaling.

Figure 2:
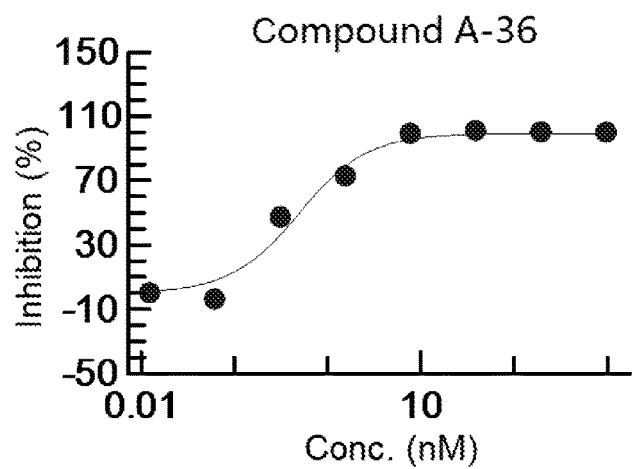
FIG. 2 depicts the IC50 curve of compound A-36 of the present invention in the primary assay.
Figure 3:
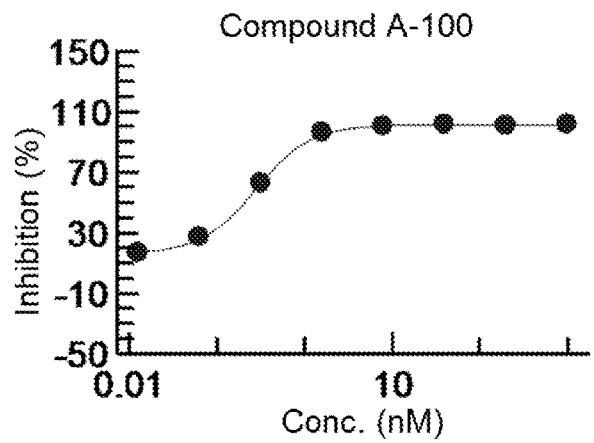
FIG. 3 depicts the IC50 curve of compound A-100 of the present invention in the primary assay.
Figure 4:
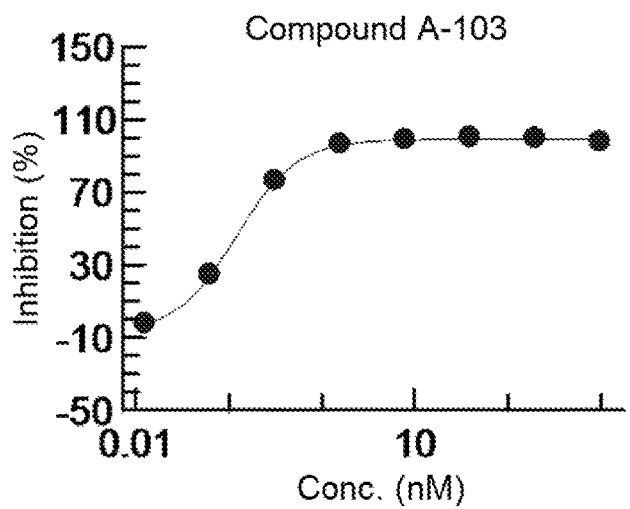
FIG. 4 depicts the IC50 curve of compound A-103 of the present invention in the primary assay.
Figure 5:
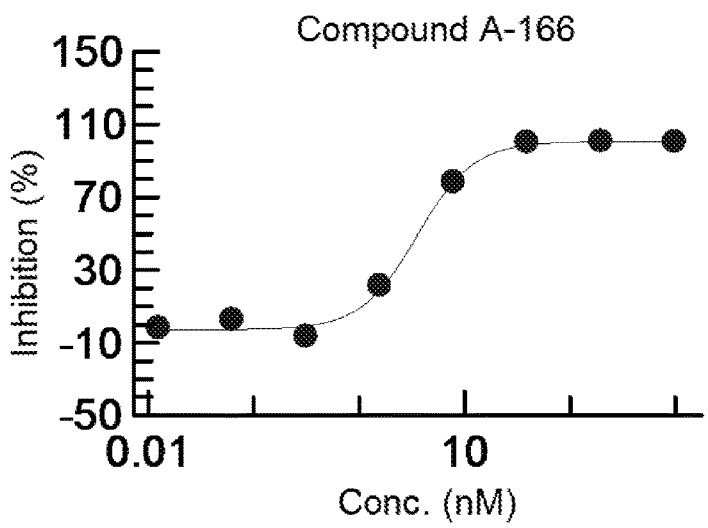
FIG. 5 depicts the IC50 curve of compound A-166 of the present invention in the primary assay.
Figure 6:
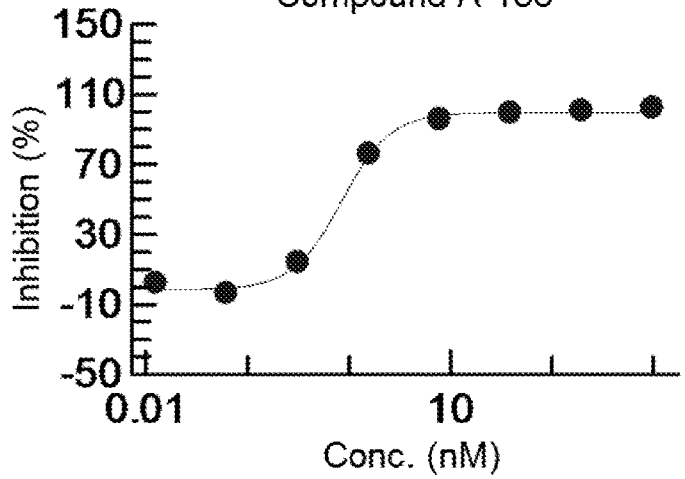
FIG. 6 depicts the IC50 curve of compound A-168 of the present invention in the primary assay.
Figure 7:
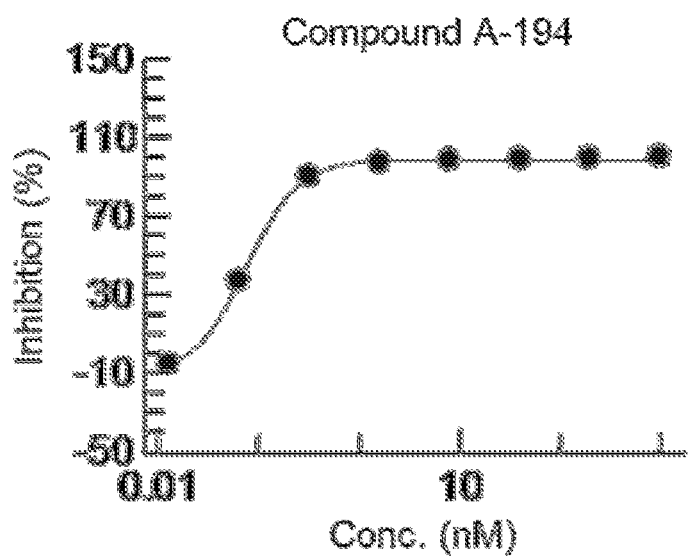
FIG. 7 depicts the IC50 curve of compound A-194 of the present invention in the primary assay.
Figure 8:
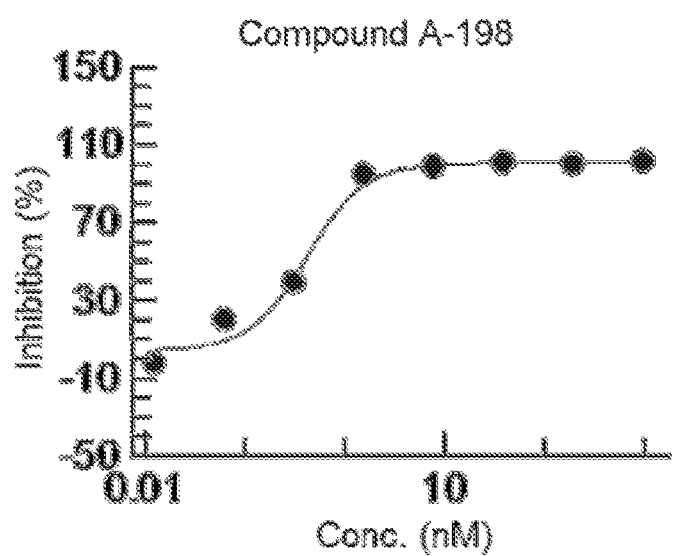
FIG. 8 depicts the IC50 curve of compound A-198 of the present invention in the primary assay.

The above mentioned compounds were tested in the primary assay described above and the data were summarized in Table 3. In particular, IC50 curves for compounds A-12, A-36, A-100, A-103, A-166, A-168, A-194, and A-198 are shown in FIGS. 1-8, respectively.

TABLE 3

Results of selected compounds (A-1 to A-202) of the present invention when tested in the primary assay.

| Compound number | $IC_{50}$ (nM) | Compound number | $IC_{50}$ (nM) | Compound number | $IC_{50}$ (nM) |
|---|---|---|---|---|---|
| A-1 | 1.4 | A-2 | 2.9 | A-3 | 36 |
| A-4 | 0.3 | A-5 | 2.1 | A-6 | 4.7 |
| A-7 | 7.4 | A-8 | 1.5 | A-9 | 2.8 |
| A-10 | 285 | A-11 | 1.6 | A-12 | 0.3 |
| A-13 | 99 | A-14 | 5.9 | A-15 | 19 |
| A-16 | 27 | A-17 | >1000 | A-18 | 480 |
| A-19 | 14 | A-20 | 211 | A-21 | 14 |
| A-22 | 14 | A-23 | 15 | A-24 | 37 |
| A-25 | >1000 | A-26 | 1.5 | A-27 | 937 |
| A-28 | 17 | A-29 | 577 | A-30 | 23 |
| A-31 | 1 | A-32 | 2 | A-33 | 1.4 |
| A-34 | 3 | A-35 | 4 | A-36 | 0.5 |
| A-37 | 2.4 | A-38 | 5 | A-39 | 129 |
| A-40 | >1000 | A-41 | 55 | A-42 | 0.7 |
| A-43 | 75 | A-44 | 1 | A-45 | 0.4 |
| A-46 | 4.9 | A-47 | 0.94 | A-48 | 2.1 |
| A-49 | 0.39 | A-50 | 1.0 | A-51 | 1.0 |
| A-52 | 17 | A-53 | 89 | A-54 | 0.67 |
| A-55 | 3000 | A-56 | 1 | A-57 | 0.39 |
| A-58 | 34 | A-59 | 230 | A-60 | 0.81 |
| A-61 | 1.3 | A-62 | 6.2 | A-63 | 2 |
| A-64 | 16 | A-65 | 0.44 | A-66 | 58 |
| A-67 | 10 | A-68 | 16 | A-69 | 73 |
| A-70 | 147 | A-71 | 0.29 | A-72 | 0.64 |
| A-73 | 1.3 | A-74 | 1.6 | A-75 | 0.52 |
| A-76 | 1.3 | A-77 | 1.6 | A-78 | 777 |
| A-79 | 416 | A-80 | 768 | A-81 | 625 |
| A-82 | 338 | A-83 | 3000 | A-84 | 0.26 |
| A-85 | 0.14 | A-86 | 0.34 | A-87 | 0.51 |
| A-88 | 7.7 | A-89 | 14 | A-90 | 1.2 |

TABLE 3-continued

Results of selected compounds (A-1 to A-202) of the present invention when tested in the primary assay.

| Compound number | $IC_{50}$ (nM) | Compound number | $IC_{50}$ (nM) | Compound number | $IC_{50}$ (nM) |
|---|---|---|---|---|---|
| A-91 | 53 | A-92 | 10 | A-93 | 40 |
| A-94 | 0.8 | A-95 | 15 | A-96 | 0.2 |
| A-97 | 0.18 | A-98 | 0.06 | A-99 | 0.11 |
| A-100 | 0.27 | A-101 | 0.31 | A-102 | 0.54 |
| A-103 | 0.12 | A-104 | 0.11 | A-105 | 5.2 |
| A-106 | 0.24 | A-107 | 16 | A-108 | 1 |
| A-109 | 10 | A-110 | 1 | A-111 | 10 |
| A-112 | 10 | A-113 | 16 | A-114 | 8 |
| A-115 | 7 | A-116 | 8 | A-117 | 2 |
| A-118 | 318 | A-119 | 10 | A-120 | 12 |
| A-121 | 0.06 | A-122 | 0.13 | A-123 | 0.12 |
| A-124 | 0.12 | A-125 | 0.06 | A-126 | 0.04 |
| A-127 | 0.34 | A-128 | 1.8 | A-129 | 0.4 |
| A-130 | 0.11 | A-131 | 1.0 | A-132 | 0.25 |
| A-133 | 34 | A-134 | 24 | A-135 | 3000 |
| A-136 | 4000 | A-137 | 3000 | A-138 | 712 |
| A-139 | 3000 | A-140 | 3000 | A-141 | 3000 |
| A-142 | 3000 | A-143 | 2000 | A-144 | 40 |
| A-145 | 1131 | A-146 | 68 | A-147 | 40 |
| A-148 | 10 | A-149 | 603 | A-150 | 250 |
| A-151 | 2000 | A-152 | 4.9 | A-153 | 3000 |
| A-154 | 1.2 | A-155 | 229 | A-156 | 12 |
| A-157 | 3000 | A-158 | 3000 | A-159 | 17 |
| A-160 | 6.7 | A-161 | 3000 | A-162 | 2000 |
| A-162 | 3.2 | A-164 | 3000 | A-165 | 0.71 |
| A-166 | 3.6 | A-167 | 120 | A-168 | 0.85 |
| A-169 | 4.9 | A-170 | 3.7 | A-171 | 0.31 |
| A-172 | 1.7 | A-173 | 106 | A-174 | 2.7 |
| A-175 | 0.74 | A-176 | 18 | A-177 | 100 |
| A-178 | 200 | A-179 | 500 | A-180 | 300 |
| A-181 | 350 | A-182 | 0.64 | A-183 | 2.1 |
| A-184 | 1 | A-185 | 4.3 | A-186 | 0.27 |
| A-187 | 51 | A-188 | 4.6 | A-189 | 3000 |
| A-190 | 0.4 | A-191 | 0.38 | A-192 | 0.1 |
| A-193 | 0.07 | A-194 | 0.09 | A-195 | 0.84 |
| A-196 | 0.78 | A-197 | 0.31 | A-198 | 0.42 |
| A-199 | 0.17 | A-200 | 25 | A-201 | 0.8 |
| A-202 | 0.5 | | | | |

What is claimed is:
1. A compound of Formula I:

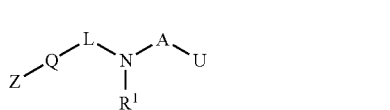

or a pharmaceutically acceptable salt, solvate, stereoisomer or a tautomer thereof, wherein A is A2 or A3;
U is U1;
L is L1, L2, or L3;
A2 is

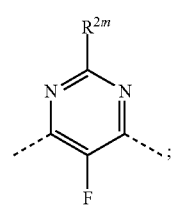

A3 is

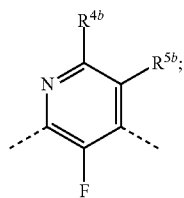

U1 is

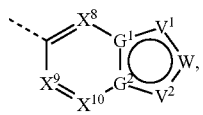

wherein $X^8$ and $X^{10}$ are independently selected from N and $C—R^{14}$;

$G^1$ and $G^2$ are independently selected from N and C;

$V^1$ and $V^2$ are independently selected from N, O, S and $C—R^{15}$;

W is $V^3$, $V^4—V^5$ or $V^4=V^5$, wherein $V^3$ to $V^5$ are independently selected from N, O, S and $C—R^{16}$, wherein $V^4$ connects with $V^1$; and $V^5$ connects with $V^2$;

L1 is

L2 is

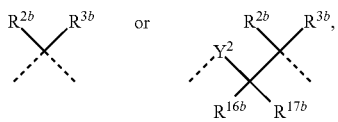

wherein $Y^2$ is blank, —O—, —S—, —N($R^{18b}$)— or —C($R^{18b}$)($R^{19b}$)—;

L3 is —C($R^2c$)($R^3c$)— or —NHCH$_2$CH$_2$—;

Q is

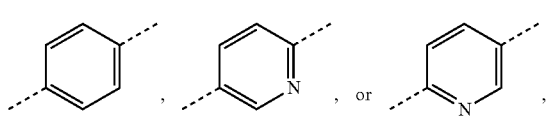

each of which is unsubstituted or substituted with 1 to 3 $R^{4a}$ groups;

Z is

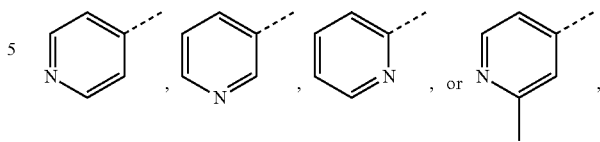

each of which is unsubstituted or substituted with 1 to 3 $R^{5a}$ groups;

$R^1$ to $R^3$ are independently selected from H and $C_1$-$C_6$ alkyl, wherein $C_1$-$C_6$ alkyl is unsubstituted or substituted with 1 to 3 halide, —CN, —OH, $C_1$-$C_3$ alkyl, $C_3$-$C_5$ cycloalkyl, or $C_1$-$C_3$ alkoxy groups;

$R^{14}$ to $R^{16}$ are independently selected from H, halide, —CN, —OH, amino, $C_1$-$C_6$ alkyl, $C_3$-$C_6$ cycloalkyl, $C_1$-$C_6$ alkoxy and $C_1$-$C_6$ alkylthio, wherein amino, $C_1$-$C_6$ alkyl and $C_1$-$C_6$ alkoxy are unsubstituted or substituted with 1 to 3 halide, $C_1$-$C_3$ alkyl or $C_3$-$C_6$ cycloalkyl groups;

$R^{4a}$ and $R^{5a}$ are independently selected from halide, —CN, and —OH, or $R^{4a}$ and $R^{5a}$ are independently selected from $C_1$-$C_8$ alkyl, $C_3$-$C_8$ cycloalkyl, $C_1$-$C_8$ alkoxy, $C_2$-$C_8$ alkenyl, $C_2$-$C_8$ alkynyl, $C_1$-$C_8$ alkylsulfonyl, $C_1$-$C_8$ acyl, aminoacyl, $C_1$-$C_8$ acylamino, $C_1$-$C_8$ alkylcarbamoylamino, $C_1$-$C_8$ alkoxycarbamoyl, $C_1$-$C_8$ alkylsulfonamido, $_1$-$C_8$ alkylaminosulphonyl, $C_2$-$C_8$ alkoxyacyl, and 3-8 membered heterocycle, all of which are unsubstituted or substituted with 1-3 halide, —OH, —CN, $C_1$-$C_3$ alkyl, $C_1$-$C_3$ alkoxyl or $C_3$-$C_8$ cycloalkyl groups, wherein 3-8 membered heterocycle comprises one or more hetero atoms selected from N, O or S;

$R^{2m}$ is H, deuterium, tritium, halide, —OH, —CN, $C_3$-$C_8$ cycloalkyl or $C_1$-$C_8$ alkoxy;

$R^{2b}$ and $R^{3b}$ are independently selected from H, $C_1$-$C_6$ alkyl unsubstituted or substituted with 1-3 groups selected from halide, —CN, —OH, $C_1$-$C_6$ alkyl, $C_3$-$C_5$ cycloalkyl and $C_1$-$C_3$ alkoxy;

$R^{4b}$ and $R^{5b}$ are independently selected from H, halide, —CN, amino, $C_1$-$C_8$ alkyl, $C_3$-$C_8$ cycloalkyl, $C_1$-$C_8$ alkoxy, and $C_1$-$C_3$ alkylamino;

$R^{16b}$ to $R^{19b}$ are independently selected from H and $C_1$-$C_6$ alkyl unsubstituted or substituted with halide;

$R^{2c}$ and $R^{3c}$ are independently selected from H and $C_1$-$C_6$ alkyl unsubstituted or substituted with 1-3 halide.

2. The compound of claim 1, wherein U is

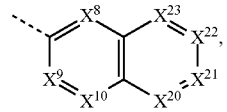

wherein $X^{20}$ to $X^{23}$ are independently N or $C—R^{15}$.

3. The compound of claim 1, wherein U is selected from:

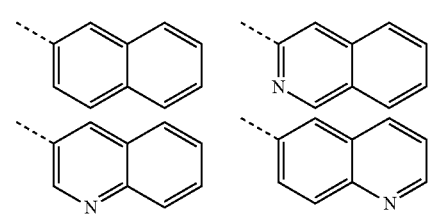

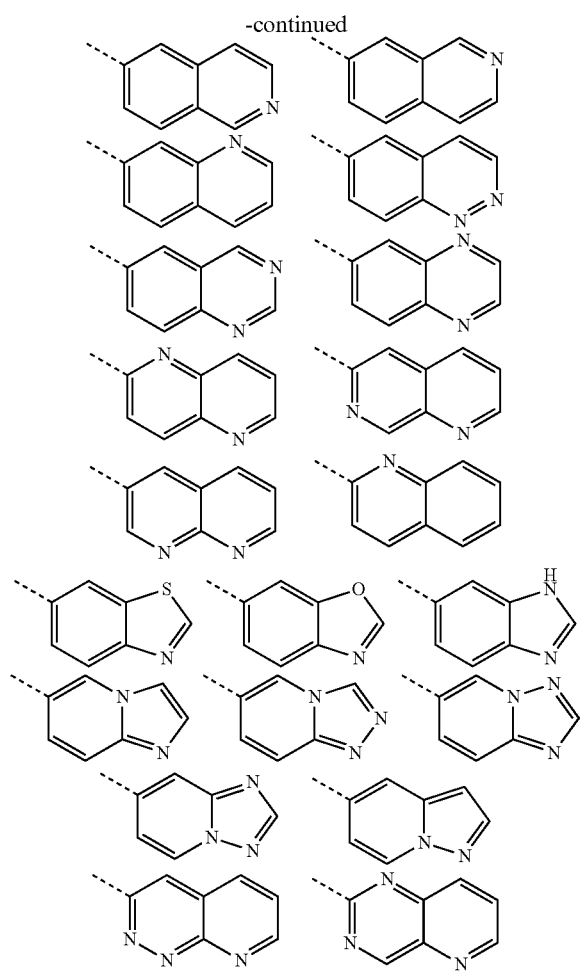
unsubstituted or substituted with 1 to 3 R[15] groups.
4. The compound of claim 1, wherein U is selected from:
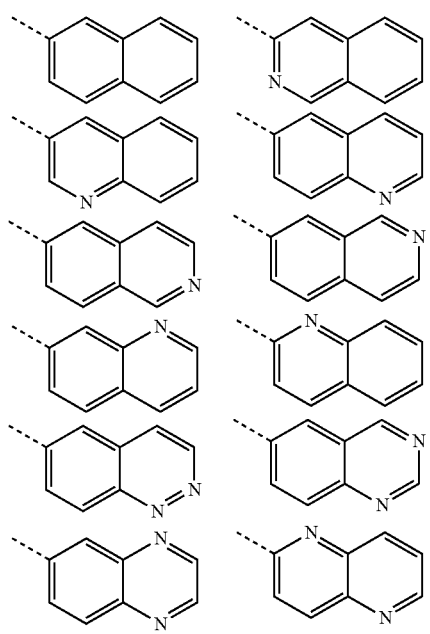
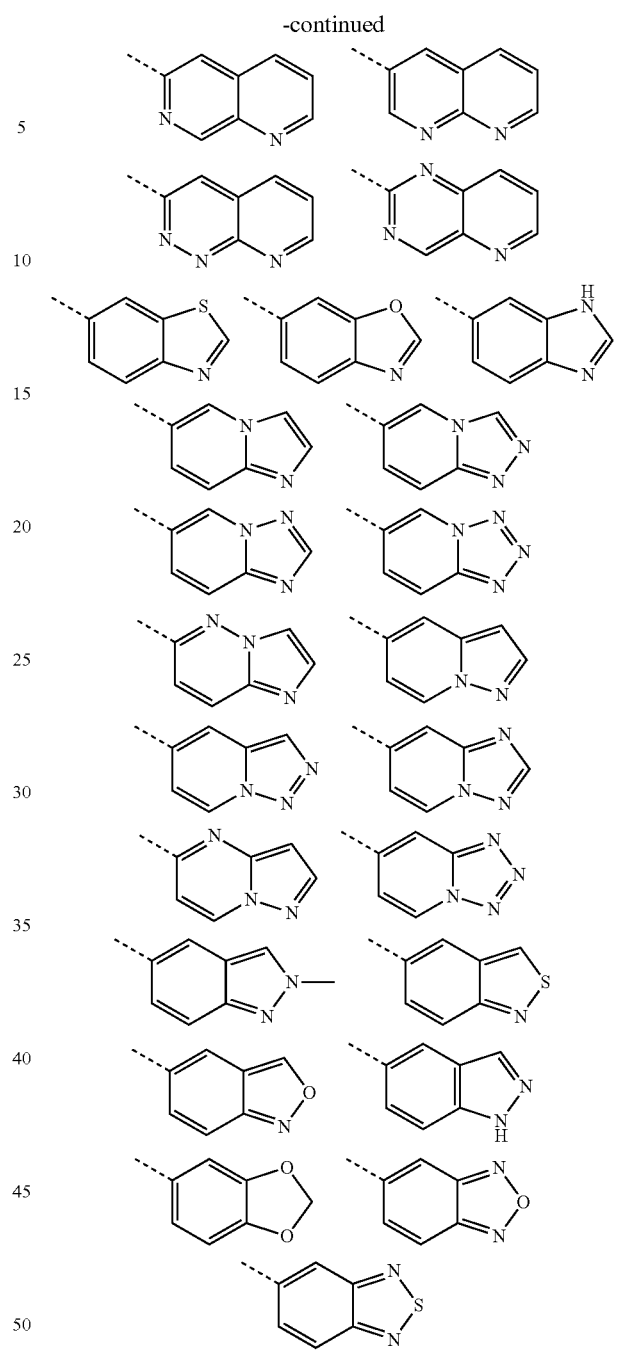
5. The compound of claim 1, wherein the compound is selected from the group consisting of:
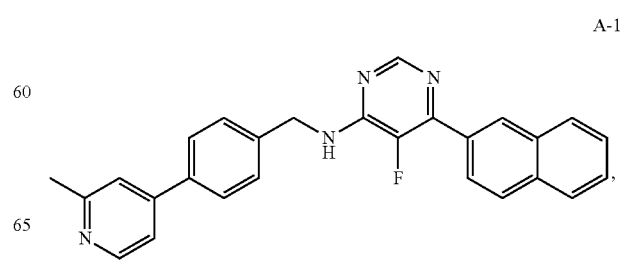
A-1

A-2
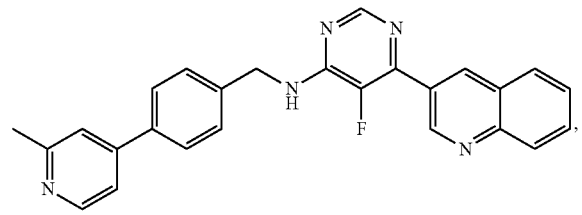
A-3
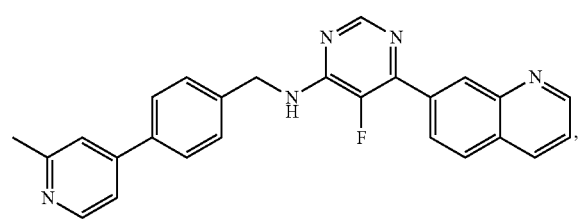
A-4
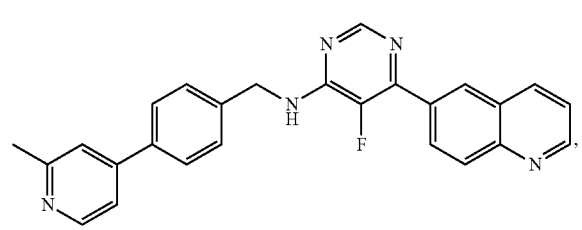
A-5
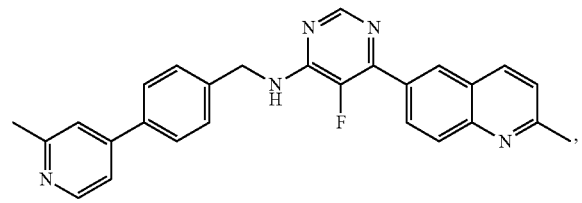
A-6
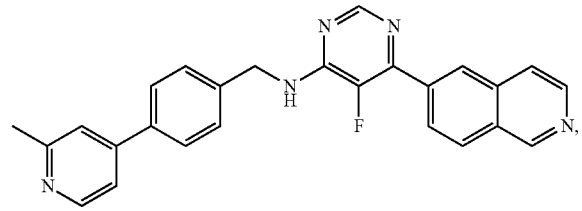
A-7
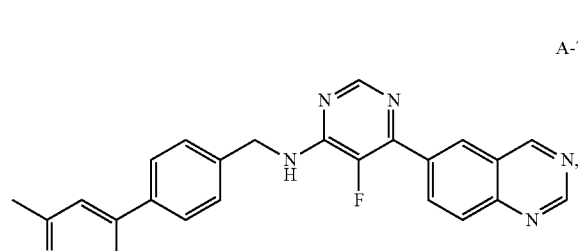
A-8
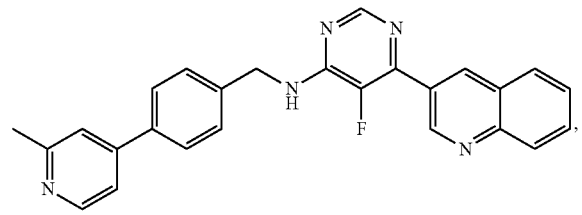
A-9
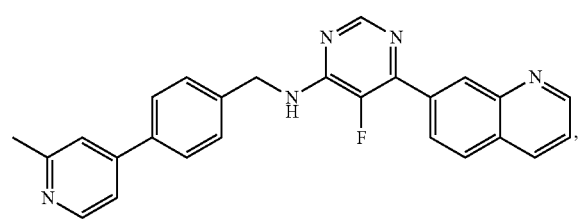
A-10
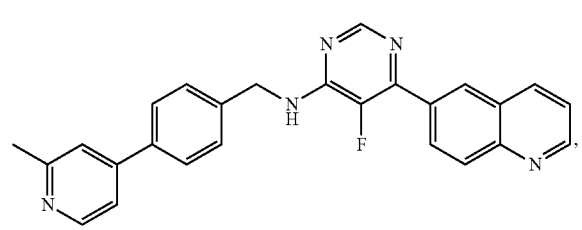
A-11
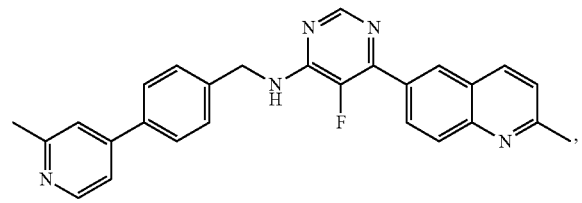
A-12
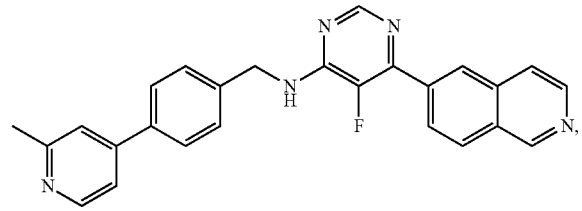
A-13
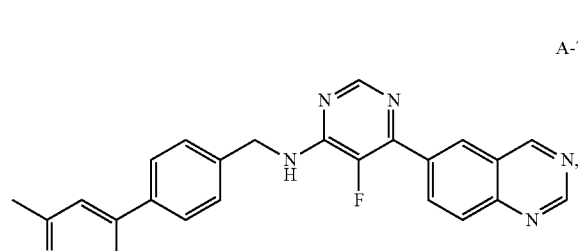

-continued

A-14, A-15, A-27, A-28, A-30, A-31, A-33, A-34, A-35, A-36, A-37, A-38

A-48
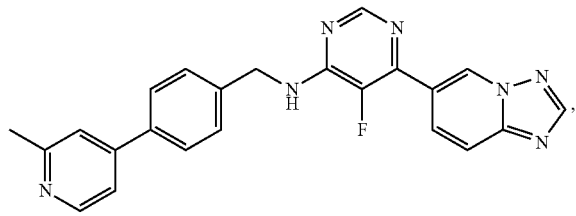
A-49
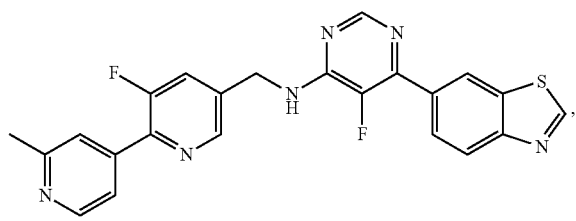
A-50
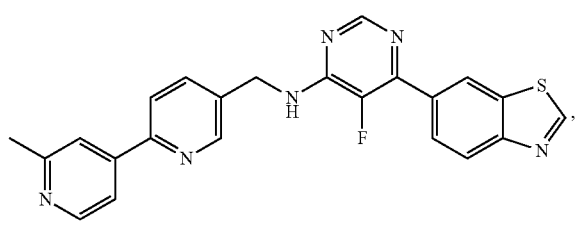
A-51
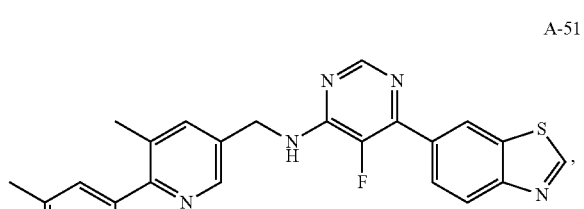
A-55
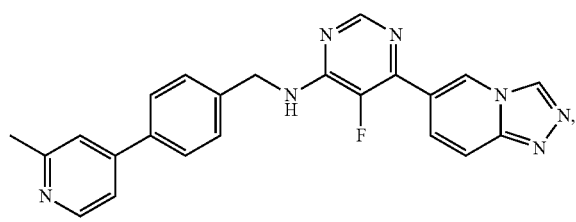
A-57
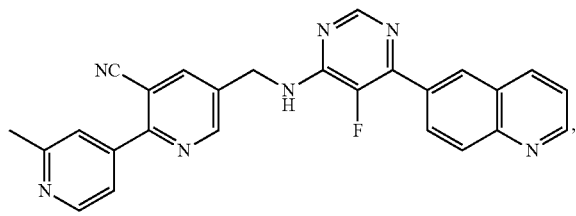
A-65
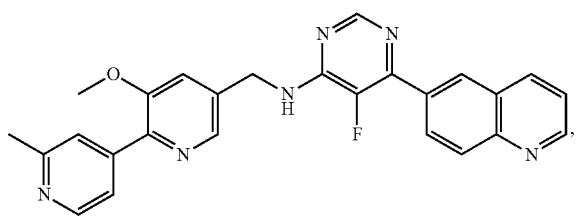
A-84
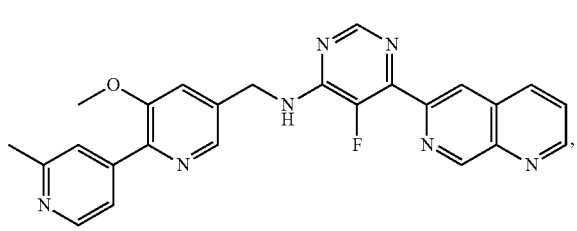
A-85
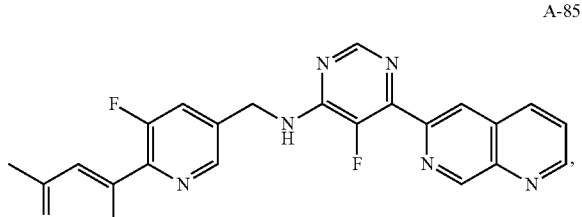
A-86
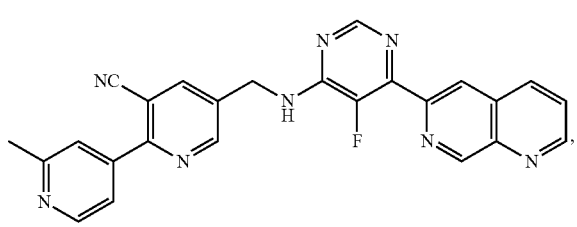
A-96
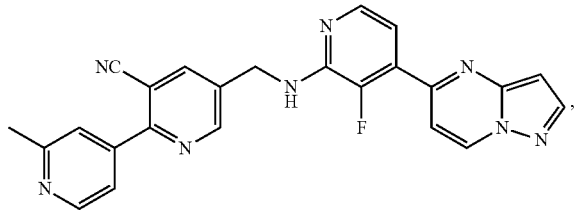
A-97
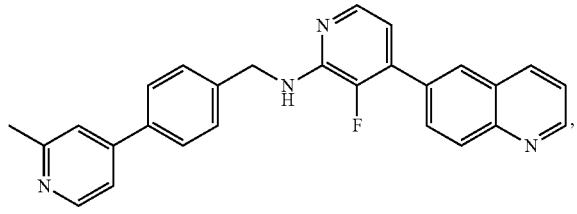

A-98
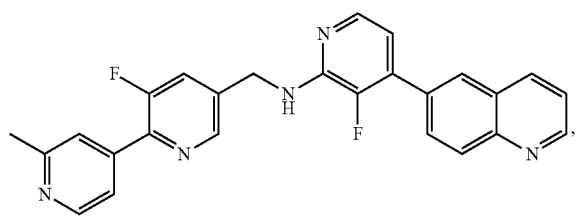
A-106
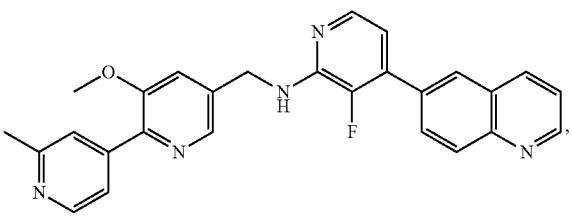
A-99
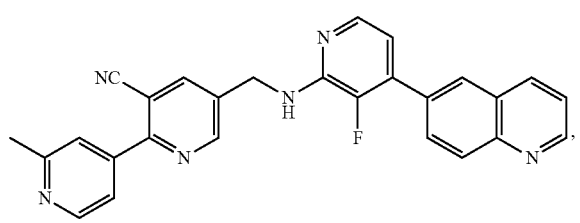
A-108
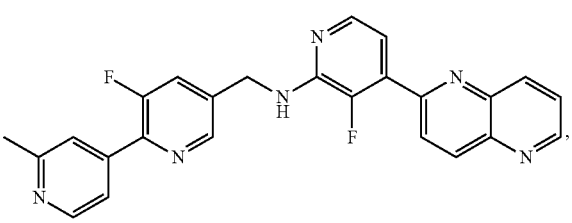
A-101
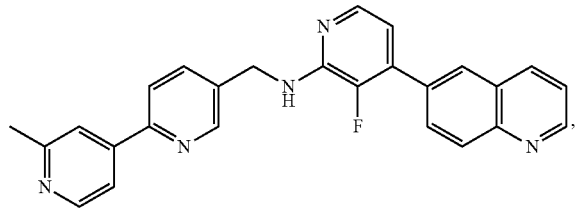
A-110
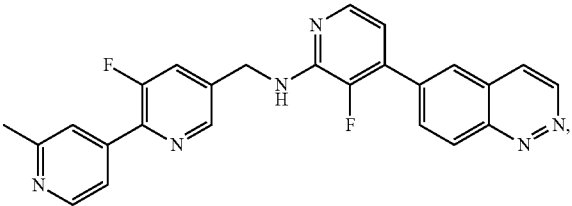
A-102
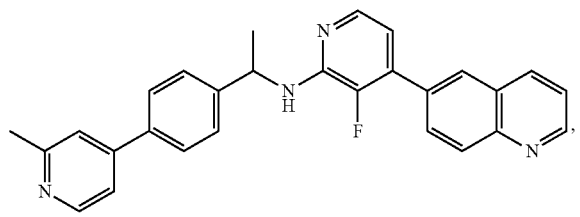
A-114
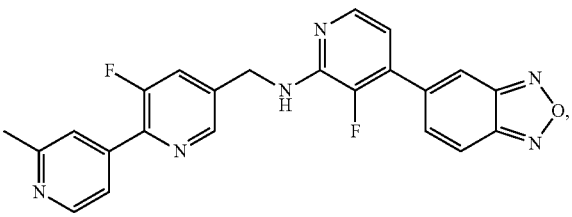
A-103
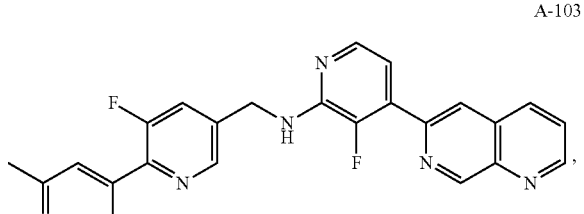
A-121
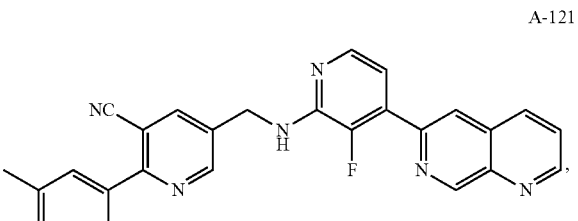
A-104
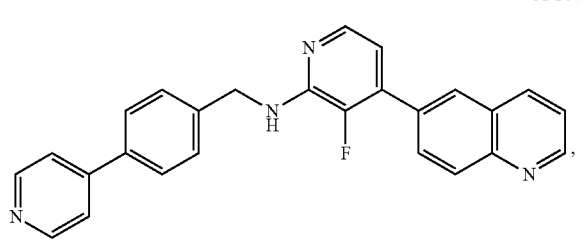
A-122
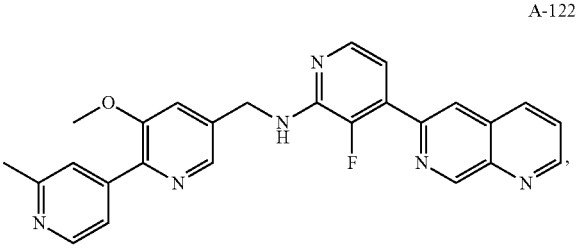

A-123

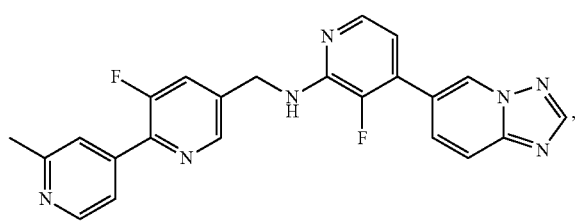

A-124

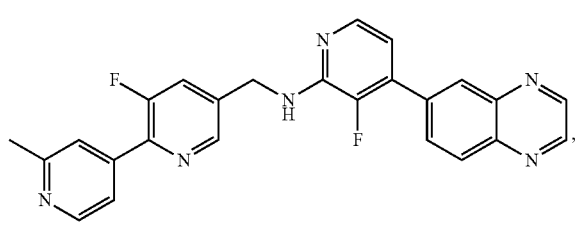

A-125

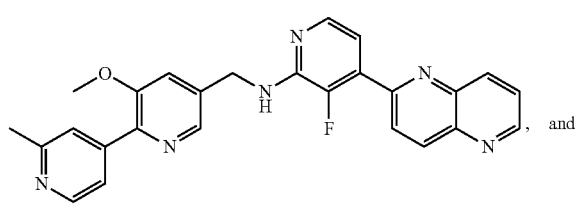
, and

A-126

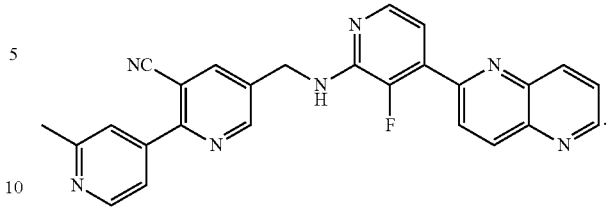

6. A pharmaceutical composition comprising a therapeutically effective amount of a compound of claim 1 and a pharmaceutically acceptable carrier.

7. A method for treating a Wnt-mediated disorder in a mammal suffering therefrom, comprising administering to the mammal a therapeutically effective amount of at least one compound of claim 1, or a pharmaceutical composition thereof, and optionally in combination with a second therapeutic agent, wherein the disorder is a cell proliferative disorder selected from the group consisting of systemic sclerosis, skin fibrosis, idiopathic pulmonary fibrosis, renal fibrosis, liver fibrosis, drug-induced fibrosis, radiation-induced fibrosis, colorectal cancer, breast cancer, head and neck squamous cell carcinoma, esophageal squamous cell carcinoma, non-small cell lung cancer, gastric cancer, pancreatic cancer, leukemia, lymphoma, neuroblastoma, retinoblastoma, sarcoma, osteosarcoma, chondosarcoma, Ewing's sarcoma, rhabdomysarcoma, brain tumor, Wilms' tumor, basal cell carcinoma, melanoma, head and neck cancer, cervical cancer, and prostate cancer.

* * * * *